US007968720B2

(12) United States Patent
Bezencon et al.

(10) Patent No.: US 7,968,720 B2
(45) Date of Patent: Jun. 28, 2011

(54) SECONDARY AMINES AS RENIN INHIBITORS

(75) Inventors: Olivier Bezencon, Riehen (CH); Daniel Bur, Therwil (CH); Olivier Corminboeuf, Allschwil (CH); Daniel Dube, Kirkland (CA); Corinna Grisostomi, Allschwil (CH); Dwight MacDonald, Kirkland (CA); Dan McKay, Kirkland (CA); David Powell, Kirkland (CA); Lubos Remen, Allschwil (CH); Sylvia Richard-Bildstein, Dietwiller (FR); John Scheigetz, Kirkland (CA); Michel Therien, Kirkland (CA); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 217 days.

(21) Appl. No.: 12/223,597

(22) PCT Filed: Jan. 31, 2007

(86) PCT No.: PCT/IB2007/050327

§ 371 (c)(1),
(2), (4) Date: Aug. 1, 2008

(87) PCT Pub. No.: WO2007/088514

PCT Pub. Date: Aug. 9, 2007

(65) Prior Publication Data

US 2009/0176823 A1    Jul. 9, 2009

(30) Foreign Application Priority Data

Feb. 2, 2006 (WO) .................. PCT/IB2006/050356

(51) Int. Cl.
*C07D 221/02* (2006.01)
*C07C 211/00* (2006.01)

(52) U.S. Cl. ...................................... 546/122; 564/305
(58) Field of Classification Search .................. 564/305; 514/646, 300; 546/122

See application file for complete search history.

(56) References Cited

U.S. PATENT DOCUMENTS

| 5,380,758 | A | 1/1995 | Stamler |
| 5,703,073 | A | 12/1997 | Garvey |
| 5,994,294 | A | 11/1999 | Garvey |
| 6,218,417 | B1 | 4/2001 | del Soldato |
| 6,242,432 | B1 | 6/2001 | del Soldato |
| 7,427,613 | B2 | 9/2008 | Bezencon et al. |
| 2008/0161313 | A1 | 7/2008 | Bezencon et al. |
| 2008/0214598 | A1* | 9/2008 | Bezencon et al. ............ 514/300 |
| 2009/0062342 | A1* | 3/2009 | Bezencon et al. ............ 514/318 |
| 2009/0176823 | A1 | 7/2009 | Bezencon et al. |
| 2009/0306123 | A1 | 12/2009 | Bezencon et al. |

FOREIGN PATENT DOCUMENTS

| WO | WO97/09311 | 3/1997 |
| WO | WO98/19672 | 5/1998 |
| WO | WO03/093267 | 11/2003 |
| WO | WO2004/002957 | 1/2004 |
| WO | WO2004/096366 | 11/2004 |
| WO | WO2004/096769 | 11/2004 |
| WO | WO2004/096799 | 11/2004 |
| WO | WO2004/096803 | 11/2004 |
| WO | WO2006/069788 | 7/2006 |
| WO | WO2006/129237 | 12/2006 |

OTHER PUBLICATIONS

Patani et. al., "Bioisosterism: A Rational Approach in Drug Design", Chem. Rev. 1996, 96, pp. 3147-3176.*
U.S. Appl. No. 11/915,594, Bezencon, et al.
Azizi et al., Blood pressure effects of acute intravenous rennin or oral angiotensin converting enzyme inhibition in essential hypertension, J. Hypertens, 1994, 12, 419.
Blough et al., Synthesis and transporter binding properties of 3β-[4'-Phenylalkyl,-phenylakenyl, and -phenylalkynl)phenyl] topane-2β-carboxylic acid methyl ester: evidence of a remote phenyl binding domain on the dopamine transporter, Med.Chem., 2002, 45, 4029.
Breyer et al., Angiotensin converting enzyme inhibition in diabetic nephropathy, Kidney International, 1994, 45, S156.
Carroll et al., Monoamine transporter binding, locomotor activity, and drug discrimination properties of 3-(4-substituted-phenyl) tropane-2-carboxylic acid methyl ester isomers, J.Med.Chem., 2004, 47, 6401.
Cossy et al., A formal synthesis of (-)-paroxetine by enantioselective ring enlargement of a trisubstituted prolinol, European J. Org. Chem., 2002, 21, 3543.
Fischli et al., Ro 42-5892 is a potent orally active renin inhibitor in primates, Hypertension, 1991, 18:22-31.
Fouad-Tarazi et al., The renin-angiotensin system and treatment of heart failure, Am. J. Med., 1988, 84 (Suppl.3A), 83.
Gibson, Editor, Pharmaceutical Preformulation and Formulation, IHS Health Group, Englewood CO, USA 2001.
Gould, Salt selection for basic drugs, Int. J. Pharm. 1986, 33, 201-217.
Husain, The chymase-angiotensin system in humans, J. Hypertens., 1993, 11, 1155.
Israili et al., Cough and angioneurotic edema associated with angiotensin-converting enzyme inhibitor therapy, Annals of Internal Medicine, 1992, 117, 234. Jurkauskas et al., Conjugate reduction of α,β-unsaturated carbonyl compounds catalyzed by a copper carbene complex, Org.Letters, 2003, 5, 2417.
Kleinert, Renin inhibition, Cardiovasc. Drugs, 1995, 9, 645.
Marki et al., Piperidine renin inhibitors: from leads to drug candidates, IL Farmaco, 2001, 56, 21.
Mealy et al., Aliskiren fumarate, Drugs of the Future, 2001, 26, 1139.
Meltzer et al., Synthesis and biological activity of 2-carbomethoxy-3-catechol-8-azabicyclo[3.2.1]octanes, Bioorg. Med. Chem. Letters, 2003, 13, 4133.
Murthy et al., Enantioselective synthesis of 3-substituted-4-aryl piperdines useful for the preparation of paroxetine, Science Direct, Tetrahedron Letters, 2003, 44, 5355.

(Continued)

*Primary Examiner* — Janet L Andres
*Assistant Examiner* — Heidi Reese
(74) *Attorney, Agent, or Firm* — Hoxie & Associates LLC

(57) ABSTRACT

The invention relates to novel secondary amine derivatives of formula (I) and the use thereof as active ingredients in the preparation of pharmaceutical compositions. The invention also concerns related aspects including processes for the preparation of the compounds, pharmaceutical compositions containing one or more of those compounds and especially their use as inhibitors of renin.

23 Claims, No Drawings

OTHER PUBLICATIONS

Neutel et al., Immediate blood pressure effects of the renin inhibitor enalkiren and the angiotensis-converting enzyme inhibitor enalaprilat, Am. Heart, 1991, 122, 1094.

Oae et al., Organic thionitrites and related substances, a review, Org. Prep. Proc. Int. 15(3): 165-198, 1983.

Oefner et al., Renin inhibition by substituted piperidines: a novel paradigm for the inhibition of monomeric aspartic proteinases?, Chem. Biol., 1999, 6, 127.

Pfeffer et al., Effect of captopril on mortality and morbidity in patients with left ventricular dysfunction after myocardial infarction, N.Engl. J. Med., 1992, 327, 669.

Rahuel et al., Structure-based drug design: the discovery of novel nonpeptide orally active inhibitors of human renin, Chem. Biol., 2000, 7, 493.

Remington: The Science and Practice of Pharmacy, $20^{th}$ Edition, Philadelphia College of Pharmacy and Science, table of contents.

Rosenberg et al., The paradox of the renin-angiotensin system in chronic renal disease, Kidney International, 1994, 45, 403.

Vaughan et al., Angiotensin converting enzyme inhibitors and cardiovascular remodelling, Cardiovasc. Res., 1994, 28, 159.

Waeber et al., The renin-angiotensin system: role in experimental and human hypertension, Hypertension, Amsterdam, Elsevier Science Publishing Co., 1986, 489-519.

Weber, Clinical experience with the angiotensin II receptor antanoists losartan, Am. J. Hypertens., 1992, 5, 247S.

* cited by examiner

SECONDARY AMINES AS RENIN INHIBITORS

CROSS REFERENCE TO RELATED APPLICATIONS

This application is a United States Application filed under 35 USC § 371 claiming benefit of PCT/IB2007/050327, the contents of each of which are incorporated herein by reference.

The invention relates to novel compounds of the formula (I). The invention also concerns related aspects including processes for the preparation of the compounds, pharmaceutical compositions containing one or more compounds of formula (I) and especially their use as renin inhibitors in cardiovascular events and renal insufficiency.

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.,* 1992, 5, 247S). In addition, ACE inhibitors are used for renal protection (Rosenberg M. E. et al., *Kidney International,* 1994, 45, 403; Breyer J. A. et al., *Kidney International,* 1994, 45, S156), in the prevention of congestive heart failure (Vaughan D. E. et al., *Cardiovasc. Res.,* 1994, 28, 159; Fouad-Tarazi F. et al., *Am. J. Med.,* 1988, 84 (Suppl. 3A), 83) and myocardial infarction (Pfeffer M. A. et al., *N. Engl. J. Med.,* 1992, 327, 669).

The rationale to develop renin inhibitors is the specificity of renin (Kleinert H. D., *Cardiovasc. Drugs,* 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.,* 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine,* 1992, 117, 234). ACE inhibitors do not inhibit Chymase. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

Only limited clinical experience (Azizi M. et al., *J. Hypertens.,* 1994, 12, 419; Neutel J. M. et al., *Am. Heart,* 1991, 122, 1094) has been created with renin inhibitors because of their insufficient oral activity due to their peptidomimetic character (Kleinert H. D., *Cardiovasc. Drugs,* 1995, 9, 645). The clinical development of several compounds has been stopped because of this problem together with the high cost of goods. Only one compound containing four chiral centers has entered clinical trials (Rahuel J. et al., *Chem. Biol.,* 2000, 7, 493; Mealy N. E., *Drugs of the Future,* 2001, 26, 1139). Thus, renin inhibitors with good oral bioavailability and long duration of action are required. Recently, the first non-peptide renin inhibitors were described which show high in vitro activity (Oefner C. et al., *Chem. Biol.,* 1999, 6, 127; Patent Application WO 97/09311; Märki H. P. et al., *Il Farmaco,* 2001, 56, 21). However, the development status of these compounds is not known.

The present invention relates to renin inhibitors of a non-peptidic nature and of low molecular weight. Described are orally active renin inhibitors of formula (I) which have a long duration of action and which are active in indications beyond blood pressure regulation where the tissular renin-chymase system may be activated leading to pathophysiologically altered local functions such as renal, cardiac and vascular remodelling, atherosclerosis, and possibly restenosis. So, the present invention describes these non-peptidic renin inhibitors of formula (I).

In particular, the present invention relates to novel compounds of the formula (I)

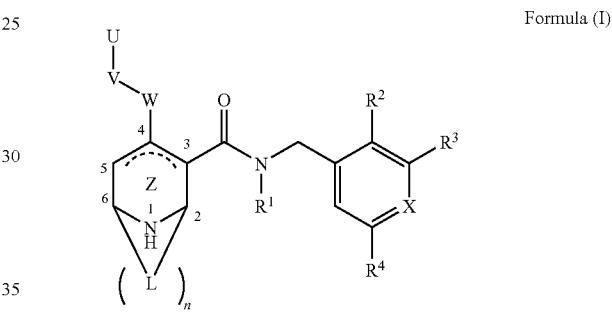

Formula (I)

wherein
the dotted line in the 6-membered nitrogen containing ring Z of formula (I) (said ring Z consisting of the numbered ring atoms 1 to 6) indicates that either a double bond is present at the 3,4- or at the 4,5-position of the ring Z of formula (I) or that no double bond is present in the ring Z of formula (I); and wherein
if n=0, a double bond can be present at the 3,4- or at the 4,5-position of the ring Z of formula (I); or
if n=1, a double bond can be present at the 3,4-position of the ring Z of formula (I);
or:
no double bond may be present in the ring Z of formula (I) if:
  i) n represents the integer 0 and X represents N or $N^+$—$O^-$, or
  ii) n represents the integer 0 and V represents —O—$CH_2$-Q-, or
  iii) n represents the integer 0, W represents para-substituted phenyl or especially para-substituted pyridinyl, and V represents a pyrrolidinyl of the formula:

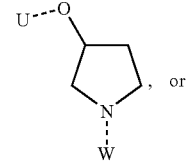

, or iv) n represents the integer 1 and L represents —CH$_2$—CH$_2$—, —CH$_2$—CH(R$^5$)—CH$_2$—, —CH$_2$—O—CH$_2$—, or —CH$_2$—S—CH$_2$—, or v) n represents the integer 1, L represents —CH$_2$—N(R$^6$)—CH$_2$—, and X represents N or N$^+$—O$^-$;

X represents CH, N, or N$^+$—O$^-$;

W represents a para-substituted phenyl, a para-substituted pyridinyl, or a thiazolyl, especially a para-substituted phenyl or a para-substituted pyridinyl;

V represents —CH$_2$CH$_2$CH$_2$—, —CH$_2$CH$_2$-A-, —CH$_2$-A-CH$_2$—, -A-CH$_2$CH$_2$—, —CH$_2$CH$_2$CH$_2$CH$_2$—, -A-CH$_2$CH$_2$CH$_2$—, —CH$_2$-A-CH$_2$CH$_2$—, —CH$_2$CH$_2$-A-CH$_2$—, —CH$_2$CH$_2$CH$_2$-A-, -A-CH$_2$CH$_2$—B—, —CH$_2$CH$_2$CH$_2$CH$_2$CH$_2$—, -A-CH$_2$CH$_2$CH$_2$CH$_2$—, —CH$_2$-A-CH$_2$CH$_2$CH$_2$—, —CH$_2$CH$_2$-A-CH$_2$CH$_2$—, —CH$_2$CH$_2$CH$_2$-A-CH$_2$—, —CH$_2$CH$_2$CH$_2$CH$_2$-A-, -A-CH$_2$CH$_2$CH$_2$—B—, —CH$_2$-A-CH$_2$CH$_2$—B—, -A-CH$_2$CH$_2$—B—CH$_2$—, -A-CH$_2$CH$_2$CH$_2$—B—CH$_2$—, —CH$_2$-A-CH$_2$CH$_2$CH$_2$—B—, or —O—CH$_2$-Q-, wherein Q is bound to the group U of formula (I); or:

if i) n represents the integer 0, or ii) n represents the integer 1 and X represents N or N$^+$—O$^-$, or iii) L represents —CH$_2$—CH$_2$—, or iv) L represents —CH$_2$—N(R$^6$)—CH$_2$—, and W represents a para-substituted pyridinyl, V can in addition represent a pyrrolidinyl of the formula:

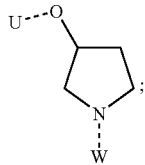

U represents unsubstituted aryl, especially phenyl; mono-, di-, tri- or tetra-substituted aryl (especially mono- di-, tri-, or tetra-substituted phenyl), wherein the substituents are independently selected from C$_{1-7}$-alkyl, —CF$_3$, halogen and hydroxy-C$_{1-7}$-alkyl; or five-membered heteroaryl containing two heteroatoms independently selected from nitrogen, oxygen and sulfur (preferably pyrazolyl or isoxazolyl), wherein said heteroaryl radical is optionally mono-, di- or tri-substituted, wherein the substitutents are independently selected from C$_{1-7}$-alkyl, C$_{1-7}$-alkoxy, —CF$_3$, —OCF$_3$, and halogen;

Q represents a five-membered heteroaryl with two or three heteroatoms independently selected from O and N;

L represents —CH$_2$—CH$_2$—, —CH$_2$—CH(R$^5$)—CH$_2$—, —CH$_2$—N(R$^6$)—CH$_2$—, —CH$_2$—O—CH$_2$—, or —CH$_2$—S—CH$_2$—;

A and B represent independently from each others —O— or —S—;

R$^1$ represents C$_{1-7}$-alkyl or cycloalkyl, preferably cycloalkyl such as especially cyclopropyl;

R$^2$ represents halogen or C$_{1-7}$-alkyl, preferably chloro or methyl, especially chloro;

R$^3$ represents halogen, C$_{1-7}$-alkyl, C$_{1-7}$-alkoxy, —CF$_3$, or hydrogen, preferably hydrogen;

R$^4$ represents C$_{1-7}$-alkyl-O—(CH$_2$)$_{0-4}$—CH$_2$—; CF$_3$—O—(CH$_2$)$_{0-4}$—CH$_2$—; R'R''N—(CH$_2$)$_{0-4}$—CH$_2$—, wherein R' and R'' are independently selected from the group consisting of hydrogen, C$_{1-7}$-alkyl (optionally but preferably substituted by one to three fluorine), cyclopropyl (optionally substituted by one to three fluorine), cyclopropyl-C$_{1-7}$-alkyl (optionally but preferably substituted by one to three fluorine), and —C(=O)—R''' wherein R''' is C$_{1-4}$-alkyl, C$_{1-4}$-alkoxy, —CF$_3$, —CH$_2$—CF$_3$, or cyclopropyl; or R$^{12}$NH—C(=O)—(O)$_{0-1}$—(CH$_2$)$_{0-4}$—, wherein R$^{12}$ is C$_{1-4}$-alkyl, C$_{1-4}$-alkoxy, or cyclopropyl; wherein R' and R''' preferably do not both simultaneously represent hydrogen;

R$^5$ represents —H, —CH$_2$OR$^8$, —CH$_2$NR$^7$R$^8$, —CH$_2$NR$^7$COR$^8$, —CH$_2$NR$^7$SO$_2$R$^8$, —CO$_2$R$^8$, —CH$_2$OCONR$^7$R$^8$, —CONR$^7$R$^8$, —CH$_2$NR$^7$CONR$^7$R$^8$, —CH$_2$SO$_2$NR$^7$R$^8$, —CH$_2$SR$^8$, —CH$_2$SOR$^8$, or —CH$_2$SO$_2$R$^8$;

R$^6$ represents —R$^8$, —COR$^8$, —COOR$^{10}$, —CONR$^7$R$^8$, —C(NR$^7$)NR$^7$R$^8$, —CSNR$^7$R$^8$, —SO$_2$R$^8$, or —SO$_2$NR$^7$R$^8$; or R$^6$ represents a radical of the formula:

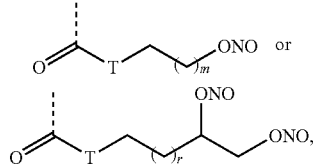

wherein T represents —CH$_2$—, —NH— or —O—, m is an integer from 1 to 6 and r is an integer from 1 to 4;

R$^7$ and R$^{7'}$ independently represent hydrogen, C$_{1-7}$-alkyl, C$_{2-7}$-alkenyl, cycloalkyl, or cycloalkyl-C$_{1-7}$-alkyl, wherein C$_{1-7}$-alkyl, cycloalkyl, and cycloalkyl-C$_{1-7}$-alkyl can be substituted by one, two, or three halogens;

R$^8$ represents hydrogen, C$_{1-7}$-alkyl, cycloalkyl, or cycloalkyl-C$_{1-7}$-alkyl, wherein C$_{1-7}$-alkyl, cycloalkyl, or cycloalkyl-C$_{1-7}$-alkyl may be mono-, di- or tri-substituted, wherein the substituents are independently selected from the group consisting of halogen, hydroxy, —OCOR$^{11}$, —COOR$^{11}$, C$_{1-7}$-alkoxy, cyano, SO$_2$R$^{11}$, —CONR$^{11}$R$^{11'}$, morpholin-4-yl-CO—, ((4-C$_{1-7}$-alkyl)piperazin-1-yl)-CO—, —NHC(NH)NH$_2$, —NR$^9$R$^{9'}$ and C$_{1-7}$-alkyl, with the proviso that a carbon atom is attached at the most to one heteroatom in case this carbon atom is sp$^3$-hybridized;

R$^9$ and R$^{9'}$ independently represent hydrogen, C$_{1-7}$-alkyl, cycloalkyl, cycloalkyl-C$_{1-7}$-alkyl, hydroxy-C$_{1-7}$-alkyl, —COOR$^7$, or —CONH$_2$;

R$^{10}$ represents halogen, C$_{1-7}$-alkyl, C$_{1-7}$-alkoxy, —CF$_3$, or hydrogen;

R$^{11}$ and R$^{11'}$ independently represent hydrogen, C$_{1-7}$-alkyl, C$_{2-7}$-alkenyl, cycloalkyl, or cycloalkyl-C$_{1-7}$-alkyl, wherein C$_{1-7}$-alkyl, cycloalkyl, and cycloalkyl-C$_{1-7}$-alkyl can be substituted by one, two, or three halogens; and n represents the integer 0 or 1;

and salts thereof.

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference to a compound of formula (I) is to be understood as referring also to salts (especially pharmaceutically acceptable salts) of a compound of formula (I), as appropriate and expedient.

The term C$_{1-7}$-alkyl, alone or in combination with other groups, means saturated, straight or branched chain groups with one to seven carbon atoms, preferably one to four carbon atoms, i.e. C$_{1-4}$-alkyl. Examples of C$_{1-7}$-alkyl groups are methyl, ethyl, n-propyl, iso-propyl, n-butyl, iso-butyl, secbutyl, tert-butyl, pentyl, hexyl and heptyl. The methyl, ethyl and isopropyl groups are preferred.

The term $C_{1-7}$-alkoxy, alone or in combination with other groups, refers to an R—O— group, wherein R is a $C_{1-7}$-alkyl group. Examples of $C_{1-7}$-alkoxy groups are methoxy, ethoxy, propoxy, iso-propoxy, iso-butoxy, sec-butoxy and tert-butoxy.

The term hydroxy-$C_{1-7}$-alkyl, alone or in combination with other groups, refers to an HO—R group, wherein R is a $C_{1-7}$-alkyl group. Examples of hydroxy-$C_{1-7}$-alkyl groups are HO—$CH_2$—, HO—$CH_2CH_2$—, HO—$CH_2CH_2CH_2$— and $CH_3CH(OH)$—.

The term $C_{2-7}$-alkenyl, alone or in combination with other groups, means straight or branched chain groups comprising an olefinic bond and consisting of two to seven carbon atoms, preferably two to four carbon atoms. Examples of $C_{2-7}$-alkenyl are vinyl, propenyl and butenyl.

The term halogen means fluorine, chlorine, bromine or iodine, preferably fluorine, chlorine or bromine. In a more preferred embodiment of the invention the term halogen means fluorine or chlorine.

The term cycloalkyl, alone or in combination with other groups, means a saturated cyclic hydrocarbon ring system with 3 to 7 carbon atoms, i.e. cyclopropyl, cyclobutyl, cyclopentyl, cyclohexyl or cycloheptyl, preferably cyclopropyl.

The term aryl, alone or in combination, refers to a phenyl, naphthyl or indanyl group, preferably a phenyl group.

The term $sp^3$-hybridized refers to a carbon atom and means that this carbon atom forms four bonds to four substituents placed in a tetragonal fashion around this carbon atom.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or in case the compound of formula (I) is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

The compounds of the formula (I) may contain asymmetric carbon atoms. Substituents at a double bond or a ring may be present in cis- (=Z—) or trans (=E-) form unless indicated otherwise. The compounds of formula (I) may thus be present as mixtures of stereoisomers or preferably as pure stereoisomers. Mixtures of stereoisomers may be separated in a manner known per se, e.g. by column chromatography, thin layer chromatography, HPLC or crystallization.

Compounds of the invention also include nitrosated compounds of formula (I) that have been nitrosated through one or more sites such as oxygen (hydroxyl condensation), sulfur (sulfhydryl condensation) and/or nitrogen.

The nitrosated compounds of the present invention can be prepared using conventional methods known to one skilled in the art. For example, known methods for nitrosating compounds are described in U.S. Pat. Nos. 5,380,758, 5,703,073, 5,994,294, 6,242,432 and 6,218,417; WO 98/19672; and Oae et al., Org. Prep. Proc. Int., 15(3): 165-198 (1983).

A preferred embodiment of the present invention relates to a compound of formula (I), wherein if n=0, a double bond can be present at the 3,4- or at the 4,5-position of the ring Z of formula (I); or if n=1, a double bond can be present at the 3,4-position of the ring Z of formula (I);

or:

no double bond may be present in the ring Z of formula (I) if:
  i) n represents the integer 0 and X represents N, or
  ii) n represents the integer 0 and V represents —O—$CH_2$-Q-, or
  iii) n represents the integer 1 and L represents —$CH_2$—$CH_2$—, —$CH_2$—$CH(R^5)$—$CH_2$—, —$CH_2$—O—$CH_2$—, or —$CH_2$—S—$CH_2$—, or
  iv) n represents the integer 1, L represents —$CH_2$—N($R^6$)—$CH_2$—, and X represents N;

X represents CH or N;

V represents —$CH_2CH_2CH_2$—, —$CH_2CH_2$-A-, —$CH_2$-A-$CH_2$—, -A-$CH_2CH_2$—, —$CH_2CH_2CH_2CH_2$—, -A-$CH_2CH_2CH_2$—, —$CH_2$-A-$CH_2CH_2$—, —$CH_2CH_2$-A-$CH_2$—, —$CH_2CH_2CH_2$-A-, -A-$CH_2CH_2$—B—, —$CH_2CH_2CH_2CH_2CH_2$—, -A-$CH_2CH_2CH_2CH_2$—, —$CH_2$-A-$CH_2CH_2CH_2$—, —$CH_2CH_2$-A-$CH_2CH_2$—, —$CH_2CH_2CH_2$-A-$CH_2$—, —$CH_2CH_2CH_2CH_2$-A-, -A-$CH_2CH_2CH_2$—B—, —$CH_2$-A-$CH_2CH_2$—B—, -A-$CH_2CH_2$—B—$CH_2$—, -A-$CH_2CH_2CH_2$—B—$CH_2$—, —$CH_2$-A-$CH_2CH_2CH_2$—B—, or —O—$CH_2$-Q-, wherein Q is bound to the group U of formula (I); or:

if
  i) n represents the integer 0, or
  ii) n represents the integer 1 and X represents N, or
  iii) L represents —$CH_2$—$CH_2$—, or
  iv) L represents —$CH_2$—N($R^6$)—$CH_2$—, and W represents a para-substituted pyridinyl, V can in addition represent a pyrrolidinyl of the formula:

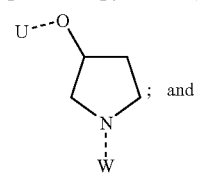 ; and $R^4$ represents $C_{1-7}$-alkyl-O—$(CH_2)_{0-4}$—$CH_2$—; $CF_3$—O—$(CH_2)_{0-4}$—$CH_2$—; or R'R"N—$(CH_2)_{0-4}$—$CH_2$—, wherein R' and R" are independently selected from the group consisting of hydrogen, $C_{1-7}$-alkyl (optionally substituted by one to three fluorine), cyclopropyl (optionally substituted by one to three fluorine), cyclopropyl-$C_{1-7}$-alkyl (optionally substituted by one to three fluorine), and —C(=O)—R''' wherein R''' is $C_{1-4}$-alkyl, —$CF_3$, —$CH_2$—$CF_3$, or cyclopropyl.

A preferred embodiment of the present invention relates to a compound of formula (I), wherein X represents CH or $N^+$—$O^-$.

A preferred embodiment of the present invention relates to a compound of formula (I), wherein $R^6$ represents —$R^8$, —$COR^8$, —$COOR^{10}$, —$CONR^7R^8$, —$C(NR^7)NR^7'R^8$, —$CSNR^7R^8$, —$SO_2R^8$, or —$SO_2NR^7R^8$.

A preferred embodiment of the present invention relates to a compound of formula (I), wherein A and B both represent —O—.

A preferred embodiment of the present invention relates to a compound of formula (I), wherein $R^5$ represents —$CO_2CH_3$ or —$CO_2H$.

A preferred embodiment of the present invention relates to a compound of formula (I), wherein $R^6$ represents —H, —$COCH_3$, —C(NH)$NH_2$, —$CONHCH_2C(CH_3)_2CONH_2$, —$CONHCH(CH_2)_2$, or —$CONHC(CH_2)_2CN$.

A preferred embodiment of the present invention relates to a compound of formula (I), wherein $R^6$ represents —H.

A preferred embodiment of the present invention relates to a compound of formula (I), wherein L represents —$CH_2$—$CH_2$— or —$CH_2$—NH—$CH_2$—

A preferred embodiment of the present invention relates to a compound of formula (I), wherein $R^1$ represents cyclopropyl.

A preferred embodiment of the present invention relates to a compound of formula (I), wherein W represents a para-substituted phenyl, or

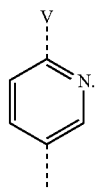

A preferred embodiment of the present invention relates to a compound of formula (I), wherein V represents —O—$CH_2$—$CH_2$—O—, —O—$CH_2$-Q-, —$CH_2$—$CH_2$—O— wherein the —$CH_2$ part of —$CH_2$—$CH_2$—O— is bound to the group W of formula (I), or

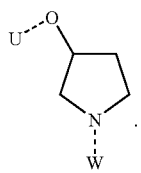

A preferred embodiment of the present invention relates to a compound of formula (I), wherein V represents —O—$CH_2$—$CH_2$—O—, or —O—$CH_2$-Q-. A preferred embodiment of the present invention relates to a compound of formula (I), wherein V—W represents:

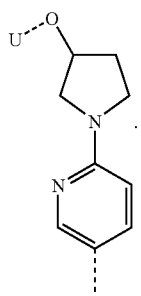

A preferred embodiment of the present invention relates to a compound of formula (I), wherein U represents

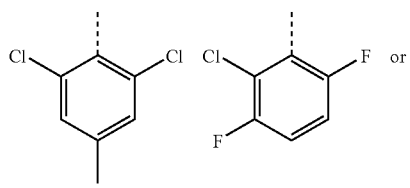

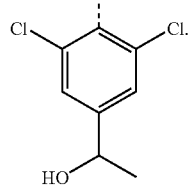

A preferred embodiment of the present invention relates to a compound of formula (I), wherein U represents

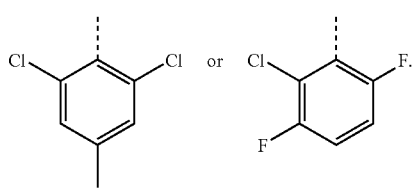

A preferred embodiment of the present invention relates to a compound of formula (I), wherein Q represents an isoxazolyl or an oxadiazolyl.

A preferred embodiment of the present invention relates to a compound of formula (I), wherein Q represents an isoxazolyl, especially an isoxazolyl that is connected to the rest of the molecule of formula (I) as follows:

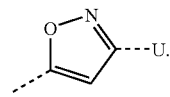

A preferred embodiment of the present invention relates to a compound of formula (I), wherein $R^2$ represents Cl, and $R^3$ represents hydrogen.

A preferred embodiment of the present invention relates to a compound of formula (I), wherein $R^4$ represents $CH_3$—O—$(CH_2)_{2-3}$—, or $CH_3$—C(=O)—NH—$CH_2$—$CH_2$—.

A preferred embodiment of the present invention relates to a compound of formula (I), wherein $R^4$ represents —$CH_2CH_2CH_2$—O—$CH_3$ or —$CH_2CH_2$—O—$CH_3$.

A preferred embodiment of the present invention relates to a compound of formula (I), wherein $R^4$ represents —$CH_2CH_2$—O—$CH_3$.

A preferred embodiment of the present invention relates to a compound of formula (I), wherein the moiety

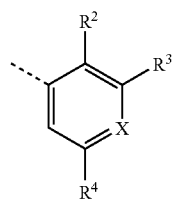

represents one of the following possibilities:

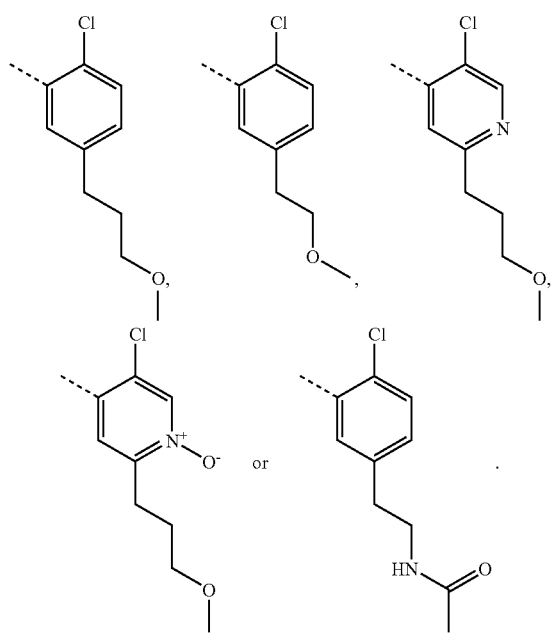

A preferred embodiment of the present invention relates to a compound of formula (I), wherein n represents the integer 0.

A preferred embodiment of the present invention relates to a compound of formula (I), wherein no double bond is present in the ring Z of formula (I), or a double bond is present at the 3,4-position of the ring Z of formula (I).

A preferred embodiment of the present invention relates to a compound of formula (I), wherein no double bond is present in the ring Z of formula (I), and the 3- and 4-substituents of the ring Z of formula (I) are trans to each others.

A preferred embodiment of the present invention relates to a compound of formula (I), wherein no double bond is present in the ring Z of formula (I), and the absolute configuration is (R) at the position 3 of the ring Z of formula (I), and the 4-substituent of the ring Z of formula (I) is trans to the 3-substituent of the ring Z of formula (I).

In an especially preferred embodiment, the present invention relates to a compound of formula (I), wherein
X represents CH or N;
W represents a para-substituted phenyl or a para-substituted pyridinyl;
V represents —CH$_2$CH$_2$-A- wherein the —CH$_2$ part of —CH$_2$CH$_2$-A- is bound to the group W of formula (I), -A-CH$_2$CH$_2$—B—, or —O—CH$_2$-Q-;
U represents tri-substituted phenyl, wherein the substituents are independently selected from C$_{1-7}$-alkyl and halogen;
Q represents an isoxazolyl;
L represents —CH$_2$—CH$_2$— or —CH$_2$—N(R$^6$)—CH$_2$—;
A and B both represent —O—;
R$^1$ represents cycloalkyl, preferably cyclopropyl;
R$^2$ represents halogen or C$_{1-7}$-alkyl;
R$^3$ represents halogen or hydrogen;
R$^4$ represents C$_{1-7}$-alkyl-O—(CH$_2$)$_{0-4}$—CH$_2$—;
R$^6$ represents —R$^8$, —COR$^8$, —CONR$^7$R$^8$, or —C(NR$^7$)NR$^{7'}$R$^8$;
R$^7$ and R$^{7'}$ both represent hydrogen;
R$^8$ represents hydrogen, C$_{1-7}$-alkyl, or cycloalkyl, wherein C$_{1-7}$-alkyl or cycloalkyl may be mono-substituted with cyano or —CONR$^{11}$R$^{11'}$, wherein R$^{11}$ and R$^{11'}$ both represent hydrogen; and
n represents the integer 0 or 1.

In another especially preferred embodiment, the present invention relates to a compound of formula (I), wherein
a double bond can be present at the 3,4-position of the ring Z of formula (I);
or:
no double bond may be present in the ring Z of formula (I) if:
i) n represents the integer 0 and X represents N or N$^+$—O$^-$, or
ii) n represents the integer 0 and V represents —O—CH$_2$-Q-, or
iii) n represents the integer 0, W represents para-substituted pyridinyl and V represents a pyrrolidinyl of the formula:

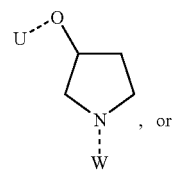

, or iv) n represents the integer 1 and L represents —CH$_2$—CH$_2$—;
X represents CH, N, or N$^+$—O$^-$;
W represents a para-substituted phenyl, or a para-substituted pyridinyl;
V represents —CH$_2$CH$_2$-A-, -A-CH$_2$CH$_2$—B—, or —O—CH$_2$-Q-, wherein Q is bound to the group U of formula (I); or:
if
i) n represents the integer 0, or
ii) L represents —CH$_2$—CH$_2$—, or
iii) L represents —CH$_2$—N(R$^6$)—CH$_2$— such as especially —CH$_2$—NH—CH$_2$—, and W represents a para-substituted pyridinyl,
V can in addition represent a pyrrolidinyl of the formula:

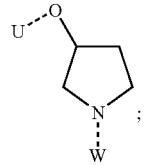

;

U represents tri-substituted phenyl, wherein the substituents are independently selected from C$_{1-7}$-alkyl and halogen, especially from methyl and halogen;
Q represents an isoxazolyl;
L represents —CH$_2$—CH$_2$— or —CH$_2$—N(R$^6$)—CH$_2$—;
A and B both represent —O—;
R$^1$ represents cyclopropyl;
R$^2$ represents halogen or C$_{1-7}$-alkyl, preferably chloro or methyl, especially chloro;
R$^3$ represents halogen (especially chloro) or hydrogen, preferably hydrogen;
R$^4$ represents C$_{1-7}$-alkyl-O—(CH$_2$)$_{0-4}$—CH$_2$— such as especially CH$_3$—O—(CH$_2$)$_{1-2}$—CH$_2$—; R'R''N—(CH$_2$)$_{0-4}$—CH$_2$—, wherein R' and R'' are independently selected from the group consisting of hydrogen, C$_{1-7}$-alkyl substituted by one to three fluorine (especially F$_2$CH—CH$_2$—), cyclopropyl, and —C(=O)—R''' wherein R''' is C$_{1-4}$-alkyl (especially methyl or ethyl), C$_{1-4}$-alkoxy (especially methoxy), —CH$_2$—CF$_3$, or cyclopropyl, such as especially R'NH—(CH$_2$)$_{0-1}$—CH$_2$—, wherein R' is as defined before; or R$^{12}$NH—C(═O)—(O)$_{0-1}$—(CH$_2$)$_{0-4}$— (especially R$^{12}$NH—C(═O)—(O)$_{0-1}$—(CH$_2$)$_{1-2}$—), wherein R$^{12}$ is C$_{1-4}$-alkyl (especially methyl or ethyl) or cyclopropyl; with the proviso that R' and R" cannot both simultaneously represent hydrogen;

R$^6$ represents —H, C$_{1-7}$-alkyl-CO— (especially CH$_3$—CO—), —CONHR$^8$, or —C(NH)NH$_2$;

R$^8$ represents cycloalkyl (especially cyclopropyl); or C$_{1-7}$-alkyl (especially C$_4$-alkyl) or cycloalkyl (especially cyclopropyl) which are both mono-substituted with cyano or —CONH$_2$; and n represents the integer 0 or 1.

The present invention also relates to compounds of formula (I) wherein the meanings of one or more of the substituents and symbols as defined for formula (I), or a preferred embodiment of formula (I), are replaced by their preferred meanings as defined herein, such as those defined for the above-given preferred embodiments.

A very preferred embodiment of the present invention relates to a compound of formula (I) selected from the group consisting of:
(1R*,5S*)-7-{4-[2-(2,6-dichloro-4-methyl-phenoxy)-ethyl]-phenyl}-3,9-diaza-bicyclo[3.3.1]non-6-ene-6-carboxylic acid [2-chloro-5-(3-methoxy-propyl)-benzyl]-cyclopropyl-amide,
(1R*,5S*)-6-{[2-chloro-5-(2-methoxy-ethyl)-benzyl]-cyclopropyl-carbamoyl}-7-{4-[2-(2,6-dichloro-4-methyl-phenoxy)-ethyl]-phenyl}-3,9-diaza-bicyclo[3.3.1]non-6-ene,
(1R*,5S*)-7-{4-[2-(2,6-dichloro-4-methyl-phenoxy)-ethoxy]-phenyl}-3,9-diaza-bicyclo[3.3.1]non-6-ene-6-carboxylic acid [2-chloro-5-(3-methoxy-propyl)-benzyl]-cyclopropyl-amide,
(1R,5S)-7-{4-[2-(2,6-dichloro-4-methyl-phenoxy)-ethoxy]-phenyl}-3,9-diaza-bicyclo[3.3.1]non-6-ene-6-carboxylic acid [2-chloro-5-(3-methoxy-propyl)-benzyl]-cyclopropyl-amide,
(1S,5R)-7-{4-[2-(2,6-dichloro-4-methyl-phenoxy)-ethoxy]-phenyl}-3,9-diaza-bicyclo[3.3.1]non-6-ene-6-carboxylic acid [2-chloro-5-(3-methoxy-propyl)-benzyl]-cyclopropyl-amide,
(1R*,5S*)-7-{4-[2-(2,6-dichloro-4-methyl-phenoxy)-ethoxy]-phenyl}-3,9-diaza-bicyclo[3.3.1]non-6-ene-6-carboxylic acid [2-chloro-5-(2-methoxy-ethyl)-benzyl]-cyclopropyl-amide,
(1R,5S)-7-{4-[2-(2,6-dichloro-4-methyl-phenoxy)-ethoxy]-phenyl}-3,9-diaza-bicyclo[3.3.1]non-6-ene-6-carboxylic acid [2-chloro-5-(2-methoxy-ethyl)-benzyl]-cyclopropyl-amide,
(1R,5S)-7-{4-[2-(2,6-dichloro-4-methyl-phenoxy)-ethoxy]-phenyl}-3,9-diaza-bicyclo[3.3.1]non-6-ene-6-carboxylic acid cyclopropyl-[5-(2-methoxy-ethyl)-2-methyl-benzyl]-amide,
(1R,5S)-7-{4-[2-(2,6-dichloro-4-methyl-phenoxy)-ethoxy]-phenyl}-3,9-diaza-bicyclo[3.3.1]non-6-ene-6-carboxylic acid cyclopropyl-[5-(3-methoxy-propyl)-2-methyl-benzyl]-amide,
(1R,5S)-7-{4-[2-(2,6-dichloro-4-methyl-phenoxy)-ethoxy]-phenyl}-3,9-diaza-bicyclo[3.3.1]non-6-ene-6-carboxylic acid cyclopropyl-[2,3-dichloro-5-(3-methoxy-propyl)-benzyl]-amide,
(1R,5S)-3-carbamimidoyl-7-{4-[2-(2,6-dichloro-4-methyl-phenoxy)-ethoxy]-phenyl}-3,9-diaza-bicyclo[3.3.1]non-6-ene-6-carboxylic acid cyclopropyl-[2-chloro-5-(3-methoxy-propyl)-benzyl]-amide,
(1R,5S)-7-{4-[2-(2,6-dichloro-4-methyl-phenoxy)-ethoxy]-phenyl}-3,9-diaza-bicyclo[3.3.1]non-6-ene-3,6-dicarboxylic acid 3-[(1-cyano-cyclopropyl)-amide] 6-{cyclopropyl-[2-chloro-5-(3-methoxy-propyl)-benzyl]-amide},
(1R,5S)-7-{4-[2-(2,6-dichloro-4-methyl-phenoxy)-ethoxy]-phenyl}-3,9-diaza-bicyclo[3.3.1]non-6-ene-3,6-dicarboxylic acid 3-cyclopropylamide 6-{cyclopropyl-[2-chloro-5-(3-methoxy-propyl)-benzyl]-amide},
(1R,5S)-7-{4-[2-(2,6-dichloro-4-methyl-phenoxy)-ethoxy]-phenyl}-3,9-diaza-bicyclo[3.3.1]non-6-ene-3,6-dicarboxylic acid 3-[(2-carbamoyl-2-methyl-propyl)-amide] 6-{cyclopropyl-[2-chloro-5-(3-methoxy-propyl)-benzyl]-amide},
(1R,5S)-3-{4-[2-(2,6-dichloro-4-methyl-phenoxy)-ethoxy]-phenyl}-8-aza-bicyclo[3.2.1]oct-2-ene-2-carboxylic acid [2-chloro-5-(3-methoxy-propyl)-benzyl]-cyclopropyl-amide,
4-{4-[2-(2,6-dichloro-4-methyl-phenoxy)-ethoxy]-phenyl}-1,2,5,6-tetrahydro-pyridine-3-carboxylic acid [2-chloro-5-(3-methoxy-propyl)-benzyl]-cyclopropyl-amide,
(1R,5S)-3-acetyl-7-{6-[2-(2,6-dichloro-4-methyl-phenoxy)-ethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide,
6-[2-(2,6-dichloro-4-methyl-phenoxy)-ethoxy]-1',2',5',6'-tetrahydro-[3,4']bipyridinyl-3'-carboxylic acid [2-chloro-5-(3-methoxy-propyl)-benzyl]-cyclopropyl-amide,
4-{4-[3-(2-chloro-3,6-difluoro-phenyl)-isoxazol-5-ylmethoxy]-phenyl}-1,2,5,6-tetrahydro-pyridine-3-carboxylic acid [2-chloro-5-(3-methoxy-propyl)-benzyl]-cyclopropyl-amide,
4-{4-[2-(2,6-dichloro-4-methyl-phenoxy)-ethoxy]-phenyl}-1,2,5,6-tetrahydro-pyridine-3-carboxylic acid [5-chloro-2-(3-methoxy-propyl)-pyridin-4-ylmethyl]-cyclopropyl-amide,
(1R,5S)-7-{6-[2-(2,6-dichloro-4-methyl-phenoxy)-ethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide,
(1S,5R)-7-{6-[2-(2,6-dichloro-4-methyl-phenoxy)-ethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide,
(3R,4S)-4-{4-[3-(2-chloro-3,6-difluoro-phenyl)-isoxazol-5-ylmethoxy]-phenyl}-piperidine-3-carboxylic acid [2-chloro-5-(3-methoxy-propyl)-benzyl]-cyclopropyl-amide,
6-[3-(2-chloro-3,6-difluoro-phenyl)-isoxazol-5-ylmethoxy]-1',2',5',6'-tetrahydro-[3,4']bipyridinyl-3'-carboxylic acid [2-chloro-5-(3-methoxy-propyl)-benzyl]-cyclopropyl-amide, and
(1R,5S)-3-acetyl-7-{6-[2-(2,6-dichloro-4-methyl-phenoxy)-ethoxy]-pyridin-3-yl}-3,9-diaza-bicyclo[3.3.1]non-6-ene-6-carboxylic acid [5-chloro-2-(3-methoxy-propyl)-pyridin-4-ylmethyl]-cyclopropyl-amide, and salts of these compounds.

A further very preferred embodiment of the present invention relates to a compound of formula (I) selected from the group consisting of:
(1R,2R,3S,5S)-3-{4-[2-(2,6-dichloro-4-methyl-phenoxy)-ethoxy]-phenyl}-8-aza-bicyclo[3.2.1]octane-2-carboxylic acid [2-chloro-5-(2-methoxy-ethyl)-benzyl]-cyclopropyl-amide,
(1R,2R,3S,5S)-3-{4-[2-(2,6-dichloro-4-methyl-phenoxy)-ethoxy]-phenyl}-8-aza-bicyclo[3.2.1]octane-2-carboxylic acid [2-chloro-5-(3-methoxy-propyl)-benzyl]-cyclopropyl-amide, (1R,5S)-3-{4-[3-(2-chloro-3,6-difluoro-phenyl)-isoxazol-5-ylmethoxy]-phenyl}-8-aza-bicyclo[3.2.1]oct-2-ene-2-carboxylic acid [2-chloro-5-(3-methoxy-propyl)-benzyl]-cyclopropyl-amide, (1R,5S)-3-acetyl-7-{6-[3-(2-chloro-3,6-difluoro-phenyl)-isoxazol-5-ylmethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide, 6-[2-(2,6-dichloro-4-methyl-phenoxy)-ethoxy]-1',2',5',6'-tetrahydro-[3,4']bipyridinyl-3'-carboxylic acid [5-chloro-2-(3-methoxy-propyl)-pyridin-4-ylmethyl]-cyclopropyl-amide, (3'R,4'S)-6-[2-(2,6-dichloro-4-methyl-phenoxy)-ethoxy]-1',2',3',4',5',6'-hexahydro-[3,4']bipyridinyl-3'-carboxylic acid [5-chloro-2-(3-methoxy-propyl)-pyridin-4-ylmethyl]-cyclopropyl-amide, (1R,5S)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [5-chloro-2-(3-methoxy-propyl)-pyridin-4-ylmethyl]-cyclopropyl-amide, (1S,5R)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [5-chloro-2-(3-methoxy-propyl)-pyridin-4-ylmethyl]-cyclopropyl-amide, 4-{4-[3-(2-chloro-3,6-difluoro-phenyl)-isoxazol-5-ylmethoxy]-phenyl}-1,2,5,6-tetrahydro-pyridine-3-carboxylic acid [5-chloro-2-(3-methoxy-propyl)-pyridin-4-ylmethyl]-cyclopropyl-amide, (1R,5S)-3-{6-[2-(2,6-dichloro-4-methyl-phenoxy)-ethoxy]-pyridin-3-yl}-8-aza-bicyclo[3.2.1]oct-2-ene-2-carboxylic acid [2-chloro-5-(3-methoxy-propyl)-benzyl]-cyclopropyl-amide, (1R,5S)-3-{6-[3-(2-chloro-3,6-difluoro-phenyl)-isoxazol-5-ylmethoxy]-pyridin-3-yl}-8-aza-bicyclo[3.2.1]oct-2-ene-2-carboxylic acid [2-chloro-5-(3-methoxy-propyl)-benzyl]-cyclopropyl-amide, (1R,5S)-3-{4-[(R)-3-(2,6-dichloro-4-methyl-phenoxy)-pyrrolidin-1-yl]-phenyl}-8-aza-bicyclo[3.2.1]oct-2-ene-2-carboxylic acid [2-chloro-5-(3-methoxy-propyl)-benzyl]-cyclopropyl-amide, (1R,5S)-7-{6-[(R)-3-(2,6-dichloro-4-methyl-phenoxy)-pyrrolidin-1-yl]-pyridin-3-yl}-3,9-diaza-bicyclo[3.3.1]non-6-ene-6-carboxylic acid [2-chloro-5-(2-methoxy-ethyl)-benzyl]-cyclopropyl-amide, (1S,5R)-7-{6-[(R)-3-(2,6-dichloro-4-methyl-phenoxy)-pyrrolidin-1-yl]-pyridin-3-yl}-3,9-diaza-bicyclo[3.3.1]non-6-ene-6-carboxylic acid [2-chloro-5-(2-methoxy-ethyl)-benzyl]-cyclopropyl-amide, (1R,5S)-7-{6-[(R)-3-(2-chloro-3,6-difluoro-phenoxy)-pyrrolidin-1-yl]-pyridin-3-yl}-3,9-diaza-bicyclo[3.3.1]non-6-ene-6-carboxylic acid [2-chloro-5-(2-methoxy-ethyl)-benzyl]-cyclopropyl-amide, (1S,5R)-7-{6-[(R)-3-(2-chloro-3,6-difluoro-phenoxy)-pyrrolidin-1-yl]-pyridin-3-yl}-3,9-diaza-bicyclo[3.3.1]non-6-ene-6-carboxylic acid [2-chloro-5-(2-methoxy-ethyl)-benzyl]-cyclopropyl-amide, (1R,5S)-7-{6-[2-(2,6-dichloro-4-methyl-phenoxy)-ethoxy]-pyridin-3-yl}-3,9-diaza-bicyclo[3.3.1]non-6-ene-6-carboxylic acid [5-chloro-2-(3-methoxy-propyl)-pyridin-4-ylmethyl]-cyclopropyl-amide, (1S,5R)-7-{6-[2-(2,6-dichloro-4-methyl-phenoxy)-ethoxy]-pyridin-3-yl}-3,9-diaza-bicyclo[3.3.1]non-6-ene-6-carboxylic acid [5-chloro-2-(3-methoxy-propyl)-pyridin-4-ylmethyl]-cyclopropyl-amide, (3R,4S)-4-{4-[2-(2,6-dichloro-4-methyl-phenoxy)-ethoxy]-phenyl}-piperidine-3-carboxylic acid [5-chloro-2-(3-methoxy-propyl)-pyridin-4-ylmethyl]-cyclopropyl-amide, (1R,2R,3S,5S)-3-{6-[2-(2,6-dichloro-4-methyl-phenoxy)-ethoxy]-pyridin-3-yl}-8-aza-bicyclo[3.2.1]octane-2-carboxylic acid [2-chloro-5-(2-methoxy-ethyl)-benzyl]-cyclopropyl-amide, (1R,5S)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(3-methoxy-propyl)-benzyl]-cyclopropyl-amide, (1S,5R)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(3-methoxy-propyl)-benzyl]-cyclopropyl-amide, (1R,5S)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(2-methoxy-ethyl)-benzyl]-cyclopropyl-amide, (1S,5R)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(2-methoxy-ethyl)-benzyl]-cyclopropyl-amide, (1R,5S)-3-acetyl-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(3-methoxy-propyl)-benzyl]-cyclopropyl-amide, (1R,5S)-3-acetyl-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(2-methoxy-ethyl)-benzyl]-cyclopropyl-amide, (1R,5S)-7-{6-[3-(2-chloro-3,6-difluoro-phenyl)-isoxazol-5-ylmethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide, (1S,5R)-7-{6-[3-(2-chloro-3,6-difluoro-phenyl)-isoxazol-5-ylmethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide, (1R,2R,3S,5S)-3-{4-[(R)-3-(2,6-dichloro-4-methyl-phenoxy)-pyrrolidin-1-yl]-phenyl}-8-aza-bicyclo[3.2.1]octane-2-carboxylic acid [2-chloro-5-(2-methoxy-ethyl)-benzyl]-cyclopropyl-amide, (1R,2R,3S,5S)-3-{6-[(R)-3-(2,6-dichloro-4-methyl-phenoxy)-pyrrolidin-1-yl]-pyridin-3-yl}-8-aza-bicyclo[3.2.1]octane-2-carboxylic acid [2-chloro-5-(2-methoxy-ethyl)-benzyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-methoxy-ethyl)-benzyl]-cyclopropyl-amide, (1R,5S)-3-{4-[2-(2,6-dichloro-4-methyl-phenoxy)-ethoxy]-phenyl}-8-aza-bicyclo[3.2.1]oct-2-ene-2-carboxylic acid [5-chloro-2-(3-methoxy-propyl)-pyridin-4-ylmethyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [5-chloro-2-(3-methoxy-propyl)-pyridin-4-ylmethyl]-cyclopropyl-amide, (1R,2R,3S,5S)-3-{4-[3-(2-chloro-3,6-difluoro-phenyl)-isoxazol-5-ylmethoxy]-phenyl}-8-aza-bicyclo[3.2.1]octane-2-carboxylic acid [2-chloro-5-(3-methoxy-propyl)-benzyl]-cyclopropyl-amide, (1R,2R,3S,5S)-3-{4-[3-(2-chloro-3,6-difluoro-phenyl)-isoxazol-5-ylmethoxy]-phenyl}-8-aza-bicyclo[3.2.1]octane-2-carboxylic acid [2-chloro-5-(2-methoxy-ethyl)-benzyl]-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-methoxy-ethyl)-benzyl]-cyclopropyl-amide, (1R,2R,3S,5S)-3-{4-[3-(2-chloro-3,6-difluoro-phenyl)-isoxazol-5-ylmethoxy]-phenyl}-8-aza-bicyclo[3.2.1]octane-2-carboxylic acid [5-chloro-2-(3-methoxy-propyl)-pyridin-4-ylmethyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid [5-chloro-2-(3-methoxy-propyl)-pyridin-4-ylmethyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid [5-(acetylamino-methyl)-2-chloro-benzyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [5-(acetylamino-methyl)-2-chloro-benzyl]-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [5-(acetylamino-methyl)-2-chloro-benzyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[(3,3,3-trifluoro-propionylamino)-methyl]-benzyl}-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[(3,3,3-trifluoro-propionylamino)-methyl]-benzyl}-cyclopropyl-amide, (3R,4S)-4-{4-[3-(2-chloro-3,6-difluoro-phenyl)-isoxazol-5-ylmethoxy]-phenyl}-piperidine-3-carboxylic acid (2-chloro-5-cyclopropylaminomethyl-benzyl)-cyclopropyl-amide, (3R,4S)-4-{4-[3-(2-chloro-3,6-difluoro-phenyl)-isoxazol-5-ylmethoxy]-phenyl}-piperidine-3-carboxylic acid [5-chloro-2-(3-methoxy-propyl)-1-oxy-pyridin-4-ylmethyl]-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-cyclopropylaminomethyl-benzyl)-cyclopropyl-amide, (3R,4S)-4-{4-[3-(2-chloro-3,6-difluoro-phenyl)-isoxazol-5-ylmethoxy]-phenyl}-piperidine-3-carboxylic acid [5-(2-acetylamino-ethyl)-2-chloro-benzyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid [2-chloro-5-(2-cyclopropylamino-ethyl)-benzyl]-cyclopropyl-amide, (3R,4S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-cyclopropylamino-ethyl)-benzyl]-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-cyclopropylamino-ethyl)-benzyl]-cyclopropyl-amide, (3'R,4'S)-6-[2-(2,6-dichloro-4-methyl-phenoxy)-ethoxy]-1',2',3',4',5',6'-hexahydro-[3,4']bipyridinyl-3'-carboxylic acid [5-chloro-2-(3-methoxy-propyl)-1-oxy-pyridin-4-ylmethyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid {2-chloro-5-[(2,2-difluoro-ethylamino)-methyl]-benzyl}-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[(2,2-difluoro-ethylamino)-methyl]-benzyl}-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-cyclopropylcarbamoylmethyl-benzyl)-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-methylcarbamoylmethyl-benzyl)-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-ethylcarbamoylmethyl-benzyl)-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(propionylamino-methyl)-benzyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid {2-chloro-5-[(cyclopropanecarbonyl-amino)-methyl]-benzyl}-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[(cyclopropanecarbonyl-amino)-methyl]-benzyl}-cyclopropyl-amide, (4-chloro-3-{[((3R,4S)-4-{4-[3-(2-chloro-3,6-difluoro-phenyl)-isoxazol-5-ylmethoxy]-phenyl}-piperidine-3-carbonyl)-cyclopropyl-amino]-methyl}-benzyl)-carbamic acid methyl ester, {4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-benzyl}-carbamic acid methyl ester, {4-chloro-3-[(cyclopropyl-{(3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-benzyl}-carbamic acid methyl ester, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [5-(2-acetylamino-ethyl)-2-chloro-benzyl]-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [5-(2-acetylamino-ethyl)-2-chloro-benzyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-[(2,2-difluoro-ethylamino)-methyl]-benzyl)-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-cyclopropylcarbamoylmethyl-benzyl)-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-methylcarbamoylmethyl-benzyl)-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'- carboxylic acid {2-chloro-5-[(cyclopropanecarbonyl-amino)-methyl]-benzyl}-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [5-chloro-2-(3-methoxy-propyl)-1-oxy-pyridin-4-ylmethyl]-cyclopropyl-amide, (3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [5-chloro-2-(3-methoxy-propyl)-1-oxy-pyridin-4-ylmethyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid (2-chloro-5-cyclopropylcarbamoylmethyl-benzyl)-cyclopropyl-amide, (3R,4S)-4-{4-[3-(2-chloro-3,6-difluoro-phenyl)-isoxazol-5-ylmethoxy]-phenyl}-piperidine-3-carboxylic acid (2-chloro-5-methylcarbamoylmethyl-benzyl)-cyclopropyl-amide, (3R,4S)-4-{4-[3-(2-chloro-3,6-difluoro-phenyl)-isoxazol-5-ylmethoxy]-phenyl}-piperidine-3-carboxylic acid (2-chloro-5-ethylcarbamoylmethyl-benzyl)-cyclopropyl-amide, (3R,4S)-4-{4-[3-(2-chloro-3,6-difluoro-phenyl)-isoxazol-5-ylmethoxy]-phenyl}-piperidine-3-carboxylic acid [2-chloro-5-(propionylamino-methyl)-benzyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-ethylcarbamoylmethyl-benzyl)-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(propionylamino-methyl)-benzyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid [2-chloro-5-(2-methylcarbamoyl-ethyl)-benzyl]-cyclopropyl-amide, (3R,4S)-4-{4-[3-(2-chloro-3,6-difluoro-phenyl)-isoxazol-5-ylmethoxy]-phenyl}-piperidine-3-carboxylic acid {2-chloro-5-[2-(2,2-difluoro-ethylamino)-ethyl]-benzyl}-cyclopropyl-amide, (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [5-(2-acetylamino-ethyl)-2-chloro-benzyl]-cyclopropyl-amide, (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [5-chloro-2-(3-methoxy-propyl)-1-oxy-pyridin-4-ylmethyl]-cyclopropyl-amide, (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [5-chloro-2-(3-methoxy-propyl)-pyridin-4-ylmethyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-methylcarbamoyl-ethyl)-benzyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[2-(2,2-difluoro-ethylamino)-ethyl]-benzyl}-cyclopropyl-amide, methyl-carbamic acid 4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-benzyl ester, methyl-carbamic acid 2-{4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-phenyl}-ethyl ester, (2-{4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-phenyl}-ethyl)-carbamic acid methyl ester, and (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [2-chloro-5-(2-methoxy-ethyl)-benzyl]-cyclopropyl-amide, and salts of these compounds.

The compounds of formula (I) are useful for the treatment and/or prophylaxis of diseases such as or related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases related to the renin-angiotensin system.

The compounds of formula (I) are especially useful for the treatment and/or prophylaxis of hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment and/or prophylaxis of the above-mentioned diseases, said methods comprising administering to a patient a pharmaceutically active amount of a compound of formula (I).

A further aspect of the present invention relates to pharmaceutical compositions comprising a compound of formula (I) and a pharmaceutically acceptable carrier material. These pharmaceutical compositions may be used for the treatment and/or prophylaxis of the above-mentioned diseases. The pharmaceutical compositions can be used for enteral, parenteral, or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The invention also relates to the use of a compound of formula (I) for the preparation of pharmaceutical compositions for the treatment and/or prophylaxis of the above-mentioned diseases.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Compounds of formula (I) or the above-mentioned pharmaceutical compositions are also of use in combination with other pharmacologically active compounds such as ACE-inhibitors, neutral endopeptidase inhibitors, aldosterone antagonists, angiotensin II receptor antagonists, endothelin receptors antagonists, vasodilators, calcium antagonists, potassium activators, diuretics, sympatholitics, beta-adrenergic antagonists, alpha-adrenergic antagonists, 11beta-hydroxysteroid dehydrogenase type 1 inhibitors, soluble guanylate cyclase activators and/or other drugs beneficial for the prevention or the treatment of the above-mentioned diseases.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient.

The compounds of formula (I) can be manufactured by the methods outlined below, by the methods described in the examples or by analogous methods.

A compound of type A as depicted in Scheme 1 can be prepared as described in the patent applications WO 2003/093267, WO 2004/002957, WO 2004/096769, WO 2004/096803, WO 2004/096799, and WO 2004/096366. PG stands for a suitable protecting group, typically a carbamate. $R^a$ stands for a suitable ester substituent, typically a methyl, an ethyl, or a benzyl group. L' stands for a precursor of the L-group as defined for formula (I). Generally, the main chain of the L-substituent is already completed in the L'-group, but the $R^5$- and $R^6$-groups have to be built in later on. The $R^a$- and L'-groups can be modified along the synthesis. A coupling catalysed by a transition metal, typically palladium, more commonly a Negishi or a Suzuki coupling, leads to a compound of type B, wherein $V^a$ stands for a precursor of the V-substituent as defined for formula (I). $V^a$ can be modified along the synthesis. Completion of the U—V-fragment leads to a compound of type C. Sometimes it is possible to build in the full U—V—W-fragment from a compound of type A, yielding a compound of type C directly. Reduction of the double bond on a compound of type C, followed by equilibrating conditions, leads to a compound of type D, wherein the U—V—W— and $R^a$OCO-substituents are often trans to each others. If n=1, two diastereoisomers are obtained; they can be separated by chromatographic methodologies. Sometimes it is more convenient to reduce the double bond on a compound of type C; in this case a compound of type E is obtained, which is transformed into a compound of type D after achievement of the U—V—W-substituent.

Scheme 1

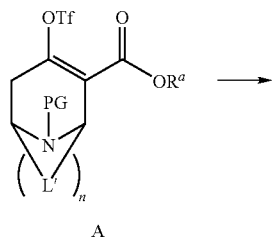

A

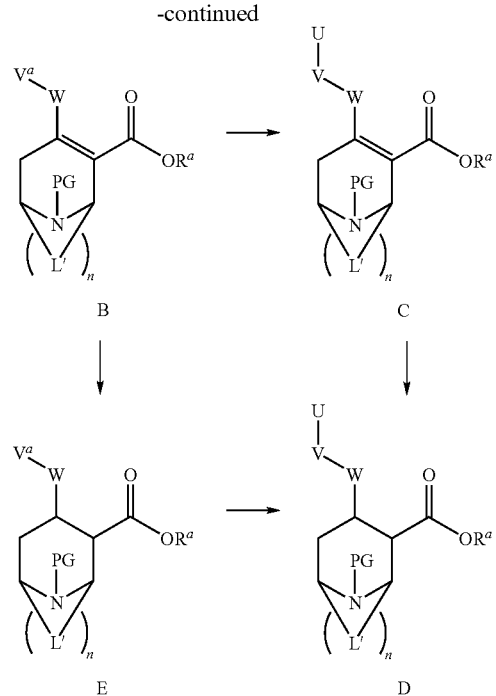

The U—V—W— or $V^a$—W-fragments that are coupled to a compound of type A have to be prepared separately. The preparation of several such substituents is described in the patent applications mentioned earlier. Otherwise a pyrrolidine substituent can be attached to an aromatic ring by a copper- or palladium-catalysed coupling as described in Scheme 2. Under certain circumstances a transition metal is not necessary to catalyse this reaction. A compound of type F, wherein PG' stands for a suitable protecting group, will be transformed into a compound of type G, wherein X' stands for CH or N. If W in formula (I) represents a thiazolyl, the same chemistry can be applied as well.

Scheme 2

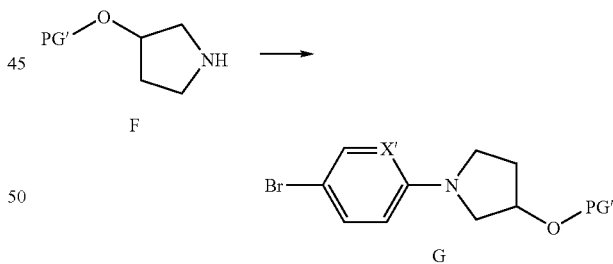

If V represents —O—CH$_2$-Q-, the isoxazolyl moiety is prepared by cycloaddition. This cycloaddition can be realized on the W—$V^a$-fragment in a compound of type B, leading to a compound of type C as described in Scheme 1. Otherwise the cycloaddition can be performed separately as, for instance, described in Scheme 3. Cycloaddition on a compound of type H with an often commercially available aldehyde leads to a compound of type J. Of course an aldehyde moiety can be built on the W—V'-fragment, and a compound of the form U—CCH can be constructed, to give after cycloaddition, another isoxazolyl moiety. The same principles can be used to prepare oxadiazolyl moieties, using methodologies described in the literature.

Scheme 3

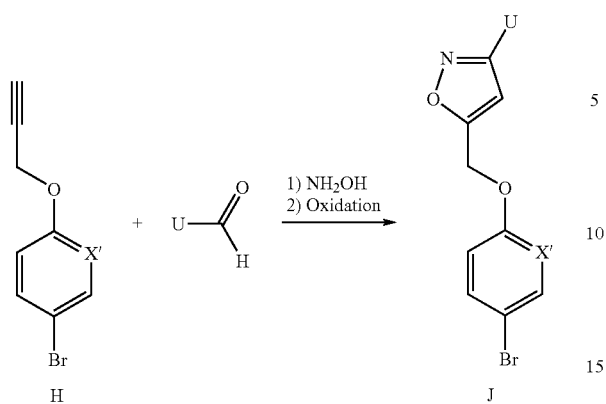

Also a hydroxymethyl isoxazole (Scheme 4) can be prepared from the aldehyde mentioned in Scheme 3 and propargyl alcohol. Coupling to a phenyl or heteroaryl derivative, wherein X" typically stands for —OH, —Br, or —I, leads to a compound of type J.

Scheme 4

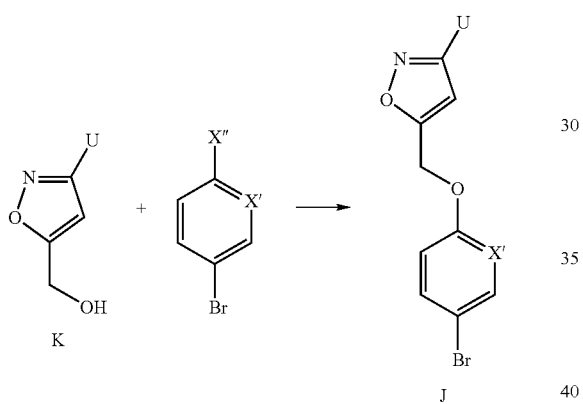

The ester group of a compound of type C or D can be cleaved to yield a compound of type K, as described in Scheme 5. If a double bond is present, it can partially migrate and a mixture of two isomeric carboxylic acids is obtained. This mixture is not separated. An amide coupling on a compound of type K yields a compound of type L. If a mixture of isomers with the double bond in the 3,4- or in the 4,5-positions is obtained, this mixture is separated on this stage by chromatographic methodologies.

Scheme 5

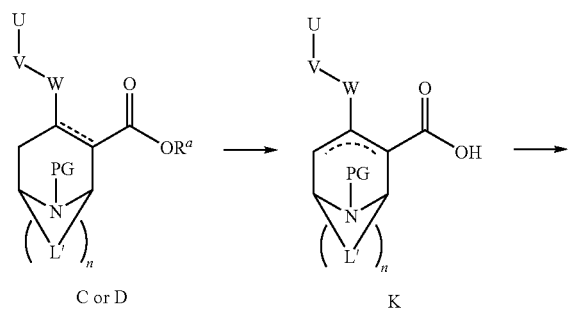

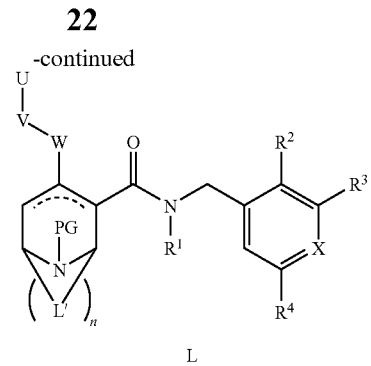

The amines used for such amide couplings have to be prepared separately, as described specifically in the examples, vide infra.

Final construction of the L-group, if necessary, leads to a compound of type M, as described in Scheme 6. Final removal of the protecting group PG leads to a compound of formula (I).

Scheme 6

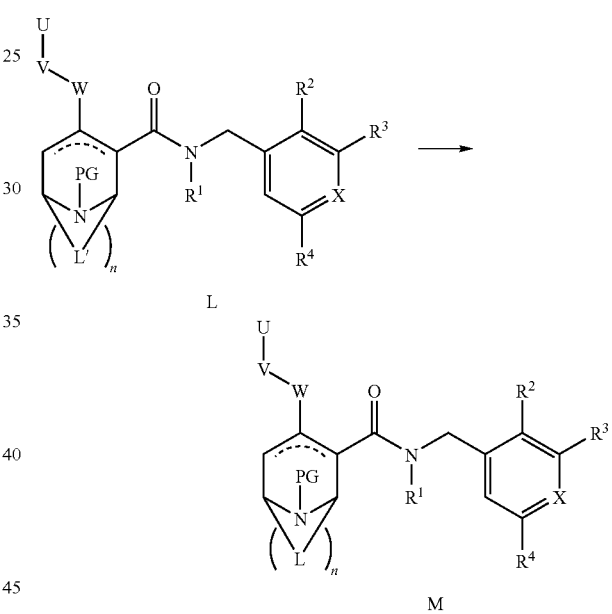

Enantiomerically pure compounds can always be obtained by chromatographic separation of the corresponding racemate, using a chiral solid support. Enantioselective synthesis of several systems are known as well in the literature (Murthy, K. S. K., Rey, A. W., Tjepkema, M., *Tetrahedron Lett.,* 2003, 44, 5355; Cossy, J., Mirguet, O., Pardo, Domingo G., Desmurs, J.-R., *European J. Org. Chem.,* 2002, 21, 3543; Carroll, F. I., Runyon, S. P., Abraham, P., Navarro, H., Kuhar, M. J., Pollard, G. T., Howard, J. L., *J. Med. Chem.,* 2004, 47, 6401; Meltzer, P. C., McPhee, M., Madras, B. K., *Bioorg. Med. Chem. Lett.,* 2003, 13, 4133; Blough, B. E., Keverline, K. I., Nie, Z., Navarro, H., Kuhar, M. J., Carroll, F. I., *J. Med. Chem.,* 2002, 45, 4029). It should also be mentioned that a resolution of 9-methyl-7-oxo-3,9-diaza-bicyclo[3.3.1]nonane-3,6-dicarboxylic acid 3-tert-butyl ester 6-ethyl ester is possible with tartaric acid.

The following examples serve to illustrate the present invention in more details. They are, however, not intended to limit its scope in any manner.

Chemistry

| Abbreviations (as used herein) | |
|---|---|
| Ac | acetyl |
| AcCl | acetyl chloride |
| AcOH | acetic acid |
| ADDP | azodicarboxylic dipiperidide |
| Ang | angiotensin |
| aq. | aqueous |
| 9-BBN | 9-borabicyclo[3.3.1]nonane |
| Boc | tert-butyloxycarbonyl |
| bp | boiling point |
| BSA | bovine serum albumine |
| Bu | butyl |
| BuLi | n-butyllithium |
| CDI | carbonyldiimidazole |
| ca. | about |
| cat. | catalytic |
| conc. | concentrated |
| Cy | cyclohexyl |
| dba | dibenzylidene acetone |
| DIPEA | diisopropylethylamine |
| DMAP | 4-N,N-dimethylaminopyridine |
| DME | 1,2-dimethoxyethane |
| DMF | N,N-dimethylformamide |
| DMSO | dimethylsulfoxide |
| dppp | 1,3-bis(diphenylphosphino)propane |
| EDC·HCl | ethyl-N,N-dimethylaminopropylcarbodiimide hydrochloride |
| EIA | enzyme immunoassay |
| ELSD | evaporative light-scattering detection |
| eq. | equivalent(s) |
| ES+ | electro-spray, positive ionization |
| ESI | electro-spray ionization |
| Et | ethyl |
| EtOAc | ethyl acetate |
| EtOH | ethanol |
| FC | flash chromatography |
| h | hour(s) |
| HOBt | hydroxybenzotriazol |
| HPLC | high performance liquid chromatography |
| LC-MS | liquid chromatography-mass spectrometry |
| MCPBA | meta-chloro perbenzoic acid |
| Me | methyl |
| MeOH | methanol |
| min | minute(s) |
| MS | mass spectrometry |
| NCS | N-chlorosuccinimide |
| NMO | N-methylmorpholine oxide |
| NMR | nuclear magnetic resonance |
| OAc | acetate |
| org. | organic |
| p | para |
| p-TsOH | para-toluene sulfonic acid |
| PG | protecting group |
| Ph | phenyl |
| Q+ | positive ionisation |
| rt | room temperature |
| sat. | saturated |
| sol. | solution |
| TBAC | tetra-n-butylammonium chloride |
| TBAF | tetra-n-butylammonium fluoride |
| TBDMS | tert-butyl-dimethyl-silyl |
| TBME | tert-butyl-methyl-ether |
| TBTU | O-(benzotriazol-1-yl)-N,N',N'-tetramethyluronium tetrafluoroborate |
| tBu | tert-butyl |
| Tf | trifluoromethylsulfonyl |
| TFA | trifluoroacetic acid |
| THF | tetrahydrofuran |
| TLC | thin layer chromatography |
| $t_R$ | retention time (in LC-MS or HPLC) given in minutes |
| UV | ultra violet |
| Vis | visible |
| xantphos | 4,5-bis(diphenylphosphino)-9,9-dimethylxanthene |

Temperatures are indicated in degrees Celsius (° C.). Unless otherwise indicated, the reactions take place at rt.

HPLC- or LC-MS-Conditions (if not Indicated Otherwise):
Analytic: Zorbax 59 SB Aqua column, 4.6×50 mm from Agilent Technologies. Eluents: A: acetonitrile; B: $H_2O$+0.5% TFA. Gradient: 90% B→5% B over 2 min. Flow: 1 mL/min. Detection: UV/Vis+MS.

Preparative: Zorbax SB Aqua column, 20×500 mm from Agilent Technologies. Eluent: A: acetonitrile; B: $H_2O$+0.05% ammonium hydroxide (25% aq.). Gradient: 80% B→10% B over 6 min. Flow: 40 mL/min. Detection: UV+MS, or UV+ELSD.

Chiral, Analytic:
a) Regis Whelk column, 4.6×250 mm, 10 μm. Eluent A: EtOH+0.05% $Et_3N$. Eluent B: hexane. Flow 1 mL/min.
b) ChiralPak AD, 4.6×250 mm, 5 μm. Eluent A: EtOH+ 0.05% $Et_3N$. Eluent B: hexane. Flow 1 mL/min.
c) ChiralCel OD, 4.6×250 mm, 10 μm. Eluent A: EtOH+ 0.1% $Et_3N$. Eluent B: hexane. Flow 0.8 mL/min.

Chiral, Preparative:
a) Regis Whelk 01 column, 50×250 mm and a flow of 100 mL/min.
b) ChiralPak AD, 20×250 mm, flow 10 mL/min.
c) ChiralCel OD, 20 μm, 50 mm×250 mm, flow 100 mL/min.

EXPERIMENTAL PART

Bromo-2,3-dichlorobenzaldehyde

Into a flame dried 250 mL round-bottom flask equipped with a magnetic stir bar and under $N_2$ was added anhydrous THF (75 mL) and diisopropylamine (3.74 mL, 26.6 mmol). The sol. was cooled to 0° C. and BuLi (11.8 mL, 26.6 mmol, 2.25 M sol. in hexanes) was added dropwise via syringe. The resulting yellow sol. was stirred at 0° C. for 30 min and cooled to −78° C. A sol. of 1-bromo-3,4-dichlorobenzene (5.00 g, 22.1 mmol) in 10 mL of THF was added by syringe and the resulting sol. was stirred at −78° C. for 1 h. After this time, DMF (8.51 mL, 111 mmol) was added in a single addition, and the reaction mixture was stirred at −78° C. for 2 h, and then allowed to warm to rt overnight. The mixture was quenched with aq. sat. $NH_4Cl$ (15 mL), and poured into a 500 mL separatory funnel containing aq. sat. $NH_4Cl$ (250 mL). The mixture was extracted with $Et_2O$ (3×50 mL). The combined org. layers were washed with brine, dried over $MgSO_4$, filtered and concentrated under reduced pressure. Purification of the crude by FC (hexanes→95:5 hexanes/$Et_2O$) yielded the title compound (4.57 g, 82% yield).
$^1H$ NMR ($CDCl_3$, 500 MHz) δ 10.44 (1H, s), 7.98 (1H, d, J=2.5 Hz), 7.87 (1H, d, J=2.5 Hz).
$^{13}C$ NMR ($CDCl_3$, 125 MHz) δ 187.7, 137.7, 135.3, 135.0, 134.7, 130.5, 121.1.

5-Chloro-2-methylbenzaldehyde

Into a flame-dried 250 mL round-bottom flask equipped with a magnetic stir bar and under $N_2$ was added 2-bromo-4-chlorotoluene (10.0 mL, 75.0 mmol) in anhydrous THF (150 mL). The clear sol. was cooled to −78° C. and BuLi (36.6 mL, 82.4 mmol, 2.25 M sol. in hexanes) was added dropwise over 20 min. The resulting light orange sol. was stirred at −78° C. for 1 h, and DMF (30 mL, 375 mmol) was added in a single addition. The resulting mixture was allowed to warm to rt over 4 h. The reaction was quenched by addition of aq. 1M HCl (20 mL), and stirred at rt overnight. The reaction mixture was poured into a 500 mL separatory funnel containing aq. 1M HCl (200 mL). The mixture was extracted with $Et_2O$ (3×100 mL). The combined org. layers were washed with brine, dried over MgSO₄, filtered, and concentrated under reduced pressure to a yellow oil. Purification by short-path distillation under reduced pressure (≈1 mm Hg) yielded the title compound as a light yellow oil (7.99 g, 69%). bp=70-72° C. at 1 mm Hg.

¹H NMR (CDCl₃, 500 MHz) δ 10.23 (1H, s), 7.77 (1H, d, J=2.5 Hz), 7.45 (1H, dd, J=8.0, 2.5 Hz), 7.22 (1H, d, J=8.0 Hz), 2.65 (3H, s).

5-Bromo-2-chloro-N-cyclopropylbenzamide

Into a flame-dried 250 mL round-bottom flask equipped with a magnetic stir bar and under N₂ were added 5-bromo-2-chlorobenzoic acid (10.0 g, 42.5 mmol) and DMF (3.9 mL, 51.0 mmol) in toluene (80 mL). The sol. was cooled to 0° C., and oxalyl chloride (4.4 mL, 51.0 mmol) was added dropwise over 1 h. The resulting mixture was stirred at 0° C. for 2 h and then the volatiles were removed. The resulting crude reaction mixture was dissolved in CH₂Cl₂ (100 mL) and cooled to 0° C. in an ice bath. Cyclopropylamine (4.5 mL, 63.7 mmol) was added dropwise over 1 h followed by addition of DIPEA (11.8 mL, 85.0 mmol). The resulting sol. was stirred at rt for 16 h. The reaction mixture was poured into a 1 L separatory funnel containing aq. 1M HCl (600 mL). The mixture was extracted with CH₂Cl₂ (6×250 mL). The combined org. layers were washed with brine, dried over MgSO₄, filtered and concentrated under reduced pressure. The product was crystallized from hexane/CH₂Cl₂ and isolated by filtration to give the title compound (8.24 g, 71%).

N-(5-bromo-2-chlorobenzyl)cyclopropylamine

A sol. of 5-bromo-2-chloro-N-cyclopropylbenzamide (12.0 g, 43.7 mmol) in THF (100 mL) was placed into a 250 mL round-bottom flask, equipped with a magnetic stir bar and under N₂. The sol. was treated with dropwise addition of BH₃.Me₂S (13.1 mL, 131 mmol), and the resulting suspension was stirred at rt for 1 h. The mixture was heated to reflux for 1 h, cooled to rt, and slowly quenched with dropwise addition of aq. 1M HCl (25 mL). The suspension was again refluxed for 1 h, cooled to rt, and basified to pH=10-11 with aq. 1M NaOH. The mixture was poured into a 500 mL separatory funnel containing aq. 1M NaOH (350 mL). The mixture was extracted with EtOAc (3×100 mL). The combined org. layers were washed with brine, dried over MgSO₄, filtered and concentrated under reduced pressure. The crude amine was used directly in the next step.

General Procedure for the Reductive Amination of Substituted Benzaldehydes with Cyclopropylamine:

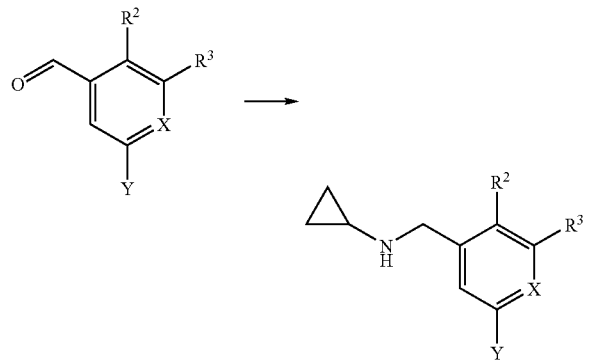

Y = Cl, Br, or I

A sol. of substituted benzaldehyde (17.8 mmol, 1.0 eq.), cyclopropylamine (3.13 mL, 44.5 mmol, 2.5 eq.) and sodium cyanoborohydride (1.34 g, 21.4 mmol, 1.2 eq.) in MeOH (100 mL) was treated with dropwise addition of glacial AcOH (3.06 mL, 53.4 mmol, 3.0 eq.). The resulting sol. was stirred at rt for 16 h overnight. The reaction mixture was quenched with dropwise addition of aq. sat. NaHCO₃, and concentrated under reduced pressure to remove the MeOH. The crude residue was poured into a 250 mL separatory funnel containing aq. sat. NaHCO₃ (150 mL), and extracted with EtOAc (3×50 mL). The combined org. layers were washed with brine, dried over MgSO₄, filtered and concentrated under reduced pressure. Purification by FC yielded the benzamine product.

General Procedure for the Boc-protection of Cyclopropylbenzamines:

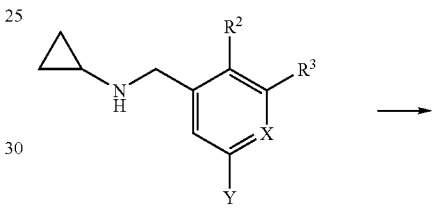

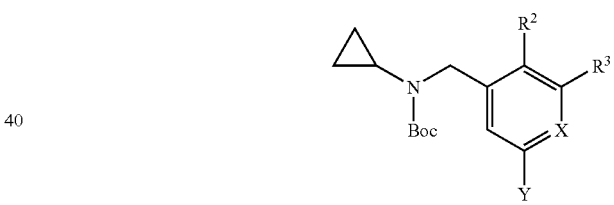

Y = Cl, Br, or I

A sol. of the cyclopropylbenzamine (43.7 mmol, 1.0 eq.) in a biphasic mixture of CH₂Cl₂ (50 mL) and 1M aq. NaOH (50 mL) was treated with Boc₂O (15.1 mL, 65.6 mmol, 1.5 eq.). The mixture was stirred at rt vigorously for 16 h. The mixture was poured into a 500 mL separatory funnel containing H₂O (300 mL), and extracted with CH₂Cl₂ (3×100 mL). The combined org. layers were washed with brine, dried over MgSO₄, filtered and concentrated under reduced pressure. Purification by FC yielded the Boc-protected amine.

General Procedure for the Allylation of Boc-protected Cyclopropylbenzamines:

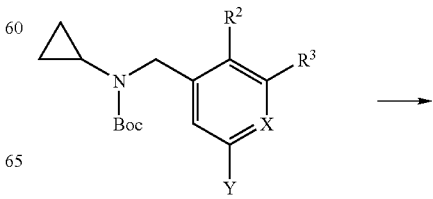

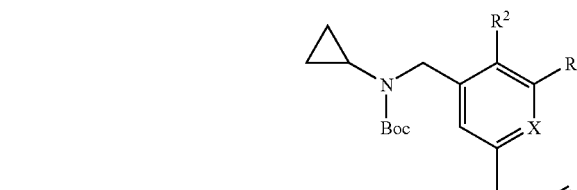

Y = Cl, Br, or I

Into a flame-dried round-bottom flask or Schlenk tube, under $N_2$ was added $Pd[PCy_3]_2$ (0.05 eq.), CsF (2.0 eq.) and the corresponding aryl bromide (1.0 eq.). If the aryl chloride was being used as a starting material, the $(Pd[PtBu_3]Br)_2$ dimer (0.025 eq.) was used in place of the $Pd[PCy_3]_2$ catalyst. The flask was evacuated under reduced pressure (0.1 mm Hg) and backfilled with $N_2$ (repeated 3 times). The resulting solids were dissolved in anhydrous THF or dioxane (0.15 M sol.) and tri-n-butyl allyltin (1.5 eq.) was added and the resulting mixture was refluxed for 8-16 h, until TLC shows complete consumption of starting material. The reaction mixture was cooled to rt, and filtered through a pad of silica gel on a sintered glass funnel, washing with $Et_2O$. The filtrate was concentrated and purified by FC to give the corresponding allylbenzamide derivative.

General Procedure for the Hydroboration/Oxidation of Allylbenzamines:

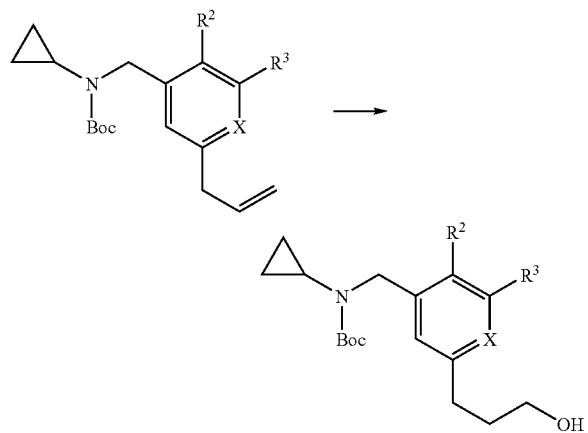

Into a flame-dried round-bottom flask equipped with a magnetic stir bar was added the allylbenzamine (1.0 eq.) and anhydrous THF (0.3 M sol.). The sol. was cooled to 0° C. and $BH_3 \cdot Me_2S$ (1.1 eq.) was added dropwise over 20 min. The sol. was stirred at 0° C. for 1 h, then allowed to warm to rt, and stirred for an additional 2 h. The sol. was cooled to 0° C. and aq. 1M NaOH was added dropwise (CAUTION—EXOTHERMIC REACTION) followed by dropwise addition of 30% aq. $H_2O_2$. The mixture was allowed to warm to rt, and stirred for 2 h. The mixture was poured into a separatory funnel containing $H_2O$ and extracted with $Et_2O$ (3 times). The combined org. layers were washed with brine, dried over $MgSO_4$, filtered and concentrated under reduced pressure. Purification by FC yielded the desired alcohol product.

General Procedure for the Oxidative Cleavage/Reduction of Allylbenzamines:

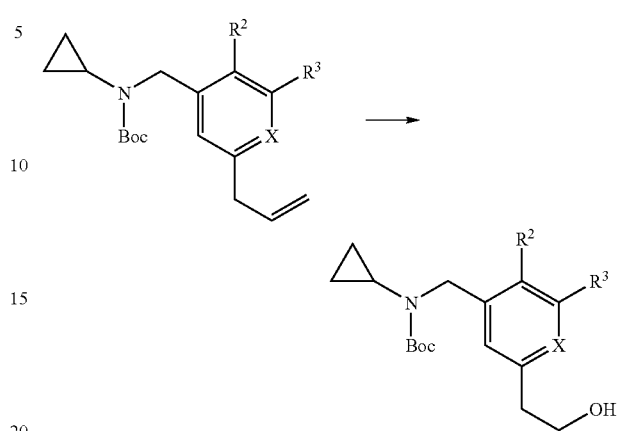

A sol. of allylbenzamine (1.0 eq.) in $CH_2Cl_2$ (0.4 M sol.) was cooled to −78° C. and $O_3$ gas was introduced into the sol. using a gas dispersion tube. The ozone gas was introduced until all of the starting material had been consumed, as determined by TLC, and the reaction mixture maintained a slight blue colour. The reaction was stirred at −78° C. for 20 min, then EtOH (0.5 M sol.) and $NaBH_4$ (2.5 eq.) were added. The mixture was allowed to warm to rt overnight (16 h). The reaction mixture was quenched with dropwise addition of aq. sat. $NH_4Cl$ (5 mL), and poured into a separatory funnel containing aq. sat. $NH_4Cl$. The mixture was extracted with $Et_2O$ (3 times). The combined org. layers were washed with brine, dried over $MgSO_4$, filtered and concentrated under reduced pressure. Purification by FC yielded the desired alcohol.

General Procedure for the Etherification of Aromatic Primary Alcohols with Methyl Iodide:

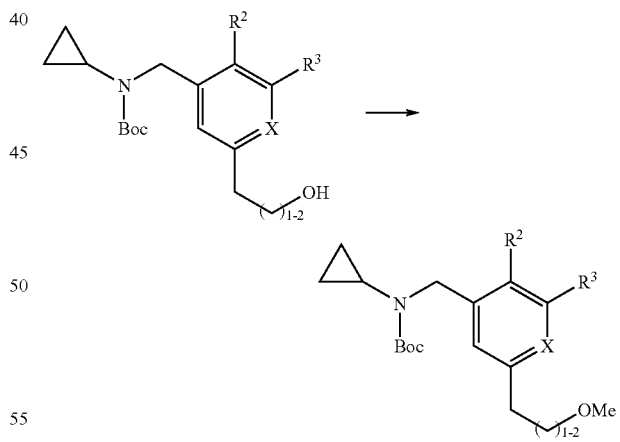

A suspension of the primary alcohol (1.0 eq.) in THF (0.25 M sol.) was cooled to 0° C. and treated with NaH (60% in oil, 2.0 eq.). The resulting mixture was stirred at 0° C. for 30 min and then at rt for another 30 min. The suspension was re-cooled to 0° C. and then MeI (8.0 eq.) was added in a single portion. The reaction mixture was stirred at 0° C. for 30 min, at rt for 30 min, and then heated to reflux for 4 h until all of the starting material was consumed as determined by TLC. The cooled reaction mixture was quenched with dropwise addition of aq. sat. $NH_4Cl$ and poured into a separatory funnel containing aq. sat. NH₄Cl, and extracted with EtOAc (3 times). The combined org. layers were washed with brine, dried over MgSO₄, filtered and concentrated under reduced pressure. Purification by FC yielded the methyl ether.

General Procedure for the Deprotection of Boc-protected Cyclopropylbenzamines:

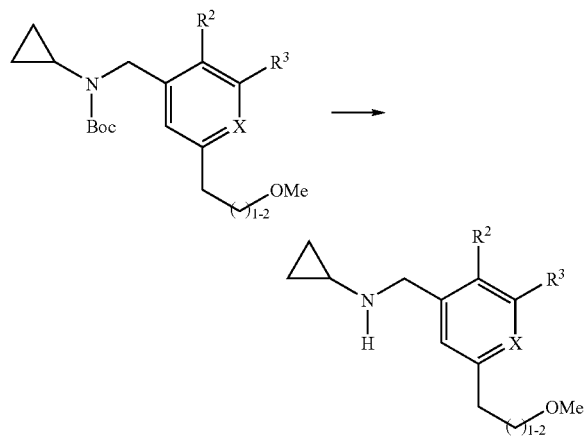

To a sol. of Boc-protected cyclopropylbenzamine (1.0 eq.) in CH₂Cl₂ (0.1-0.5 M sol.) was added 4 M HCl in dioxane (5.0 eq.). The resulting mixture was stirred at rt for 8-16 h until TLC shows complete conversion of starting material. The reaction was poured into a separatory funnel containing 1M aq. NaOH, and extracted with CH₂Cl₂ (3 times). Purification by FC yielded the corresponding free amine.

2-(4-Bromo-phenoxy)-ethanol

4-Bromophenol (100 g, 0.58 mol) was dissolved in in xylenes (220 mL). [1,3]Dioxolan-2-one (53.7 g, 0.61 mol) and imidazole (592 mg, 8.70 mmol) were added. The mixture was heated to 140° C. for 3 days. The mixture was allowed to cool to rt, and the solvents were removed under reduced pressure. Drying the residue under high vacuum yielded the title compound (130 g, quantitative). LC-MS: $t_R$=0.81 min.

Methanesulfonic Acid 2-(4-bromo-phenoxy)-ethyl Ester 2-(4-Bromo-phenoxy)-ethanol (125 g, 0.576 mol) was dissolved in CH₂Cl₂ (650 mL), and the sol. was cooled to 0° C. Et₃N (110 mL, 0.864 mol), then mesyl chloride (67.1 mL, 0.864 mol) were dropped at such a speed that the temperature did not raise above 10° C. (about 60 min). The mixture was stirred at 0° C. for 1 h, then at rt overnight. The mixture was diluted with CH₂Cl₂, and washed with brine (2×). The aq. phase was extracted back with CH₂Cl₂. The combined org. extracts were dried over MgSO₄, filtered, and the solvents were removed under reduced pressure. Drying the residue under high vacuum yielded the crude title compound (174 g, quantitative yield) that was used further without purification. LC-MS: $t_R$=0.92 min.

1-[2-(4-Bromo-phenoxy)-ethoxy]-2,6-dichloro-4-methyl-benzene

K₂CO₃ (29.3 g, 212 mmol) was dissolved in water (162 mL). 1-Propanol (150 mL) was added. A sol. of 2,6-dichloro-para-cresol (25 g, 141 mmol) in 1-propanol (150 mL) was added. Methanesulfonic acid 2-(4-bromo-phenoxy)-ethyl ester (41.6 g, 141 mmol) was added. The mixture was stirred at 85° C. for 6 h. The heating oil bath was removed, and water (330 mL) was added dropwise when the internal temperature had reached 78° C. The beige suspension was allowed to cool to rt. The mixture was filtered, and the precipitate was washed with water. Drying the precipitate under high vacuum at 30° C. for 48 h yielded the title compound (43 g, 81%). LC-MS: $t_R$=1.15 min.

2-(2,6-Dichloro-4-methyl-phenoxy)-ethanol

In a three-necked flask equipped with a gas droplet counter and an efficient cooling system, a mixture of 2,6-dichloro-p-cresol (20.0 g, 113 mmol), [1,3]dioxolan-2-one (9.95 g, 113 mmol) and imidazole (115 mg, 1.70 mmol) was heated to 160° C. for 25 h. The mixture was allowed to cool to rt. Purification by FC (Et₂O/heptane 1:1) yielded the title compound (18.7 g, 75%). LC-MS: $t_R$=0.88 min.

5-Bromo-2-[2-(2,6-dichloro-4-methyl-phenoxy)-ethoxy]-pyridine

A sol. of 2-(2,6-dichloro-4-methyl-phenoxy)-ethanol (18.6 g, 84 mmol) in THF (360 mL) was cooled to 0° C. NaH (about 55% in oil, 6.60 g, about 153 mmol) was added in portions, and the mixture was stirred at rt for 30 min. A sol. of 2,5-dibromopyridine (18.0 g, 76.3 mmol) in THF (60 mL) was added dropwise, and the mixture was heated to reflux for 90 min. The mixture was allowed to cool to rt, and ice was added carefully. The solvents were partially removed under reduced pressure, and the residue was diluted with EtOAc. This mixture was washed with aq. sat. NH₄Cl. The aq. layer was extracted back with EtOAc (2×). The combined org. extracts were washed with brine, dried over MgSO₄, filtered, and the solvents were removed under reduced pressure. Purification of the crude by FC (EtOAc/heptane 3:97) yielded the title compound (22.7 g, 79%). LC-MS: $t_R$=1.13 min; ES+: 378.08.

2-Chloro-3,6-difluoro-benzaldehyde Oxime

2-Chloro-3,6-difluoro-benzaldehyde (25.0 g, 142 mmol) was dissolved in CH₃CN (175 mL). To this sol. was added NaHCO₃ (35.7 g, 424 mmol), and the mixture was stirred vigorously for 5 min. Water (350 mL) was added, and the mixture was stirred for 10 min. NH₂OH.HCl (19.7 g, 283 mmol) and TBAC (1.97 g, 7.08 mmol) were added, and the reaction mixture was stirred at rt for 1 h. AcOH (20 mL) was added dropwise to pH 6-7. The mixture was extracted with Et₂O (3×). The combined org. extracts were washed with brine, dried over Na₂SO₄, filtered, and the solvents were removed under reduced pressure. Drying under high vacuum yielded the title compound (25.0 g, 92%). LC-MS: $t_R$=0.93 min.

[3-(2-Chloro-3,6-difluoro-phenyl)-isoxazol-5-yl]-methanol

A sol. of 2-chloro-3,6-difluoro-benzaldehyde oxime (21.3 g, 111 mmol) in DMF (66.7 mL) was added dropwise to a sol. of NCS (14.9 g, 111 mmol) and pyridine (1.78 mL) in DMF (222 mL). The mixture was stirred for 1 h at rt, and a sol. of propargyl alcohol (4.99 g, 89.1 mmol) in DMF (71 mL) was dropwise added. The reaction mixture was heated to 85° C., and a sol. of Et₃N (15.5 mL, 111 mmol) in DMF (89.3 mL) was slowly added. The reaction mixture was stirred at 85° C.

for 60 min, and was allowed to cool to rt. The mixture was diluted with water (533 mL), and was extracted with EtOAc (2×). The combined org. extracts were washed with water and brine, were dried over Na$_2$SO$_4$, filtered, and the solvents were removed under reduced pressure. Purification of the residue by FC (EtOAc/heptane 40:60) yielded the title compound (17.0 g, 78%). LC-MS: t$_R$=0.84 min; ES+: 287.12.

2-Bromo-5-chloro-pyridine-4-carbaldehyde

To a stirred sol. of diisopropylamine (20.9 mL, 148 mmol) in dry THF (350 mL) at −5° C. was added dropwise BuLi (1.6M in hexane, 89.5 mL, 143 mmol), and the resulting sol. was stirred for 30 min at −5° C. The sol. was allowed to cool to −70° C., and a sol. of 2-bromo-5-chloropyridine (25.0 g, 130 mmol) in THF (100 mL) was added dropwise at −70° C. over 15 min such as the internal temperature did not exceed −65° C. The mixture was stirred at −70° C. for 30 min. DMF (10.5 mL, 136 mmol) was added dropwise over 20 min at such a rate that the internal temperature did not exceed −70° C. The orange mixture was stirred at −70° C. for 40 min. The mixture was allowed to warm up to rt, and was poured onto a mixture of water (200 mL) and aq. 1M NaOH (50 mL). The mixture was extracted with EtOAc (2×), and the combined org. extracts were washed back with aq. 1M NaOH (2×). The org. extracts were dried over MgSO$_4$, filtered, and the solvents were removed under reduced pressure. Purification of the crude by FC (EtOAc/heptane 1:9→1:8→1:6→1:4→1:2→1:1) yielded the title compound (21.6 g, 72%). LC-MS: t$_R$=0.74 min; ES+: 295.01.

2-Bromo-5-chloro-4-dimethoxymethyl-pyridine

To a sol. of 2-bromo-5-chloro-pyridine-4-carbaldehyde (43.9 g, 199 mmol) in MeOH (800 mL) were successively added at rt trimethyl orthoformate (65.3 mL, 597 mmol) and p-TsOH (1.90 g, 10.0 mmol). This reaction mixture was then heated to reflux for 3 h. The mixture was allowed to cool to rt, and was concentrated under reduced pressure. The residue was dissolved in CH$_2$Cl$_2$, and the mixture was washed with aq. 10% K$_2$CO$_3$. The org. layer was dried over MgSO$_4$, filtered, and the solvents were removed under reduced pressure. Drying the residue under high vacuum yielded the crude title compound (51.7 g, 97%) that was used further without purification. LC-MS: t$_R$=0.92 min; ES+: 309.06.

5-Chloro-4-dimethoxymethyl-2-(3-methoxy-propyl)-pyridine

To a suspension of Mg (911 mg, 37.5 mmol) and iodine (one crystal) in dry THF (30 mL) was added dropwise 5% of the total amount of 1-bromo-3-methoxypropane (4.59 g, 30.0 mmol). The mixture was heated to reflux with the help of a heat gun until the Grignard-formation started. The rest of the 1-bromo-3-methoxypropane was added slowly, while an exothermic reaction proceeded. After the end of the addition, the reaction mixture was stirred under reflux for 20 min, and was allowed to cool to rt. This Grignard-sol. (1M in THF, 23.5 mL, 23.5 mmol) was added dropwise to a mixture of 2-bromo-5-chloro-4-dimethoxymethyl-pyridine (2.50 g, 9.38 mmol) and Ni(dppp)Cl$_2$ (495 mg, 0.938 mmol) in THF (50 mL) at 0° C. The reaction mixture was stirred at rt for 30 min, and was then heated to reflux for 2 h. The mixture was allowed to cool to rt, and was dissolved with EtOAc. This mixture was washed with aq. sat. NaHCO$_3$. The org. layer was dried over MgSO$_4$, filtered, and the solvents were removed under reduced pressure. Purification of the residue by FC (heptane→EtOAc/heptane 1:1) yielded the title compound (1.51 g, 62%). LC-MS: t$_R$=0.80 min; ES+: 260.15.

5-Chloro-2-(3-methoxy-propyl)-pyridine-4-carbaldehyde

5-Chloro-4-dimethoxymethyl-2-(3-methoxy-propyl)-pyridine (25.5 g, 98.2 mmol) was dissolved in aq. 1M HCl (500 mL), and the mixture was heated to 80° C. for 2 h. The mixture was allowed to cool to rt, and EtOAc was added. The mixture was cooled to 0° C., and was basified with aq. 2.5M NaOH to pH=10. The layers were separated, and the org. layer was dried over MgSO$_4$, filtered, and concentrated under reduced pressure. Drying the residue under high vacuum yielded the crude title compound (98.1 mmol, 99%) that was used further without purification. LC-MS: t$_R$=0.62 min; ES+: 246.12.

[5-Chloro-2-(3-methoxy-propyl)-pyridin-4-ylmethyl]-cyclopropyl-amine

A mixture of 5-chloro-2-(3-methoxy-propyl)-pyridine-4-carbaldehyde (21.0 g, 98.2 mmol) and cyclopropylamine (13.8 mL, 196 mmol) in MeOH (450 mL) was stirred at rt overnight. NaBH$_4$ (4.83 g, 128 mmol) was added at 0° C., and the mixture was stirred at rt overnight. Ice was added, and the mixture was concentrated under reduced pressure. The crude product was dissolved in EtOAc, and this mixture was washed with aq. 1M NaOH. The aq. layer was extracted back with EtOAc. The combined org. extracts were dried over MgSO$_4$, filtered, and the solvents were removed under reduced pressure. Purification of the crude by FC (EtOAc/heptane 1:5→1:4→1:3→1:1→3:1→EtOAc) yielded the title compound (11.8 g) and [5-chloro-2-(3-methoxy-propyl)-pyridin-4-ylmethylene]-cyclopropyl-amine (10.7 g). This unreacted imine was dissolved in MeOH (20 mL), and this sol. was cooled to 0° C. NaBH$_4$ (3.20 g, 84.6 mmol) was added, and the mixture was stirred at rt overnight. NaBH$_4$ (3.20 g, 84.6 mmol) was added again, and the mixture was stirred for 3 days. Ice was added to the reaction mixture, and the mixture was concentrated under reduced pressure. The crude product was dissolved in EtOAc and the resulting mixture was washed with aq. 1M NaOH. The aq. phase was extracted back with EtOAc. The combined org. extracts were dried over MgSO$_4$, filtered, and the solvents were removed under reduced pressure. Purification of the crude by FC (EtOAc/heptane 1:3→1:2→1:1→EtOAc) yielded the title compound (9.40 g). The fractions of the title compounds were mixed together (21.2 g, 85%). LC-MS: t$_R$=0.55 min; ES+: 296.16.

2-[3-(2-Chloro-3,6-difluoro-phenyl)-isoxazol-5-ylmethoxy]-5-(4,4,5,5-tetramethyl-[1,3,2]dioxaborolan-2-yl)-pyridine Et$_3$N (11.3 mL, 79.2 mmol) and PdCl$_2$(PPh$_3$)$_2$ (936 mg, 1.31 mmol) were added to a sol. of compound J1 (10.6 g, 26.4 mmol) in dioxane (60 mL), and the resulting mixture was stirred at 100° C. overnight. The mixture was allowed to cool to rt, and was diluted with EtOAc. The resulting mixture was washed with water (2×) and brine (1×). The org. layer was dried over MgSO$_4$, filtered, and the solvents were removed under reduced pressure. Drying the residue under high vacuum yielded the crude title compound (9.28 g, 78%) that was used further without purification.

(5-Bromo-2-chloro-benzyloxy)-tert-butyl-dimethyl-silane

TBDMS-Cl (10.6 g, 66.7 mmol) was added to a sol. of (5-bromo-2-chloro-phenyl)-methanol (12.8 g, 55.6 mmol)

and imidazole (9.42 g, 138 mmol) in DMF (190 mL) at 0° C. The mixture was stirred for 2 h at 0° C., and aq. sat. NH₄Cl was added. The mixture was extracted with heptane (2×). The combined org. extracts were dried over MgSO₄, filtered, and the solvents were removed under reduced pressure. Purification of the residue by FC (heptane→EtOAc/heptane 1:49) yielded the title compound (18.0 g, 96%). LC-MS: $t_R$=1.22 min.

3-(tert-Butyl-dimethyl-silanyloxymethyl)-4-chloro-benzaldehyde

BuLi (1.6M in hexane, 46.6 mL, 74.6 mmol) was added to a sol. of (5-bromo-2-chloro-benzyloxy)-tert-butyl-dimethyl-silane (16.7 g, 49.7 mmol) in THF (500 mL). The mixture was stirred for 30 min at −78° C., and DMF (19.2 mL, 249 mmol) was added at such a rate that the temperature did not raise above −70° C. The mixture was stirred for 30 min at −78° C., and was allowed to warm up to rt. The mixture was poured onto aq. sat. NH₄Cl. The resulting mixture was extracted several times with EtOAc. The combined org. extracts were dried over MgSO₄, filtered, and the solvents were removed under reduced pressure. Purification of the residue by FC (EtOAc/heptane 1:4) yielded the title compound (11.2 g, 79%). LC-MS: $t_R$=1.15 min.

3-(tert-Butyl-dimethyl-silanyloxymethyl)-4-chloro-benzaldehyde Oxime 3-(tert-Butyl-dimethyl-silanyloxymethyl)-4-chloro-benzaldehyde (12.7 g, 44.6 mmol) was dissolved in CH₃CN (53 mL). To this sol. was added NaHCO₃ (11.2 g, 134 mmol), and the mixture was stirred vigorously for 5 min. Water (96 mL) was added and the mixture was stirred for 10 min. NH₂OH.HCl (6.20 g, 89.2 mmol) was added dropwise, followed by TBAC (622 mg, 2.24 mmol). The mixture was stirred at rt for 1 h, and AcOH (4.00 mL) was added dropwise to pH 6-7. The mixture was diluted with water (100 mL), and this mixture was extracted with Et₂O (3×). The combined org. extracts were dried over MgSO₄, filtered, and the solvents were removed under reduced pressure. Drying the residue under high vacuum yielded the crude title compound (15.1 g, 98%) that was used further without purification. LC-MS: $t_R$=1.09 min; ES+: 341.13.

3-(tert-Butyl-dimethyl-silanyloxymethyl)-4-chloro-benzylamine

LiAlH₄ (4.11 g, 108 mmol) was added in portions to a sol. of 3-(tert-butyl-dimethyl-silanyloxymethyl)-4-chloro-benzaldehyde oxime (13.0 g, 43.4 mmol) in Et₂O (433 mL). The mixture was stirred for 1 h at rt. Aq. sat. potassium sodium tartrate (400 mL) was carefully added to the mixture. The mixture was stirred for 3 h, and was extracted with Et₂O (3×). The combined org. extracts were dried over MgSO₄, filtered, and the solvents were removed under reduced pressure. Drying under high vacuum yielded the crude title compound (12.4 g, quantitative yield) that was used further without purification. LC-MS: $t_R$=0.84 min; ES+: 327.37.

N-[3-(tert-Butyl-dimethyl-silanyloxymethyl)-4-chloro-benzyl]-acetamide

AcCl (0.547 mL, 7.70 mmol) was added to a sol. of 3-(tert-butyl-dimethyl-silanyloxymethyl)-4-chloro-benzylamine (2.00 g, 7.00 mmol) and DIPEA (4.80 mL, 28.0 mmol) in CH₂Cl₂ (70 mL) at 0° C. The mixture was stirred for 1 h while warming up to rt. CH₂Cl₂ (30 mL) was added, and the mixture was washed with aq. sat. NH₄Cl (2×), aq. 1M NaOH (1×) and brine (1×). The org. layer was dried over MgSO₄, filtered, and the solvents were removed under reduced pressure. Purification of the crude by FC (EtOAc/heptane 60:40) yielded the title compound (2.10 g, 91%). LC-MS: $t_R$=1.07 min; ES+: 369.19.

N-(4-Chloro-3-hydroxymethyl-benzyl)acetamide

TBAF (1M in THF, 12.0 mL, 12.0 mmol) was added to a sol. of N-[3-(tert-butyl-dimethyl-silanyloxymethyl)-4-chloro-benzyl]-acetamide (2.05 g, 6.00 mmol) in THF (60 mL) at 0° C. The mixture was stirred for 2 h while warming up to rt. EtOAc (100 mL) was added, and the mixture was washed with aq. sat. NH₄Cl (1×) and water (4×). The org. layer was dried over MgSO₄, filtered, and the solvents were removed under reduced pressure. Purification of the crude by FC(CH₂Cl₂/MeOH 90:10) yielded the title compound (750 mg, 59%). LC-MS: $t_R$=0.63 min; ES+: 237.09.

N-(4-Chloro-3-formyl-benzyl)-acetamide

NMO (1.15 g, 8.26 mmol) was added to a sol. of N-(4-chloro-3-hydroxymethyl-benzyl)-acetamide (588 mg, 2.75 mmol) in CH₃CN (27 mL). The sol. was stirred for 30 min at rt, and tetrapropylammonium perruthenate (97 mg, 0.28 mmol) was added. The mixture was stirred for 1 h at rt, and was filtered over celite. The precipitate was washed with CH₃CN. The filtrate was evaporated under reduced pressure. Purification of the crude by FC (CH₂Cl₂/MeOH 95:5) yielded the title compound (382 mg, 66%). LC-MS: $t_R$=0.71 min; ES+: 253.07.

N-(4-Chloro-3-cyclopropylaminomethyl-benzyl)-acetamide

A mixture of N-(4-chloro-3-formyl-benzyl)-acetamide (382 mg, 1.81 mmol) and cyclopropylamine (0.194 mL, 2.71 mmol) in MeOH (18 mL) was heated to reflux for 4 h. The mixture was allowed to cool to rt, and NaBH₄ (102 mg, 2.71 mmol) was added in portions. The mixture was stirred for 1 h, and the solvents were removed under reduced pressure. EtOAc (50 mL) was added, and the resulting mixture was washed with aq. sat. NaHCO₃ and brine. The org. layer was dried over MgSO₄, filtered, and the solvents were removed under reduced pressure. Purification of the crude by FC(CH₂Cl₂/MeOH 95:5) yielded the title compound (371 mg, 81%). LC-MS: $t_R$=0.53 min; ES+: 253.11.

N-[3-(tert-Butyl-dimethyl-silanyloxymethyl)-4-chloro-benzyl]-3,3,3-trifluoro-propionamide TBTU (3.37 g, 10.5 mmol) was added to a sol. of 3-(tert-butyl-dimethyl-silanyloxymethyl)-4-chloro-benzylamine (2.00 g, 7.00 mmol), DIPEA (4.80 mL, 28.0 mmol) and 3,3,3-trifluoropropionic acid (0.927 mL, 10.5 mmol) in CH₂Cl₂ (70 mL). The mixture was stirred at rt for 1 h. CH₂Cl₂ (30 mL) was added, and the mixture was washed with aq. sat. NH₄Cl (2×), aq. 1M NaOH (1×) and brine (1×). The org. layer was dried over MgSO₄, filtered, and the solvents were removed under reduced pressure. Purification of the crude by FC (EtOAc/heptane 40:60) yielded the title compound (1.80 g, 65%). LC-MS: $t_R$=1.10 min; ES+: 396.15.

N-(4-Chloro-3-hydroxymethyl-benzyl)-3,3,3-trifluoro-propionamide

TBAF (1M in THF, 9.10 mL, 9.10 mmol) was added to a sol. of N-[3-(tert-butyl-dimethyl-silanyloxymethyl)-4- chloro-benzyl]-3,3,3-trifluoro-propionamide (1.80 g, 4.55 mmol) in THF (45 mL) at 0° C. The mixture was stirred for 1 h while warming up to rt. EtOAc (100 mL) was added, and the mixture was washed with aq. sat. NH$_4$Cl (3×) and water (4×). The org. layer was dried over MgSO$_4$, filtered, and the solvents were removed under reduced pressure. Purification of the crude by FC (EtOAc/heptane 70:30) yielded the title compound (835 mg, 65%). LC-MS: t$_R$=0.76 min; ES+: 323.02.

N-(4-Chloro-3-formyl-benzyl)-3,3,3-trifluoro-propionamide

MnO$_2$ (1.44 g, 14.9 mmol) was added to a sol. of N-(4-chloro-3-hydroxymethyl-benzyl)-3,3,3-trifluoro-propionamide (841 mg, 2.99 mmol) in CH$_3$CN (60 mL). The mixture was stirred at rt for 3 h. MnO$_2$ (1.44 g, 14.9 mmol) was added again, and the mixture was stirred for 90 min. The mixture was filtered over celite, and the precipitate was washed with CH$_3$CN and CH$_2$Cl$_2$. The solvents were removed under reduced pressure, and the residue was dried under high vacuum, yielding the crude title compound (840 mg, quantitative yield) that was used further without purification. LC-MS: t$_R$=0.84 min; ES+: 341.21.

N-(4-Chloro-3-cyclopropylaminomethyl-benzyl)-3,3,3-trifluoro-propionamide

A mixture of N-(4-chloro-3-formyl-benzyl)-3,3,3-trifluoro-propionamide (840 mg, 3.00 mmol) and cyclopropylamine (0.320 mL, 4.51 mmol) in MeOH (30 mL) was heated to reflux for 4 h. The mixture was allowed to cool to rt. NaBH$_4$ (170 mg, 4.51 mmol) was added in portions. The mixture was stirred for 1 h, and the solvents were removed under reduced pressure. The residue was diluted with EtOAc, and the resulting mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 90:10) yielded the title compound (929 mg, 96%). LC-MS: t$_R$=0.64 min; ES+: 321.05.

[3-(tert-Butyl-dimethyl-silanyloxymethyl)-4-chloro-benzyl]-cyclopropyl-carbamic Acid tert-butyl Ester A mixture of 3-(tert-butyl-dimethyl-silanyloxymethyl)-4-chloro-benzaldehyde (1.73 g, 6.06 mmol) and cyclopropylamine (0.64 mL, 9.1 mmol) in MeOH (60 mL) was heated to reflux for 4 h. The mixture was allowed to cool to rt, and NaBH$_4$ (344 mg, 9.09 mmol) was added in portions. The mixture was stirred for 1 h, and water (20 mL) was added. The solvents were partially removed under reduced pressure. The resulting aq. suspension was diluted with water (50 mL), and extracted with EtOAc. The org. extracts were washed with aq. sat. NaHCO$_3$, and brine. The org. layer was dried over MgSO$_4$, filtered, and the solvents were removed under reduced pressure to yield the crude [3-(tert-butyl-dimethyl-silanyloxymethyl)-4-chloro-benzyl]-cyclopropyl-amine (1.54 g). This crude material was dissolved in CH$_2$Cl$_2$ (60 mL). DIPEA (3.1 mL, 18 mmol) was added, followed by Boc$_2$O (1.98 g, 9.09 mmol). The mixture was stirred at rt for 2 h. CH$_2$Cl$_2$ (40 mL) was added, and the mixture was washed with aq. 1M HCl, aq. sat. NaHCO$_3$, and brine. The org. layer was dried over MgSO$_4$, filtered, and the solvents were removed under reduced pressure. Purification of the crude by FC (heptane→EtOAc/heptane 5:95) yielded the title compound (1.54 g, 78%). LC-MS: t$_R$=1.26 min; ES+: 426.14.

(4-Chloro-3-hydroxymethyl-benzyl)-cyclopropyl-carbamic Acid tert-butyl Ester

Aq. 1M NaOH (16 mL) was added to a sol. of [3-(tert-butyl-dimethyl-silanyloxymethyl)-4-chloro-benzyl]-cyclopropyl-carbamic acid tert-butyl ester (700 mg, 1.64 mmol) in MeOH (32 mL). The mixture was heated to reflux for 2 h, and was allowed to cool to rt. The solvents were partially removed under reduced pressure, and the resulting aq. layer was diluted with water (100 mL). The mixture was extracted with Et$_2$O (3×). The combined org. layers were dried over MgSO$_4$, filtered, and the solvents were removed under reduced pressure. Purification of the crude by FC (EtOAc/heptane 40:60) yielded the title compound (550 mg, quantitative yield). LC-MS: t$_R$=0.98 min; ES+: 312.04.

(4-Chloro-3-formyl-benzyl)-cyclopropyl-carbamic Acid tert-butyl Ester

MnO$_2$ (815 mg, 8.44 mmol) was added to a sol. of (4-chloro-3-hydroxymethyl-benzyl)-cyclopropyl-carbamic acid tert-butyl ester (526 mg, 1.69 mmol) in CH$_3$CN (34 mL). The mixture was stirred at rt for 3 h, and was filtered over celite, and washed with CH$_3$CN and CH$_2$Cl$_2$. Evaporation of the solvents under reduced pressure yielded the crude title compound (563 mg, quantitative yield) that was used further without purification. LC-MS: t$_R$=1.05 min; ES+: 310.04.

(4-Chloro-3-cyclopropylaminomethyl-benzyl)-cyclopropyl-carbamic Acid tert-butyl Ester A mixture of (4-chloro-3-formyl-benzyl)-cyclopropyl-carbamic acid tert-butyl ester (563 mg, 1.82 mmol) and cyclopropylamine (0.195 mL, 2.73 mmol) in MeOH (18 mL) was heated to reflux for 4 h. The mixture was allowed to cool to rt, and NaBH$_4$ (103 mg, 2.73 mmol) was added in portions. The mixture was stirred for 1 h, and the solvents were removed under reduced pressure. The resulting oil was diluted with EtOAc (100 mL), and the resulting mixture was washed with aq. sat. NaHCO$_3$ and brine. The org. layer was dried over MgSO$_4$, filtered, and the solvents were removed under reduced pressure. Purification of the crude by FC(CH$_2$Cl$_2$/MeOH 95:5) yielded the title compound (343 mg, 54%). LC-MS: t$_R$=0.78 min; ES+: 351.39.

tert-Butyl-[2-chloro-5-(2-nitro-vinyl)-benzyloxy]-dimethyl-silane

A mixture of 3-(tert-butyl-dimethyl-silanyloxymethyl)-4-chloro-benzaldehyde (14.0 g, 49.1 mmol) and ammonium acetate (3.79 g, 49.1 mmol) in nitromethane (8.19 mL, 152 mmol) and AcOH (39 mL) was heated to reflux for 3 h. The mixture was allowed to cool to rt, and was poured onto water. The resulting mixture was extracted several times with EtOAc. The combined org. extracts were washed with water and aq. sat. NaHCO$_3$ several times. The org. layer was dried over MgSO$_4$, filtered, and the solvents were removed under reduced pressure. The residue was dried under high vacuum overnight, and was dissolved in DMF (217 mL). The sol. was cooled to 0° C., and imidazole (8.36 g, 123 mmol) and TBDMS-Cl (8.84 g, 58.6 mmol) were added. The mixture was stirred for 2 h at 0° C., and was poured onto aq. sat. NH$_4$Cl. The resulting mixture was extracted with EtOAc several times. The combined org. extracts were washed with water and brine. The org. layer was dried over MgSO$_4$, filtered, and the solvents were removed under reduced pressure.

Purification of the crude by FC (EtOAc/heptane 2:8) yielded the title compound (9.50 g, 59%). LC-MS: $t_R$=1.18 min.

2-[3-(tert-Butyl-dimethyl-silanyloxymethyl)-4-chloro-phenyl]-ethylamine

LiAlH$_4$ (1.09 g, 28.7 mmol) was added to a sol. of tert-butyl-[2-chloro-5-(2-nitro-vinyl)-benzyloxy]-dimethyl-silane (3.95 g, 11.5 mmol) in Et$_2$O (115 mL). The mixture was stirred for 1 h at rt, and aq. sat. potassium sodium tartrate was added. The mixture was stirred for 1 h, and the layers were separated. The aq. layer was extracted several times with Et$_2$O. The combined org. extracts were dried over MgSO$_4$, filtered, and the solvents were removed under reduced pressure. Drying the residue under high vacuum yielded the crude title compound (3.20 g, 93%) that was used further without purification. LC-MS: $t_R$=0.90 min; ES+: 341.18.

N-{2-[3-(tert-Butyl-dimethyl-silanyloxymethyl)-4-chloro-phenyl]-ethyl}-acetamide AcCl (0.063 mL, 0.88 mmol) was added to a sol. of 2-[3-(tert-butyl-dimethyl-silanyloxymethyl)-4-chloro-phenyl]-ethylamine (252 mg, 0.840 mmol) and DIPEA (0.575 mL, 3.36 mmol) in CH$_2$Cl$_2$ (8.4 mL). The mixture was stirred at rt for 30 min, and aq. sat. NH$_4$Cl was added. The layers were separated, and the org. layer was washed with aq. 1M NaOH, dried over MgSO$_4$, filtered, and the solvents were removed under reduced pressure. Purification of the crude by FC(CH$_2$Cl$_2$/MeOH 19:1) yielded the title compound (190 mg, 66%). LC-MS: $t_R$=1.09 min; ES+: 342.19.

N-[2-(4-Chloro-3-hydroxymethyl-phenyl)-ethyl]-acetamide

TBAF (1M in THF, 1.12 mL, 1.12 mmol) was added to a sol. of N-{2-[3-(tert-butyl-dimethyl-silanyloxymethyl)-4-chloro-phenyl]-ethyl}-acetamide (190 mg, 0.555 mmol) in THF (7.10 mL) at 0° C. The mixture was stirred for 1 h while warming up to rt. Aq. sat. NH$_4$Cl was added, and the mixture was extracted with EtOAc (3×). The org. layer was dried over MgSO$_4$, filtered, and the solvents were removed under reduced pressure. Purification of the crude by FC(CH$_2$Cl$_2$/MeOH 19:1) yielded the title compound (100 mg, 79%). LC-MS: $t_R$=0.67 min; ES+: 284.11.

N-[2-(4-Chloro-3-formyl-phenyl)-ethyl]-acetamide

NMO (184 mg, 1.32 mmol) was added to a sol. of N-[2-(4-chloro-3-hydroxymethyl-phenyl)-ethyl]-acetamide (100 mg, 0.439 mmol) in CH$_2$Cl$_2$ (9.22 mL). The mixture was stirred for 30 min, and tetrapropylammonium perruthenate (15.5 mg, 0.044 mmol) was added. The mixture was stirred for 1 h at rt, and was filtered over celite. The filtrate was evaporated under reduced pressure. Purification of the crude by FC(CH$_2$Cl$_2$/MeOH 49:1) yielded the title compound (50 mg, 50%). LC-MS: $t_R$=0.75 min; ES+: 267.10.

N-[2-(4-Chloro-3-cyclopropylaminomethyl-phenyl)-ethyl]-acetamide

A mixture of N-[2-(4-chloro-3-formyl-phenyl)-ethyl]-acetamide (50.1 mg, 0.222 mmol), Et$_3$N (0.046 mL, 0.332 mmol) and cyclopropylamine (0.023 mL, 0.332 mmol) in MeOH (0.50 mL) was heated to reflux for 4 h. The mixture was allowed to cool to rt, and NaBH$_4$ (21.0 mg, 0.554 mmol) was added in portions. The mixture was stirred for 1 h, and aq. sat. NaHCO$_3$ was added. The mixture was extracted with EtOAc several times, and the combined org. extracts were washed with brine. The org. layer was dried over MgSO$_4$, filtered, and the solvents were removed under reduced pressure. Purification of the residue by FC(CH$_2$Cl$_2$/MeOH 95:5) yielded the title compound (35 mg, 59%). LC-MS: $t_R$=0.59 min; ES+: 267.17.

tert-Butyl-(2-chloro-5-vinyl-benzyloxy)-dimethyl-silane

Pd(PPh$_3$)$_4$ (173 mg, 0.149 mmol) was added to a sol. of (5-bromo-2-chloro-benzyloxy)-tert-butyl-dimethyl-silane (1.00 g, 2.98 mmol) in DME (30 mL). The mixture was stirred at rt for 20 min, and K$_2$CO$_3$ (411 mg, 2.98 mmol), water (10 mL) and 4,4,5,5-tetramethyl-2-vinyl-1,3,2-dioxaborolane (0.53 mL, 2.98 mmol) were added. The mixture was heated rapidly to reflux, and stirred under reflux for 2 h. The mixture was allowed to cool to rt, and was diluted with Et$_2$O (100 mL). The mixture was washed with water, and the aq. layer was extracted back with Et$_2$O (3×). The combined org. extracts were dried over MgSO$_4$, filtered, and the solvents were removed under reduced pressure. Purification of the crude by FC (EtOAc/heptane 5:95) yielded the title compound (822 mg, 98%). LC-MS: $t_R$=1.22 min.

2-[3-(tert-Butyl-dimethyl-silanyloxymethyl)-4-chloro-phenyl]-ethanol

9-BBN (0.5M in THF, 34.0 mL, 17.0 mmol) was added dropwise over 30 min to a sol. of tert-butyl-(2-chloro-5-vinyl-benzyloxy)-dimethyl-silane (800 mg, 2.83 mmol) in THF (28 mL) at 0° C. The mixture was stirred for 30 min at 0° C., and for 4 h at rt. The mixture was cooled again to 0° C., and aq. 1M NaOH (39.0 mL) and H$_2$O$_2$ (33%, 9.80 mL, 113 mmol) were added dropwise. The mixture was stirred for 2 h while warming up to rt, and was cooled to 0° C. Aq. sat. Na$_2$S$_2$O$_3$ (100 mL) was carefully added, and this mixture was allowed to gently warm up to rt overnight. The solvents were partially removed under reduced pressure, and the aq. residue was extracted with EtOAc (3×). The combined org. extracts were washed with brine. The org. layer was dried over MgSO$_4$, filtered, and the solvents were removed under reduced pressure. Purification of the crude by FC (EtOAc/heptane 40:60) yielded the title compound (677 mg, 80%). LC-MS: $t_R$=1.10 min; ES+: 301.08.

Methanesulfonic Acid 2-[3-(tert-butyl-dimethyl-silanyloxymethyl)-4-chloro-phenyl]-ethyl Ester To a sol. of 2-[3-(tert-butyl-dimethyl-silanyloxymethyl)-4-chloro-phenyl]-ethanol (2.00 g, 6.65 mmol) in CH$_2$Cl$_2$ (66 mL) at 0° C. were added dropwise Et$_3$N (1.02 mL, 7.31 mmol) and methanesulfonyl chloride (0.57 mL, 7.3 mmol). The reaction was stirred at 0° C. for 1 h, and was diluted with CH$_2$Cl$_2$ (40 mL). The resulting mixture was washed with aq. sat. NH$_4$Cl (2×). The org. layer was dried over MgSO$_4$, filtered, and the solvents were removed under reduced pressure to yield the crude title compound (2.55 g, quantitative yield) that was used further without purification. LC-MS: $t_R$=1.13 min; ES+: 379.29.

{2-[3-(tert-Butyl-dimethyl-silanyloxymethyl)-4-chloro-phenyl]-ethyl}-cyclopropyl-amine Cyclopropylamine (1.14 mL, 16.3 mmol) was added to a sol. of methanesulfonic acid 2-[3-(tert-butyl-dimethyl-silanyloxymethyl)-4-chloro-phenyl]-ethyl ester (1.76 g, 4.65 mmol) in EtOH (46 mL). The mixture was heated to reflux for 2 h, and cyclopropylamine (0.57 mL, 8.2 mmol) was added again. The mixture was heated to reflux overnight, and was allowed to cool to rt. The solvents were removed under reduced pressure, and the residue was purified by FC (EtOAc/heptane 50:50→7M NH$_3$/MeOH) to yield the title compound (865 mg, 68%). LC-MS: $t_R$=0.92 min; ES+: 340.39.

{2-[3-(tert-Butyl-dimethyl-silanyloxymethyl)-4-chloro-phenyl]-ethyl}-cyclopropyl-carbamic Acid tert-butyl Ester DIPEA (2.61 mL, 5.60 mmol) and Boc$_2$O (1.22 g, 5.60 mmol) were added to a sol. of {2-[3-(tert-butyl-dimethyl-silanyloxymethyl)-4-chloro-phenyl]-ethyl}-cyclopropyl-amine (1.73 g, 5.09 mmol) in CH$_2$Cl$_2$ (50 mL). The mixture was stirred at rt for 4 h. The mixture was diluted with CH$_2$Cl$_2$ (50 mL), washed with aq. sat. NaHCO$_3$, aq. sat. NH$_4$Cl and brine. The org. layer was dried over MgSO$_4$, filtered, and the solvents were removed under reduced pressure. Purification of the crude by FC (EtOAc/heptane 10:90) yielded the title compound (2.14 g, 96%). LC-MS: $t_R$=1.26 min.

[2-(4-Chloro-3-hydroxymethyl-phenyl)-ethyl]-cyclopropyl-carbamic Acid tert-butyl Ester Aq. 1M NaOH (48 mL) was added to a suspension of {2-[3-(tert-butyl-dimethyl-silanyloxymethyl)-4-chloro-phenyl]-ethyl}-cyclopropyl-carbamic acid tert-butyl ester (2.10 g, 4.77 mmol) in MeOH (96 mL). The mixture was heated to reflux for 90 min. The mixture was allowed to cool to rt, and the solvents were partially removed under reduced pressure. The resulting aq. mixture was diluted with water (100 mL), and was extracted with Et$_2$O (3×). The combined org. extracts were dried over MgSO$_4$, filtered, and the solvents were removed under reduced pressure. Purification of the crude by FC (EtOAc/heptane 40:60) yielded the title compound (1.34 g, 86%). LC-MS: $t_R$=0.98 min; ES+: 326.30.

[2-(4-Chloro-3-formyl-phenyl)ethyl]-cyclopropyl-carbamic Acid tert-butyl Ester

MnO$_2$ (1.97 g, 20.4 mmol) was added to a sol. of [2-(4-chloro-3-hydroxymethyl-phenyl)-ethyl]-cyclopropyl-carbamic acid tert-butyl ester (1.33 g, 4.08 mmol) in CH$_3$CN (41 mL). The mixture was stirred overnight at rt. The mixture was filtered over celite, and was washed with CH$_3$CN and CH$_2$Cl$_2$. Evaporation of the filtrate under reduced pressure yielded the crude title compound (1.32 g, quantitative yield) that was used further without purification. LC-MS: $t_R$=1.05 min.

[2-(4-Chloro-3-cyclopropylaminomethyl-phenyl)-ethyl]-cyclopropyl-carbamic Acid tert-butyl ester A mixture of [2-(4-chloro-3-formyl-phenyl)-ethyl]-cyclopropyl-carbamic acid tert-butyl ester (1.32 g, 4.08 mmol) and cyclopropylamine (0.438 mL, 6.26 mmol) in MeOH (41 mL) was heated to reflux for 4 h. The mixture was allowed to cool to rt, and NaBH$_4$ (232 mg, 6.14 mmol) was added in portions. The mixture was stirred for 1 h, and the solvents were removed under reduced pressure. EtOAc (100 mL) was added, and the mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 95:5) yielded the title compound (883 mg, 59%). LC-MS: $t_R$=0.82 min; ES+: 365.38.

[5-Chloro-2-(3-methoxy-propyl)-pyridin-4-ylmethyl]-cyclopropyl-carbamic Acid tert-butyl Ester Boc$_2$O (10.2 g, 45.9 mmol) was added to a sol. of [5-chloro-2-(3-methoxy-propyl)-pyridin-4-ylmethyl]-cyclopropyl-amine (7.79 g, 30.6 mmol) and DIPEA (13.1 mL, 76.5 mmol) in CH$_2$Cl$_2$ (270 mL). The mixture was stirred at rt for 1 h, and was cooled to 0° C. The mixture was neutralized to pH 6 with aq. 1M HCl under efficient stirring, and the layers were separated. The aq. layer was extracted with CH$_2$Cl$_2$ (2×). The combined org. extracts were dried over MgSO$_4$, filtered, and the solvents were removed under reduced pressure. Purification of the crude by FC (EtOAc/heptane 1:3→1:2) yielded the title compound (7.83 g, 72%). LC-MS: $t_R$=0.97 min; ES+: 355.09.

[5-Chloro-2-(3-methoxy-propyl)-1-oxy-pyridin-4-ylmethyl]-cyclopropyl-carbamic Acid tert-butyl Ester MCPBA (70%, 8.33 g, 33.8 mmol) was added to a sol. of [5-chloro-2-(3-methoxy-propyl)-pyridin-4-ylmethyl]-cyclopropyl-carbamic acid tert-butyl ester (7.83 g, 30.7 mmol) in CH$_2$Cl$_2$ (210 mL), and the mixture was stirred for 2 h at rt. The mixture was washed with aq. 1M NaOH and with brine. The combined aq. layers were extracted back with CH$_2$Cl$_2$. The combined org. extracts were dried over MgSO$_4$, filtered, and the solvents were removed under reduced pressure to yield the crude title compound (8.26 g, 72%) that was used further without purification. LC-MS: $t_R$=0.94 min; ES+: 371.14.

[5-Chloro-2-(3-methoxy-propyl)-1-oxy-pyridin-4-ylmethyl]-cyclopropyl-amine

HCl (4M in dioxane, 83 mL) was added to a sol. of [5-chloro-2-(3-methoxy-propyl)-1-oxy-pyridin-4-ylmethyl]-cyclopropyl-carbamic acid tert-butyl ester (8.26 g, 22.3 mmol) in CH$_2$Cl$_2$ (83 mL) at 0° C. The mixture was stirred for 45 min at 0° C., and for 3 h at rt. The solvents were removed under reduced pressure, and the residue was diluted with CH$_2$Cl$_2$. The mixture was washed with aq. 1M NaOH. The org. layer was dried over MgSO$_4$, filtered, and the solvents were removed under reduced pressure. Purification of the crude by FC (MeOH/CH$_2$Cl$_2$ 1:19) yielded the title compound (5.71 g, 95%). LC-MS: $t_R$=0.46 min; ES+: 271.42.

[3-(tert-Butyl-dimethyl-silanyloxymethyl)-4-chloro-benzyl]-(2-fluoro-ethyl)-carbamic Acid tert-butyl Ester A mixture of 3-(tert-butyl-dimethyl-silanyloxymethyl)-4-chloro-benzaldehyde (1.50 g, 5.27 mmol), DIPEA (1.80 mL, 10.5 mmol) and 2-fluoroethylamine hydrochloride (873 mg, 7.90 mmol) in MeOH (53 mL) was heated to reflux for 4 h. The reaction was allowed to cool to rt, and NaBH$_4$ (300 mg, 7.91 mmol) was added in portions. The mixture was stirred for 1 h, and the solvents were removed under reduced pressure. EtOAc (100 mL) was added, and the mixture was washed with aq. sat. NaHCO$_3$ and brine. The org. layer was dried over MgSO$_4$, filtered, and the solvents were removed under reduced pressure to yield the crude [3-(tert-butyl-dimethyl-silanyloxymethyl)-4-chloro-benzyl]-(2-fluoro-ethyl)-amine. This crude product was dissolved in CH$_2$Cl$_2$ (70 mL).

DIPEA (2.70 mL, 15.8 mmol) was added, followed by Boc$_2$O (1.70 g, 7.91 mmol). The mixture was stirred at rt for 1 h. The mixture was diluted with CH$_2$Cl$_2$ (50 mL), and was washed with aq. 1M HCl, aq. sat. NaHCO$_3$, and brine. The org. layer was dried over MgSO$_4$, filtered, and the solvents were removed under reduced pressure. Purification of the crude by FC (EtOAc/heptane 10:90) yielded the title compound (1.92 g, 85%). LC-MS: $t_R$=1.22 min; ES+: 417.17.

(4-Chloro-3-hydroxymethyl-benzyl)-(2-fluoro-ethyl) carbamic Acid tert-butyl Ester TBAF (1M in THF, 8.84 mL, 8.84 mmol) was added to a sol. of [3-(tert-butyl-dimethyl-silanyloxymethyl)-4-chlorobenzyl]-(2-fluoro-ethyl)-carbamic acid tert-butyl ester (1.91 g, 4.42 mmol) in THF (44.2 mL) at 0° C. The mixture was stirred for 1 h while warming up to rt. EtOAc (100 mL) was added, and the resulting mixture was washed with aq. sat. NH$_4$Cl (2×) and brine (1×). The org. layer was dried over MgSO$_4$, filtered, and the solvents were removed under reduced pressure. Purification of the crude by FC (EtOAc/heptane 30:70) yielded the title compound (901 mg, 64%). LC-MS: $t_R$=0.64 min; ES+: 318.07.

(4-Chloro-3-formyl-benzyl)-(2-fluoro-ethyl)-carbamic Acid tert-butyl Ester

MnO$_2$ (1.22 g, 12.6 mmol) was added to a sol. of (4-chloro-3-hydroxymethyl-benzyl)-(2-fluoro-ethyl)-carbamic acid tert-butyl ester (801 mg, 2.52 mmol) in CH$_3$CN (50 mL). The mixture was stirred at rt for 4.5 h, and MnO$_2$ (1.22 g, 12.6 mmol) was added again. The mixture was stirred for 1 h, and was filtered over celite. The precipitate was washed with CH$_3$CN and CH$_2$Cl$_2$. The filtrate was evaporated under reduced pressure. Drying the residue under high vacuum yielded the crude title compound (800 mg, quantitative yield) that was used further without purification. LC-MS: $t_R$=1.01 min.

(4-Chloro-3-cyclopropylaminomethyl-benzyl)-(2-fluoro-ethyl)-carbamic Acid tert-butyl Ester A mixture of (4-chloro-3-formyl-benzyl)-(2-fluoro-ethyl)-carbamic acid tert-butyl ester (850 mg, 2.69 mmol) and cyclopropylamine (0.290 mL, 4.05 mmol) in MeOH (27 mL) was heated to reflux for 4 h. The mixture was allowed to cool to rt, and NaBH$_4$ (153 mg, 4.40 mmol) was added in portions. The mixture was stirred for 1 h. The solvents were removed under reduced pressure, and EtOAc was added. The resulting mixture was washed with aq. sat. NaHCO$_3$ and brine. The org. layer was dried over MgSO$_4$, filtered, and the solvents were removed under reduced pressure. Purification of the crude by FC (CH$_2$Cl$_2$/MeOH 95:5) yielded the title compound (845 mg, 88%). LC-MS: $t_R$=0.76 min; ES+: 357.19.

{3-[(tert-Butoxycarbonyl-cyclopropyl-amino)-methyl]4-chloro-phenyl}-acetic Acid

Conc. H$_2$SO$_4$ (98%, 5.80 mL) was carefully added to a suspension of CrO$_3$ (6.70 g, 67.0 mmol) in water (12.5 mL). Water was slowly added up to a total volume of 22.5 mL, at which stage the mixture was a clear sol. This sol. was added dropwise to a sol. of [2-chloro-5-(2-hydroxy-ethyl)-benzyl]-cyclopropyl-carbamic acid tert-butyl ester (13.0 g, 39.9 mmol) in acetone (140 mL) at 0° C. When the addition was complete, the mixture was stirred at 0° C. for 30 min. The mixture was filtered, and the filtrate was evaporated under reduced pressure. The residue was diluted with EtOAc, and the resulting mixture was washed with aq. 1M HCl. The org. layer was dried over MgSO$_4$, filtered, and the solvents were removed under reduced pressure. Drying the residue under high vacuum yielded the crude title compound (12.2 g, 90%) that was used further without purification. LC-MS: $t_R$=0.95 min; ES+: 325.35.

(2-Chloro-5-cyclopropylcarbamoylmethyl-benzyl)-cyclopropyl-carbamic Acid tert-butyl Ester To a sol. of {3-[(tert-butoxycarbonyl-cyclopropyl-amino)-methyl]-4-chloro-phenyl}-acetic acid (4.30 g, 12.6 mmol) in CH$_2$Cl$_2$ (130 mL) was added 1-chloro-N,N-2-trimethylpropenyl amine (1.87 mL, 15.2 mmol), and the mixture was stirred for 60 min. A sol. of cyclopropylamine (3.62 mL, 50.6 mmol) in CH$_2$Cl$_2$ (50 mL) was added, and the mixture was stirred for 60 min. More CH$_2$Cl$_2$ was added, and the mixture was washed with water and brine, was dried over MgSO$_4$, filtered, and the solvents were removed under reduced pressure. Purification of the crude by FC (EtOAc/heptane 7:3) yielded the title compound (3.14 g, 65%). LC-MS: $t_R$=0.97 min; ES+: 323.29.

2-(4-Chloro-3-cyclopropylaminomethyl-phenyl)-N-cyclopropyl-acetamide

HCl (4M in dioxane, 31 mL) was added to a sol. of (2-chloro-5-cyclopropylcarbamoylmethyl-benzyl)-cyclopropyl-carbamic acid tert-butyl ester (3.14 g, 8.29 mmol) in CH$_2$Cl$_2$ (31 mL) at 0° C. The mixture was stirred for 2 h at 0° C., and was carefully neutralized with aq. 1M NaOH. The layers were separated, and the aq. layer was extracted with CH$_2$Cl$_2$. The combined org. extracts were dried over MgSO$_4$, filtered, and the solvents were removed under reduced pressure to yield the crude title compound (2.11 g, 91%) that was used further without purification. LC-MS: $t_R$=0.59 min; ES+: 279.32.

(2-Chloro-5-methylcarbamoylmethyl-benzyl)-cyclopropyl-carbamic Acid tert-butyl Ester To a sol. of {3-[(tert-butoxycarbonyl-cyclopropyl-amino)-methyl]-4-chloro-phenyl}-acetic acid (4.30 g, 12.6 mmol) in CH$_2$Cl$_2$ (130 mL) was added 1-chloro-N,N-2-trimethylpropenyl amine (1.87 mL, 15.2 mmol), and the mixture was stirred for 60 min. Methylamine (2M in THF, 25.0 mL, 50.0 mmol) was added, and the mixture was stirred overnight. More CH$_2$Cl$_2$ was added, and the mixture was washed with water and brine, was dried over MgSO$_4$, filtered, and the solvents were removed under reduced pressure. Purification of the crude by FC (EtOAc/heptane 7:3) yielded the title compound (2.01 g, 45%). LC-MS: $t_R$=0.95 min; ES+: 325.30.

2-(4-Chloro-3-cyclopropylaminomethyl-phenyl)-N-methyl-acetamide

HCl (4M in dioxane, 20 mL) was added to a sol. of (2-chloro-5-methylcarbamoylmethyl-benzyl)-cyclopropyl-carbamic acid tert-butyl ester (2.01 g, 5.97 mmol) in CH$_2$Cl$_2$ (20 mL) at 0° C. The mixture was stirred for 2 h at 0° C., and was carefully neutralized with aq. 1M NaOH. The layers were separated, and the aq. layer was extracted with CH$_2$Cl$_2$. The combined org. extracts were dried over MgSO$_4$, filtered, and the solvents were removed under reduced pressure to yield the crude title compound (1.42 g, 99%) that was used further without purification. LC-MS: $t_R$=0.54 min; ES+: 294.33.

(2-Chloro-5-ethylcarbamoylmethyl-benzyl)-cyclopropyl-carbamic Acid tert-butyl Ester To a sol. of {3-[(tert-butoxycarbonyl-cyclopropyl-amino)-methyl]-4-chloro-phenyl}-acetic acid (4.30 g, 12.6 mmol) in $CH_2Cl_2$ (130 mL) was added 1-chloro-N,N-2-trimethylpropenyl amine (1.87 mL, 15.2 mmol), and the mixture was stirred for 60 min. Ethylamine (2M in THF, 25.0 mL, 50.0 mmol) was added, and the mixture was stirred overnight. More $CH_2Cl_2$ was added, and the mixture was washed with water and brine, was dried over $MgSO_4$, filtered, and the solvents were removed under reduced pressure. Purification of the crude by FC (EtOAc/heptane 7:3) yielded the title compound (2.94 g, 63%). LC-MS: $t_R$=0.97 min; ES+: 311.28.

2-(4-Chloro-3-cyclopropylaminomethyl-phenyl)-N-ethyl-acetamide

HCl (4M in dioxane, 29 m-L) was added to a sol. of (2-chloro-5-ethylcarbamoylmethyl-benzyl)-cyclopropyl-carbamic acid tert-butyl ester (2.94 g, 8.01 mmol) in $CH_2Cl_2$ (29 mL) at 0° C. The mixture was stirred for 2 h at 0° C., and was carefully neutralized with aq. 1M NaOH. The layers were separated, and the aq. layer was extracted with $CH_2Cl_2$. The combined org. extracts were dried over $MgSO_4$, filtered, and the solvents were removed under reduced pressure to yield the crude title compound (1.90 g, 89%) that was used further without purification. LC-MS: $t_R$=0.58 min; ES+: 308.03.

N-[3-(tert-Butyl-dimethyl-silanyloxymethyl)-4-chloro-benzyl]-propionamide

Propionyl chloride (2.02 mL, 23.1 mmol) and DIPEA (14.4 mL, 84.0 mL) were added to a sol. of 3-(tert-butyl-dimethyl-silanyloxymethyl)-4-chloro-benzylamine (6.00 g, 20.9 mmol) in $CH_2Cl_2$ (195 mL). The mixture was stirred for 15 min at rt, and more $CH_2Cl_2$ was added. The mixture was washed with aq. sat. $NH_4Cl$ (2×), with aq. 1M NaOH (1×) and with brine (1×). The org. layer was dried over $MgSO_4$, filtered, and the solvents were removed under reduced pressure. Purification of the crude by FC (EtOAc/heptane 1:9→3:2) yielded the title compound (5.08 g, 71%). LC-MS: $t_R$=1.09 min; ES+: 383.41.

N-(4-Chloro-3-hydroxymethyl-benzyl)-propionamide

Aq. 1M NaOH (92 mL) was added to a sol. of N-[3-(tert-butyl-dimethyl-silanyloxymethyl)-4-chloro-benzyl]-propionamide (5.08 g, 14.9 mmol) in MeOH (184 mL). The mixture was heated to 80° C., and stirred at this temperature for 30 min. The mixture was allowed to cool to rt, and the solvents were partially removed under reduced pressure. The aq. residue was diluted with water, and was extracted with EtOAc (3×). The combined org. extracts were washed with brine, dried over $MgSO_4$, filtered, and the solvents were removed under reduced pressure. Purification of the crude by FC($CH_2Cl_2$→MeOH/$CH_2Cl_2$ 1:9) yielded the title compound (2.99 g, 88%). LC-MS: $t_R$=0.67 min; ES+: 269.31.

N-(4-Chloro-3-formyl-benzyl)-propionamide $MnO_2$ (5.61 g, 65.7 mmol) was added to a sol. of N-(4-chloro-3-hydroxymethyl-benzyl)-propionamide (2.99 g, 13.1 mmol) in $CH_3CN$ (255 mL) at rt. The mixture was stirred for 3 h at rt, and $MnO_2$ (2.24 g, 26.2 mmol) was added again. The mixture was stirred for 1 h at rt, and the mixture was filtered through celite. The filtrate was evaporated under reduced pressure, and the residue was dried under high vacuum to yield the crude title compound (2.74 g, 93%) that was used further without purification. LC-MS: $t_R$=0.76 min; ES+: 267.27.

N-(4-Chloro-3-cyclopropylaminomethyl-benzyl)-propionamide

Cyclopropylamine (1.28 mL, 18.2 mmol) was added to a sol. of N-(4-chloro-3-formyl-benzyl)-propionamide (2.74 g, 12.1 mmol) in MeOH (42 mL). The mixture was stirred overnight, and $NaBH_4$ (918 mg, 24.3 mmol) was added in portions. The mixture was stirred for 4 h, and aq. 1M NaOH (70 mL) was added. The solvents were partially removed under reduced pressure, and the aq. residue was extracted with EtOAc (2×). The combined org. extracts were washed with brine, dried over $MgSO_4$, filtered, and the solvents were removed under reduced pressure. Purification of the crude by FC($CH_2Cl_2$→MeOH/$CH_2Cl_2$ 1:9) yielded the title compound (2.62 g, 81%). LC-MS: $t_R$=0.58 min; ES+: 267.38.

Cyclopropanecarboxylic Acid 3-(tert-butyl-dimethyl-silanyloxymethyl)-4-chloro-benzylamide Cyclopropylcarbonyl chloride (2.88 mL, 31.0 mmol) and $Et_3N$ (4.38 mL, 31.0 mmol) were added to a sol. of 3-(tert-butyl-dimethyl-silanyloxymethyl)-4-chloro-benzylamine (6.00 g, 20.9 mmol) in $CH_2Cl_2$ (125 mL). The mixture was stirred for 30 min at rt, and more $CH_2Cl_2$ was added. The mixture was washed with aq. sat. $NH_4Cl$ (2×), with aq. 1M NaOH (2×) and with brine (1×). The org. layer was dried over $MgSO_4$, filtered, and the solvents were removed under reduced pressure. Purification of the crude by FC (MeOH/$CH_2Cl_2$ 1:19) yielded the title compound (6.10 g, 82%). LC-MS: $t_R$=1.09 min; ES+: 395.42.

Cyclopropanecarboxylic acid 4-chloro-3-hydroxymethyl-benzylamide

Aq. 1M NaOH (111 mL) was added to a sol. of cyclopropanecarboxylic acid 3-(tert-butyl-dimethyl-silanyloxymethyl)-4-chloro-benzylamide (6.10 g, 17.2 mmol) in MeOH (222 mL). The mixture was heated to 80° C., and stirred at this temperature for 30 min. The mixture was allowed to cool to rt, and the solvents were partially removed under reduced pressure. The aq. residue was diluted with water, and was extracted with EtOAc (3×). The combined org. extracts were washed with brine, dried over $MgSO_4$, filtered, and the solvents were removed under reduced pressure. Purification of the crude by FC($CH_2Cl_2$→MeOH/$CH_2Cl_2$ 1:9) yielded the title compound (3.47 g, 84%). LC-MS: $t_R$=0.71 min; ES+: 281.31.

Cyclopropanecarboxylic Acid 4-chloro-3-formyl-benzylamide $MnO_2$ (6.29 g, 72.0 mmol) was added to a sol. of cyclopropanecarboxylic acid 4-chloro-3-hydroxymethyl-benzylamide (3.47 g, 14.0 mmol) in $CH_3CN$ (300 mL) at rt. The mixture was stirred for 3 h at rt, and $MnO_2$ (2.52 g, 29.0 mmol) was added again. The mixture was stirred for 1 h at rt, and $MnO_2$ (1.26 g, 14.0 mmol) was added again. The mixture was stirred for 1.5 h, and was filtered through celite. The filtrate was evaporated under reduced pressure, and the residue was dried under high vacuum to yield the crude title compound (3.13 g, 91%) that was used further without purification. LC-MS: $t_R$=0.80 min; ES+: 279.31.

Cyclopropanecarboxylic Acid 4-chloro-3-cyclopropylaminomethyl-benzylamide

Cyclopropylamine (1.39 mL, 19.8 mmol) was added to a sol. of cyclopropanecarboxylic acid 4-chloro-3-formyl-benzylamide (3.13 g, 13.2 mmol) in MeOH (28 mL). The mixture was stirred overnight, and NaBH$_4$ (996 mg, 26.0 mmol) was added in portions. The mixture was stirred for 3 h, and aq. 1M NaOH (70 mL) was added. The solvents were partially removed under reduced pressure, and the aq. residue was extracted with EtOAc (2×). The combined org. extracts were washed with brine, dried over MgSO$_4$, filtered, and the solvents were removed under reduced pressure. Purification of the crude by FC (CH$_2$Cl$_2$→MeOH/CH$_2$Cl$_2$ 1:9) yielded the title compound (3.37 g, 92%). LC-MS: $t_R$=0.62 min; ES+: 279.35.

[3-(tert-Butyl-dimethyl-silanyloxymethyl)-4-chloro-benzyl]-carbamic Acid Methyl Ester Methyl chloroformate (1.98 mL, 25.2 mmol) was added to a sol. of 3-(tert-butyl-dimethyl-silanyloxymethyl)-4-chloro-benzylamine (6.00 g, 20.9 mmol) and DIPEA (7.33 mL, 42.0 mmol) in CH$_2$Cl$_2$ (100 mL) at rt. The mixture was stirred for 1 h at rt, and more CH$_2$Cl$_2$ was added. The mixture was washed with aq. sat. NH$_4$Cl, aq. 1M NaOH, and brine. The org. layer was dried over MgSO$_4$, filtered, and the solvents were removed under reduced pressure. Purification of the crude by FC (EtOAc/heptane 1:5) yielded the title compound (5.39 g, 75%). LC-MS: $t_R$=1.02 min; ES+: 344.38.

(4-Chloro-3-hydroxymethyl-benzyl)-carbamic Acid Methyl Ester

A mixture of [3-(tert-butyl-dimethyl-silanyloxymethyl)-4-chloro-benzyl]-carbamic acid methyl ester (5.39 g, 15.7 mmol) in MeOH (160 mL) and aq. 1M NaOH (80 mL) was heated to 80° C. for 1.5 h. The mixture was allowed to cool to rt, and was partially evaporated under reduced pressure. The aq. residue was extracted with EtOAc (3×). The combined org. extracts were dried over MgSO$_4$, filtered, and the solvents were removed under reduced pressure. Drying the residue under high vacuum yielded the crude title compound (3.53 g, 98%) that was used further without purification. LC-MS: $t_R$=0.72 min; ES+: 230.25.

(4-Chloro-3-formyl-benzyl)-carbamic Acid Methyl Ester

MnO$_2$ (6.68 g, 76.9 mmol) was added to a sol. of (4-chloro-3-hydroxymethyl-benzyl)-carbamic acid methyl ester (3.53 g, 15.4 mmol) in CH$_3$CN (300 mL). The mixture was stirred at rt for 3 h, and MnO$_2$ (2.67 g, 30.7 mmol) was added again. The mixture was stirred for 1 h, and MnO$_2$ (1.34 g, 15.4 mmol) was added again. The mixture was stirred for 2 h, and was filtered through celite. The precipitate was washed with CH$_2$Cl$_2$, and the filtrate was evaporated under reduced pressure. Drying the residue under high vacuum yielded the crude title compound (3.22 g, 92%) that was used further without purification.

(4-Chloro-3-cyclopropylaminomethyl-benzyl)-carbamic Acid Methyl Ester

A mixture of (4-chloro-3-formyl-benzyl)-carbamic acid methyl ester (3.22 g, 14.1 mmol) and cyclopropylamine (1.49 mL, 21.2 mmol) in MeOH (50 mL) was stirred at rt overnight. NaBH$_4$ (1.07 g, 28.3 mmol) was added in portions, and the mixture was stirred at rt for 3 h. Aq. 1M NaOH (90 mL) was added, and the solvents were partially removed under reduced pressure. The aq. residue was extracted with EtOAc (3×). The combined org. extracts were washed with brine, dried over MgSO$_4$, filtered, and the solvents were removed under reduced pressure. Purification of the crude by FC (EtOAc/heptane 1:1) yielded the title compound (3.24 g, 85%). LC-MS: $t_R$=0.59 min; ES+: 310.31.

3-(4-Chloro-3-hydroxymethyl-phenyl)-propionic Acid

A mixture of 3-(tert-butyl-dimethyl-silanyloxymethyl)-4-chloro-benzaldehyde (1.84 g, 6.46 mmol), Meldrum acid (931 mg, 6.46 mmol), and formic acid-triethylamine 5:2 complex (1.62 mL, 23.4 mmol) in DMF (6.00 mL) was heated to 100° C. for 3.5 h. Meldrum acid (466 mg, 3.23 mmol) was added again, and the mixture was stirred for 1 h at 100° C. The mixture was allowed to cool to rt, and was diluted with a mixture of water and ice. The resulting mixture was extracted several times with EtOAc. The combined org. extracts were washed with water, dried over MgSO$_4$, filtered, and the solvents were removed under reduced pressure. The residue was dissolved in Et$_2$O, and the resulting mixture was extracted several times with aq. 1M NaOH. The combined aq. extracts were acidified to pH 2 with aq. 1M HCl, and this aq. mixture was extracted back with Et$_2$O several times. The combined org. extracts were dried over MgSO$_4$, filtered, and the solvents were removed under reduced pressure. Drying the residue under high vacuum yielded the crude title compound (1.20 g, 87%) that was used further without purification. LC-MS: $t_R$=0.71 min.

3-(4-Chloro-3-hydroxymethyl-phenyl)-N-methyl-propionamide

MeNH$_2$ (2M in THF, 28.0 mL, 56.1 mmol) and TBTU (1.98 g, 6.17 mmol) were added to a sol. of 3-(4-chloro-3-hydroxymethyl-phenyl)-propionic acid (1.20 g, 5.59 mmol) in CH$_2$Cl$_2$ (42 mL). The mixture was stirred at rt for 2.5 h, and CH$_2$Cl$_2$ (150 mL) was added. The mixture was washed with brine. The org. layer was dried over MgSO$_4$, filtered, and the solvents were removed under reduced pressure. Purification of the crude by FC (MeOH/CH$_2$Cl$_2$ 1:9) yielded the title compound (250 mg, 20%). LC-MS: $t_R$=0.67 min; ES+: 269.34.

3-(4-Chloro-3-formyl-phenyl)-N-methyl-propionamide

MnO$_2$ (10.6 g, 110 mmol) was added to a sol. of 3-(4-chloro-3-hydroxymethyl-phenyl)-N-methyl-propionamide (2.50 g, 11.0 mmol) in CH$_3$CN (223 mL). The mixture was stirred for 1 h at rt. The mixture was filtered over celite and washed with CH$_3$CN and CH$_2$Cl$_2$. The filtrate was evaporated under reduced pressure, and the residue was dried under high vacuum to yield the crude title compound (2.30 g, 93%) that was used without further purification. LC-MS: $t_R$=0.76 min; ES+: 267.30.

3-(4-Chloro-3-cyclopropylaminomethyl-phenyl)-N-methyl-propionamide

A mixture of 3-(4-chloro-3-formyl-phenyl)-N-methyl-propionamide (2.30 g, 10.2 mmol) and cyclopropylamine (1.09 mL, 15.3 mmol) in MeOH (109 mL) was stirred for 2 h.

Cyclopropylamine (0.364 mL, 5.09 mmol) was added, and the mixture was heated to reflux for 4 h. The mixture was allowed to cool down to rt, and NaBH$_4$ (771 mg, 20.4 mmol) was added by portion. The mixture was stirred for 2 h at rt. The solvents were removed under reduced pressure, and the resulting oil was diluted with EtOAc (500 mL). The resulting mixture was washed with aq. sat. NaHCO$_3$ and brine. The org. layer was dried over MgSO$_4$, filtered, and the solvents were removed under reduced pressure. Purification of the crude by FC (MeOH/CH$_2$Cl$_2$ 5:95) yielded the title compound (2.05 g, 75%). LC-MS: $t_R$=0.58 min; ES+: 267.39.

{2-[3-(tert-Butyl-dimethyl-silanyloxymethyl)-4-chloro-phenyl]-ethyl}-(2,2-difluoro-ethyl)carbamic Acid tert-butyl Ester A mixture of methanesulfonic acid 2-[3-(tert-butyl-dimethyl-silanyloxymethyl)-4-chloro-phenyl]-ethyl ester (7.50 g, 19.8 mmol) and 2,2-difluoroethylamine (5.05 g, 62.3 mmol) in EtOH (20 mL) was stirred at 60° C. overnight. The mixture was allowed to cool to rt, and the solvents were removed under reduced pressure. The residue was dried under high vacuum, and was dissolved in CH$_2$Cl$_2$ (200 mL). The mixture was cooled to 0° C., and Et$_3$N (9.64 mL, 69.2 mmol) and Boc$_2$O (6.05 g, 27.7 mmol) were added. The mixture was stirred overnight while warming up to rt. CH$_2$Cl$_2$ (120 mL) was added, and the mixture was washed with aq. 1M HCl, aq. sat. NaHCO$_3$, and brine. The org. layer was dried over MgSO$_4$, filtered, and the solvents were removed under reduced pressure. Purification of the crude by FC (heptane→EtOAc/heptane 1:19) yielded the title compound (8.00 g, quantitative yield) that still contained tert-butanol as impurity. LC-MS: $t_R$=0.91 min; ES+: 364.49.

[2-(4-Chloro-3-hydroxymethyl-phenyl)-ethyl]-(2,2-difluoro-ethyl)-carbamic Acid tert-butyl Ester {2-[3-(tert-Butyl-dimethyl-silanyloxymethyl)-4-chloro-phenyl]-ethyl}-(2,2-difluoro-ethyl)-carbamic acid tert-butyl ester (7.50 g, 16.2 mmol) was dissolved in MeOH (323 mL). Aq. 1M NaOH (161 mL) was added, and the mixture was heated to reflux for 1 h. The solvents were partially removed under reduced pressure, and the aq. residue was diluted with water (900 mL). The mixture was extracted with Et$_2$O (3×). The combined org. extracts were dried over MgSO$_4$, filtered, and the solvents were removed under reduced pressure to yield to crude title compound (4.60 g, 81%) that was used further without purification. LC-MS: $t_R$=1.00 min; ES+: 317.31.

[2-(4-Chloro-3-formyl-phenyl)ethyl]-(2,2-difluoro-ethyl)carbamic Acid tert-butyl Ester MnO$_2$ (6.35 g, 65.7 mmol) was added to a sol. of [2-(4-chloro-3-hydroxymethyl-phenyl)-ethyl]-(2,2-difluoro-ethyl)-carbamic acid tert-butyl ester (4.60 g, 13.2 mmol) in CH$_3$CN (133 mL). The mixture was stirred at rt for 4 h. The mixture was filtered over celite, and the precipitate was washed with CH$_3$CN and CH$_2$Cl$_2$. The filtrate was evaporated under reduced pressure to yield to crude title compound (4.30 g, 94%) that was used further without purification. LC-MS: $t_R$=1.06 min.

[2-(4-Chloro-3-cyclopropylaminomethyl-phenyl)ethyl]-(2,2-difluoro-ethyl)-carbamic Acid tert-butyl Ester A mixture of [2-(4-chloro-3-formyl-phenyl)-ethyl]-(2,2-difluoro-ethyl)-carbamic acid tert-butyl ester (4.30 g, 12.4 mmol) and cyclopropylamine (1.77 mL, 12.4 mmol) in MeOH (125 mL) was stirred for 2 h at rt. Cyclopropylamine (0.44 mL, 6.2 mmol) was added, and the mixture was heated to reflux for 4 h. The mixture was allowed to cool to rt. NaBH$_4$ (935 mg, 24.7 mmol) was added in portions. The mixture was stirred for 1 h. The solvents were removed under reduced pressure, and the residue was taken in EtOAc (800 mL). The resulting mixture was washed with aq. sat. NaHCO$_3$ and brine. The org. layer was dried over MgSO$_4$, filtered, and the solvents were removed under reduced pressure. Purification of the crude by FC (MeOH/CH$_2$Cl$_2$ 5:95) yielded the title compound (3.53 g, 73%). LC-MS: $t_R$=0.83 min; ES+: 389.52.

(2-Chloro-5-vinyl-benzyl)-cyclopropyl-carbamic Acid tert-butyl Ester

To a sol. of (5-bromo-2-chloro-benzyl)-cyclopropyl-carbamic acid tert-butyl ester (105 g, 0.292 mol) in DME (800 mL) under N$_2$ at rt was added Pd(PPh$_3$)$_4$ (16.9 g, 14.6 mmol). The mixture was stirred at rt for 30 min, and K$_2$CO$_3$ (40.7 g, 292 mmol), water (350 mL) and 4,4,5,5-tetramethyl-2-vinyl-[1,3,2]dioxaborolane (52.0 mL, 292 mmol) were added. The mixture was heated to reflux for 3 h. The mixture was allowed to cool to rt, and water (500 mL) was added. The mixture was extracted with Et$_2$O (4×). The combined org. extracts were dried over MgSO$_4$, filtered, and the solvents were removed under reduced pressure. Purification of the crude by FC (heptane/EtOAc 9:1) yielded the title compound (70.9 g, 79%). LC-MS: $t_R$=1.10 min; ES+: 293.38.

(2-Chloro-5-formyl-benzyl)-cyclopropyl-carbamic Acid tert-butyl Ester

A O$_3$/O$_2$-mixture (generated by a Fischer ozonolyser) was gently bubbled through a sol. of (2-chloro-5-vinyl-benzyl)-cyclopropyl-carbamic acid tert-butyl ester (10.0 g, 32.5 mmol) in CH$_2$Cl$_2$ (356 mL) and MeOH (44 mL) at −78° C. for 60 min. The mixture turned light blue, and pure O$_2$ was bubbled through the mixture until it became colourless. The mixture was purged with a stream of nitrogen for 60 min, and Me$_2$S (44.0 mL) was added. The mixture was stirred at −78° C. for 2 h. The solvents were removed under reduced pressure, and the residue was dried under high vacuum overnight to yield to crude title compound (11.7 g, quantitative yield) that was used further without purification. LC-MS: $t_R$=1.04 min; ES+: 295.34.

(2-Chloro-5-hydroxymethyl-benzyl)-cyclopropyl-carbamic Acid tert-butyl Ester

NaBH$_4$ (1.48 g, 37.7 mmol) was added to a sol. of (2-chloro-5-formyl-benzyl)-cyclopropyl-carbamic acid tert-butyl ester (11.7 g, 37.7 mmol) in CH$_3$CN (113 mL) under N$_2$. The mixture was stirred at rt for 1 h, and water (113 mL) was added. The mixture was stirred at rt for 5 min, and extracted with CH$_2$Cl$_2$ (3×). The combined org. layers were dried over MgSO$_4$, filtered, and the solvents were removed under reduced pressure. Purification of the crude by FC (heptane/EtOAc 7:3) yielded the title compound (6.53 g, 56%). LC-MS: $t_R$=0.96 min; ES+: 297.37.

(2-Chloro-5-methylcarbamoyloxymethyl-benzyl)-cyclopropyl-carbamic Acid tert-butyl Ester 4-Nitrophenyl chloroformate (5.08 g, 24.4 mmol) and DIPEA (8.37 mL, 48.9 mmol) were added to a sol. of (2-chloro-5-hydroxymethyl-benzyl)-cyclopropyl-carbamic acid tert-butyl ester (3.05 g, 9.78 mmol) in $CH_3CN$ (50 mL). The mixture was stirred at 60° C. for 20 h, and was allowed to cool to rt. $MeNH_2$ (2M in THF, 49.0 mL, 98.0 mmol) was added, and the mixture was stirred at rt for 4 h. The mixture was partitioned between $CH_2Cl_2$ and water. The org. layer was washed with water and brine, dried over $MgSO_4$, filtered, and the solvents were removed under reduced pressure. Purification of the crude by FC ($CH_2Cl_2/Et_2O$ 9:1) yielded the title compound (2.67 g, 74%). LC-MS: $t_R$=1.01 min; ES+: 313.37.

Methyl-carbamic Acid 4-chloro-3-cyclopropylaminomethyl-benzyl Ester

HCl (4M in dioxane, 35 mL) was added to a sol. of (2-chloro-5-methylcarbamoyloxymethyl-benzyl)-cyclopropyl-carbamic acid tert-butyl ester (3.48 g, 9.43 mmol) in $CH_2Cl_2$ (35 mL) at 0° C. The mixture was stirred for 2 h at 0° C., and more $CH_2Cl_2$ was added. The mixture was washed with aq. 1M NaOH and brine. The org. layer was dried over $MgSO_4$, filtered, and the solvents were removed under reduced pressure to yield the crude title compound (2.48 g, 98%) that was used further without purification. LC-MS: $t_R$=0.61 min; ES+: 310.38.

[2-Chloro-5-(2-methylcarbamoyloxy-ethyl)-benzyl]-cyclopropyl-carbamic Acid tert-butyl Ester 4-Nitrophenyl chloroformate (3.25 g, 15.7 mmol) and DIPEA (7.88 mL, 46.0 mmol) were added to a sol. of [2-chloro-5-(2-hydroxy-ethyl)-benzyl]-cyclopropyl-carbamic acid tert-butyl ester (3.00 g, 9.21 mmol) in $CH_3CN$ (46 mL). The mixture was stirred at 60° C. for 20 h, and was allowed to cool to rt. $MeNH_2$ (2M in THF, 46.0 mL; 92.0 mmol) was added, and the mixture stirred at rt for 4 h. The mixture was partitioned between $CH_2Cl_2$, and water. The org. layer was washed with water and brine, dried over $MgSO_4$, filtered, and the solvents were removed under reduced pressure. Purification of the crude by FC ($CH_2Cl_2/Et_2O$ 9:1) yielded the title compound (1.76 g, 50%). LC-MS: $t_R$=1.02 min; ES+: 283.42.

Methyl-carbamic Acid 2-(4-chloro-3-cyclopropylaminomethyl-phenyl)ethyl Ester

HCl (4M in dioxane, 18 mL) was added to a sol. of [2-chloro-5-(2-methylcarbamoyloxy-ethyl)-benzyl]-cyclopropyl-carbamic acid tert-butyl ester (1.76 g, 4.60 mmol) in $CH_2Cl_2$ (18 mL) at 0° C. The mixture was stirred for 2 h at 0° C., and more $CH_2Cl_2$ was added. The mixture was washed with aq. 1M NaOH and brine. The org. layer was dried over $MgSO_4$, filtered, and the solvents were removed under reduced pressure to yield the crude title compound (1.46 g, quantitative yield) that was used further without purification. LC-MS: $t_R$=0.64 min; ES+: 283.40.

Toluene-4-sulfonic Acid 2-{3-[(tert-butoxycarbonyl-cyclopropyl-amino)-methyl]-4-chloro-phenyl}-ethyl Ester $Et_3N$ (2.56 mL, 18.4 mmol) and DMAP (153 mg, 1.23 mmol) were added to a sol. of [2-chloro-5-(2-hydroxy-ethyl)-benzyl]-cyclopropyl-carbamic acid tert-butyl ester (4.00 g, 12.3 mmol) in $CH_2Cl_2$ (110 mL) at 0° C. A sol. of p-toluene-sulfonyl chloride (2.80 g, 14.7 mmol) in $CH_2Cl_2$ (18 mL) was added dropwise, and the mixture was stirred for 3 days while warming up to rt. The mixture was partitioned between $CH_2Cl_2$ and water, and the aq. layer was extracted with $CH_2Cl_2$ (3×). The combined org. layers were washed with brine, dried over $MgSO_4$, filtered, and the solvents were removed under reduced pressure. Purification of the crude by FC (heptane/EtOAc 8:2) yielded the title compound (4.90 g, 83%). LC-MS: $t_R$=1.13 min; ES+: 480.53.

[5-(2-Azido-ethyl)-2-chloro-benzyl]-cyclopropyl-carbamic Acid tert-butyl Ester $NaN_3$ (1.17 g, 18.0 mmol) was added to a sol. of toluene-4-sulfonic acid 2-{3-[(tert-butoxycarbonyl-cyclopropyl-amino)-methyl]-4-chloro-phenyl}-ethyl ester (2.16 g, 4.50 mmol) in DMF (45 mL). The mixture was heated to 65° C., and stirred at this temperature for 1.5 h. The mixture was allowed to cool to rt, and poured onto water. The mixture was extracted with TBME (3×). The combined org. extracts were washed with brine, dried over $MgSO_4$, filtered, and the solvents were removed under reduced pressure. Purification of the crude by FC (heptane/EtOAc 95:5) yielded the title compound (1.49 g, 94%). LC-MS: $t_R$=1.11 min; ES+: 336.43.

[5-(2-Amino-ethyl)-2-chloro-benzyl]-cyclopropyl-carbamic Acid tert-butyl Ester $Me_3P$ (1M in toluene, 4.20 mL, 4.20 mmol) was added to a sol. of [5-(2-azido-ethyl)-2-chloro-benzyl]-cyclopropyl-carbamic acid tert-butyl ester (1.49 g, 4.25 mmol) in THF (13.0 mL), and the mixture was stirred at rt for 5 h. Phosphate buffer (pH 7.4, DPBS Gibco 14200, diluted 10×) was added, and the mixture was extracted with $CH_2Cl_2$ several times. The combined org. extracts were dried over $MgSO_4$, filtered, and the solvents were removed under reduced pressure. Drying the residue under high vacuum yielded the crude title compound (1.34 g, 97%) that was used further without purification. LC-MS: $t_R$=0.81 min; ES+: 325.18.

(2-{3-[(tert-Butoxycarbonyl-cyclopropyl-amino)-methyl]-4-chloro-phenyl}-ethyl)-carbamic Acid Methyl Ester Methyl chloroformate (1.72 mL, 21.9 mmol) and $K_2CO_3$ (7.65 g, 54.8 mmol) were added to a sol. of [5-(2-amino-ethyl)-2-chloro-benzyl]-cyclopropyl-carbamic acid tert-butyl ester (1.78 g, 5.48 mmol) in acetone (8.00 mL). The mixture was refluxed overnight, and was allowed to cool to rt. The mixture was partitioned between water and $CH_2Cl_2$, and the aq. layer was extracted with $CH_2Cl_2$ (3×). The combined org. extracts were dried over $MgSO_4$, filtered, and the solvents were removed under reduced pressure. Purification of the crude by FC (heptane/EtOAc 6:4) yielded the title compound (1.41 g, 67%). LC-MS: $t_R$=1.03 min; ES+: 383.50.

[2-(4-Chloro-3-cyclopropylaminomethyl-phenyl) ethyl]-carbamic Acid Methyl Ester

HCl (4M in dioxane, 17 mL) was added to a sol. of (2-{3-[(tert-butoxycarbonyl-cyclopropyl-amino)-methyl]-4-chloro-phenyl}-ethyl)-carbamic acid methyl ester (1.73 g, 4.52 mmol) in $CH_2Cl_2$ (17 mL) at 0° C. The mixture was stirred at 0° C. for 2.5 h, and was washed with aq. 1M NaOH. The aq. layer was extracted back with $CH_2Cl_2$. The combined org. extracts were washed with brine, dried over $MgSO_4$, filtered, and the solvents were removed under reduced pressure. Drying the residue under high vacuum yielded the crude title compound (1.27 g, 99%) that was used further without purification. LC-MS: $t_R$=0.64 min; ES+: 283.41.

[3-(tert-Butyl-dimethyl-silanyloxymethyl)-4-chloro-benzyl]-(2,2-difluoro-ethyl)-carbamic Acid tert-butyl Ester 2,2-Difluoro-ethylamine hydrochloride (1.70 g, 14.4 mmol) and DIPEA (2.47 mL, 14.4 mmol) were added to a sol. of 3-(tert-butyl-dimethyl-silanyloxymethyl)-4-chloro-benzaldehyde (2.74 g, 9.62 mmol) in MeOH (80 mL). The mixture was heated to reflux for 5 h, and was allowed to cool to rt. NaBH$_4$ (546 mg, 14.4 mmol) was added in portions, and the mixture was stirred for 2 h at rt. The solvents were removed under reduced pressure, and the residue was taken in EtOAc. The mixture was washed with aq. sat. NaHCO$_3$ and brine. The org. layer was dried over MgSO$_4$, filtered, and the solvents were removed under reduced pressure. The residue was dissolved in CH$_2$Cl$_2$ (53 mL), and DIPEA (4.94 mL, 28.9 mmol) and Boc$_2$O (3.15 g, 14.4 mmol) were added. The mixture was stirred for 1 h at rt, and was washed with aq. 1M HCl, aq. sat. NaHCO$_3$ and brine. The org. layer was dried over MgSO$_4$, filtered, and the solvents were removed under reduced pressure to yield the crude title compound (4.35 g, quantitative yield) that was used further without purification. LC-MS: $t_R$=1.25 min; ES+: 394.08.

(4-Chloro-3-hydroxymethyl-benzyl)-(2,2-difluoro-ethyl)-carbamic Acid tert-butyl Ester

[3-(tert-Butyl-dimethyl-silanyloxymethyl)-4-chloro-benzyl]-(2,2-difluoro-ethyl)-carbamic acid tert-butyl ester (4.35 g, 9.67 mmol) was suspended in MeOH (100 mL), and aq. 1M NaOH (50 mL) was added. The mixture was heated to reflux for 3 h, and the solvents were partially removed under reduced pressure. The aq. residue was diluted with water (100 mL), and the mixture was extracted with EtOAc (3×). The combined org. extracts were washed with brine, dried over MgSO$_4$, filtered, and the solvents were removed under reduced pressure. Purification of the crude by FC (EtOAc/heptane 2:8→3:7) yielded the title compound (2.70 g, 83%). LC-MS: $t_R$=0.99 min; ES+: 302.96.

(4-Chloro-3-formyl-benzyl)(2,2-difluoro-ethyl)-carbamic Acid tert-butyl Ester

MnO$_2$ (3.89 g, 40.2 mmol) was added to a sol. of (4-chloro-3-hydroxymethyl-benzyl)-(2,2-difluoro-ethyl)-carbamic acid tert-butyl ester (2.71 g, 18.2 mmol) in CH$_3$CN (85 mL) at rt. The mixture was stirred at rt for 4 h, and MnO$_2$ (2.71 g, 18.2 mmol) was added again. The mixture was stirred overnight. The mixture was filtered over Celite, and the precipitate was washed with CH$_3$CN and CH$_2$Cl$_2$. The filtrate was evaporated under reduced pressure to yield the crude title compound (2.80 g, quantitative yield) that was used further without purification. LC-MS: $t_R$=1.03 min; ES+: not visible.

(4-Chloro-3-cyclopropylaminomethyl-benzyl)-(2,2-difluoro-ethyl)-carbamic Acid tert-butyl Ester (4-Chloro-3-formyl-benzyl)-(2,2-difluoro-ethyl)-carbamic acid tert-butyl ester (563 mg, 1.69 mmol) was dissolved in MeOH (18 mL). Cyclopropylamine (0.181 mL, 2.53 mmol) was added, and the mixture was heated to reflux for 4 h. The mixture was allowed to cool to rt, and NaBH$_4$ (96 mg, 95.7 mg, 2.53 mmol) was added in portions. The mixture was stirred for 1 h, and the solvents were removed under reduced pressure. The residue was taken in EtOAc, and the mixture was washed with aq. sat. NaHCO$_3$ (1×) and brine (1×). The org. layer was dried over MgSO$_4$, filtered, and the solvents were removed under reduced pressure. Purification of the crude by FC(CH$_2$Cl$_2$/MeOH 95:5) yielded the title compound (558 mg, 88%). LC-MS: $t_R$=0.76 min; ES+: 375.15.

(S)-(4-Bromo-phenyl)-pyrrolidin-3-ol

A mixture of 1-bromo-4-iodo-benzene (50.0 g, 177 mmol), (S)-pyrrolidin-3-ol (28.6 mL, 353 mmol), CuI (6.73 g, 35.3 mmol) and K$_3$PO$_4$.H$_2$O (81.4 g, 353 mmol) in N,N-dimethylaminoethanol (177 mL) was stirred at 55° C. for 60 h. The mixture was allowed to cool to rt, and water was added. The mixture was extracted several times with CH$_2$Cl$_2$. The combined org. extracts were washed with a 1:1 mixture of aq. conc. NH$_3$ and water. The NH$_3$-containing aq. layer was extracted with CH$_2$Cl$_2$. The combined org. extracts were dried over MgSO$_4$, filtered, and the solvents were removed under reduced pressure. Crystallization of the crude from EtOAc/heptane yielded the title compound (36.1 g, 84%).

(S)-1-(4-Bromo-phenyl)-3-(tert-butyl-dimethyl-silanyloxy)-pyrrolidine (S)-1-(4-Bromo-phenyl)-pyrrolidin-3-ol (14.0 g, 57.7 mmol) was dissolved in DMF (100 mL), and TBDMS-Cl (10.4 g, 69.2 mmol) and imidazole (9.81 g, 144 mmol) were added. The mixture was stirred at rt overnight. Aq. sat. NH$_4$Cl (100 mL) was added, and the mixture was extracted with heptane (2×). The combined org. extracts were dried over MgSO$_4$, filtered, and the solvents were removed under reduced pressure. Purification of the residue by FC (EtOAc/heptane 1:15→1:4) yielded the title compound (17.3 g, 84%).

(R)-5-Bromo-2-[3-(2,6-dichloro-4-methyl-phenoxy)-pyrrolidin-1-yl]-pyridine

ADDP (11.7 g, 45.4 mmol) was added to a sol. of compound G1 (8.82 g, 36.3 mmol) and 2,6-dichloro-p-cresol (7.37 g, 40.0 mmol) in toluene (200 mL). The mixture was degassed with nitrogen for 5 min, and PBu$_3$ (85%, 15.8 mL, 46.2 mmol) was added. The mixture was heated rapidly to 100° C., and stirred at this temperature for 2 h. The mixture was allowed to cool to rt, and was diluted with heptane (200 mL). The mixture was filtered, and the filtrate was evaporated under reduced pressure. Purification of the residue by FC (EtOAc/heptane 1:7) yielded a crude title compound that was diluted with CH$_2$Cl$_2$. This mixture was washed with aq. 1M NaOH. The org. layer was dried over MgSO$_4$, filtered, and the solvents were removed under reduced pressure. Drying the residue under high vacuum yielded the pure title compound (13.5 g, 93%). LC-MS: $t_R$=0.92 min; ES+: 402.98.

(S5-Bromo-2-[3-(2,6-dichloro-4-methyl-phenoxy)-pyrrolidin-1-yl]-pyridine

ADDP (11.4 g, 44.2 mmol) was added to a sol. of compound G3 (8.61 g, 35.4 mmol) and 2,6-dichloro-p-cresol (7.19 g, 39.0 mmol) in toluene (200 mL). The mixture was degassed with nitrogen for 5 min, and PBu$_3$ (85%, 15.4 mL, 45.0 mmol) was added. The mixture was heated rapidly to 100° C., and stirred at this temperature for 2 h. The mixture was allowed to cool to rt, and was diluted with heptane (200 mL). The mixture was filtered, and the filtrate was evaporated under reduced pressure. Purification of the residue by FC (EtOAc/heptane 1:7) yielded a crude title compound that was diluted with $CH_2Cl_2$. This mixture was washed with aq. 1M NaOH. The org. layer was dried over $MgSO_4$, filtered, and the solvents were removed under reduced pressure. Drying the residue under high vacuum yielded the pure title compound (13.4 g, 94%). LC-MS: $t_R$=0.93 min; ES+: 402.97.

3-Oxo-8-aza-bicyclo[3.2.1]octane-8-carboxylic Acid tert-butyl Ester

A mixture of 8-methyl-8-aza-bicyclo[3.2.1]octan-3-one (50.5 g, 359 mmol) and 1-chloroethyl chloroformate (117 mL, 1.08 mol) in $CH_2ClCH_2Cl$ (500 mL) was heated to 80° C. for 5 h. The mixture was allowed to cool to rt, and the solvents were removed under reduced pressure. The residue was dried under high vacuum for 3 h, and was added in portions to MeOH (250 mL) over 30 min. The mixture was stirred at 75° C. for 1 h, and allowed to cool to rt. The solvents were removed under reduced pressure. The residue was diluted with $Et_2O$ (250 mL), and the mixture was sonicated for 15 min. The mixture was then stirred for 30 min, and filtered. The precipitate was washed with $Et_2O$ (125 mL), and dried under high vacuum. The residue was diluted with dioxane (400 mL), and the mixture was cooled to 0° C. Aq. 1M NaOH (400 mL) was added. $Boc_2O$ (82.3 g, 377 mmol) was added, and the mixture was stirred overnight while warming up to rt. The mixture was extracted with $Et_2O$ (2×). The combined org. extracts were dried over $MgSO_4$, filtered, and the solvents were removed under reduced pressure. Purification of the crude by FC (EtOAc/heptane 3:7) yielded the title compound (59.0 g, 73%). LC-MS: $t_R$=0.83 min.

(rac.)-(1R*,5S*)-3-Hydroxy-8-aza-bicyclo[3.2.1]oct-2-ene-2,8-dicarboxylic Acid 8-tert-butyl Ester 2-methyl Ester To a suspension of NaH (55-65% mineral oil, 9.82 g, about 225 mmol) in cyclohexane (87.5 mL) was added dimethyl carbonate (21.0 mL, 250 mmol). The mixture was heated to reflux, and a sol. of 3-oxo-8-aza-bicyclo[3.2.1]octane-8-carboxylic acid tert-butyl ester (25.6 g, 113 mmol) in MeOH (0.25 mL) and cyclohexane (62.5 mL) was added over 35 min. The mixture was heated to reflux for 3 h, and was cooled to 0° C. Aq. sat. $NH_4Cl$ was added carefully until the phases separated. The org. layer was extracted with $CH_2Cl_2$ several times. The combined org. extracts were washed with brine, dried over $MgSO_4$, filtered, and the solvents were removed under reduced pressure. Purification of the residue by FC (EtOAc/heptane 3:7) yielded the title compound (29.7 g, 93%). LC-MS: $t_R$=0.96 min.

(rac.)-(1R*,5S*)-3-Trifluoromethanesulfonyloxy-8-aza-bicyclo[3.2.1]oct-2-ene-2,8-dicarboxylic Acid 8-tert-butyl Ester 2-methyl Ester (A1)

NaH (55-65% suspension in oil, 6.69 g, about 153 mmol) was added over 35 min to a sol. of (rac.)-(1R*,5S*)-3-hydroxy-8-aza-bicyclo[3.2.1]oct-2-ene-2,8-dicarboxylic acid 8-tert-butyl ester 2-methyl ester (34.7 g, 123 mmol) in THF (600 mL) at 0° C. The mixture was stirred for 75 min, and $PhN(Tf)_2$ (52.5 g, 147 mmol) was added. The mixture was stirred overnight while warming up to rt. The mixture was poured onto ice-water. The solvents were partially removed under reduced pressure, and the residue was extracted with EtOAc several times. The combined org. extracts were washed with water, with brine, were dried over $MgSO_4$, filtered, and the solvents were removed under reduced pressure.

Purification of the residue by FC (EtOAc/heptane 2:8) yielded the title compound (52.0 g, quantitative yield). LC-MS: $t_R$=1.07 min.

4-Trifluoromethanesulfonyloxy-5,6-dihydro-2H-pyridine-1,3-dicarboxylic Acid 1-tert-butyl Ester 3-ethyl Ester (A2)

4-Oxo-piperidine-1,3-dicarboxylic acid 1-tert-butyl ester 3-ethyl ester (30.9 g, 114 mmol) was dissolved in $CH_2Cl_2$ (800 mL). DIPEA (48.7 mL, 285 mmol) was added, and the reaction mixture was cooled to −78° C. A sol. of $Tf_2O$ (24.4 mL, 148 mmol) in $CH_2Cl_2$ (25 mL) was added slowly, while maintaining the temperature at −78° C. The mixture was stirred for 30 min at −78° C. The mixture was allowed to warm to rt, and aq. 10% $Na_2CO_3$ (400 mL) and ice were added. The layers were separated and the aq. layer was extracted with $CH_2Cl_2$ (2×). The combined org. layers were dried over $MgSO_4$, filtered, and the solvents were removed under reduced pressure. Purification of the residue by FC (heptane→EtOAc/heptane 25:75) yielded the title compound (44.0 g, 91%). LC-MS: $t_R$=1.05 min; ES+: 404.44.

4-[4-(tert-Butyl-dimethyl-silanyloxy)-phenyl]-5,6-dihydro-2H-pyridine-1,3-dicarboxylic Acid 1-tert-butyl Ester 3-methyl Ester (B1)

BuLi (1.6M in hexanes, 27.0 mL, 43.1 mmol) was added to a sol. of (4-bromophenoxy)-tert-butyldimethylsilane (12.4 g, 43.1 mmol) in THF (300 mL) at −78° C. The mixture was stirred for 30 min at −78° C., and $ZnCl_2$ (1M in THF, 52.4 mL, 52.4 mmol) was added. The mixture was allowed to warm to rt, and a sol. of 4-trifluoromethanesulfonyloxy-5,6-dihydro-2H-pyridine-1,3-dicarboxylic acid 1-tert-butyl ester 3-methyl ester (WO 2004/002957; 12.0 g, 30.8 mmol) in THF (20 mL) and $Pd(PPh_3)_4$ (1.00 g, 0.863 mmol) were added. The mixture was stirred at rt overnight, and aq. sat. $NH_4Cl$ was added. The mixture was extracted with EtOAc. The combined org. extracts were dried over $MgSO_4$, filtered, and the solvents were removed under reduced pressure. Purification of the crude by FC (EtOAc/heptane 1:9→1:1) yielded the title compound (13.3 g, 96%). LC-MS: $t_R$=1.20 min; ES+: 448.35.

4-(4-Hydroxy-phenyl)-5,6-dihydro-2H-pyridine-1,3-dicarboxylic Acid 1-tert-butyl Ester 3-methyl Ester (B2)

TBAF (9.50 g, 30 mmol) was added to a sol. of compound B1 (13.4 g, 30 mmol) in THF (100 mL) at 0° C. The mixture was stirred at 0° C. for 1 h. $CH_2Cl_2$ was added, and the mixture was washed with aq. sat. $NH_4Cl$, water, and brine. The org. layer was dried over $MgSO_4$, filtered, and the solvents were removed under reduced pressure. Drying the residue under high vacuum yielded the crude title compound (10.0 g, quantitative yield) that was used further without purification. LC-MS: $t_R$=0.92 min; ES+: 334.23.

4-(4-Benzyloxy-phenyl)-5,6-dihydro-2H-pyridine-1,3-dicarboxylic Acid 1-tert-butyl Ester 3-methyl Ester (B3)

To a sol. of 4-benzoxy-bromo-benzene (18.4 g, 70.0 mmol) in THF (450 mL) at −78° C. was added BuLi (1.6M in hexane, 50.0 mL, 80.0 mmol). The mixture was stirred for 30 min at −78° C., and $ZnCl_2$ (1M in THF, 86 mL, 86 mmol) was added. The mixture was allowed to warm up to rt. A sol. of 4-trifluoromethanesulfonyloxy-5,6-dihydro-2H-pyridine-1,3-dicarboxylic acid 1-tert-butyl ester 3-methyl ester (WO 2004/002957; 19.5 g, 50.0 mmol) in THF (20 mL) and Pd(PPh$_3$)$_4$ (1.43 g, 1.23 mmol) were added. The mixture was quickly heated to 50° C., and stirred at this temperature for 40 min. Aq. sat. NH$_4$Cl was added, and the mixture was extracted with EtOAc (3×). The combined org. extracts were washed with brine, dried over Na$_2$SO$_4$, filtered, and the solvents were removed under reduced pressure. Purification of the residue by FC (EtOAc/heptane 1:9→2:8) yielded the title compound (20.8 g, 98%). LC-MS: t$_R$=1.12 min; ES+: 424.25.

(rac.)-(1R*,5S*)-3-(4-Hydroxy-phenyl)-8-aza-bicyclo[3.2.1]oct-2-ene-2,8-dicarboxylic Acid 8-tert-butyl Ester 2-methyl Ester (B4)

Aq. 2M Na$_2$CO$_3$ (90.0 mL) was added to a mixture of compound A1 (10.1 g, 24.4 mmol) and 4-hydroxybenzeneboronic acid (3.37 g, 24.4 mmol) in DME (180 mL). The mixture was degassed with N$_2$ for 3 min, and Pd(PPh$_3$)$_4$ (1.42 g, 1.23 mmol) was added. The mixture was heated quickly to 80° C., and stirred at this temperature for 1 h. The mixture was allowed to cool to rt, and was partitioned between EtOAc (250 mL) and water (250 mL). The org. phase was washed with water. The combined aq. layers were extracted with EtOAc. The combined org. extracts were dried over MgSO$_4$, filtered, and the solvents were removed under reduced pressure. Purification of the crude by FC (EtOAc/heptane 1:1) yielded the title compound (7.27 g, 83%). LC-MS: t$_R$=0.94 min; ES+: 360.29.

(rac.)-(1R*,5S*)-7-[4-(tert-Butyl-dimethyl-silanyloxy)-phenyl]-9-methyl-3,9-diaza-bicyclo[3.3.1]non-7-ene-3,6-dicarboxylic Acid 3-tert-butyl Ester 6-ethyl Ester (B9)

BuLi (1.6M in hexane, 31.9 mL, 51.0 mmol) was added to a sol. of (4-bromo-phenoxy)-tert-butyl-dimethyl-silane (12.8 g, 44.5 mmol) in THF (150 mL) at −78° C. The mixture was stirred for 60 min at −78° C., and ZnCl$_2$ (1.1M, 50.5 mL, 55.6 mmol) was added. The mixture was allowed to warm to rt, and a sol. of (rac.)-(1R*,5S*)-9-methyl-7-trifluoromethanesulfonyloxy-3,9-diaza-bicyclo[3.3.1]non-6-ene-3,6-dicarboxylic acid 3-tert-butyl ester 6-ethyl ester (WO 2003/093267; 17.0 g, 37.1 mmol) in THF (10 mL) and Pd(PPh$_3$)$_4$ (1.07 g, 0.927 mmol) were added. The mixture was stirred at 50° C. for 25 min, and was allowed to cool to rt. Aq. sat. NH$_4$Cl was added, and the mixture was extracted with EtOAc (3×). The combined org. extracts were dried over Na$_2$SO$_4$, filtered, and the solvents were removed under reduced pressure. Purification of the residue by FC (EtOAc/heptane 6:4) yielded the title compound (15.9 g, 83%). LC-MS: t$_R$=0.95 min, ES+: 517.25.

(rac.)-(1R*,5S*)-7-[4-(tert-Butyl-dimethyl-silanyloxy)-phenyl]-3,9-diaza-bicyclo[3.3.1]non-6-ene-3,6,9-tricarboxylic Acid 3-tert-butyl Ester 6-ethyl Ester 9-(2,2,2-trichloro-1,1-dimethyl-ethyl) Ester (B10)

A mixture of compound B9 (6.16 g, 11.9 mmol) and 2,2,2-trichloro-1,1-dimethylethyl chloroformate (3.15 g, 13.1 mmol) in 1,2-dichloroethane (200 mL) was heated to 60° C. for 20 h. The mixture was allowed to cool to rt, and the solvents were removed under reduced pressure. Purification of the residue by FC (EtOAc/heptane 8:2) yielded the title compound (7.58 g, 90%). LC-MS: t$_R$=1.29 min, ES+: 707.36.

(rac.)-(1R*,5S*)-7-(4-Hydroxy-phenyl)-3,9-diaza-bicyclo[3.3.1]non-6-ene-3,6,9-tricarboxylic Acid 3-tert-butyl Ester 6-ethyl Ester 9-(2,2,2-trichloro-1,1-dimethyl-ethyl) Ester (B11)

Compound B10 (7.58 g, 10.7 mmol) was dissolved in MeOH (110 mL) and p-TsOH (2.03 g, 11.8 mmol) was added. The mixture was stirred at rt for 2 h, and aq. 10% Na$_2$CO$_3$ (200 mL) was added. The solvents were partially removed under reduced pressure, and the resulting suspension was extracted with EtOAc. The org. extracts were filtered and washed with aq. 10% Na$_2$CO$_3$ and brine. The org. layer was dried over Na$_2$SO$_4$, filtered, and the solvents were removed under reduced pressure. Purification of the crude by FC (EtOAc/heptane) yielded the title compound (2.10 g, 33%). LC-MS: t$_R$=1.09 min, ES+: 593.25.

(rac.)-(1R*,5S*)-3-(6-Bromo-pyridin-3-yl)-8-aza-bicyclo[3.2.1]oct-2-ene-2,8-dicarboxylic Acid 8-tert-butyl Ester 2-methyl Ester (B12)

6-Bromopyridine-3-boronic acid (5.00 g, 24.8 mmol), Pd(OAc)$_2$ (278 mg, 1.24 mmol) and PPh$_3$ (650 mg, 2.48 mmol) were suspended in EtOH (67 mL). A sol. of Na$_2$CO$_3$ (3.15 g, 29.7 mmol) in water (25.3 mL) was added. A sol. of compound A1 (10.3 g, 24.8 mmol) in THF (25 mL) was added, and the mixture was heated to reflux for 4 h. 6-Bromopyridine-3-boronic acid (5.00 g, 24.8 mmol) was added again, and 1 h later Pd(OAc)$_2$ (278 mg, 1.24 mmol) and PPh$_3$ (650 mg, 2.48 mmol) and Na$_2$CO$_3$ (3.15 g, 29.7 mmol) were added. The mixture was stirred at reflux for 1 h, and was allowed to cool to rt. The solvents were removed under reduced pressure. EtOAc was added, and the mixture was washed with aq. sat. NaHCO$_3$ (2×), with aq. sat. NH$_4$Cl, and with brine. The org. layer was dried over Na$_2$SO$_4$, filtered, and the solvents were removed under reduced pressure. Purification of the crude by FC (EtOAc/heptane 20:80) yielded the title compound (4.24 g, 40%). LC-MS: t$_R$=1.01 min, ES+: 423.19.

Mixture of (1R,5S)-3-{4-[(S)-3-(tert-butyl-dimethyl-silanyloxy)-pyrrolidin-1-yl]-phenyl}-8-aza-bicyclo[3.2.1]oct-2-ene-2,8-dicarboxylic Acid 8-tert-butyl Ester 2-methyl Ester and (1S,5R)-3-{4-[(S)-3-(tert-butyl-dimethyl-silanyloxy)-pyrrolidin-1-yl]-phenyl}-8-aza-bicyclo[3.2.1]oct-2-ene-2,8-dicarboxylic Acid 8-tert-butyl Ester 2-methyl Ester (B13)

BuLi (1.6M in hexane, 30.5 mL, 48.8 mmol) was added over 20 min to a sol. of (S)-1-(4-bromo-phenyl)-3-(tert-butyl-dimethyl-silanyloxy)-pyrrolidine (8.40 g, 23.6 mmol) in THF (350 mL) at −78° C. The mixture was stirred for 1.75 h at −78° C., and BuLi (7.85 mL, 12.7 mmol) was added again. The mixture was stirred for 15 min at −78° C., and ZnCl$_2$ (1M in THF, 53.6 mL, 53.6 mmol) was added. The mixture was allowed to warm up to rt, and a sol. of compound A1 (6.53 g, 15.7 mmol) in THF (20 mL), and Pd(PPh$_3$)$_4$ (451 mg, 0.390 mmol) were added. The mixture was rapidly heated to 45° C., and was stirred at this temperature for 45 min. The mixture was allowed to cool to rt, and aq. sat. NH$_4$Cl (200 mL) was added. The layers were separated, and the aq. layer was extracted with CH$_2$Cl$_2$ (2×). The combined org. extracts were dried over MgSO$_4$, filtered, and the solvents were removed under reduced pressure. Purification of the residue by FC (EtOAc/heptane 2:8) yielded the title compounds mixture (7.17 g, 84%). LC-MS: $t_R$=1.24 min, ES+: 543.26.

Mixture of (1R,5S)-3-[4-((S)-3-hydroxy-pyrrolidin-1-yl)-phenyl]-8-aza-bicyclo[3.2.1]oct-2-ene-2,8-dicarboxylic Acid 8-tert-butyl Ester 2-methyl Ester and (1S,5R)-3-[4-((S)-3-hydroxy-pyrrolidin-1-yl)-phenyl]-8-aza-bicyclo[3.2.1]oct-2-ene-2,8-dicarboxylic Acid 8-tert-butyl Ester 2-methyl Ester (B14)

TBAF (4.87 g, 15.5 mmol) was added to a sol. of compounds B13 (7.22 g, 13.3 mmol) in THF (75 mL) at 0° C. The mixture was stirred overnight while warming up to rt. EtOAc (185 mL) was added, and the mixture was washed with brine (4×). The org. layer was dried over MgSO$_4$, filtered, and the solvents were removed under reduced pressure. Purification of the crude by FC (MeOH/CH$_2$Cl$_2$ with 1% Et$_3$N) yielded the title compounds mixture (5.51 g, 97%). LC-MS: $t_R$=0.96 min, ES+: 429.32.

Mixture of (1R,5S)-7-{6-[(S)-3-(tert-butyl-dimethyl-silanyloxy)-pyrrolidin-1-yl]-pyridin-3-yl}-9-methyl-3,9-diaza-bicyclo[3.3.1]non-6-ene-3,6-dicarboxylic Acid 3-tert-butyl Ester 6-ethyl Ester and (1S,5R)-7-{6-[(S)-3-(tert-butyl-dimethyl-silanyloxy)-pyrrolidin-1-yl]-pyridin-3-yl}-9-methyl-3,9-diaza-bicyclo[3.3.1]non-6-ene-3,6-dicarboxylic Acid 3-tert-butyl Ester 6-ethyl Ester (B15)

BuLi (1.6M in hexane, 20.6 mL, 33.2 mmol) was added to a sol. of compound G2 (9.30 g, 26.0 mmol) in THF (300 ml) at −78° C. The mixture was stirred for 60 min at −78° C., and ZnCl$_2$ (1M in THF, 41.4 mL, 41.4 mmol) was added. The mixture was allowed to warm up to rt, and was stirred at this temperature for 30 min. A sol. of (rac.)-(1R*,5S*)-9-methyl-7-trifluoromethanesulfonyloxy-3,9-diaza-bicyclo[3.3.1]non-6-ene-3,6-dicarboxylic acid 3-tert-butyl ester 6-ethyl ester (WO 2003/093267; 9.50 g, 20.7 mmol) in THF (50 mL) and Pd(PPh$_3$)$_4$ (578 mg, 0.500 mmol) in THF (10 mL) were added, and the reaction mixture was heated to 70° C. for 2 h. The mixture was allowed to cool to rt, and was quenched with aq. sat. NH$_4$Cl. The mixture was extracted with EtOAc (3×). The combined org. extracts were dried over MgSO$_4$, filtered, and the solvents were removed under reduced pressure. Purification of the residue by FC (heptane/EtOAc 5:1→3:1→1:1→1:3→EtOAc/MeOH 49:1) yielded the title compounds mixture (12.1 g, 99%). LC-MS: $t_R$=0.81 min, ES+: 587.56.

Mixture of (1R,5S)-7-[6-((S)-3-hydroxy-pyrrolidin-1-yl)-pyridin-3-yl]-3,9-diaza-bicyclo[3.3.1]non-6-ene-3,6,9-tricarboxylic Acid 3,9-di-tert-butyl Ester 6-ethyl Ester and (1S,5R)-7-[6-((S)-3-hydroxy-pyrrolidin-1-yl)-pyridin-3-yl]-3,9-diaza-bicyclo[3.3.1]non-6-ene-3,6,9-tricarboxylic Acid 3,9-di-tert-butyl Ester 6-ethyl Ester (B16)

To a sol. of the compounds B15 (12.0 g, 20.5 mmol) in CH$_2$ClCH$_2$Cl (250 mL) was added NaHCO$_3$ (17.2 g, 204 mmol) and 1-chloroethyl chloroformate (22.3 mL, 204 mmol). The mixture was heated to reflux overnight, and was allowed to cool to rt. The mixture was filtered, and the filtrate was thoroughly evaporated under reduced pressure. The residue was dried under high vacuum for 1 h, and was dissolved in MeOH (200 mL). The mixture was stirred at 60° C. for 3 h, and the solvents were removed under reduced pressure. The residue was dried under high vacuum for 5 h. The residue was dissolved in CH$_2$Cl$_2$ (250 mL), and was cooled to 0° C. DIPEA (21.0 mL, 122 mmol) and Boc$_2$O (13.4 g, 61.3 mmol) were added. The mixture was stirred at 0° C. for 30 min, and at rt overnight. The mixture was diluted with CH$_2$Cl$_2$, and was washed with aq. 1M HCl and aq. sat. NaHCO$_3$. The org. layer was dried over MgSO$_4$, filtered, and the solvents were removed under reduced pressure. Purification of the residue by FC(CH$_2$Cl$_2$/MeOH 99:1→98:2→97:3→96:4→95:5) yielded the title compounds mixture (7.31 g, 64%). LC-MS: $t_R$=0.82 min, ES+: 559.43.

(S)-6-[3-(tert-Butyl-dimethyl-silanyloxy)-pyrrolidin-1-yl]-5',6'-dihydro-2'H-[3,4']bipyridinyl-1',3'-dicarboxylic Acid 1'-tert-butyl Ester 3'-methyl Ester (B17)

BuLi (1.6M in hexane, 32.8 mL, 52.4 mmol) was added to a sol. of compound G2 (13.2 g, 37.0 mmol) in THF (300 mL) at −78° C. The mixture was stirred at −78° C. for 1 h, and ZnCl$_2$ (1M in THF, 61.6 mL, 61.6 mmol) was added. The mixture was allowed to warm to rt, and 4-trifluoromethanesulfonyloxy-5,6-dihydro-2H-pyridine-1,3-dicarboxylic acid 1-tert-butyl ester 3-methyl ester (WO 2004/002957; 12.0 g, 30.8 mmol) in THF (20 mL) and Pd(PPh$_3$)$_4$ (887 mg, 0.768 mmol) were added. The mixture was rapidly heated to 70° C., and stirred at this temperature for 90 min. The mixture was allowed to cool to rt, and aq. sat. NH$_4$Cl was added. The mixture was extracted with EtOAc. The org. extracts were washed with aq. sat. NH$_4$Cl, dried over MgSO$_4$, filtered, and the solvents were removed under reduced pressure. Purification of the crude by FC (heptane/EtOAc 9:1 with 1% Et$_3$N→heptane/EtOAc 5:5 with 1% Et$_3$N) yielded the title compound (27.3 g, 89%). LC-MS: $t_R$=0.97 min, ES+: 518.50.

(rac.)-(1R*,5S*)-3-(4-Hydroxy-phenyl)-8-aza-bicyclo[3.2.1]oct-2-ene-2,8-dicarboxylic Acid 8-tert-butyl Ester 2-methyl Ester (B18)

To a sol. of compound A1 (10.0 g, 24.1 mmol) and 4-hydroxybenzeneboronic acid (3.42 g, 24.1 mmol) in DME (171 mL) was added aq. 2 M Na$_2$CO$_3$ (86 mL). The mixture was stirred at rt for a few minutes, and Pd(PPh$_3$)$_4$ (1.39 g, 1.20 mmol) was added. The mixture was heated rapidly to 80° C., and stirred at this temperature for 60 min. The mixture was partitioned between EtOAc and water, and the aq. layer was extracted with EtOAc. The combined org. extracts were dried over MgSO$_4$, filtered, and the solvents were removed under reduced pressure. Purification of the crude by FC (heptane/EtOAc 6:4) yielded the title compound (7.70 g, 89%). LC-MS: $t_R$=0.95 min, ES+: 360.18.

(rac.)-(1R*,5S*)-3-(4-Benzyloxy-phenyl)-8-aza-bicyclo[3.2.1]oct-2-ene-2,8-dicarboxylic Acid 8-tert-butyl Ester 2-methyl Ester (B19)

To a sol. of compound B18 (7.70 g, 21.4 mmol) in CH$_3$CN (54 mL) was added K$_2$CO$_3$ (2.96 g, 21.4 mmol), followed by LiBr (cat. amount). The mixture was refluxed for 60 min, and a sol. of benzyl bromide (2.55 mL, 21.4 mmol) in CH$_3$CN (54 mL) was added dropwise. The mixture was refluxed for 3 h. The mixture was allowed to cool to rt, and the solvents were removed under reduced pressure. CH$_2$Cl$_2$ was added, the mixture was washed with aq. sat. NH$_4$Cl. The aq. layer was extracted back with CH$_2$Cl$_2$ (3×). The combined org. extracts were washed with brine, dried over MgSO$_4$, filtered, and the solvents were removed under reduced pressure. Purification of the crude by FC (heptane/EtOAc 7:3) yielded the title compound (9.36 g, 97%). LC-MS: $t_R$=1.13 min, ES+: 450.17.

(rac.)-(1R*,5S*)-3-{4-[2-(2,6-Dichloro-4-methyl-phenoxy)-ethoxy]-phenyl}-8-methyl-8-aza-bicyclo[3.2.1]oct-2-ene-2-carboxylic Acid Methyl Ester (C1)

1-[2-(4-Bromo-phenoxy)-ethoxy]-2,6-dichloro-4-methyl-benzene (10.5 g, 28.0 mmol) was dissolved in THF (90 mL), and the sol. was cooled to −78° C. BuLi (1.6M in hexane, 18.2 mL, 29.1 mmol) was added, and the sol. was stirred at −78° C. for 1 h. $ZnCl_2$ (1M in THF, 30.8 mL, 30.8 mmol) was added, and the mixture was allowed to warm to rt. A sol. of (rac.)-(1R*,5S*)-8-methyl-3-trifluoromethanesulfonyloxy-8-aza-bicyclo[3.2.1]oct-2-ene-2-carboxylic acid methyl ester (WO 2004/096799; 4.60 g, 14.0 mmol) in THF (10 mL), and then $Pd(PPh_3)_4$ (324 mg, 0.280 mmol) were added. The mixture was heated rapidly to 55° C., and stirred at this temperature for 30 min. The mixture was cooled to 0° C., and EtOAc (250 mL) was added. This mixture was washed with cold aq. 1M NaOH (1×), and brine. The org. layer was dried over $MgSO_4$, filtered, and the solvents were removed under reduced pressure. Purification of the crude by FC ($MeOH/CH_2Cl_2$ 5:95) yielded the title compound (5.77 g, 87%). LC-MS: $t_R$=0.86 min; ES+: 476.26.

(rac.)-(1R*,5S*)-3-{4-[2-(2,6-Dichloro-4-methyl-phenoxy)-ethoxy]-phenyl}-8-aza-bicyclo[3.2.1]oct-2-ene-2,8-dicarboxylic Acid 8-tert-butyl Ester 2-methyl Ester (C2)

$NaHCO_3$ (4.65 g, 55.3 mmol) and 1-chloroethyl chloroformate (6.03 mL, 55.3 mmol) were added to a sol. of compound C1 (5.27 g, 11.1 mmol) in $CH_2ClCH_2Cl$ (100 mL). The mixture was heated to reflux for 4 h, and allowed to cool to rt. The mixture was filtered, the precipitate washed with $CH_2ClCH_2Cl$, and the filtrate was evaporated under reduced pressure. The residue was dried under high vacuum overnight, and dissolved in MeOH (100 mL). The mixture was rapidly heated to 50° C., and stirred at this temperature for 20 min. The solvents were removed under reduced pressure, and the residue was dried under high vacuum. The residue was dissolved in $CH_2Cl_2$ (100 mL), and DIPEA (9.47 mL, 55.3 mmol) was added. The mixture was cooled to 0° C., and $Boc_2O$ (3.62 g, 16.6 mmol) was added. The mixture was stirred at 0° C. for 2 h, and diluted with $CH_2Cl_2$. This mixture was washed with aq. 1M HCl (2×) and aq. sat. $NaHCO_3$ (1×). The org. layer was dried over $MgSO_4$, filtered, and the solvents were removed under reduced pressure. Purification by FC (EtOAc/heptane 1:8→1:4→1:1→EtOAc) yielded the title compound (3.56 g, 57%). LC-MS: $t_R$=1.19 min; ES+: 562.34.

4-{4-[2-(2,6-Dichloro-4-methyl-phenoxy)-ethoxy]-phenyl}-5,6-dihydro-2H-pyridine-1,3-dicarboxylic Acid 1-tert-butyl Ester 3-methyl Ester (C3)

1-[2-(4-Bromo-phenoxy)-ethoxy]-2,6-dichloro-4-methyl-benzene (16.6 g, 44.2 mmol) was dissolved in THF (150 mL), and the sol. was cooled to −78° C. BuLi (1.6M in hexane, 31.4 mL, 50.3 mmol) was added, and the mixture was stirred at −78° C. for 30 min. $ZnCl_2$ (1M in THF, 56.0 mL, 56.0 mmol) was added, and the mixture was allowed to warm up to rt. The mixture was stirred at rt for 1 h. A sol. of 4-trifluoromethanesulfonyloxy-5,6-dihydro-2H-pyridine-1,3-dicarboxylic acid 1-tert-butyl ester 3-methyl ester (WO 2004/002957; 14.3 g, 36.7 mmol) in THF (30 mL), and then a sol. of $Pd(PPh_3)_4$ (1.23 g, 1.06 mmol) in THF (30 mL) were added. The mixture was stirred at 50° C. over 20 min, and cooled to 0° C. Aq. 10% $NH_4Cl$ was added. The mixture was extracted with EtOAc. The org. extracts were washed with aq. 10% $NH_4Cl$, water, and brine. The org. layer was dried over $MgSO_4$, filtered, and the solvents were removed under reduced pressure. Purification of the residue by FC (EtOAc/heptane 1:4→EtOAc) yielded the title compound (19.7 g, quantitative yield). LC-MS: $t_R$=1.20 min; ES+: 536.77.

(rac.)-(1R*,5S*)-7-{6-[2-(2,6-Dichloro-4-methyl-phenoxy)-ethoxy]-pyridin-3-yl}-9-methyl-3,9-diaza-bicyclo[3.3.1]non-6-ene-3,6-dicarboxylic Acid 3-tert-butyl Ester 6-ethyl Ester (C4)

A sol. of 5-bromo-2-[2-(2,6-dichloro-4-methyl-phenoxy)-ethoxy]-pyridine (790 mg, 2.10 mmol) in THF (18 mL) was cooled to −78° C. BuLi (1.6M in hexane, 2.65 mL, 4.20 mmol) was added. The mixture was stirred at −78° C. for 1 h, and $ZnCl_2$ (1M in THF, 6.30 mL, 6.30 mmol) was added. The mixture was allowed to warm to rt. A sol. of (rac.)-(1R*,5S*)-9-methyl-7-trifluoromethanesulfonyloxy-3,9-diaza-bicyclo[3.3.1]non-6-ene-3,6-dicarboxylic acid 3-tert-butyl ester 6-ethyl ester (WO 2003/093267; 641 mg, 1.40 mmol) in THF (3.00 mL), and then $Pd(PPh_3)_4$ (40 mg, 0.035 mmol) were added. The mixture was rapidly heated to 55° C., and was stirred at this temperature for 20 min. The mixture was allowed to cool to rt, and aq. sat. $NH_4Cl$ was added. The solvents were partially removed under reduced pressure, and the rest was diluted with EtOAc. This mixture was washed with water. The aq. layer was extracted back with EtOAc (3×). The combined org. extracts were dried over $MgSO_4$, filtered, and the solvents were removed under reduced pressure. Purification of the crude by FC (EtOAc/heptane 1:3→EtOAc) yielded the title compound (444 mg, 52%). LC-MS: $t_R$=0.94 min; ES+: 606.28.

(rac.)-(1R*,5S*)-7-{6-[2-(2,6-Dichloro-4-methyl-phenoxy)-ethoxy]-pyridin-3-yl}-3,9-diaza-bicyclo[3.3.1]non-6-ene-3,6,9-tricarboxylic Acid 3-tert-butyl Ester 6-ethyl Ester 9-(2,2,2-trichloro-1,1-dimethyl-ethyl) Ester (C5)

2,2,2-Trichloro-1,1-dimethylethyl chloroformate (2.77 g, 11.6 mmol) was added to a sol. of compound C4 (1.40 g, 2.31 mmol) in $CH_2ClCH_2Cl$ (30 mL), and the mixture was heated to reflux for 2 h. 2,2,2-Trichloro-1,1-dimethylethyl chloroformate (1.40 g, 5.5 mmol) was added again, and the mixture was heated to reflux for 2 h. The mixture was allowed to cool to rt, and the solvents were removed under reduced pressure. The residue was diluted with EtOAc, and washed with aq. 1M NaOH (2×). The combined aq. layers were extracted back with EtOAc (2×). The combined org. extracts were dried over $MgSO_4$, filtered, and the solvents were removed under reduced pressure. Purification of the residue by FC (EtOAc/heptane 1:4) yielded the title compound (815 mg, 44%). LC-MS: $t_R$=1.25 min; ES+: 796.32.

6-[2-(2,6-Dichloro-4-methyl-phenoxy)-ethoxy]-5',6'-dihydro-2'H-[3,4']bipyridinyl-1',3'-dicarboxylic Acid 1'-tert-butyl Ester 3'-methyl Ester (C6)

BuLi (1.6M in hexane, 39.3 mL, 45.2 mmol) was added to a sol. of 5-bromo-2-[2-(2,6-dichloro-4-methyl-phenoxy)-ethoxy]-pyridine (11.0 g, 28.3 mmol) in THF (700 mL) at −78° C. The mixture was stirred for 1 h, and $ZnCl_2$ (0.71M in THF, 78.6 mL, 56.5 mmol) was added. This sol. was allowed to warm up to rt. A sol. of 4-trifluoromethanesulfonyloxy-5,6-dihydro-2H-pyridine-1,3-dicarboxylic acid 1-tert-butyl ester 3-methyl ester (WO 2004/002957; 13.0 g, 34.5 mmol) in THF (30 mL) and Pd(PPh$_3$)$_4$ (814 mg, 0.704 mmol) were added. The mixture was stirred for 30 min at rt. Aq. sat. NH$_4$Cl was added, and the mixture was extracted with EtOAc (2×). The combined org. extracts were dried over MgSO$_4$, filtered, and the solvents were removed under reduced pressure. Purification of the crude by FC (EtOAc/heptane 1:9→1:1) yielded the title compound (10.7 g, 70%). LC-MS: t$_R$=1.16 min; ES+: 537.33.

4-{4-[3-(2-Chloro-3,6-difluoro-phenyl)-isoxazol-5-ylmethoxy]-phenyl}-5,6-dihydro-2H-pyridine-1,3-dicarboxylic Acid 1-tert-butyl Ester 3-methyl Ester (C7)

To a sol. of compound B2 (10.0 g, 30 mmol) and [3-(2-chloro-3,6-difluoro-phenyl)-isoxazol-5-yl]-methanol (8.84 g, 30 mmol) in toluene (60 mL) were added ADDP (15.1 g, 60 mmol) and PBu$_3$ (90%, 30.0 mL; 108 mmol). The mixture was stirred for 2 h at 80° C., and was allowed to cool to rt. The solvents were removed under reduced pressure. Purification of the residue by FC (EtOAc/heptane 1:4→EtOAc) yielded the title compound (8.64 g, 51%). LC-MS: t$_R$=1.15 min; ES+: 561.25.

6-[3-(2-Chloro-3,6-difluoro-phenyl)-isoxazol-5-ylmethoxy]-5',6'-dihydro-2'H-[3,4']bipyridinyl-1',3'-dicarboxylic Acid 1'-tert-butyl Ester 3'-methyl Ester (C8)

A mixture of 4-trifluoromethanesulfonyloxy-5,6-dihydro-2H-pyridine-1,3-dicarboxylic acid 1-tert-butyl ester 3-methyl ester (WO 2004/002957; 6.04 g, 15.5 mmol), 2-[3-(2-chloro-3,6-difluoro-phenyl)-isoxazol-5-ylmethoxy]-5-(4,4,5,5-tetramethyl-[1,3,2]dioxaborolan-2-yl)-pyridine (9.28 g, 20.7 mmol) and aq. 2M Na$_2$CO$_3$ (93.1 mL, 186 mmol) in DME (150 mL) was prepared, and Pd(PPh$_3$)$_4$ (1.00 g, 0.866 mmol) was added in portions. The mixture was heated to 80° C., and stirred at this temperature for 1 h. The mixture was allowed to cool to rt, and was diluted with EtOAc. The resulting mixture was washed with water and brine. The org. layer was dried over MgSO$_4$, filtered, and the solvents were removed under reduced pressure. Purification of the residue by FC (EtOAc/heptane 1:2→2:1) yielded the title compound (4.64 g, 40%). LC-MS: t$_R$=1.34 min; ES+: 562.34.

(rac.)-(1R*,5S*)-3-Acetyl-7-{6-[2-(2,6-dichloro-4-methyl-phenoxy)-ethoxy]-pyridin-3-yl}-3,9-diaza-bicyclo[3.3.1]non-6-ene-6,9-dicarboxylic Acid 6-ethyl Ester 9-(2,2,2-trichloro-1,1-dimethyl-ethyl) Ester (C9)

HCl (4M in dioxane, 30 mL) was added to a sol. of compound C5 (3.34 g, 4.20 mmol) in CH$_2$Cl$_2$ (30 mL) at 0° C. The mixture was stirred for 1 h at 0° C., then for 1 h at rt. The solvents were removed under reduced pressure, and the residue was dried under high vacuum. The residue was dissolved in CH$_2$Cl$_2$ (30 mL), and DIPEA (2.88 mL, 16.8 mmol) was added. The mixture was cooled to −20° C., and AcCl (0.315 mL, 4.41 mmol) was added carefully. The mixture was stirred for 20 min at −20° C., and CH$_2$Cl$_2$ was added. The mixture was washed with aq. 1M HCl and aq. 1M NaOH. The org. layer was dried over MgSO$_4$, filtered, and the solvents were removed under reduced pressure. Purification of the residue by FC (EtOAc/heptane 1:4→1:3→1:2) yielded the title compound (3.03 g, 98%). LC-MS: t$_R$=1.18 min; ES+: 738.14.

(rac.)-(1R*,5S*)-3-{4-[3-(2-Chloro-3,6-difluoro-phenyl)-isoxazol-5-ylmethoxy]-phenyl}-8-aza-bicyclo[3.2.1]oct-2-ene-2,8-dicarboxylic Acid 8-tert-butyl Ester 2-methyl Ester (C10)

A mixture of compound B4 (6.80 g, 18.9 mmol), [3-(2-chloro-3,6-difluoro-phenyl)-isoxazol-5-yl]-methanol (6.97 g, 28.3 mmol), ADDP (9.55 g, 37.8 mmol) and PBu$_3$ (85%, 13.8 mL, 56.6 mmol) in toluene (280 mL) was heated to reflux for 1 h. The mixture was allowed to cool to rt, and the solvents were removed under reduced pressure. Purification of the residue by FC (EtOAc/heptane 1:1) yielded the title compound (11.0 g, 99%). LC-MS: t$_R$=1.14 min; ES+: 587.30.

(rac.)-(1R*,5S*)-7-{6-[3-(2-Chloro-3,6-difluoro-phenyl)-isoxazol-5-ylmethoxy]-pyridin-3-yl}-9-methyl-3,9-diaza-bicyclo[3.3.1]non-6-ene-3,6-dicarboxylic Acid 3-tert-butyl Ester 6-ethyl Ester (C11)

(rac.)-(1R*,5S*)-9-Methyl-7-trifluoromethanesulfonyloxy-3,9-diaza-bicyclo[3.3.1]non-6-ene-3,6-dicarboxylic acid 3-tert-butyl ester 6-ethyl ester (WO 2003/093267; 1.00 g, 2.18 mmol) and 2-[3-(2-chloro-3,6-difluoro-phenyl)-isoxazol-5-ylmethoxy]-5-(4,4,5,5-tetramethyl-[1,3,2]dioxaborolan-2-yl)-pyridine (1.41 g, 3.27 mmol) were dissolved in DME (14.5 mL), and aq. 2M Na$_2$CO$_3$ (11.0 mL) was added. The mixture was degassed with N$_2$ (5 min). Pd(PPh$_3$)$_4$ (126 mg, 0.109 mmol) was added, and the mixture was rapidly heated to 80° C. The mixture was stirred at this temperature for 1 h, and was allowed to cool to rt. The mixture was diluted with EtOAc (100 mL), and was washed with water (100 mL). The org. layer was dried over MgSO$_4$, filtered, and the solvents were removed under reduced pressure. Purification of the crude by FC(CH$_2$Cl$_2$/MeOH 95:5) yielded the title compound (1.12 g, 81%). LC-MS: t$_R$=0.91 min; ES+: 631.34.

(rac.)-(1R*,5S*)-7-{6-[3-(2-Chloro-3,6-difluoro-phenyl)-isoxazol-5-ylmethoxy]-pyridin-3-yl}-3,9-diaza-bicyclo[3.3.1]non-6-ene-3,6,9-tricarboxylic Acid 3-tert-butyl Ester 6-ethyl Ester 9-(2,2,2-trichloro-1,1-dimethyl-ethyl) Ester (C12)

A mixture of compound C11 (1.10 g, 1.74 mmol) and 2,2,2-trichloro-1,1-dimethylethyl chloroformate (4.18 g, 17.4 mmol) in 1,2-dichloroethane (18.0 mL) was stirred at 70° C. for 2 h. The mixture was allowed to cool to rt, the solvents were removed under reduced pressure, and the crude product was purified by FC (EtOAc/heptane 40:60) to yield the title compound (1.04 g, 73%). LC-MS: t$_R$=1.22 min; ES+: 821.16.

(rac.)-(1R*,5S*)-3-Acetyl-7-{6-[3-(2-chloro-3,6-difluoro-phenyl)-isoxazol-5-ylmethoxy]-pyridin-3-yl}-3,9-diaza-bicyclo[3.3.1]non-6-ene-6,9-dicarboxylic Acid 6-ethyl Ester 9-(2,2,2-trichloro-1,1-dimethyl-ethyl) Ester (C13)

To a sol. of compound C12 (4.14 g, 5.04 mmol) in CH$_2$Cl$_2$ (41 mL) at 0° C. was added HCl (4M in dioxane, 41 mL). The mixture was stirred at 0° C. for 90 min, and at rt for 30 min. The solvents were removed under reduced pressure, and the residue was dried under high vacuum. This residue was dissolved in CH$_2$Cl$_2$ (41 mL), and DIPEA (3.45 mL, 20.2 mmol) was added. The mixture was cooled to 0° C., and acetyl chloride (0.376 mL, 5.29 mmol) was added dropwise. The mixture was stirred at rt for 30 min, and CH$_2$Cl$_2$ was added. This mixture was washed with aq. sat. NH$_4$Cl. The org.

extracts were washed with aq. 1M NaOH, dried over MgSO$_4$, filtered, and the solvents were removed under reduced pressure. Purification of the crude by FC (heptane/EtOAc 7:3) yielded the title compound (3.35 g, 87%). LC-MS: $t_R$=1.15 min; ES+: 763.07.

(rac.)-(1R*,5S*)-7-{4-[3-(2-Chloro-3,6-difluoro-phenyl)-isoxazol-5-ylmethoxy]-phenyl}-3,9-diaza-bicyclo[3.3.1]non-6-ene-3,6,9-tricarboxylic Acid 3-tert-butyl Ester 6-ethyl Ester 9-(2,2,2-trichloro-1,1-dimethyl-ethyl Ester (C20)

A mixture of compound B11 (2.10 g, 3.55 mmol), [3-(2-chloro-3,6-difluoro-phenyl)-isoxazol-5-yl]-methanol (5.32 g, 10.1 mmol), ADDP (1.79 g, 7.10 mmol) and PBu$_3$ (85%, 2.60 ml, 10.5 mmol) in toluene (70 mL) was heated to reflux for 1 h. The mixture was allowed to cool to rt, and the solvents were removed under reduced pressure. Purification of the residue by FC (EtOAc/heptane: 1:1) yielded the title compound (2.87 g, 99%). LC-MS: $t_R$=1.22 min; ES+ not visible.

(rac.)-(1R*,5S*)-3-{6-[2-(2,6-Dichloro-4-methyl-phenoxy)-ethoxy]-pyridin-3-yl}-8-aza-bicyclo[3.2.1]oct-2-ene-2,8-dicarboxylic Acid 8-tert-butyl Ester 2-methyl Ester (C21)

BuLi (1.6 M in hexane, 12.0 mL, 19.2 mmol) was added to the sol. of 5-bromo-2-[2-(2,6-dichloro-4-methyl-phenoxy)-ethoxy]-pyridine (5.45 g, 14.4 mmol) in THF (120 mL) at −78° C. The mixture was stirred at −78° C. for 60 min, and ZnCl$_2$ (1M in THF, 28.9 mL, 28.9 mmol) was added. The mixture was allowed to warm up to rt, and compound A1 (4.00 g, 9.63 mmol) in dry THF (50 mL) and Pd(PPh$_3$)$_4$ (277 mg, 0.240 mmol) in THF (2 mL) were added. The mixture was heated to 70° C. for 1 h, and was quenched with aq. sat. NH$_4$Cl (70 mL). The mixture was extracted with EtOAc (3×). The combined org. layers were dried over MgSO$_4$, filtered, and the solvents were removed under reduced pressure. Purification of crude by FC(CH$_2$Cl$_2$/MeOH 99:1→98:2→97:3→96:4→95:5) yielded the title compound (4.25 g, 78%). LC-MS: $t_R$=1.16 min; ES+: 563.11.

(rac.)-(1R*,5S*)-3-{6-[3-(2-Chloro-3,6-difluoro-phenyl)-isoxazol-5-ylmethoxy]-pyridin-3-yl}-8-aza-bicyclo[3.2.1]oct-2-ene-2,8-dicarboxylic Acid 8-tert-butyl Ester 2-methyl Ester (C22)

Compound B12 (2.49 g, 5.88 mmol) and [3-(2-chloro-3,6-difluoro-phenyl)-isoxazol-5-yl]-methanol (1.88 g, 7.65 mmol) were dissolved in toluene (58 mL). tert-BuONa (848 mg, 8.83 mmol), xantphos (204 mg, 0.353 mmol) and Pd$_2$(dba)$_3$ (110 mg, 0.120 mmol) were added to the mixture. The reaction was heated to reflux for 1 h, and was allowed to cool to rt. The mixture was evaporated to dryness under reduced pressure. Purification of the residue by FC (EtOAc/heptane 25:75) yielded the title compound (1.71 g, 50%). LC-MS: $t_R$=1.13 min; ES+: 588.23.

Mixture of (1R,5S)-3-{4-[(R)-3-(2,6-dichloro-4-methyl-phenoxy)-pyrrolidin-1-yl]-phenyl}-8-aza-bicyclo[3.2.1]oct-2-ene-2,8-dicarboxylic Acid 8-tert-butyl Ester 2-methyl Ester and (1S,5R)-3-{4-[(R)-3-(2,6-dichloro-4-methyl-phenoxy)-pyrrolidin-1-yl]-phenyl}-8-aza-bicyclo[3.2.1]oct-2-ene-2,8-dicarboxylic Acid 8-tert-butyl Ester 2-methyl Ester (C23)

A mixture of compounds B14 (2.75 g, 6.42 mmol), 2,6-dichloro-p-cresol (2.27 g, 12.8 mmol), ADDP (2.43 g, 9.63 mmol) and PBu$_3$ (3.90 g, 19.2 mmol) in toluene (43 mL) was heated to reflux for 1 h. The mixture was allowed to cool to rt, and EtOAc (65 mL) was added. The mixture was washed with aq. 1M NaOH (2×) and brine (1×). The org. layer was dried over MgSO$_4$, filtered, and the solvents were removed under reduced pressure. Purification of the residue by FC (EtOAc/heptane 1:5) yielded the title compounds mixture (2.54 g, 67%). LC-MS: $t_R$=1.23 min; ES+: 587.26.

Mixture of (1R,5S)-7-{6-[(R)-3-(2,6-dichloro-4-methyl-phenoxy)-pyrrolidin-1-yl]-pyridin-3-yl}-3,9-diaza-bicyclo[3.3.1]non-6-ene-3,6,9-tricarboxylic Acid 3,9-di-tert-butyl Ester 6-ethyl Ester and (1S,5R)-7-{6-[(R)-3-(2,6-dichloro-4-methyl-phenoxy)-pyrrolidin-1-yl]-pyridin-3-yl}-3,9-diaza-bicyclo[3.3.1]non-6-ene-3,6,9-tricarboxylic Acid 3,9-di-tert-butyl Ester 6-ethyl Ester (C24)

A mixture of compounds B16 (5.00 g, 8.95 mmol), 2,6-dichloro-p-cresol (3.17 g, 17.9 mmol), ADDP (4.52 g, 17.9 mmol) and PBu$_3$ (85%, 6.97 mL, 26.8 mmol) in toluene (80 mL) was heated to reflux for 2 h. The mixture was allowed to cool to rt, and was diluted with EtOAc (200 mL). The mixture was washed with aq. 1M NaOH (3×). The org. layer was dried over MgSO$_4$, filtered, and the solvents were removed under reduced pressure. Purification of the residue by FC (EtOAc/heptane 1:19→1:1) yielded the title compounds mixture (5.60 g, 87%). LC-MS: $t_R$=1.01 min, ES+: 717.33.

Mixture of (1R,5S)-7-{6-[(R)-3-(2-chloro-3,6-difluoro-phenoxy)-pyrrolidin-1-yl]-pyridin-3-yl}-3,9-diaza-bicyclo[3.3.1]non-6-ene-3,6,9-tricarboxylic Acid 3,9-di-tert-butyl Ester 6-ethyl Ester and (1S,5R)-7-{6-[(R)-3-(2-chloro-3,6-difluoro-phenoxy)-pyrrolidin-1-yl]-pyridin-3-yl}-3,9-diaza-bicyclo[3.3.1]non-6-ene-3,6,9-tricarboxylic Acid 3,9-di-tert-butyl Ester 6-ethyl Ester (C25)

A mixture of compounds B16 (5.00 g, 8.95 mmol), 2-chloro-3,6-difluorophenol (2.95 g, 17.9 mmol), ADDP (4.52 g, 17.9 mmol) and PBu$_3$ (85%, 6.97 mL, 26.8 mmol) in toluene (80 mL) was heated to reflux for 2 h. The mixture was allowed to cool to rt, and was diluted with EtOAc (200 mL). The mixture was washed with aq. 1M NaOH (3×). The org. layer was dried over MgSO$_4$, filtered, and the solvents were removed under reduced pressure. Purification of the residue by FC (EtOAc/heptane 1:19→1:1) yielded the title compounds mixture (4.96 g, 79%). LC-MS: $t_R$=0.98 min, ES+: 705.37.

(rac.)-(1R*,5S*)-7-{4-[3-(2-Chloro-3,6-difluoro-phenyl)-isoxazol-5-ylmethoxy]-phenyl}-3,9-diaza-bicyclo[3.3.1]non-6-ene-3,6-dicarboxylic Acid 3-tert-butyl Ester 6-ethyl Ester (C26)

Zn (2.00 g, 30.7 mmol) was added to a sol. of compound C20 (2.50 g, 3.05 mmol) in THF (31 mL) and AcOH (3.80 mL), and the mixture was stirred efficiently at rt for 6.5 h. The mixture was filtered through celite, and the filtrate was evaporated under reduced pressure. The residue was diluted with CH$_2$Cl$_2$, and the mixture was washed with aq. sat. NaHCO$_3$. The org. layer was dried over MgSO$_4$, filtered, and the solvents were removed under reduced pressure. Purification of the crude by FC (MeOH/CH$_2$Cl$_2$ 1:19) yielded the title compound (1.52 g, 81%). LC-MS: $t_R$=0.90 min, ES+: 657.21.

(rac.)-(1R*,5S*)-7-{4-[3-(2-Chloro-3,6-difluoro-phenyl)-isoxazol-5-ylmethoxy]-phenyl}-3,9-diaza-bicyclo[3.3.1]non-6-ene-3,6,9-tricarboxylic Acid 3,9-di-tert-butyl Ester 6-ethyl Ester (C27)

A sol. of compound C26 (1.52 g, 2.47 mmol), DIPEA (2.11 mL, 12.3 mmol), and Boc$_2$O (1.62 g, 7.40 mmol) in CH$_2$Cl$_2$ (12 mL) was stirred at rt overnight. The mixture was diluted with CH$_2$Cl$_2$, and was washed with aq. sat. NH$_4$Cl. The aq. layer was extracted back with CH$_2$Cl$_2$. The combined org. extracts were dried over MgSO$_4$, filtered, and the solvents were removed under reduced pressure. Purification of the crude by FC (heptane/EtOAc 7:3) yielded the title compound (1.58 g, 59%). LC-MS: $t_R$=1.16 min, ES+: 716.20.

(rac.)-(1R*,5S*)-3-Acetyl-7-{4-[3-(2-chloro-3,6-difluoro-phenyl)-isoxazol-5-ylmethoxy]-phenyl}-3,9-diaza-bicyclo[3.3.1]non-6-ene-6,9-dicarboxylic Acid 6-ethyl Ester 9-(2,2,2-trichloro-1,1-dimethyl-ethyl) Ester (C28)

HCl (4M in dioxane, 15 m-L) was added to a sol. of compound C20 (1.50 g, 1.83 mmol) in CH$_2$Cl$_2$ (15 mL), and the mixture was stirred at rt for 90 min. The solvents were removed under reduced pressure, and the residue was dried under high vacuum. The residue was diluted with CH$_2$Cl$_2$ (15 mL), and DIPEA (1.25 mL, 7.33 mmol) and AcCl (0.136 mL, 1.92 mmol) were added. The mixture was stirred at rt for 30 min, and CH$_2$Cl$_2$ was added. The mixture was washed with aq. 1M HCl and aq. 1M NaOH. The org. layer was dried over MgSO$_4$, filtered, and the solvents were removed under reduced pressure. Purification of the crude by FC (heptane/EtOAc 1:1) yielded the title compound (1.10 g, 79%). LC-MS: $t_R$=1.14 min, ES+: 761.99.

(rac.)-(1R*,5S*)-3-Acetyl-7-{4-[3-(2-chloro-3,6-difluoro-phenyl)-isoxazol-5-ylmethoxy]-phenyl}-3,9-diaza-bicyclo[3.3.1]non-6-ene-6-carboxylic Acid Ethyl Ester (C29)

Zn powder (944 mg, 14.4 mmol) was added to a sol. of compound C28 (1.10 g, 1.45 mmol) in THF (15 mL) and glacial AcOH (1.30 mL). The mixture was stirred at rt for 3 h. The mixture was filtered through celite, and the filtrate was evaporated under reduced pressure. The residue was partitioned between CH$_2$Cl$_2$ and aq. sat. NaHCO$_3$, and the org. layer was extracted with CH$_2$Cl$_2$. The combined org. extracts were dried over MgSO$_4$, filtered, and the solvents were removed under reduced pressure. Purification of the crude by FC(CH$_2$Cl$_2$/MeOH 95:5) yielded the title compound (640 mg, 79%). LC-MS: $t_R$=0.84 min, ES+: 599.48.

(rac.)-(1R*,5S*)-3-Acetyl-7-{4-[3-(2-chloro-3,6-difluoro-phenyl)-isoxazol-5-ylmethoxy]-phenyl}-3,9-diaza-bicyclo[3.3.1]non-6-ene-6,9-dicarboxylic Acid 9-tert-butyl Ester 6-ethyl Ester (C30)

A mixture of compound C29 (640 mg, 1.15 mmol), DIPEA (0.983, 5.74 mmol) and Boc$_2$O (753 mg, 3.45 mmol) in CH$_2$Cl$_2$ (6.00 mL) was stirred at rt overnight. The mixture was partitioned between CH$_2$Cl$_2$ and aq. sat. NH$_4$Cl. The aq. layer was extracted with CH$_2$Cl$_2$. The combined org. extracts were dried over MgSO$_4$, filtered, and the solvents were removed under reduced pressure. Purification of the crude by FC (EtOAc) yielded the title compound (750 mg, 99%). LC-MS: $t_R$=1.09 min, ES+: 658.15.

(rac.)-(1R*,5S*)-7-{6-[3-(2-Chloro-3,6-difluoro-phenyl)-isoxazol-5-ylmethoxy]-pyridin-3-yl}-3,9-diaza-bicyclo[3.3.1]non-6-ene-3,6,9-tricarboxylic Acid 3,9-di-tert-butyl Ester 6-methyl Ester (C31)

(rac.)-(1R*,5S*)-7-Trifluoromethanesulfonyloxy-3,9-diaza-bicyclo[3.3.1]non-6-ene-3,6,9-tricarboxylic acid 3,9-di-tert-butyl ester 6-methyl ester (WO 2006/021402, 4.72 g, 8.90 mmol) and 2-[3-(2-chloro-3,6-difluoro-phenyl)-isoxazol-5-ylmethoxy]-5-(4,4,5,5-tetramethyl-[1,3,2]dioxaborolan-2-yl)-pyridine (5.77 g crude, about 13.4 mmol) were dissolved in a mixture of DME (59.3 mL) and aq. 2M Na$_2$CO$_3$ (44.5 mL). The mixture was degassed with N$_2$, and Pd(PPh$_3$)$_4$ (514 mg, 0.445 mmol) was added. The mixture was heated rapidly to 80° C., and was stirred at this temperature for 1 h. The mixture was diluted with EtOAc (100 mL), and washed with water (100 mL). The org. layer was dried over MgSO$_4$, filtered, and the solvents were removed under reduced pressure. Purification of the crude by FC (EtOAc 100%→EtOAc/MeOH 95:5) yielded the title compound (4.56 g, 73%). LC-MS: $t_R$=1.15 min, ES+: 703.25.

Mixture of (1R,5S)-3-{6-[(R)-3-(2,6-dichloro-4-methyl-phenoxy)-pyrrolidin-1-yl]-pyridin-3-yl}-8-aza-bicyclo[3.2.1]oct-2-ene-2,8-dicarboxylic Acid 8-tert-butyl Ester 2-methyl Ester and (1S,5R)-3-{6-[(R)-3-(2,6-dichloro-4-methyl-phenoxy)-pyrrolidin-1-yl]-pyridin-3-yl}-8-aza-bicyclo[3.2.1]oct-2-ene-2,8-dicarboxylic Acid 8-tert-butyl Ester 2-methyl Ester (C32)

A sol. of (R)-5-bromo-2-[3-(2,6-dichloro-4-methyl-phenoxy)-pyrrolidin-1-yl]-pyridine (8.52 g, 21.2 mmol) in THF (212 mL) at −78° C. was treated with BuLi (1.6M in hexane, 22.1 mL). After 30 min of stirring at −78° C., ZnCl$_2$ (1.03M in THF, 41.1 mL, 42.4 mmol) was added. The mixture was allowed to warm up to rt. Compound A1 (9.78 g, 23.5 mmol) in THF (5 mL) and Pd(PPh$_3$)$_4$ (816 mg, 0.706 mmol) were added. The mixture was heated rapidly to 75° C., and was stirred at this temperature for 1 h. The mixture was allowed to cool to rt, and aq. sat. NH$_4$Cl was added. The mixture was extracted with EtOAc. The org. extracts were washed with aq. sat. NH$_4$Cl, dried over MgSO$_4$, filtered, and the solvents were removed under reduced pressure. Purification of the residue by FC (heptane→heptane/EtOAc 60:40) yielded the title compounds mixture (6.18 g, 45%). LC-MS: $t_R$=0.96 min, ES+: 588.19.

(S)-6-[3-(2,6-Dichloro-4-methyl-phenoxy)-pyrrolidin-1-yl]-5',6'-dihydro-2'H-[3,4']bipyridinyl-1',3'-dicarboxylic Acid 1'-tert-butyl Ester 3'-methyl Ester (C33)

A sol. of (S)-5-bromo-2-[3-(2,6-dichloro-4-methyl-phenoxy)-pyrrolidin-1-yl]-pyridine (8.52 g, 21.2 mmol) in THF (212 mL) at −78° C. was treated with BuLi (1.6M in hexane, 22.1 mL, 35.3 mmol). The mixture was stirred −78° C. for 30 min, and ZnCl$_2$ (1.03M in THF, 41.1 mL, 42.4 mmol) was added. The mixture was allowed to warm up to rt. A sol. of 4-trifluoromethanesulfonyloxy-5,6-dihydro-2H-pyridine-1,3-dicarboxylic acid 1-tert-butyl ester 3-methyl ester (WO 2004/002957; 9.17 g, 23.5 mmol) in THF (5 mL), and Pd(PPh$_3$)$_4$ (816 mg, 0.701 mmol) were added. The mixture was rapidly heated to 75° C., and stirred at this temperature for 1 h. The mixture was allowed to cool to rt, and aq. sat. NH$_4$Cl was added. The mixture was extracted with EtOAc. The org. extracts were washed with aq. sat. NH$_4$Cl, dried over MgSO₄, filtered, and the solvents were removed under reduced pressure. Purification of the crude by FC (heptane→heptane:EtOAc 65:35) yielded the title compound (6.83 g, 52%). LC-MS: $t_R$=0.92 min, ES+: 562.36.

6-[3-(2-Chloro-3,6-difluoro-phenyl)isoxazol-5-yl-methoxy]-5',6'-dihydro-2'H-[3,4']bipyridinyl-1',3'-dicarboxylic Acid 1'-tert-butyl Ester 3'-ethyl Ester (C34)

Compound A2 (9.52 g, 23.6 mmol) and 2-[3-(2-chloro-3,6-difluoro-phenyl)-isoxazol-5-ylmethoxy]-5-(4,4,5,5-tetramethyl-[1,3,2]dioxaborolan-2-yl)-pyridine (13.2 g, 29.5 mmol) were dissolved in DME (164 mL), and aq. 2M Na₂CO₃ (118 mL) was added. The mixture was degassed with N₂ (5 min), and Pd(PPh₃)₄ (1.36 g, 1.18 mmol) was added. The mixture was heated rapidly to 80° C., and was stirred at this temperature for 1 h. The mixture was allowed to cool to rt, and was diluted with EtOAc (200 mL). The mixture was washed with water (200 mL). The org. layer was dried over MgSO₄, filtered, and the solvents were removed under reduced pressure. Purification of the crude by FC (heptane→EtOAc/heptane 30:70) yielded the title compound (8.45 g, 62%). LC-MS: $t_R$=1.13 min, ES+: 576.41.

(rac.)-(3R*,4S*)-4-{4-[3-(2-Chloro-3,6-difluoro-phenyl)-isoxazol-5-ylmethoxy]-phenyl}-piperidine-1,3-dicarboxylic Acid 1-tert-butyl Ester 3-methyl Ester (D1)

ADDP (2.78 g, 11.0 mmol) was added to a sol. of compound E3 (1.85 g, 5.52 mmol) and [3-(2-chloro-3,6-difluoro-phenyl)-isoxazol-5-yl]-methanol (1.63 g, 6.62 mmol) in toluene (20 mL). PBu₃ (90%, 5.44 mL, 20.0 mmol) was added, and the mixture was stirred for 2 h at 80° C. The mixture was allowed to cool to rt, and was diluted with EtOAc. The resulting mixture was washed with water (1×) and brine (2×). The org. layer was dried over MgSO₄, filtered, and the solvents were removed under reduced pressure. Purification of the crude by FC (EtOAc/heptane 2:8→EtOAc) yielded the title compound (2.67 g, 86%). LC-MS: $t_R$=1.14 min; ES+: 563.26.

(rac.)-(1R*,2R*,3S*,5S*)-3-{4-[2-(2,6-Dichloro-4-methyl-phenoxy)-ethoxy]-phenyl}-8-aza-bicyclo[3.2.1]octane-2,8-dicarboxylic Acid 8-tert-butyl Ester 2-methyl Ester (D2)

Mg (1.02 g, 41.8 mmol) was added to a sol. of compound C2 (4.70 g, 8.36 mmol) in MeOH (230 mL). The reaction mixture was stirred at rt for 2 h. Mg (1.02 g, 41.8 mmol) was added again, and the mixture was stirred for 2 h again. The reaction mixture was heated to 70° C. and stirred at this temperature for 16 h. The mixture was allowed to cool down to rt, and was quenched with aq. sat. NH₄Cl (5 mL). EtOAc was added, and the mixture was washed with water (2×) and brine (1×). The org. phase was dried over MgSO₄, filtered, and concentrated under reduced pressure. Purification of the crude by FC (EtOAc/heptane 5:45→6:44→7:43→8:42) yielded the title compound (595 mg, 13%). LC-MS: $t_R$=1.18 min; ES+: 564.18.

Mixture of all Possible Stereoisomers of 6-[2-(2,6-dichloro-4-methyl-phenoxy)-ethoxy]-3',4',5',6'-tetrahydro-2'H-[3,4']bipyridinyl-1',3'-dicarboxylic Acid 1'-tert-butyl Ester 3'-methyl Ester (D3)

Compound C6 (7.00 g, 13.0 mmol) was dissolved in MeOH (130 mL). Mg (500 mg, 20.6 mmol) was added slowly. The mixture was stirred for 1 h, and Mg (608 mg, 25.0 mmol) was added again. The mixture was stirred 3 h. Aq. 1M HCl was added slowly, and the mixture was stirred 1 h at rt. The solvents were evaporated under reduced pressure, and the mixture was extracted with EtOAc. The org. extracts were dried over MgSO₄, filtered, and the solvents were removed under reduced pressure. Drying under high vacuum yielded the crude title compounds mixture (4.92 g, 70%) that was used further without purification. LC-MS: $t_R$=1.16 min, ES+=539.43.

(rac.)-(3R*,4S*)-6-[2-(2,6-Dichloro-4-methyl-phenoxy)-ethoxy]-3',4',5',6'-tetrahydro-2'H-[3,4']bipyridinyl-1',3'-dicarboxylic Acid 1'-tert-butyl Ester 3'-methyl Ester (D4)

A mixture of compounds D3 (5.40 g, 10.0 mmol) and MeONa (540 mg, 10.0 mmol) in MeOH (250 mL) was stirred overnight at 70° C. MeONa (54 mg, 1.00 mmol) was added again, and the mixture was stirred for 5 h at 70° C. MeONa (54 mg, 1.00 mmol) was added again, and the mixture was stirred overnight at 70° C. Aq. 1M HCl was added until a pH of 6-7 was reached. The solvents were evaporated under reduced pressure, and the mixture was extracted with EtOAc. The combined org. extracts were washed with water, and with brine. The org. layer was dried over MgSO₄, filtered, and the solvents were removed under reduced pressure. Purification of the residue by FC (heptane/EtOAc 8:2 with 1% Et₃N) yielded the title compound (4.92 g, 91%). LC-MS: $t_R$=1.16 min, ES+=539.43.

Mixture of all Four Possible Stereoisomers of 4-{4-[2-(2,6-dichloro-4-methyl-phenoxy)-ethoxy]-phenyl}-piperidine-1,3-dicarboxylic Acid 1-tert-butyl Ester 3-methyl Ester (D5)

Mg (2.21 g, 91 mmol) was added in portions to a sol. of compound C3 (22.5 g, 42 mmol) in MeOH (200 mL) at 0° C. The mixture was stirred for 1.5 h at 0° C., and EtOAc was added. The mixture was washed with aq. 1M HCl and brine. The org. layer was dried over MgSO₄, filtered, and the solvents were removed under reduced pressure. Drying the residue under high vacuum yielded the crude title compounds mixture (22.6 g, quantitative yield). LC-MS: $t_R$=1.19 min, ES+=538.39.

(rac.)-(3R*,4S*)-4-{4-[2-(2,6-Dichloro-4-methyl-phenoxy)-ethoxy]-phenyl}-piperidine-1,3-dicarboxylic Acid 1-tert-butyl Ester 3-methyl Ester (D6)

MeONa (2.27 g, 42 mmol) was added to a sol. of compounds D5 (22.6 g, 42 mmol) in MeOH (200 mL). The mixture was stirred at 70° C. for 6 h, and MeONa (2.27 g, 42 mmol) was added again. The mixture was stirred at 70° C. for 2 days, and was allowed to cool to rt. EtOAc was added, and the resulting mixture was washed with aq. 1M HCl and brine. The org. layer was dried over MgSO₄, filtered, and the solvents were removed under reduced pressure. Purification of the crude by FC (MeOH/CH₂Cl₂ 5:95→10:90) yielded the title compound (10.7 g, 47%). LC-MS: $t_R$=1.19 min, ES+=538.39.

(3R,4S)-4-{4-[2-(2,6-Dichloro-4-methyl-phenoxy)-ethoxy]-phenyl}-piperidine-1,3-dicarboxylic Acid 1-tert-butyl Ester 3-methyl Ester (D7)

Compound D6 (24.2 g, 45 mmol) was separated by HPLC (Regis R, R Whelk, isocratic conditions, eluent B 65%). The title compound was obtained (6.61 g, 27%). LC-MS: $t_R$=1.19 min, ES+=538.39. Chiral HPLC column: $t_R$=13.8 min.

(rac.)-(1R*,2R*,3S*,5S*)-3-{6-[2-(2,6-Dichloro-4-methyl-phenoxy)-ethoxy]-pyridin-3-yl}-8-aza-bicyclo[3.2.1]octane-2,8-dicarboxylic Acid 8-tert-butyl Ester 2-methyl Ester (D8)

Mg (600 mg, 24.7 mmol) was added to a sol. of compound C21 (6.48 g, 11.5 mmol) in MeOH (350 mL). The mixture was efficiently stirred at rt for 2 h, and Mg (1.20 g, 49.4 mmol) was added again. The mixture was stirred for 4 h, and Mg (600 mg, 24.7 mmol) was added again. The mixture was stirred overnight, and Mg (300 mg, 12.3 mmol) was added again. The mixture was stirred for 3 h at rt, and was heated to reflux overnight. The mixture was allowed to cool to rt, and EtOAc (400 mL) was added. The mixture was washed with water and brine. The org. layer was dried over MgSO$_4$, filtered, and the solvents were removed under reduced pressure. Purification of the crude by FC (EtOAc/heptane 1:19→3:47→6:75→1:9→9:75→2:15) yielded the title compound (1.12 g, 17%). LC-MS: $t_R$=1.16 min, ES+=565.33.

Mixture of (1R,2R,3S,5S)-3-{4-[(R)-3-(2,6-dichloro-4-methyl-phenoxy)-pyrrolidin-1-yl]-phenyl}-8-aza-bicyclo[3.2.1]octane-2,8-dicarboxylic Acid 8-tert-butyl Ester 2-methyl Ester and (1S,2S,3R,5R)-3-{4-[(R)-3-(2,6-dichloro-4-methyl-phenoxy)pyrrolidin-1-yl]-phenyl}-8-aza-bicyclo[3.2.1]octane-2,8-dicarboxylic Acid 8-tert-butyl Ester 2-methyl Ester (D9)

Mg (1.01 g, 41.4 mmol) was added to a sol. of compounds C23 (4.86 g, 8.27 mmol) in MeOH (83 mL). The mixture was stirred at rt for 2 h. Mg (1.01 g, 41.4 mmol) was added again, and the mixture was stirred at rt until the whole amount of Mg had reacted. The mixture was heated to 70° C. for 16 h, and was allowed to cool down to rt. Aq. 1M HCl was added to a pH=6-7, and the solvents were partially evaporated under reduced pressure. The aq. residue was extracted with EtOAc. The org. extracts were washed with water and brine, were dried over MgSO$_4$, filtered, and the solvents were removed under reduced pressure. Repetitive purification of the crude by FC (heptane→heptane/EtOAc 90:10) yielded the title compounds mixture (820 mg, 17%). LC-MS: $t_R$=1.21 min, ES+=589.16.

Mixture of (1R,2R,3S,5S)-3-{6-[(R)-3-(2,6-dichloro-4-methyl-phenoxy)-pyrrolidin-1-yl]-pyridin-3-yl}-8-aza-bicyclo[3.2.1]octane-2,8-dicarboxylic Acid 8-tert-butyl Ester 2-methyl Ester, (1S,2S,3R,5R)-3-{6-[(R)-3-(2,6-dichloro-4-methyl-phenoxy)-pyrrolidin-1-yl]-pyridin-3-yl}-8-aza-bicyclo[3.2.1]octane-2,8-dicarboxylic Acid 8-tert-butyl Ester 2-methyl Ester, (1R,2S,3R,5S)-3-{6-[(R)-3-(2,6-dichloro-4-methyl-phenoxy)pyrrolidin-1-yl]-pyridin-3-yl}-8-aza-bicyclo[3.2.1]octane-2,8-dicarboxylic Acid 8-tert-butyl Ester 2-methyl Ester and (1S,2R,3S,5R)-3-{6-[(R)-3-(2,6-dichloro-4-methyl-phenoxy)pyrrolidin-1-yl]-pyridin-3-yl}-8-aza-bicyclo[3.2.1]octane-2,8-dicarboxylic Acid 8-tert-butyl Ester 2-methyl Ester (D10)

Mg (1.27 g, 52.3 mmol) was added in portions to a sol. of compounds C32 (6.15 g, 10.5 mmol) in MeOH (105 mL) at rt. The mixture was stirred at rt for 2 h. Mg (1.27 g, 52.3 mmol) was added again, and the mixture was stirred until Mg had completely reacted. The mixture was heated to 70° C., and stirred at this temperature for 16 h. The mixture was allowed to cool to rt, and aq. 1M HCl was added to a pH=6-7. The solvents were partially evaporated under reduced pressure, and the aq. residue was poured in aq. sat. NH$_4$Cl, diluted with EtOAc and stirred vigorously. The mixture was then extracted with EtOAc, and the combined org. extracts were washed with water and brine. The org. layer was dried over MgSO$_4$, filtered, and the solvents were removed under reduced pressure. Purification of the crude by FC (heptane→heptane/EtOAc 6:4) yielded the title compounds mixture (3.26 g, 53%).

Mixture of (3'R,4'R)-6-[(R)-3-(2,6-dichloro-4-methyl-phenoxy)-pyrrolidin-1-yl]-3',4',5',6'-tetrahydro-2'H-[3,4']bipyridinyl-1',3'-dicarboxylic Acid 1'-tert-butyl Ester 3'-methyl Ester, (3'R,4'S)-6-[(R)-3-(2,6-dichloro-4-methyl-phenoxy)-pyrrolidin-1-yl]-3',4',5',6'-tetrahydro-2'H-[3,4']bipyridinyl-1',3'-dicarboxylic Acid 1'-tert-butyl Ester 3'-methyl Ester, (3'S,4'R)-6-[(R)-3-(2,6-dichloro-4-methyl-phenoxy)-pyrrolidin-1-yl]-3',4',5',6'-tetrahydro-2'H-[3,4']bipyridinyl-1',3'-dicarboxylic Acid 1'-tert-butyl Ester 3'-methyl Ester, and (3'S,4'S-6-[(R)-3-(2,6-dichloro-4-methyl-phenoxy)-pyrrolidin-1-yl]-3',4',5',6'-tetrahydro-2'H-[3,4']bipyridinyl-1',3'-dicarboxylic Acid 1'-tert-butyl Ester 3'-methyl Ester (D11)

A mixture of compounds E5 (7.02 g, 17.3 mmol), 2,6-dichloro-p-cresol (3.68 g, 20.8 mmol), ADDP (6.56 g, 26.0 mmol) and PBu$_3$ (90%, 8.55 mL, 31.1 mmol) in toluene (340 mL) was stirred at 65° C. for 5 h. The mixture was allowed to cool to rt, and EtOAc was added. The mixture was washed with water (3×). The org. layer was dried over MgSO$_4$, filtered, and the solvents were removed under reduced pressure. Purification of the crude by FC (EtOAc/heptane 1:9→4:6) yielded the title compounds mixture (6.54 g, 67%). LC-MS: $t_R$=0.95 min, ES+=564.51.

Mixture of (3'R,4'S)-6-[(R)-3-(2,6-dichloro-4-methyl-phenoxy)-pyrrolidin-1-yl]-3',4',5',6'-tetrahydro-2'H-[3,4']bipyridinyl-1',3'-dicarboxylic acid 1'-tert-butyl ester 3'-methyl ester and (3'S,4'R)-6-[(R)-3-(2,6-dichloro-4-methyl-phenoxy)-pyrrolidin-1-yl]-3',4',5',6'-tetrahydro-2'H-[3,4']bipyridinyl-1',3'-dicarboxylic acid 1'-tert-butyl ester 3'-methyl ester (D12)

MeONa (851 mg, 15.8 mmol) was added to a sol. of compounds D11 (6.54 g, 12.1 mmol) in MeOH (250 mL). The mixture was stirred overnight at 70° C., and MeONa (196 mg, 3.63 mmol) was added, and the mixture was stirred for 3 days at 70° C. Aq. 1M HCl was added until pH=6-7, and the solvents were partially removed under reduced pressure. The aq. residue was extracted with EtOAc. The combined org. extracts were washed with water and brine, dried over MgSO$_4$, filtered, and the solvents were removed under reduced pressure. Purification of the residue by FC (heptane/EtOAc 8:2→heptane/EtOAc 5:5 with always 1% Et$_3$N) yielded the title compounds mixture (2.74 g, 42%).

(rac.)-(1R*,2R*,3S*,5S*)-3-{4-[3-(2-Chloro-3,6-difluoro-phenyl)-isoxazol-5-ylmethoxy]-phenyl}-8-aza-bicyclo[3.2.1]octane-2,8-dicarboxylic acid 8-tert-butyl ester 2-methyl ester (D13)

To a sol. of compound E7 (590 mg, 1.63 mmol) in toluene (10 mL) were added ADDP (824 mg, 3.27 mmol), [3-(2- chloro-3,6-difluoro-phenyl)-isoxazol-5-yl]-methanol (441 mg, 1.80 mmol) and PBu₃ (85%, 1.19 mL, 4.85 mmol). The mixture was refluxed for 3 h, and was allowed to cool to rt. The mixture was partitioned between EtOAc and aq. 10% Na₂CO₃, and the aq. layer was extracted with EtOAc. The combined org. layers were washed with aq. sat. Na₂CO₃ and brine, dried over MgSO₄, filtered, and the solvents were removed under reduced pressure. Purification of the crude by FC (heptane/EtOAc 8:2) yielded the title compound (772 mg, 80%). LC-MS: $t_R$=1.14 min, ES+=589.20.

Mixture of (3'R,4'S)-6-[(S)-3-(2,6-dichloro-4-methyl-phenoxy)-pyrrolidin-1-yl]-3',4',5',6'-tetrahydro-2'H-[3,4']bipyridinyl-1',3'-dicarboxylic acid 1'-tert-butyl ester 3'-methyl ester and (3'S,4'R)-6-[(S)-3-(2,6-dichloro-4-methyl-phenoxy)-pyrrolidin-1-yl]-3',4',5',6'-tetrahydro-2'H-[3,4']bipyridinyl-1',3'-dicarboxylic acid 1'-tert-butyl ester 3'-methyl ester (D14)

Mg (1.03 g, 42.6 mmol) was added in four portions to a sol. of the compound C33 (5.00 g, 8.51 mmol) in MeOH (85 mL) at rt in a flask equipped with a reflux condenser and a bubble counter to control the H₂ evolution. The mixture was stirred at rt for 2 h. The mixture was heated to 70° C., and stirred at this temperature for 16 h. The mixture was allowed to cool down to rt, and aq. 1M HCl was added to a pH=6-7. The solvents were partially removed under reduced pressure, and the aq. mixture was poured in aq. sat. NH₄Cl. EtOAc was added, and the mixture was stirred vigorously. The mixture was extracted with EtOAc. The combined org. extracts were washed with water and brine, dried over MgSO₄, filtered, and the solvents were removed under reduced pressure. Purifications of the crude by FC (heptane→heptane/EtOAc 70:30) yielded the title compounds mixture (1.60 g, 33%).

(rac.)-(3'R,4'R)-6-[3-(2-Chloro-3,6-difluoro-phenyl)-isoxazol-5-ylmethoxy]-3',4',5',6'-tetrahydro-2'H-[3,4']bipyridinyl-1',3'-dicarboxylic acid 1'-tert-butyl ester 3'-ethyl ester (D15)

To a 5 mL two-neck flask, heat gun dried and inertized three times, were added 1,3-bis-(2,6-di-1-propylphenyl)imidazolium copper (I) chloride (Buchwald, S. L., et al., Org. Lett. 2003, 5, 2417, 466 mg, 0.955 mmol), NaOtBu (91.8 mg, 0.955 mmol) and toluene (9.5 if L). The suspension was stirred at rt for 10 min while turning into a clear sol. Poly (methylhydrosilane) (6.89 mL, 115 mmol) was added, and the resulting yellow/orange sol. was stirred at rt for 5 min. Compound C34 (550 mg, 9.55 mmol) in toluene (9.5 mL) was added in one portion at rt, and the mixture stirred for 1 min. Neat tBuOH (10.8 mL, 115 mmol) was added dropwise over 15 min to control the gas evolution, and the reaction mixture was stirred at rt and for 3 h. The mixture was poured onto brine, and the mixture was extracted with EtOAc several times. The combined org. layers were dried over Na₂SO₄, filtered, and the solvents were removed under reduced pressure. The residue was dissolved in MeOH whereas the poly (methylhydrosilane) precipitated, and the mixture was filtered over celite. Purification of the residue by FC (heptane→heptane/EtOAc 70:30) yielded the title compound contaminated with poly(methylhydrosilane) (7.32 g, quantitative yield). LC-MS: $t_R$=1.13 min; ES+: 578.57.

(rac.)-(3'R,4'S)-6-[3-(2-Chloro-3,6-difluoro-phenyl)-isoxazol-5-ylmethoxy]-3',4',5',6'-tetrahydro-2'H-[3,4']bipyridinyl-1',3'-dicarboxylic acid 1'-tert-butyl ester 3'-ethyl ester (D16)

A mixture of compound D15 (7.32 g, 12.7 mmol) and NaOEt (1.29 g, 19.0 mmol) in EtOH (253 mL) was stirred at 70° C. overnight. The mixture was allowed to cool to rt. Aq. 1M HCl was added until pH=6-7, and the solvents were partially evaporated under reduced pressure. The mixture was extracted with EtOAc. The combined org. extracts were washed with water and brine, dried over MgSO₄, filtered, and the solvents were evaporated under reduced pressure. Purification of the crude by FC (heptane→heptane/EtOAc 70:30) yielded the title compound (2.45 g, 33%). LC-MS: $t_R$=1.14 min; ES+: 578.42.

Mixture of (rac.)-(3R*,4R*)-4-(4-benzyloxy-phenyl)-piperidine-1,3-dicarboxylic acid 1-tert-butyl ester 3-methyl ester and (rac.)-(3R*,4S*)-4-(4-benzyloxy-phenyl)piperidine-1,3-dicarboxylic acid 1-tert-butyl ester 3-methyl ester (E1)

Mg (3.96 g, 163 mmol) was carefully added to a sol. of compound B3 (20.6 g, 46 mmol) in MeOH (20 mL). The mixture was stirred for 2 h, and was diluted with EtOAc. The resulting mixture was washed with aq. 1M HCl and brine. The org. layer was dried over MgSO₄, filtered, and the solvents were removed under reduced pressure. Drying at high vacuum yielded the title mixture (19.7 g, 95%) that was used without further purification.

(rac.)-(3R*,4S*)-4-(4-Benzyloxy-phenyl)-piperidine-1,3-dicarboxylic acid 1-tert-butyl ester 3-methyl ester (E2)

MeONa (382 mg, 7.07 mmol) was rapidly added to a sol. of compounds E1 (3.01 g, 7.07 mmol) in MeOH (20 mL). The mixture was stirred at 70° C. for 6 h. MeONa (382 mg, 7.07 mmol) was added again, and the mixture was stirred at 70° C. for 3 days. EtOAc was added, and the resulting mixture was washed with aq. 1M HCl, and brine. The org. layer was dried over MgSO₄, filtered, and the solvents were removed under reduced pressure. Purification of the crude by FC (EtOAc) yielded the title compound (2.88 g, 96%).

(rac.)-(3R*,4S*)-4-(4-Hydroxy-phenyl)-piperidine-1,3-dicarboxylic acid 1-tert-butyl ester 3-methyl ester (E3)

A sol. of compound E2 (2.61 g, 6.12 mmol) in THF (20 mL) was prepared. The mixture was flushed with Ar, and Pd(OH)₂ (20% on charcoal, 5.00 mg) was added. The mixture was flushed with H₂, and was stirred at rt overnight. The mixture was filtered over celite, and the filtrate was evaporated under reduced pressure. Drying under high vacuum yielded the crude title compound (1.85 g, 90%) that was used further without purification. LC-MS: $t_R$=0.93 min; ES+: 336.26.

Mixture of (3'R,4'S)-6-[(S)-3-(tert-butyl-dimethyl-silanyloxy)-pyrrolidin-1-yl]-3',4',5',6'-tetrahydro-2'H-[3,4']bipyridinyl-1',3'-dicarboxylic acid 1'-tert-butyl ester 3'-methyl ester, (3'R,4'R-6-[(S)-3-(tert-butyl-dimethyl-silanyloxy)-pyrrolidin-1-yl]-3',4',5',6'-tetrahydro-2'H-[3,4']bipyridinyl-1',3'-dicarboxylic acid 1'-tert-butyl ester 3'-methyl ester, (3'S,4'S)-6-[(S)-3-(tert-butyl-dimethyl-silanyloxy)-pyrrolidin-1-yl]-3',4',5',6'-tetrahydro-2'H-[3,4']bipyridinyl-1',3'-dicarboxylic acid 1'-tert-butyl ester 3'-methyl ester, and (3'S,4'R)-6-[(S)-3-(tert-butyl-dimethyl-silanyloxy)-pyrrolidin-1-yl]-3',4',5',6'-tetrahydro-2'H-[3,4']bipyridinyl-1',3'-dicarboxylic acid 1'-tert-butyl ester 3'-methyl ester (E4)

Mg (1.00 g, 41.2 mmol) was added to a sol. of compounds B17 (15.5 g, 30.0 mmol) in MeOH (300 mL). The mixture was stirred for 1 h, while a gas evolution occurred after 30 min. Mg (1.00 g, 41.2 mmol) was added again, and the mixture was stirred again for 2 h. Aq. 1M HCl was added slowly, and the mixture was stirred for 1 h at rt. The mixture was extracted with EtOAc (5×). The combined org. extracts were dried over MgSO$_4$, filtered, and the solvents were removed under reduced pressure. Purification of the residue by FC (CH$_2$Cl$_2$/MeOH 19:1→CH$_2$Cl$_2$/MeOH/Et$_3$N 9:1:0.015) yielded the title compounds mixture (5.65 g, 36%). LC-MS: $t_R$=0.97 min; ES+: 520.41.

Mixture of (3'R,4'R)-6-((S)-3-hydroxy-pyrrolidin-1-yl)-3',4',5',6'-tetrahydro-2'H-[3,4']bipyridinyl-1',3'-dicarboxylic acid 1'-tert-butyl ester 3'-methyl ester, (3'R,4'S)-6-((S)-3-hydroxy-pyrrolidin-1-yl)-3',4',5', 6'-tetrahydro-2'H-[3,4']bipyridinyl-1',3'-dicarboxylic acid 1'-tert-butyl ester 3'-methyl ester (3'S,4'R)-6-((S)-3-hydroxy-pyrrolidin-1-yl-3',4',5',6'-tetrahydro-2'H-[3,4']bipyridinyl-1',3'-dicarboxylic acid 1'-tert-butyl ester 3'-methyl ester, and (3'S,4'S)-6-((S)-3-hydroxy-pyrrolidin-1-yl)-3',4',5',6'-tetrahydro-2'H-[3, 4']bipyridinyl-1',3'-dicarboxylic acid 1'-tert-butyl ester 3'-methyl ester (E5)

TBAF (3.22 g, 10.2 mmol) was added to a sol. of compounds E4 (5.30 g, 10.2 mmol) in THF (110 mL) at 0° C. The mixture was stirred for 5 h at 0° C., and TBAF (3.22 g, 10.2 mmol) was added again. The mixture was stirred for 2 h at 0° C. EtOAc was added, and the mixture was washed with water and brine. The org. layer was dried over MgSO$_4$, filtered, and the solvents were removed under reduced pressure. Purification of the crude by FC (EtOAc/heptane 2:1→EtOAc) yielded the title compounds mixture (2.80 g, 68%). LC-MS: $t_R$=0.71 min; ES+: 406.41.

(rac.)-(1R*,2R*,3S*,5S*)-3-(4-Benzyloxy-phenyl)-8-aza-bicyclo[3.2.1]octane-2,8-dicarboxylic acid 8-tert-butyl ester 2-methyl ester (E6)

Mg (1.35 g, 55.6 mmol) was added to a sol. of compound B19 (5.00 g, 11.1 mmol) in MeOH (310 mL) at 0° C. The mixture was stirred for 2 h at rt, and Mg (1.35 g, 55.6 mmol) was added again. The mixture was stirred for 4 h at rt, and at reflux for 19 h. The mixture was allowed to cool to rt, and aq. sat. NH$_4$Cl was added. The mixture was extracted with EtOAc. The combined org. extracts were washed with water and brine, dried over MgSO$_4$, filtered, and the solvents were removed under reduced pressure. Purification of the crude by FC (heptane/EtOAc 85:15) yielded the title compound (760 mg, 15%). LC-MS: $t_R$=1.13 min; ES+: 452.23.

(rac.)-(1R*,2R*,3S*,5S*)-3-(4-Hydroxy-phenyl)-8-aza-bicyclo[3.2.1]octane-2,8-dicarboxylic acid 8-tert-butyl ester 2-methyl ester (E7)

Pd(OH)$_2$ on charcoal (20%, 76 mg) was added to a sol. of compound E6 (760 mg, 1.68 mmol) in MeOH (5.00 mL) and THF (5 mL). The mixture was purged with N$_2$, then with H$_2$. The mixture was stirred under an atmosphere of H$_2$ overnight. The mixture was filtered through celite, and the filtrate was evaporated under reduced pressure. Drying the residue under high vacuum yielded the crude title compound (590 mg, 97%) that was used further without purification. LC-MS: $t_R$=0.95 min; ES+: 347.36.

(S)-1-(5-Bromo-pyridin-2-yl)-pyrrolidin-3-ol (G1)

A mixture of 2,5-dibromopyridine (12.2 g, 51.5 mmol) and (S)-hydroxypyrrolidine (2.80 g, 32.1 mmol) in toluene (50 mL) was heated to reflux overnight. The mixture was allowed to cool to rt, and the solvents were removed under reduced pressure. The residue was dissolved with EtOAc (150 mL), and the mixture was washed with aq. 10% K$_2$CO$_3$. The org. layer was dried over MgSO$_4$, filtered, and the solvents were removed under reduced pressure. Purification of the residue by FC (heptane→heptane/EtOAc 1:2) yielded the title compound (3.62 g, 46%). LC-MS: $t_R$=0.48 min; ES+: 243.15.

(S)-5-Bromo-2-[3-(tert-butyl-dimethyl-silanyloxy)-pyrrolidin-1-yl]-pyridine (G2)

To a sol. of compound G1 (20.9 g, 85.8 mmol) in DMF (350 mL) at 0° C. were added imidazole (14.6 g, 215 mmol) and TBDMS-Cl (19.4 g, 129 mmol). This mixture was stirred at rt for 1.5 h, and aq. 10% K$_2$CO$_3$ (150 mL) was added. The mixture was extracted with heptane (2×). The combined org. extracts were dried over MgSO$_4$, filtered, and the solvents were removed under reduced pressure. Purification of the residue by FC (heptane/EtOAc 5:1→4:1→3:1→1:1) yielded the title compound (30.5 g, 99%).

(R)-1-(5-Bromo-pyridin-2-yl)-pyrrolidin-3-ol (G3)

A mixture of 2,5-dibromopyridine (10.0 g, 42.2 mmol) and (R)-hydroxypyrrolidine (11.0 g, 126 mmol) in toluene (50 mL) was heated to reflux overnight. The mixture was allowed to cool to rt, and the solvents were removed under reduced pressure. The residue was dissolved with EtOAc (150 mL), and the mixture was washed with aq. 10% K$_2$CO$_3$. The org. layer was dried over MgSO$_4$, filtered, and the solvents were removed under reduced pressure. Purification of the residue by FC (heptane→heptane/EtOAc 1:2) yielded the title compound (8.63 g, 84%). LC-MS: $t_R$=0.48 min; ES+: 243.15.

5-Bromo-2-[3-(2-chloro-3,6-difluoro-phenyl)-isoxazol-5-ylmethoxy]-pyridine (J1)

2,5-Dibromopyridine (12.6 g, 53.0 mmol) and [3-(2-chloro-3,6-difluoro-phenyl)-isoxazol-5-yl]-methanol (10.0 g, 40.7 mmol) were dissolved in toluene (400 mL). tBuONa (5.87 g, 61.1 mmol), xantphos (1.42 g, 2.45 mmol) and Pd$_2$(dba)$_3$ (732 mg, 0.800 mmol) were added to the sol. The resulting mixture was refluxed overnight, and was allowed to cool down to rt. The mixture was filtered through Celite (washed with EtOAc), and was washed with aq. sat. NaHCO$_3$ (1×) and brine (2×). The org. layer was dried over MgSO$_4$, filtered, and concentrated under reduced pressure. Purification of the crude by FC (EtOAc/heptane 10:90) yielded the title compound (10.6 g, 65%). LC-MS: $t_R$=1.10 min; ES+: 400.66.

(rac.)-(1R*,5S*)-3-{4-[2-(2,6-Dichloro-4-methyl-phenoxy)-ethoxy]-phenyl}-8-aza-bicyclo[3.2.1]oct-2-ene-2,8-dicarboxylic acid 8-tert-butyl ester (K1)

Compound C2 (3.82 g, 6.80 mmol) was dissolved in EtOH (100 mL). The sol. was heated to 70° C., and aq. 1M NaOH (80 mL, 80 mmol) was added. The mixture was stirred at 80° C. for 3 h, and allowed to cool to rt. The solvents were partially removed under reduced pressure, and the residue was poured into a separatory funnel filled with EtOAc. Aq. 1M HCl was added until the aq. phase was acidic, and the phases were shaken and separated. The aq. layer was extracted with EtOAc (2×), and the combined org. extracts were dried over MgSO$_4$, filtered, and the solvents were removed under reduced pressure. Drying the residue under high vacuum yielded the crude title compound mixed with (rac.)-(1R*,5S*)-3-{4-[2-(2,6-dichloro-4-methyl-phenoxy)-ethoxy]-phenyl}-8-aza-bicyclo[3.2.1]oct-3-ene-2,8-dicarboxylic acid 8-tert-butyl ester (3.45 g, 93%) that was used further without purification. LC-MS: $t_R$=1.13 min; ES+: 548.25.

4-{4-[2-(2,6-Dichloro-4-methyl-phenoxy)-ethoxy]-phenyl}-5,6-dihydro-2H-pyridine-1,3-dicarboxylic acid 1-tert-butyl ester (K2)

Aq. 1M LiOH (11.1 mL, 11.1 mmol) was added to a sol. of compound C3 (1.50 g, 2.72 mmol) in THF (10 mL). The mixture was stirred at 60° C. for 3 days. The mixture was allowed to cool to rt, and aq. 1M HCl was added, until the mixture was acidic. The mixture was extracted with EtOAc. The org. extracts were washed with aq. 1M HCl and brine, dried over MgSO$_4$, filtered, and the solvents were removed under reduced pressure. Purification of the crude by FC (heptane/EtOAc 1:2) yielded the title compound mixed with 4-{4-[2-(2,6-dichloro-4-methyl-phenoxy)-ethoxy]-phenyl}-3,6-dihydro-2H-pyridine-1,3-dicarboxylic acid 1-tert-butyl ester (1.41 g, 99%). LC-MS: $t_R$=1.10 min; ES+: 522.30.

(rac.)-(1R*,5S*)-7-{6-[2-(2,6-Dichloro-4-methyl-phenoxy)ethoxy]-pyridin-3-yl}-3,9-diaza-bicyclo[3.3.1]non-6-ene-3,6,9-tricarboxylic acid 3-tert-butyl ester 9-(2,2,2-trichloro-1,1-dimethyl-ethyl) ester (K3)

Compound C5 (1.02 g, 1.3 mmol) was dissolved in EtOH (14 mL), and aq. 1M NaOH (6 mL) was added. The mixture was heated to 80° C., and stirred at this temperature for 3 h. The mixture was allowed to cool to rt, and the solvents were partially removed under reduced pressure. The residue was mixed with EtOAc, and this mixture was acidified with aq. 1M HCl. The phases were partitioned, and the aq. layer was extracted with EtOAc (2×). The combined org. extracts were dried over MgSO$_4$, filtered, and the solvents were removed under reduced pressure. Drying under high vacuum yielded the crude title compound mixed with (rac.)-(1R*,5S*)-7-{6-[2-(2,6-dichloro-4-methyl-phenoxy)-ethoxy]-pyridin-3-yl}-3,9-diaza-bicyclo[3.3.1]non-7-ene-3,6,9-tricarboxylic acid 3-tert-butyl ester 9-(2,2,2-trichloro-1,1-dimethyl-ethyl) ester (864 mg, 87%), which was used further without purification. LC-MS: $t_R$=1.15 min; ES+: 768.23.

6-[2-(2,6-Dichloro-4-methyl-phenoxy)-ethoxy]-5',6'-dihydro-2'H-[3,4']bipyridinyl-1',3'-dicarboxylic acid 1'-tert-butyl ester (K4)

A mixture of compound C6 (1.00 g, 1.86 mmol) and aq. 1M LiOH (7.00 mL, 7.00 mmol) in THF (7.00 mL) was stirred at 70° C. overnight. Aq. 1M HCl was added until a pH of 4 was reached, and the mixture was extracted with EtOAc (3×). The combined org. extracts were dried over MgSO$_4$, filtered, and the solvents were removed under reduced pressure. Drying under high vacuum yielded the crude title compound mixed with 6-[2-(2,6-dichloro-4-methyl-phenoxy)-ethoxy]-3',6'-dihydro-2'H-[3,4']bipyridinyl-1',3'-dicarboxylic acid 1'-tert-butyl ester (850 mg, 87%) that was used further without purification.

4-{4-[3-(2-Chloro-3,6-difluoro-phenyl)-isoxazol-5-ylmethoxy]-phenyl}-5,6-dihydro-2H-pyridine-1,3-dicarboxylic acid 1-tert-butyl ester (K5)

Aq. 1M LiOH (15.0 mL, 15.0 mmol) was added to a sol. of compound C7 (2.04 g, 3.64 mmol) in THF (15 mL). The mixture was stirred at 60° C. for 3 days, and aq. 1M HCl was added. The mixture was extracted with EtOAc (2×). The combined org. extracts were washed with aq. 1M HCl and brine, dried over MgSO$_4$, filtered, and the solvents were removed under reduced pressure. Purification of the crude by FC (EtOAc) yielded the crude title compound mixed with 4-{4-[3-(2-chloro-3,6-difluoro-phenyl)-isoxazol-5-yl-methoxy]-phenyl}-3,6-dihydro-2H-pyridine-1,3-dicarboxylic acid 1-tert-butyl ester (600 mg, 30%). LC-MS: $t_R$=1.08 min; ES+: 547.20.

(rac.)-(3R*,4S*)-4-{4-[3-(2-Chloro-3,6-difluoro-phenyl)-isoxazol-5-ylmethoxy]-phenyl}-piperidine-1,3-dicarboxylic acid 1-tert-butyl ester (K6)

A sol. of compound D1 (2.00 g, 3.72 mmol) in THF (30 mL) and aq. 1M NaOH (30 mL) was stirred at 70° C. overnight. Aq. 1M HCl was added until a pH=4 was reached. The mixture was extracted with EtOAc (3×). The combined org. extracts were dried over MgSO$_4$, filtered, and the solvents were removed under reduced pressure. Drying under high vacuum yielded the crude title compound (2.04 g, quantitative yield) that was used further without purification. LC-MS: $t_R$=1.08 min; ES+: 549.31.

6-[3-(2-Chloro-3,6-difluoro-phenyl)-isoxazol-5-ylmethoxy]-5',6'-dihydro-2'H-[3,4']bipyridinyl-1',3'-dicarboxylic acid 1'-tert-butyl ester (K7)

A mixture of compound C8 (1.00 g, 1.78 mmol) and aq. 1M LiOH (7.00 mL, 7.00 mmol) in THF (7.00 mL) was stirred overnight at 70° C. Aq. 1M HCl was added until a pH=4 was reached. The mixture was extracted with EtOAc (3×). The combined org. extracts were dried over MgSO$_4$, filtered, and the solvents were removed under reduced pressure. Drying the residue under high vacuum yielded the title compound mixed with 6-[3-(2-chloro-3,6-difluoro-phenyl)-isoxazol-5-ylmethoxy]-3',6'-dihydro-2'H-[3,4']bipyridinyl-1',3'-dicarboxylic acid 1'-tert-butyl ester (976 mg, quantitative yield) that was used further without purification. LC-MS: $t_R$=1.06 min; ES+: 548.30.

(rac.)-(1R*,5S*)-3-Acetyl-7-{6-[2-(2,6-dichloro-4-methyl-phenoxy)-ethoxy]-pyridin-3-yl}-3,9-diaza-bicyclo[3.3.1]non-6-ene-6,9-dicarboxylic acid 9-(2,2,2-trichloro-1,1-dimethyl-ethyl) ester (K8)

To a sol. of compound C9 (3.03 g, 3.81 mmol) in EtOH (30 mL) was added aq. 1M NaOH (15 mL). This mixture was heated to 80° C., and stirred at this temperature for 2.5 h. The mixture was partially concentrated under reduced pressure. The residue was acidified with aq. 2M HCl, and the mixture was extracted with EtOAc. The combined org. extracts were dried over MgSO$_4$, filtered, and the solvents were removed under reduced pressure. Drying the residue under high vacuum yielded the crude title compound mixed with (rac.)-(1R*,5S*)-3-acetyl-7-{6-[2-(2,6-dichloro-4-methyl-phenoxy)-ethoxy]-pyridin-3-yl}-3,9-diaza-bicyclo[3.3.1]non-7-ene-6,9-dicarboxylic acid 9-(2,2,2-trichloro-1,1-dimethyl-ethyl) ester (2.70 g, quantitative yield) that was used further without purification. LC-MS: $t_R$=1.08 min; ES+: 710.09.

(rac.)-(1R*,2R*,3S*,5S*)-3-{4-[2-(2,6-Dichloro-4-methyl-phenoxy)-ethoxy]-phenyl}-8-aza-bicyclo[3.2.1]octane-2,8-dicarboxylic acid 8-tert-butyl ester (K9)

To a sol. of compound D2 (595 mg, 1.05 mmol) in EtOH (6.00 mL) was added aq. 1M NaOH (2.0 mL), and the resulting mixture was stirred at rt for 1 h, and at 70° C. overnight. The mixture was partially concentrated under reduced pressure, and the aq. residue was acidified with aq. 2M HCl. The mixture was extracted with EtOAc. The combined org. extracts were dried over MgSO$_4$, filtered, and the solvents were removed under reduced pressure. Drying the residue under high vacuum yielded the crude title compound (573 mg, 98%) that was used further without purification. LC-MS: t$_R$=1.11 min; ES+: 534.91.

(rac.)-(1R*,5S*)-3-{4-[3-(2-Chloro-3,6-difluoro-phenyl)-isoxazol-5-ylmethoxy]-phenyl}-8-aza-bicyclo[3.2.1]oct-2-ene-2,8-dicarboxylic acid 8-tert-butyl ester (K10)

A sol. of compound C10 (1.06 g, 1.80 mmol) in EtOH (26.4 mL) was heated to 70° C. Aq. 1M NaOH (20.6 mL) was added, and the mixture was stirred for 2 h at 70° C. The mixture was allowed to cool to rt, and the solvents were partially removed under reduced pressure. The residue was acidified to pH 1 with aq. 1M HCl, and was extracted with EtOAc (2×). The combined org. extracts were dried over MgSO$_4$, filtered, and the solvents were removed under reduced pressure. Drying under high vacuum yielded the crude title compound mixed with (rac.)-(1R*,5S*)-3-{4-[3-(2-chloro-3,6-difluoro-phenyl)-isoxazol-5-ylmethoxy]-phenyl}-8-aza-bicyclo[3.2.1]oct-3-ene-2,8-dicarboxylic acid 8-tert-butyl ester (1.00 g, 95%) that was used further without purification.

(rac.)-(1R*,5S*)-3-Acetyl-7-{6-[3-(2-chloro-3,6-difluoro-phenyl)-isoxazol-5-ylmethoxy]-pyridin-3-yl}-3,9-diaza-bicyclo[3.3.1]non-6-ene-6,9-dicarboxylic acid 9-(2,2,2-trichloro-1,1-dimethyl-ethyl) ester (K11)

A mixture of compounds C13 (762 mg, 1.00 mmol) in EtOH (30 mL) and aq. 1M NaOH (10 mL) was stirred at 75° C. for 2 h. The mixture was allowed to cool down to rt. The solvents were partially removed under reduced pressure, and the residue was acidified with aq. 1M HCl to a pH of 2-3. The mixture was extracted with EtOAc. The combined org. extracts were dried over MgSO$_4$, filtered, and the solvents were removed under reduced pressure. Drying the residue under high vacuum yielded the crude title compound mixed with (rac.)-(1R*,5S*)-3-acetyl-7-{6-[3-(2-chloro-3,6-difluoro-phenyl)-isoxazol-5-ylmethoxy]-pyridin-3-yl}-3,9-diaza-bicyclo[3.3.1]non-7-ene-6,9-dicarboxylic acid 9-(2,2,2-trichloro-1,1-dimethyl-ethyl) ester (690 mg, 94%) that was used without further purification. LC-MS: t$_R$=1.06 min; ES+: 735.00.

(rac.)-(3R*,4S*)-6-[2-(2,6-Dichloro-4-methyl-phenoxy)-ethoxy]-3',4',5',6'-tetrahydro-2'H-[3,4']bipyridinyl-1',3'-dicarboxylic acid 1'-tert-butyl ester (K16)

A mixture of compound D4 (4.92 g, 9.12 mmol) in aq. 1M NaOH (75 mL) and MeOH (75 mL) was stirred for 4.5 h at 70° C. Aq. 1M HCl was added until a pH of about 4 was reached. The mixture was extracted with EtOAc (3×). The combined org. extracts were washed with brine, dried over MgSO$_4$, filtered, and the solvents were removed under reduced pressure. Drying the residue under high vacuum yielded the crude title compound (4.63 g, 97%) that was used further without purification. LC-MS: t$_R$=1.08 min, ES+: 525.40.

(rac.)-(1R*,5S*)-7-{4-[3-(2-Chloro-3,6-difluoro-phenyl)-isoxazol-5-ylmethoxy]-phenyl}-3,9-diaza-bicyclo[3.3.1]non-6-ene-3,6,9-tricarboxylic acid 3-tert-butyl ester 9-(2,2,2-trichloro-1,1-dimethyl-ethyl) ester (K17)

A mixture of compound C20 (1.29 g, 1.57 mmol) in EtOH (16 mL) and aq. 1M NaOH (16 mL) was heated to reflux overnight. The mixture was allowed to cool to rt, and the solvents were partially removed under reduced pressure. The residue was acidified with aq. 1M HCl, and the resulting mixture was extracted with EtOAc (3×). The combined org. extracts were washed with brine, dried over MgSO$_4$, filtered, and the solvents were removed under reduced pressure. Drying the residue under high vacuum yielded the crude title compound mixed with (rac.)-(1R*,5S*)-7-{4-[3-(2-chloro-3,6-difluoro-phenyl)-isoxazol-5-ylmethoxy]-phenyl}-3,9-diaza-bicyclo[3.3.1]non-7-ene-3,6,9-tricarboxylic acid 3-tert-butyl ester 9-(2,2,2-trichloro-1,1-dimethyl-ethyl) ester (1.24 g, 99%) that was used further without purification. LC-MS: t$_R$=1.15 min, ES+: 792.38.

(rac.)-(1R*,5S*)-3-{6-[2-(2,6-Dichloro-4-methyl-phenoxy)-ethoxy]-pyridin-3-yl}-8-aza-bicyclo[3.2.1]oct-2-ene-2,8-dicarboxylic acid 8-tert-butyl ester (K18)

Compound C21 was dissolved in a 1:1-mixture of MeOH and THF (50 mL). Aq. 2M NaOH (27 mL) was added, and the mixture was stirred at rt overnight. The solvents were partially removed under reduced pressure, and the residue was acidified to pH 1 with aq. 1M HCl. The mixture was extracted with EtOAc. The org. extracts were dried over MgSO$_4$, filtered, and the solvents were removed under reduced pressure. Drying the residue under high vacuum yielded the crude title compound mixed with (rac.)-(1R*,5S*)-3-{6-[2-(2,6-dichloro-4-methyl-phenoxy)-ethoxy]-pyridin-3-yl}-8-aza-bicyclo[3.2.1]oct-3-ene-2,8-dicarboxylic acid 8-tert-butyl ester (1.91 g, 98%) that was used further without purification. LC-MS: t$_R$=1.09 min, ES+: 548.96.

(rac.)-(1R*,5S*)-3-{6-[3-(2-Chloro-3,6-difluoro-phenyl)-isoxazol-5-ylmethoxy]-pyridin-3-yl}-8-aza-bicyclo[3.2.1]oct-2-ene-2,8-dicarboxylic acid 8-tert-butyl ester (K19)

Compound C22 (588 Mg, 1.00 Mmol) was Dissolved in MeOH (30 Ml), and Aq. 1M NaOH (10 mL) was added. The resulting suspension was heated to reflux for 2 h. The mixture was allowed to cool to rt, and the solvents were partially removed under reduced pressure. The aq. residue was treated with aq. 1M HCl in order to reach a pH of ca. 2-3. The mixture was extracted with EtOAc (3×). The combined org. layers were dried over MgSO$_4$, filtered, and the solvents were removed under reduced pressure. Drying the residue under high vacuum yielded the crude title compound mixed with (rac.)-(1R*,5S*)-3-{6-[3-(2-chloro-3,6-difluoro-phenyl)-isoxazol-5-ylmethoxy]-pyridin-3-yl}-8-aza-bicyclo[3.2.1] oct-3-ene-2,8-dicarboxylic acid 8-tert-butyl ester (581 mg, quantitative yield) that was used further without purification. LC-MS: t$_R$=1.06 min, ES+: 574.16.

Mixture of (1R,5S)-3-{4-[(R)-3-(2,6-dichloro-4-methyl-phenoxy)-pyrrolidin-1-yl]-phenyl}-8-aza-bicyclo[3.2.1]oct-2-ene-2,8-dicarboxylic acid 8-tert-butyl ester and (1S,5R)-3-{4-[(R)-3-(2,6-dichloro-4-methyl-phenoxy)-pyrrolidin-1-yl]-phenyl}-8-aza-bicyclo[3.2.1]oct-2-ene-2,8-dicarboxylic acid 8-tert-butyl ester (K20)

A suspension of compounds C23 (587 mg, 1.00 mmol) in MeOH (30 mL) and aq. 1M NaOH (10 mL) was heated to reflux for 24 h. The mixture was allowed to cool to rt, and the solvents were partially removed under reduced pressure. The aq. residue was treated with aq. 1M HCl in order to reach a pH of ca. 2-3, and the mixture was extracted with EtOAc (3×). The combined org. extracts were dried over MgSO$_4$, filtered, and the solvents were removed under reduced pressure. Drying the residue overnight at high vacuum yielded the crude title compounds mixed with a mixture of (1R,5S)-3-{4-[(R)-3-(2,6-dichloro-4-methyl-phenoxy)-pyrrolidin-1-yl]-phenyl}-8-aza-bicyclo[3.2.1]oct-3-ene-2,8-dicarboxylic acid 8-tert-butyl ester and (1S,5R)-3-{4-[(R)-3-(2,6-dichloro-4-methyl-phenoxy)-pyrrolidin-1-yl]-phenyl}-8-aza-bicyclo[3.2.1]oct-3-ene-2,8-dicarboxylic acid 8-tert-butyl ester (592 mg, quantitative yield) that was used further without purification. LC-MS: $t_R$=1.15 min, ES+: 573.20.

Mixture of (1R,5S)-7-{6-[(R)-3-(2,6-dichloro-4-methyl-phenoxy)-pyrrolidin-1-yl]-pyridin-3-yl}-3,9-diaza-bicyclo[3.3.1]non-6-ene-3,6,9-tricarboxylic acid 3,9-di-tert-butyl ester and (1S,5R)-7-{6-[(R)-3-(2,6-dichloro-4-methyl-phenoxy)-pyrrolidin-1-yl]-pyridin-3-yl}-3,9-diaza-bicyclo[3.3.1]non-6-ene-3,6,9-tricarboxylic acid 3,9-di-tert-butyl ester (K21)

A mixture of compounds C24 (1.20 g, 1.67 mmol) in EtOH (18 mL) and aq. 1M NaOH (6.00 mL) was stirred at rt for 1 h and at 70° C. for 5.5 h. The mixture was allowed to cool to rt, and was partially concentrated under reduced pressure. The aq. residue was acidified with aq. 2M HCl, and the mixture was extracted with EtOAc. The combined org. extracts were dried over MgSO$_4$, filtered, and the solvents were removed under reduced pressure. Drying the residue under high vacuum yielded the crude title compounds mixed with (1R,5S)-7-{6-[(R)-3-(2,6-dichloro-4-methyl-phenoxy)-pyrrolidin-1-yl]-pyridin-3-yl}-3,9-diaza-bicyclo[3.3.1]non-7-ene-3,6,9-tricarboxylic acid 3,9-di-tert-butyl ester and (1S,5R)-7-{6-[(R)-3-(2,6-dichloro-4-methyl-phenoxy)-pyrrolidin-1-yl]-pyridin-3-yl}-3,9-diaza-bicyclo[3.3.1]non-7-ene-3,6,9-tricarboxylic acid 3,9-di-tert-butyl ester (1.15 g, quantitative yield) that was used further without purification. LC-MS: $t_R$=0.94 min, ES+: 689.19.

Mixture of (1R,5S)-7-{6-[(R)-3-(2-chloro-3,6-difluoro-phenoxy)-pyrrolidin-1-yl]-pyridin-3-yl}-3,9-diaza-bicyclo[3.3.1]non-6-ene-3,6,9-tricarboxylic acid 3,9-di-tert-butyl ester and (1S,5R)-7-{6-[(R)-3-(2-chloro-3,6-difluoro-phenoxy)-pyrrolidin-1-yl]-pyridin-3-yl}-3,9-diaza-bicyclo[3.3.1]non-6-ene-3,6,9-tricarboxylic acid 3,9-di-tert-butyl ester (K22)

A mixture of compounds C25 (1.18 g, 1.67 mmol) in EtOH (18 mL) and aq. 1M NaOH (6.00 mL) was stirred at rt for 1 h and at 70° C. for 5.5 h. The mixture was allowed to cool to rt, and was partially concentrated under reduced pressure. The aq. residue was acidified with aq. 2M HCl, and the mixture was extracted with EtOAc. The combined org. extracts were dried over MgSO$_4$, filtered, and the solvents were removed under reduced pressure. Drying the residue under high vacuum yielded the crude title compounds mixed with (1R,5S)-7-{6-[(R)-3-(2-chloro-3,6-difluoro-phenoxy)-pyrrolidin-1-yl]-pyridin-3-yl}-3,9-diaza-bicyclo[3.3.1]non-7-ene-3,6,9-tricarboxylic acid 3,9-di-tert-butyl ester and (1S,5R)-7-{6-[(R)-3-(2-chloro-3,6-difluoro-phenoxy)-pyrrolidin-1-yl]-pyridin-3-yl}-3,9-diaza-bicyclo[3.3.1]non-7-ene-3,6,9-tricarboxylic acid 3,9-di-tert-butyl ester (1.13 g, quantitative yield) that was used further without purification. LC-MS: $t_R$=0.92 min, ES+: 677.21.

(3R,4S)-4-{4-[2-(2,6-Dichloro-4-methyl-phenoxy)-ethoxy]-phenyl}-piperidine-1,3-dicarboxylic acid 1-tert-butyl ester (K23)

A mixture of compound D7 (4.31 g, 8 mmol) in MeOH (50 mL) and aq. 1M NaOH (79 mL) was stirred at 80° C. for 8 h. The mixture was allowed to cool to rt, and aq. 2M HCl (50 mL) was added. The mixture was extracted with EtOAc. The combined org. extracts were washed with brine, dried over MgSO$_4$, filtered, and the solvents were removed under reduced pressure. Drying the residue under high vacuum yielded the crude title compound (4.18 g, quantitative yield). LC-MS: $t_R$=1.12 min, ES+: 524.41.

(rac.)-(1R*,2R*,3S*,5S*)-3-{6-[2-(2,6-Dichloro-4-methyl-phenoxy)-ethoxy]-pyridin-3-yl}-8-aza-bicyclo[3.2.1]octane-2,8-dicarboxylic acid 8-tert-butyl ester (K24)

Aq. 1M NaOH (6.50 mL) was added to a sol. of compound D8 (1.19 g, 2.10 mmol) in EtOH (12 mL). The mixture was heated to 70° C. for 2 h. The mixture was allowed to cool to rt, and the solvents were partially removed under reduced pressure. The resulting mixture was partitioned between EtOAc and aq. 2M HCl. The phases were separated, and the aq. phase was extracted with EtOAc (2×). The combined org. extracts were dried over MgSO$_4$, filtered, and the solvents were removed under reduced pressure. Drying the residue under high vacuum yielded the crude title compound (1.07 g, 92%) that was used further without purification. LC-MS: $t_R$=1.08 min, ES+: 551.33.

(rac.)-(1R,5S*)-7-{4-[3-(2-Chloro-3,6-difluoro-phenyl)-isoxazol-5-ylmethoxy]-phenyl}-3,9-diaza-bicyclo[3.3.1]non-6-ene-3,6,9-tricarboxylic acid 3,9-di-tert-butyl ester (K25)

A mixture of compound C27 (1.58 g, 2.21 mmol) in EtOH (22 mL) and aq. 1M NaOH (22 mL) was heated to reflux for 4 h. The mixture was allowed to cool to rt, and the solvents were partially removed under reduced pressure. The residue was partitioned between aq. 1M HCl and EtOAc. The aq. layer was extracted with EtOAc. The combined org. extracts were washed with brine, dried over MgSO$_4$, filtered, and the solvents were removed under reduced pressure. Drying the residue under high vacuum yielded the crude title compound together with (rac.)-(1R*,5S*)-7-{4-[3-(2-chloro-3,6-difluoro-phenyl)-isoxazol-5-ylmethoxy]-phenyl}-3,9-diaza-bicyclo[3.3.1]non-7-ene-3,6,9-tricarboxylic acid 3,9-di-tert-butyl ester (1.49 g, 98%) that was used further without purification. LC-MS: $t_R$=1.08 min, ES+: 688.1.

(rac.)-(1R*,5S*)-3-Acetyl-7-{4-[3-(2-chloro-3,6-difluoro-phenyl)-isoxazol-5-ylmethoxy]-phenyl}-3,9-diaza-bicyclo[3.3.1]non-6-ene-6,9-dicarboxylic acid 9-tert-butyl ester (K26)

A mixture of compound C30 (750 mg, 1.14 mmol) in EtOH (11 mL) and aq. 1M NaOH (11 mL) was heated to reflux for 2 h. The mixture was allowed to cool to rt, and the solvents were removed under reduced pressure. The residue was partitioned between aq. 1M HCl and EtOAc. The aq. layer was extracted with EtOAc. The combined org. extracts were washed with brine, dried over MgSO$_4$, filtered, and the solvents were removed under reduced pressure. Drying the residue under high vacuum yielded the crude title compound together with (rac.)-(1R*,5S*)-3-acetyl-7-{4-[3-(2-chloro-3, 6-difluoro-phenyl)-isoxazol-5-ylmethoxy]-phenyl}-3,9-diaza-bicyclo[3.3.1]non-7-ene-6,9-dicarboxylic acid 9-tert-butyl ester (720 mg, quantitative yield) that was used further without purification. LC-MS: $t_R$=1.00 min, ES+: 630.15.

(rac.)-(1R*,5S*)-7-{6-[3-(2-Chloro-3,6-difluoro-phenyl)-isoxazol-5-ylmethoxy]-pyridin-3-yl}-3,9-diaza-bicyclo[3.3.1]non-6-ene-3,6,9-tricarboxylic acid 3,9-di-tert-butyl ester (K27)

A mixture of compound C31 (703 mg, 1.00 mmol) in MeOH (30 mL) and aq. 1M NaOH (10 mL) was heated to reflux for 2 h. The mixture was allowed to cool to rt, and the solvents were partially removed under reduced pressure. The aq. residue was treated with aq. 1M HCl in order to reach a pH of ca. 2-3, and the mixture was extracted with EtOAc (3×). The combined org. extracts were dried over MgSO$_4$, filtered, and the solvents were removed under reduced pressure. Drying the residue under high vacuum yielded the crude title compound mixed with (rac.)-(1R*,5S*)-7-{6-[3-(2-chloro-3,6-difluoro-phenyl)-isoxazol-5-ylmethoxy]-pyridin-3-yl}-3,9-diaza-bicyclo[3.3.1]non-7-ene-3,6,9-tricarboxylic acid 3,9-di-tert-butyl ester (726 mg, quantitative yield) that was used further without purification. LC-MS: $t_R$=1.08 min, ES+: 689.50.

Mixture of (1R,2R,3S,5S)-3-{4-[(R)-3-(2,6-dichloro-4-methyl-phenoxy)-pyrrolidin-1-yl]-phenyl}-8-aza-bicyclo[3.2.1]octane-2,8-dicarboxylic acid 8-tert-butyl ester and (1S,3R,5R)-3-{4-[(R-3-(2,6-dichloro-4-methyl-phenoxy)-pyrrolidin-1-yl]-phenyl}-8-aza-bicyclo[3.2.1]octane-2,8-dicarboxylic acid 8-tert-butyl ester (K28)

A mixture of compounds D9 (778 mg, 1.32 mmol) in EtOH (7.5 mL) and aq. 1M NaOH (2.5 mL) was heated to 70° C. overnight. The mixture was allowed to cool to rt, and EtOAc was added. The mixture was acidified with aq. 2M HCl, and was extracted with EtOAc (3×). The combined org. extracts were dried over MgSO$_4$, filtered, and the solvents were removed under reduced pressure. Drying the residue under high vacuum yielded the crude title compounds mixture (740 mg, 97%) that was used further without purification. LC-MS: $t_R$=1.17 min, ES+: 575.21.

Mixture of (1R,2R,3S,5S)-3-{6-[(R)-3-(2,6-dichloro-4-methyl-phenoxy)-pyrrolidin-1-yl]-pyridin-3-yl}-8-aza-bicyclo[3.2.1]octane-2,8-dicarboxylic acid 8-tert-butyl ester, (1S,2S,3R,5R)-3-{6-[(R)-3-(2,6-dichloro-4-methyl-phenoxy)-pyrrolidin-1-yl]-pyridin-3-yl}-8-aza-bicyclo[3.2.1]octane-2,8-dicarboxylic acid 8-tert-butyl ester, (1R,2S,3R,5S)-3-{6-[(R-3-(2,6-dichloro-4-methyl-phenoxy)-pyrrolidin-1-yl]-pyridin-3-yl}-8-aza-bicyclo[3.2.1]octane-2,8-dicarboxylic acid 8-tert-butyl ester, and (1S,2R,3S,5R)-3-{6-[(R)-3-(2,6-dichloro-4-methyl-phenoxy)-pyrrolidin-1-yl]-pyridin-3-yl}-8-aza-bicyclo[3.2.1]octane-2,8-dicarboxylic acid 8-tert-butyl ester (K29)

A mixture of compounds D10 (1.24 g, 2.10 mmol) in EtOH (12 mL) and aq. 1M NaOH (6.50 mL) was stirred at 70° C. for 2 h. The mixture was allowed to cool to rt, and the solvents were partially removed under reduced pressure. The aq. residue was partitioned between EtOAc and aq. 2M HCl. The layers were separated, and the aq. layer was extracted with EtOAc (2×). The combined org. extracts were dried over MgSO$_4$, filtered, and the solvents were removed under reduced pressure. Drying the residue under high vacuum yielded the crude title compounds mixture (1.17 g, 97%) that was used further without purification.

Mixture of (3'R,4'S)-6-[(R-3-(2,6-dichloro-4-methyl-phenoxy)-pyrrolidin-1-yl]-3',4',5',6'-tetrahydro-2'H-[3,4']bipyridinyl-1',3'-dicarboxylic acid 1'-tert-butyl ester and (3'S,4'R)-6-[(R)-3-(2,6-dichloro-4-methyl-phenoxy)-pyrrolidin-1-yl]-3',4',5',6'-tetrahydro-2'H-[3,4']bipyridinyl-[1,3']-dicarboxylic acid 1'-tert-butyl ester (K30)

A mixture of compounds D12 (2.74 g, 5.08 mmol) in MeOH (50 mL) and aq. 1M NaOH (50 mL) was stirred for 4 h at 70° C. The mixture was allowed to cool to rt, and aq. 1M HCl was added until pH~7. The solvents were partially removed under reduced pressure, and the aq. residue was extracted EtOAc (3×). The combined org. extracts were washed with brine, dried over MgSO$_4$, filtered, and the solvents were removed under reduced pressure. Drying the residue under high vacuum yielded the crude title compounds mixture (2.10 g, 75%), that was used without further purification. LC-MS: $t_R$=0.91 min, ES+: 550.15.

(rac.)-(1R*,2R*,3S*,5S*)-3-{4-[3-(2-Chloro-3,6-difluoro-phenyl)-isoxazol-5-ylmethoxy]-phenyl}-8-aza-bicyclo[3.2.1]octane-2,8-dicarboxylic acid 8-tert-butyl ester (K31)

To a sol. of compound D13 (772 mg, 1.31 mmol) in EtOH (7.00 mL) was added aq. 1M NaOH (2.60 mL), and the mixture was stirred at 70° C. for 2 h. The mixture was partially evaporated under reduced pressure, and partitioned between water and EtOAc. The aq. layer was acidified with aq. 1M HCl, and extracted with EtOAc. The combined org. extracts were washed with brine, dried over MgSO$_4$, filtered, and the solvents were removed under reduced pressure. Drying the residue under high vacuum yielded the crude title compound (706 mg, 94%) that was used further without purification. LC-MS: $t_R$=1.07 min, ES+: 575.17.

Mixture of (3'R,4'S)-6-[(S)-3-(2,6-dichloro-4-methyl-phenoxy)-pyrrolidin-1-yl]-3',4',5',6'-tetrahydro-2'H-[3,4']bipyridinyl-1',3'-dicarboxylic acid 1'-tert-butyl ester and (3'S,4'R)-6-[(S)-3-(2,6-dichloro-4-methyl-phenoxy)-pyrrolidin-1-yl]-3',4',5',6'-tetrahydro-2'H-[3,4']bipyridinyl-1',3'-dicarboxylic acid 1'-tert-butyl ester (K32)

Compound D14 (1.55 g, 2.82 mmol) was dissolved in MeOH (28 μL). Aq. 1M NaOH (14 mL) was added, and the mixture was heated to reflux for 2 h. The mixture was allowed to cool down to rt, and aq. 1M HCl was added in order to reach a pH=5-6. The solvents were partially removed under reduced pressure, and the aq. residue was extracted with EtOAc. The org. extracts were washed with aq. sat. NH$_4$Cl, dried over MgSO$_4$, filtered, and the solvents were removed under reduced pressure. Drying the crude under high vacuum yielded the crude title compounds mixture (1.38 g, 89%) that was used further without purification. LC-MS: $t_R$=0.89 min, ES+: 550.35.

(rac.)-(3'R,4'S)-6-[3-(2-Chloro-3,6-difluoro-phenyl)-isoxazol-5-ylmethoxy]-3',4',5',6'-tetrahydro-2'H-[3,4']bipyridinyl-1',3'-dicarboxylic acid 1'-tert-butyl ester (K33)

A mixture of compound D16 (800 mg, 1.38 mmol) in aq. 1M NaOH (14 mL) and EtOH (28 mL) was stirred at 80° C.

for 2 h. The mixture was allowed to cool to rt, and the solvents were partially removed under reduced pressure. Aq. 1M HCl was added until a pH=7 was reached, and the mixture was extracted with EtOAc (2×). The combined org. extracts were washed with brine, dried over MgSO$_4$, filtered, and the solvents were removed under reduced pressure. Drying the residue under high vacuum yielded the crude title compound (757 mg, 99%) that was used further without purification. LC-MS: $t_R$=1.05 min, ES+: 550.38.

(rac.)-(1R*,5S*)-6-{[2-Chloro-5-(3-methoxy-propyl)-benzyl]cyclopropyl-carbamoyl}-7-{4-[2-(2,6-dichloro-4-methyl-phenoxy)-ethyl]-phenyl}-3,9-diaza-bicyclo[3.3.1]non-6-ene-3,9-dicarboxylic acid di-tert-butyl ester (L1)

(rac.)-(1R*,5S*)-7-{4-[2-(2,6-Dichloro-4-methyl-phenoxy)-ethyl]-phenyl}-3,9-diaza-bicyclo[3.3.1]non-6-ene-3,6,9-tricarboxylic acid 3,9-di-tert-butyl ester (300 mg, 0.463 mmol) was dissolved in toluene (10 if L). DMF (1.8 µL) and oxalyl chloride (52.7 µl, 0.6 mmol) were added. The mixture was stirred at rt for 1 h. The solvents were thoroughly removed under reduced pressure, and the residue was dissolved in CH$_2$Cl$_2$ (7.5 µL). A sol. of [2-chloro-5-(3-methoxy-propyl)-benzyl]-cyclopropyl-amine (176 mg, 0.693 mmol) and Et$_3$N (97 µL, 0.693 mmol) in CH$_2$Cl$_2$ (7.5 mL) was added over 10 min, then the mixture was stirred for 30 min. The mixture was evaporated and the residue was partitioned between Et$_2$O and aq. 1M HCl. The org. fraction was washed with aq. sat. NaHCO$_3$, and brine. The org. layer was dried over MgSO$_4$, filtered, and the solvents were removed under reduced pressure. A sol. of this residue (402 mg, 0.455 mmol) and NaOEt (21% in EtOH, 0.257 mL, 0.683 mmol) in EtOH (2.84 mL) was heated at 80° C. overnight. The mixture was evaporated under reduced pressure, and the residue was dissolved in Et$_2$O. This mixture was washed with aq. 1M HCl, aq. sat. NaHCO$_3$, and brine. The org. layer was dried over MgSO$_4$, filtered, and the solvents were removed under reduced pressure. Purification of the residue by FC yielded the title compound (300 mg).

(1R,5S)-6-{Cyclopropyl-[2-chloro-5-(3-methoxy-propyl)-benzyl]-carbamoyl}-7-{4-[2-(2,6-dichloro-4-methyl-phenoxy)-ethoxy]-phenyl}-3,9-diaza-bicyclo[3.3.1]non-6-ene-9-carboxylic acid tert-butyl ester (L2)

To a sol. of Example 4 (6.77 mmol) in THF (67.7 mL) was added trityl bromide (2.298 g, 7.11 mmol) and Et$_3$N (2.85 mL, 20.31 mmol). The mixture was stirred overnight, then 2 more portions of reagents, 10% each, were added at 1 hour intervals. The solvent was evaporated under reduced pressure, and the residue was purified by FC to afford (1R,5S)-7-{4-[2-(2,6-dichloro-4-methyl-phenoxy)-ethoxy]-phenyl}-3-trityl-3,9-diaza-bicyclo[3.3.1]non-6-ene-6-carboxylic acid cyclopropyl-[2,3-dichloro-5-(3-methoxy-propyl)-benzyl]-amide (5.21 mmol). To a sol. of this compound (5.21 mmol) in CH$_2$Cl$_2$ (52.1 mL) was added Boc$_2$O (2.84 g, 13.03 mmol) and DIPEA (2.73 if L, 15.63 mmol). The mixture was stirred overnight, and the solvents were evaporated under reduced pressure. The residue was purified by FC to afford (1R,5S)-6-{cyclopropyl-[2,3-dichloro-5-(3-methoxy-propyl)-benzyl]-carbamoyl}-7-{4-[2-(2,6-dichloro-4-methyl-phenoxy)-ethoxy]-phenyl}-3-trityl-3,9-diaza-bicyclo[3.3.1]non-6-ene-9-carboxylic acid tert-butyl ester (4.46 mmol). A sol. of this compound (4.46 mmol) in AcOH (34.9 mL) and water (3.48 µL) was heated at 60° C. for 1 h 17 min. The solvent was evaporated, and azeotropically evaporated again with heptane (2×) and purified by silica gel chromatography to afford the title compound.

(rac.)-(1R*,5S*)-2-{[2-Chloro-5-(3-methoxy-propyl)-benzyl]-cyclopropyl-carbamoyl}-3-{4-[2-(2,6-dichloro-4-methyl-phenoxy)-ethoxy]-phenyl}-8-aza-bicyclo[3.2.1]oct-2-ene-8-carboxylic acid tert-butyl ester (L3)

A mixture of compound K1 (3.15 g, 5.75 mmol), DIPEA (2.97 mL, 23.0 mmol), DMAP (175 mg, 1.44 mmol), HOBt (970 mg, 7.19 mmol) and EDC.HCl (1.65 g, 8.63 mmol) in CH$_2$Cl$_2$ (110 mL) was stirred for 1 h at rt. [2-Chloro-5-(3-methoxy-propyl)-benzyl]-cyclopropyl-amine (4.38 g, 17.3 mmol) was added, and the mixture was stirred at rt for 8 days. The mixture was diluted with CH$_2$Cl$_2$, and washed with aq. 1M HCl (3×) and aq. sat. NaHCO$_3$ (1×). The org. layer was dried over MgSO$_4$, filtered, and the solvents were removed under reduced pressure. Purification of the crude by FC (EtOAc/heptane 3:7) yielded the title compound (3.45 g, 77%). LC-MS: $t_R$=1.28 min; ES+: 785.38.

5-{[2-Chloro-5-(3-methoxy-propyl)-benzyl]-cyclopropyl-carbamoyl}-4-{4-[2-(2,6-dichloro-4-methyl-phenoxy)-ethoxy]-phenyl}-3,6-dihydro-2H-pyridine-1-carboxylic Acid tert-butyl ester (L4)

To a sol. of the compound K2 (400 mg, 0.766 mmol) in CH$_2$Cl$_2$ (8 mL) were added HOBt (129 mg, 0.957 mmol), DIPEA (0.524 mL, 3.06 mmol), DMAP (23.3 mg, 0.191 mmol), [2-chloro-5-(3-methoxy-propyl)-benzyl]-cyclopropyl-amine (291 mg, 1.15 mmol), and EDC.HCl (220 mg, 1.15 mmol). The mixture was stirred for 24 h, and was diluted with CH$_2$Cl$_2$. The mixture was washed with aq. 1M HCl and water, dried over Na$_2$SO$_4$, filtered, and the solvents were evaporated under reduced pressure. Purification by FC (EtOAc/heptane/CH$_2$Cl$_2$ 3:6:1 with 1% Et$_3$N) yielded the title compound (406 mg, 70%). LC-MS: $t_R$=1.27 min; ES+: 759.42.

(rac.)-(1R*,5S*)-6-{[2-Chloro-5-(3-methoxy-propyl)benzyl]-cyclopropyl-carbamoyl}-7-{6-[2-(2,6-dichloro-4-methyl-phenoxy)-ethoxy]-pyridin-3-yl}-3,9-diaza-bicyclo[3.3.1]non-6-ene-3,9-dicarboxylic acid 3-tert-butyl ester 9-(2,2,2-trichloro-1,1-dimethyl-ethyl) ester (L5)

A mixture of compound K3 (805 mg, 1.05 mmol), DIPEA (0.72 mL, 4.20 mmol), DMAP (32.1 mg, 0.263 mmol), HOBt (177 mg, 1.31 mmol) and EDC.HCl (302 mg, 1.58 mmol) in CH$_2$Cl$_2$ (15 mL) was stirred at rt for 1 h. [2-Chloro-5-(3-methoxy-propyl)-benzyl]-cyclopropyl-amine (535 mg, 2.10 mmol) was added, and the mixture was stirred for 4 days. EDC.HCl (140 mg, 0.709 mmol), HOBt (100 mg, 0.741 mmol) and [2-chloro-5-(3-methoxy-propyl)-benzyl]-cyclopropyl-amine (270 mg, 1.06 mmol) were added again. The mixture was stirred for 6 days, and EDC.HCl (100 mg, 0.506 mmol), and HOBt (30 mg, 0.222 mmol) were added. The mixture was stirred for 24 h, and was diluted with more CH$_2$Cl$_2$. The mixture was washed with aq. 1M HCl (2×), and aq. 10% Na$_2$CO$_3$ (1×). The org. layer was dried over MgSO$_4$, filtered, and the solvents were removed under reduced pressure. Purification of the crude by FC (EtOAc/heptane 1:9) yielded the title compound (580 mg, 55%). LC-MS: $t_R$=1.32 min; ES+: 1003.40.

5'-{[2-Chloro-5-(3-methoxy-propyl)-benzyl]-cyclopropyl-carbamoyl}-6-[2-(2,6-dichloro-4-methyl-phenoxy)-ethoxy]-3',6'-dihydro-2'H-[3,4']bipyridinyl-1'-carboxylic acid tert-butyl ester (L6)

A mixture of compound K4 (484 mg, 0.925 mmol), [2-chloro-5-(3-methoxy-propyl)-benzyl]-cyclopropyl-amine (352 mg, 1.39 mmol), HOBt (156 mg, 1.16 mmol), DMAP (28.3 mg, 0.232 mmol), DIPEA (0.631 mL, 3.69 mmol), and EDC.HCl (265 mg, 1.38 mmol) in $CH_2Cl_2$ (8 mL) was stirred overnight at rt. $CH_2Cl_2$ was added, and the mixture was stirred with aq. 1M HCl (1×), water (1×), and brine (1×). The org. layer was dried over $MgSO_4$, filtered, and the solvents were removed under reduced pressure. Purification of the residue by FC (MeOH/$CH_2Cl_2$ 1:49→1:19 with 2% $Et_3N$) yielded the title compound (570 mg, 81%). LC-MS: $t_R$=1.28 min; ES+: 607.46.

4-{4-[3-(2-Chloro-3,6-difluoro-phenyl)-isoxazol-5-ylmethoxy]-phenyl}-5-{[2-chloro-5-(3-methoxy-propyl)-benzyl]-cyclopropyl-carbamoyl}-3,6-dihydro-2H-pyridine-1-carboxylic acid tert-butyl ester (L7)

A mixture of compound K5 (6004 mg, 1.10 mmol), [2-chloro-5-(3-methoxy-propyl)-benzyl]-cyclopropyl-amine (334 mg, 1.32 mmol), HOBt (185 mg, 1.37 mmol), DMAP (33.6 mg, 0.285 mmol), DIPEA (0.751 mL, 4.39 mmol), and EDC.HCl (315 mg, 1.64 mmol) in $CH_2Cl_2$ (4 mL) was stirred for 2 days at rt. The mixture was filtered through Isolute® (0.6 g) pre-washed with aq. 1M HCl. The org. extracts were dried over $MgSO_4$, filtered, and evaporated under reduced pressure. Purification of the residue by FC (EtOAc/heptane/$CH_2Cl_2$ 3:1:6 with 1% $Et_3N$) yielded the title compound (784 mg, 91%). LC-MS: $t_R$=1.22 min; ES+: 782.54.

5-{[5-Chloro-2-(3-methoxy-propyl)-pyridin-4-ylmethyl]-cyclopropyl-carbamoyl}-4-{4-[2-(2,6-dichloro-4-methyl-phenoxy)-ethoxy]-phenyl}-3,6-dihydro-2H-pyridine-1-carboxylic acid tert-butyl ester (L8)

A mixture of compound K2 (500 mg, 0.957 mmol), [5-chloro-2-(3-methoxy-propyl)-pyridin-4-ylmethyl]-cyclopropyl-amine (300 mg, 1.18 mmol), DIPEA (0.655 mL, 3.83 mmol), DMAP (29.3 mg, 0.240 mmol), HOBt (162 mg, 1.20 mmol), and EDC.HCl (275 mg, 1.43 mmol) in $CH_2Cl_2$ (2 mL) was stirred at rt for 48 h. The mixture was filtered through Isolute® (0.6 g) pre-washed with aq. 1M HCl (1 mL). The org. layer was dried over $MgSO_4$, and the solvents were removed under reduced pressure. Purification of the residue by FC (EtOAc/heptane/$CH_2Cl_2$ 3:1:6 with 1% $Et_3N$) yielded the title compound (650 mg, 89%). LC-MS: $t_R$=1.20 min; ES+: 758.52.

(rac.)-(3R*,4S*)-4-{4-[3-(2-Chloro-3,6-difluoro-phenyl)-isoxazol-5-ylmethoxy]-phenyl}-3-{2-chloro-5-(3-methoxy-propyl)-benzyl-cyclopropyl-carbamoyl}-piperidine-1-carboxylic acid tert-butyl ester (L9)

A mixture of compound K6 (1.00 g, 1.82 mmol), [2-chloro-5-(3-methoxy-propyl)-benzyl]-cyclopropyl-amine (694 mg, 2.94 mmol), HOBt (307 mg, 2.28 mmol), DMAP (55.1 mg, 0.456 mmol), DIPEA (1.24 mL, 7.26 mmol) and EDC.HCl (1.49 g, 2.72 mmol) in $CH_2Cl_2$ (16 mL) was stirred for 24 h. The mixture was diluted with $CH_2Cl_2$, and was washed with aq. 1M HCl, water, and brine. The org. layer was dried over $MgSO_4$, filtered, and the solvents were removed under reduced pressure. Purification of the crude by FC (EtOAc/heptane/$CH_2Cl_2$ with 1% $Et_3N$) yielded the title compound (1.24 g, 87%). LC-MS: $t_R$=1.23 min; ES+: 784.40.

6-[3-(2-Chloro-3,6-difluoro-phenyl)isoxazol-5-ylmethoxy]-5'-{[2-chloro-5-(3-methoxy-propyl)-benzyl]-cyclopropyl-carbamoyl}-3',6'-dihydro-2'H-[3,4'] bipyridinyl-1'-carboxylic acid tert-butyl ester (L10)

A mixture of compound K7 (500 mg, 0.913 mmol), [2-chloro-5-(3-methoxy-propyl)-benzyl]-cyclopropyl-amine (347 mg, 1.37 mmol), HOBt (154 mg, 1.14 mmol), DMAP (27.9 mg, 0.228 mmol), DIPEA (0.623 mL, 3.63 mmol) and EDC.HCl (261 mg, 1.63 mmol) in $CH_2Cl_2$ (8.0 mL) was stirred for 24 h. The mixture was diluted with $CH_2Cl_2$, and the mixture was washed with aq. 1M HCl, water, and brine. The org. layer was dried over $MgSO_4$, filtered, and the solvents were removed under reduced pressure. Purification of the residue by FC (acetone/heptane 3:1→acetone, with always 1% $Et_3N$) yielded the title compound (344 mg, 48%). LC-MS: $t_R$=1.20 min; ES+: 783.39.

(rac.)-(1R*,5S*)-3-Acetyl-6-{[5-chloro-2-(3-methoxy-propyl)-pyridin-4-ylmethyl]-cyclopropyl-carbamoyl}-7-{6-[2-(2,6-dichloro-4-methyl-phenoxy)-ethoxy]-pyridin-3-yl}-3,9-diaza-bicyclo[3.3.1]non-6-ene-9-carboxylic acid 2,2,2-trichloro-1,1-dimethyl-ethyl ester (L11)

To a sol. of compound K8 (1.00 g, 1.41 mmol) in $CH_2Cl_2$ (17 mL) were successively added at rt DIPEA (0.965 mL, 5.64 mmol), DMAP (43.1 mg, 353 mmol), HOBt (238 mg, 1.76 mmol) and EDC.HCl (675 mg, 3.53 mmol). This mixture was stirred at rt for 45 min, and [5-chloro-2-(3-methoxy-propyl)-pyridin-4-ylmethyl]-cyclopropyl-amine (664 mg, 2.61 mmol) was added. The mixture was stirred at rt for 3 days. EDC.HCl (270 mg, 1.37 mmol) and HOBt (190 mg, 1.41 mmol) were added to the mixture that was stirred at rt for 2 days. EDC.HCl (135 mg, 0.684 mmol) was added to the reaction mixture that was stirred for 2 days. EDC.HCl (135 mg, 0.684 mmol), HOBt (95 mg, 0.704 mmol), and [5-chloro-2-(3-methoxy-propyl)-pyridin-4-ylmethyl]-cyclopropyl-amine (359 mg, 1.41 mmol) were added to the reaction mixture, which was stirred for 6 days at rt. $CH_2Cl_2$ was added, and the mixture was washed with aq. 1M HCl (3×) and with $NaHCO_3$ (1×). The org. layer was dried over $MgSO_4$, filtered and concentrated under reduced pressure. Purification of the crude by FC (EtOAc/heptane 1:4→1:3→1:2→1:1→2:1→EtOAc) yielded the title compound (722 mg, 54%). LC-MS: $t_R$=1.20 min; ES+: 783.39.

(rac.)-(1R*,2R*,3S*,5S*)-2-{[2-Chloro-5-(2-methoxy-ethyl)-benzyl]-cyclopropyl-carbamoyl}-3-{4-[2-(2,6-dichloro-4-methyl-phenoxy)-ethoxy]-phenyl}-8-aza-bicyclo[3.2.1]octane-8-carboxylic acid tert-butyl ester (L12)

To a sol. of compound K9 (573 mg, 1.04 mmol) in $CH_2Cl_2$ (10 mL) were successively added DIPEA (0.713 mL, 4.16 mmol), DMAP (31.8 mg, 0.260 mmol), HOBt (176 mg, 1.30 mmol) and EDC.HCl (499 mg, 2.60 mmol). This reaction mixture was stirred at rt for 45 min, and [2-chloro-5-(2-methoxy-ethyl)-benzyl]-cyclopropyl-amine (462 mg, 1.93 mmol) was added. The mixture was stirred overnight. $CH_2Cl_2$ was added, and the mixture was washed with aq. 1M HCl (3×) and with aq. sat. NaHCO₃ (1×). The org. layer was dried over MgSO₄, filtered, and the solvents were removed under reduced pressure. Purification of the crude by FC (EtOAc/heptane 1:5→1:3→1:1→2:1) yielded the title compound (448 mg, 56%). LC-MS: $t_R$=1.25 min; ES+: 771.16.

(rac.)-(1R*,2R*,3S*,5S*)-2-{[2-Chloro-5-(3-methoxy-propyl)-benzyl]-cyclopropyl-carbamoyl}-3-{4-[2-(2,6-dichloro-4-methyl-phenoxy)-ethoxy]-phenyl}-8-aza-bicyclo[3.2.1]octane-8-carboxylic acid tert-butyl ester (L13)

To a sol. of compound K9 (130 mg, 0.236 mmol) in CH₂Cl₂ (1.5 mL) were successively added DIPEA (0.122 mL, 0.945 mmol), DMAP (7.09 mg, 0.058 mmol), HOBt (39.7 mg, 0.294 mmol) and EDC.HCl (113 mg, 0.592 mmol). This mixture was stirred at rt for 45 min, and [2-chloro-5-(3-methoxy-propyl)-benzyl]-cyclopropyl-amine (111 mg, 0.437 mmol) was added. The mixture was stirred at rt overnight. CH₂Cl₂ was added, and the mixture was washed with aq. 1M HCl (3×) and with aq. sat. NaHCO₃ (1×). The org. layer was dried over MgSO₄, filtered, and the solvents were removed under reduced pressure. Purification of the crude by FC (EtOAc/heptane 1:5→1:3→1:1→2:1) yielded the title compound (137 mg, 73%). LC-MS: $t_R$=1.27 min; ES+: 787.16.

(rac.)-(1R*,5S*)-3-{4-[3-(2-Chloro-3,6-difluoro-phenyl)-isoxazol-5-ylmethoxy]-phenyl}-2-{[2-chloro-5-(3-methoxy-propyl)-benzyl]-cyclopropyl-carbamoyl}-8-aza-bicyclo[3.2.1]oct-2-ene-8-carboxylic acid tert-butyl ester (L14)

To a sol. of compound K10 (573 mg, 1.00 mmol) in dry DMF (15 mL) were successively added at rt DIPEA (0.685 mL, 4.00 mmol), DMAP (30.5 mg, 0.250 mmol), HOBt (169 mg, 1.25 mmol) and EDC.HCl (479 mg, 2.50 mmol). The mixture was stirred at rt for 45 min, and [2-chloro-5-(3-methoxy-propyl)-benzyl]-cyclopropyl-amine (381 mg, 1.50 mmol) was added. The mixture was stirred for 6 days. The reaction mixture was diluted with EtOAc, and washed with aq. 1M HCl (3×), and aq. sat. NaHCO₃ (1×). The org. layer was dried over MgSO₄, filtered, and the solvents were removed under reduced pressure. Purification of the crude by FC (heptane→EtOAc/heptane 30:70) yielded the title compound (492 mg, 61%). LC-MS: $t_R$=1.22 min; ES+: 808.22.

(rac.)-(1R*,5S*)-3-Acetyl-7-{6-[3-(2-chloro-3,6-difluoro-phenyl)-isoxazol-5-ylmethoxy]-pyridin-3-yl}-6-{[2-chloro-5-(3-methoxy-propyl)-benzyl]-cyclopropyl-carbamoyl}-3,9-diaza-bicyclo[3.3.1]non-6-ene-9-carboxylic acid 2,2,2-trichloro-1,1-dimethyl-ethyl ester (L15)

To a sol. of compound K11 (680 mg, 0.926 mmol) in dry DMF (13.9 mL) were successively added at rt DIPEA (0.634 mL, 3.70 mmol), DMAP (28.2 mg, 0.231 mmol), HOBt (156 mg, 1.16 mmol) and EDC.HCl (444 mg, 2.32 mmol). The reaction mixture was stirred at rt for 75 min, then [2-chloro-5-(3-methoxy-propyl)-benzyl]-cyclopropyl-amine (352 mg, 1.39 mmol) was added. The mixture was stirred for 6 days, and the solvents were removed under reduced pressure. The residue was dissolved in EtOAc, and the resulting mixture was washed with aq. 1M HCl (3×), and aq. sat. NaHCO₃ (1×). The org. layer was dried over MgSO₄, filtered, and the solvents were removed under reduced pressure. Purification of the crude by FC (EtOAc/heptane 1/1) yielded the title compound (373 mg, 42%). LC-MS: $t_R$=1.27 min; ES+: 970.38.

5'-{[5-Chloro-2-(3-methoxy-propyl)-pyridin-4-ylmethyl]-cyclopropyl-carbamoyl}-6-[2-(2,6-dichloro-4-methyl-phenoxy)-ethoxy]-3',6'-dihydro-2'H-[3,4']bipyridinyl-1'-carboxylic acid tert-butyl ester (L20)

A mixture of compound K4 (700 mg, 1.34 mmol), [5-chloro-2-(3-methoxy-propyl)-pyridin-4-ylmethyl]-cyclopropyl-amine (409 mg, 1.60 mmol), DIPEA (0.915 mL, 5.35 mmol), DMAP (40.9 mg, 0.335 mmol), HOBt (226 mg, 1.67 mmol) and EDC.HCl (384 mg, 2.00 mmol) in CH₂Cl₂ (2.00 mL) was stirred for 48 h at rt. The mixture was filtered through Isolute® pre-washed with aq. 1M HCl, and eluted with CH₂Cl₂. The org. layer was dried over MgSO₄, filtered, and the solvents were removed under reduced pressure. Purification of the residue by HPLC (x-Bridge column, acetonitrile/H₂O+0.05% formic acid, 10:90→90:10, over 6 min) yielded the title compound (249 mg, 25%). LC-MS: $t_R$=1.29 min; ES+: 1004.42.

(rac.)-(3'R*,4'S*)-3'-{[5-Chloro-2-(3-methoxy-propyl)-pyridin-4-ylmethyl]-cyclopropyl-carbamoyl}-6-[2-(2,6-dichloro-4-methyl-phenoxy)-ethoxy]-3',4',5',6'-tetrahydro-2'H-[3,4']bipyridinyl-1'-carboxylic acid tert-butyl ester (L21)

A mixture of compound K16 (1.00 g, 1.90 mmol), [5-chloro-2-(3-methoxy-propyl)-pyridin-4-ylmethyl]-cyclopropyl-amine (485 mg, 1.90 mmol), DIPEA (1.30 mL, 7.61 mmol), DMAP (58.1 mg, 0.476 mmol), HOBt (221 mg, 2.38 mmol) and EDC.HCl (547 mg, 2.86 mmol) in CH₂Cl₂ (4.00 mL) was stirred for 24 h at rt. EDC.HCl (250 mg, 1.27 mmol) was added, and the mixture was stirred again for 24 h. EDC.HCl (100 mg, 0.506 mmol) was added, and the mixture was stirred again for 24 h. CH₂Cl₂ was added, and the sol. was washed with aq. 1M HCl, water and brine. The org. layer was dried over MgSO₄, filtered, and the solvents were removed under reduced pressure. Purification of the crude by FC(CH₂Cl₂/MeOH 98:2%→95:5) yielded the title compound (414 mg, 29%). LC-MS: $t_R$=1.19 min; ES+: 763.60.

(rac.)-(1R*,5S*)-7-{4-[3-(2-Chloro-3,6-difluoro-phenyl)-isoxazol-5-ylmethoxy]-phenyl}-6-{[5-chloro-2-(3-methoxy-propyl)-pyridin-4-ylmethyl]-cyclopropyl-carbamoyl}-3,9-diaza-bicyclo[3.3.1]non-6-ene-3,9-dicarboxylic acid 3-tert-butyl ester 9-(2,2,2-trichloro-1,1-dimethyl-ethyl) ester (L22)

A mixture of compound K17 (1.24 g, 1.57 mmol), DIPEA (1.07 mL, 6.27 mmol), DMAP (47.9 mg, 0.392 mmol), HOBt (300 mg, 1.96 mmol) and EDC.HCl (751 mg, 3.92 mmol) in CH₂Cl₂ (24.00 mL) was stirred for 3 h at rt. [5-Chloro-2-(3-methoxy-propyl)-pyridin-4-ylmethyl]-cyclopropyl-amine (738 mg, 2.90 mmol) was added, and the mixture was stirred for 11 days. CH₂Cl₂ was added, and the sol. was washed with aq. 1M HCl, water and brine. The org. layer was dried over MgSO₄, filtered, and the solvents were removed under reduced pressure. Purification of the crude by FC (EtOAc/heptane 9:1) yielded the title compound (850 mg, 53%). LC-MS: $t_R$=1.24 min; ES+: 1028.60.

4-{4-[3-(2-Chloro-3,6-difluoro-phenyl)-isoxazol-5-ylmethoxy]-phenyl}-5-{[5-chloro-2-(3-methoxy-propyl)-pyridin-4-ylmethyl]-cyclopropyl-carbamoyl}-3,6-dihydro-2H-pyridine-1-carboxylic acid tert-butyl ester (L23)

A mixture of compound K5 (700 mg, 1.28 mmol), [5-chloro-2-(3-methoxy-propyl)-pyridin-4-ylmethyl]-cyclopropyl-amine (391 mg, 1.54 mmol), DIPEA (0.876 mL, 5.12 mmol), DMAP (39.2 mg, 0.321 mmol), HOBt (216 mg, 1.60 mmol) and EDC.HCl (368 mg, 1.92 mmol) in CH$_2$Cl$_2$ (2.00 mL) was stirred for 2 days at rt. The mixture was filtered through Isolute®, pre-washed with aq. 1M HCl, and using CH$_2$Cl$_2$ as eluent. The org. layer was dried over MgSO$_4$, filtered, and the solvents were removed under reduced pressure. Purification of the residue by FC (EtOAc/heptane 2:8) yielded the title compound (548 mg, 55%). LC-MS: t$_R$=1.16 min.

(rac.)-(1R*,5S*)-3-{6-[3-(2-Chloro-3,6-difluoro-phenyl)-isoxazol-5-ylmethoxy]-pyridin-3-yl}-2-{[2-chloro-5-(3-methoxy-propyl)-benzyl]-cyclopropyl-carbamoyl}-8-aza-bicyclo[3.2.1]oct-2-ene-8-carboxylic acid tert-butyl ester (L24)

To a sol. of the compound K19 (574 mg, 1.00 mmol) in dry DMF (15 mL) were successively added at rt DIPEA (0.685 mL, 4.00 mmol), DMAP (30.5 mg, 0.250 mmol), HOBt (169 mg, 1.25 mmol) and EDC.HCl (479 mg, 2.50 mmol). The reaction mixture was stirred at rt for 45 min, and [2-chloro-5-(3-methoxy-propyl)-benzyl]-cyclopropyl-amine (381 mg, 1.50 mmol) was added. The mixture was stirred for 6 days. The mixture was diluted with EtOAc and washed with aq. 1M HCl (3×) and aq. sat. NaHCO$_3$ (1×). The org. layer was dried over MgSO$_4$, filtered, and the solvents were removed under reduced pressure. Purification of the crude by FC (heptane→EtOAc/heptane 40:60) yielded the title compound (486 mg, 60%). LC-MS: t$_R$=1.21 min; ES+: 809.21.

Mixture of (1R,5S)-2-{[2-chloro-5-(3-methoxy-propyl)-benzyl]-cyclopropyl-carbamoyl}-3-{4-[(R)-3-(2,6-dichloro-4-methyl-phenoxy)-pyrrolidin-1-yl]-phenyl}-8-aza-bicyclo[3.2.1]oct-2-ene-8-carboxylic acid tert-butyl ester and (1S,5RS)-2-{[2-chloro-5-(3-methoxy-propyl)-benzyl]-cyclopropyl-carbamoyl}-3-{4-[(R)-3-(2,6-dichloro-4-methyl-phenoxy)-pyrrolidin-1-yl]-phenyl}-8-aza-bicyclo[3.2.1]oct-2-ene-8-carboxylic acid tert-butyl ester (L25)

To a sol. of the compounds K20 (574 mg, 1.00 mmol) in CH$_2$Cl$_2$ (15 mL) were successively added at rt: DIPEA (0.685 mL, 4.00 mmol), DMAP (30.5 mg, 0.250 mmol), HOBt (169 mg, 1.25 mmol) and EDC.HCl (479 mg, 2.50 mmol). The mixture was stirred at rt for 45 min, and [2-chloro-5-(3-methoxy-propyl)-benzyl]-cyclopropyl-amine (381 mg, 1.50 mmol) was added. The mixture was stirred for 6 days. The mixture was diluted with EtOAc, and was washed with aq. 1M HCl (3×) and aq. sat. NaHCO$_3$ (1×). The org. layer was dried over MgSO$_4$, filtered, and the solvents were removed under reduced pressure. Purification of the crude by FC (heptane→EtOAc/heptane 30:70) yielded the title compounds mixture (525 mg, 65%). LC-MS: t$_R$=1.31 min; ES+: 810.26.

Mixture of (1R,5S)-6-{[2-chloro-5-(2-methoxy-ethyl)-benzyl]-cyclopropyl-carbamoyl}-7-{6-[(R)-3-(2,6-dichloro-4-methyl-phenoxy)-pyrrolidin-1-yl]-pyridin-3-yl}-3,9-diaza-bicyclo[3.3.1]non-6-ene-3,9-dicarboxylic acid di-tert-butyl ester and (1S,5R)-6-{[2-chloro-5-(2-methoxy-ethyl)-benzyl]-cyclopropyl-carbamoyl}-7-{6-[(R)-3-(2,6-dichloro-4-methyl-phenoxy)-pyrrolidin-1-yl]-pyridin-3-yl}-3,9-diaza-bicyclo[3.3.1]non-6-ene-3,9-dicarboxylic acid di-tert-butyl ester (L26)

To a sol. of compounds K21 (1.15 g, 1.67 mmol) in CH$_2$Cl$_2$ (25 mL) were successively added at rt: DIPEA (1.14 mL, 6.67 mmol), DMAP (50.8 mg, 0.416 mmol), HOBt (282 mg, 2.08 mmol) and EDC.HCl (799 mg, 4.17 mmol). The mixture was stirred at rt for 45 min, and [2-chloro-5-(2-methoxy-ethyl)-benzyl]-cyclopropyl-amine (719 mg, 3.00 mmol) was added. The mixture was stirred at rt for 18 days. CH$_2$Cl$_2$ was added, and the mixture was washed with aq. 1M HCl (3×) and aq. sat. NaHCO$_3$ (1×). The org. layer was dried over MgSO$_4$, filtered, and the solvents were removed under reduced pressure. Purification of the crude by FC (EtOAc/heptane 1:9→1:7→1:5→1:3→1:1→2:1) yielded the title compounds mixture (559 mg, 37%). LC-MS: t$_R$=1.08 min; ES+: 912.08.

Mixture of (1R,5S)-7-{6-[(R)-3-(2-chloro-3,6-difluoro-phenoxy)-pyrrolidin-1-yl]-pyridin-3-yl}-6-{[2-chloro-5-(2-methoxy-ethyl)-benzyl]-cyclopropyl-carbamoyl}-3,9-diaza-bicyclo[3.3.1]non-6-ene-3,9-dicarboxylic acid di-tert-butyl ester and (1S,5R)-7-{6-[(R)-3-(2-chloro-3,6-difluoro-phenoxy)-pyrrolidin-1-yl]-pyridin-3-yl}-6-{[2-chloro-5-(2-methoxy-ethyl)-benzyl]-cyclopropyl-carbamoyl}-3,9-diaza-bicyclo[3.3.1]non-6-ene-3,9-dicarboxylic acid di-tert-butyl ester (L27)

To a sol. of compounds K22 (1.13 g, 1.67 mmol) in CH$_2$Cl$_2$ (25 mL) were successively added at rt: DIPEA (1.14 mL, 6.67 mmol), DMAP (50.8 mg, 0.416 mmol), HOBt (282 mg, 2.08 mmol) and EDC.HCl (799 mg, 4.17 mmol). The mixture was stirred at rt for 45 min, and [2-chloro-5-(2-methoxy-ethyl)-benzyl]-cyclopropyl-amine (719 mg, 3.00 mmol) was added. The mixture was stirred at rt for 18 days. CH$_2$Cl$_2$ was added, and the mixture was washed with aq. 1M HCl (3×) and aq. sat. NaHCO$_3$ (1×). The org. layer was dried over MgSO$_4$, filtered, and the solvents were removed under reduced pressure. Purification of the crude by FC (EtOAc/heptane 1:9→1:7→1:5→1:3→1:1→2:1) yielded the title compounds mixture (581 mg, 39%). LC-MS: t$_R$=1.04 min; ES+: 898.10.

(rac.)-(1R*,5S*)-6-{[5-Chloro-2-(3-methoxy-propyl)-pyridin-4-ylmethyl]-cyclopropyl-carbamoyl}-7-{6-[2-(2,6-dichloro-4-methyl-phenoxy)-ethoxy]-pyridin-3-yl}-3,9-diaza-bicyclo[3.3.1]non-6-ene-3,9-dicarboxylic acid 3-tert-butyl ester 9-(2,2,2-trichloro-1,1-dimethyl-ethyl) ester (L28)

To a sol. of compound K3 (894 mg, 1.16 mmol) in CH$_2$Cl$_2$ (15 mL) were successively added at rt: DIPEA (0.797 mL, 4.66 mmol), DMAP (35.6 mg, 0.292 mmol), HOBt (197 mg, 1.46 mmol) and EDC.HCl (558 mg, 2.91 mmol). This mixture was stirred at rt for 45 min, and [5-chloro-2-(3-methoxy-propyl)-pyridin-4-ylmethyl]-cyclopropyl-amine (548 mg, 2.15 mmol) was added. The mixture was stirred for 18 days. CH$_2$Cl$_2$ was added, and the mixture was washed with aq. 1M HCl (3×) and aq. sat. NaHCO$_3$ (1×). The org. layer was dried over MgSO$_4$, filtered, and the solvents were removed under reduced pressure. Purification of the crude by FC (EtOAc/heptane 1:4→1:3→1:2→1:1→2:1→EtOAc) yielded the title compound (325 mg, 28%). LC-MS: t$_R$=1.29 min; ES+: 1004.42.

(3R,4S)-3-{[5-Chloro-2-(3-methoxy-propyl)-pyridin-4-ylmethyl]-cyclopropyl-carbamoyl}-4-{4-[2-(2,6-dichloro-4-methyl-phenoxy)-ethoxy]-phenyl}-piperidine-1-carboxylic acid tert-butyl ester (L29)

A mixture of compound K23 (399 mg, 0.761 mmol), [5-chloro-2-(3-methoxy-propyl)-pyridin-4-ylmethyl]-cyclopropyl-amine (194 mg, 0.761 mmol), HOBt (129 mg, 0.952 mmol), DMAP (23.2 mg, 0.190 mmol), DIPEA (0.521 mL, 3.05 mmol) and EDC.HCl (219 mg, 1.14 mmol) in $CH_2Cl_2$ (8.00 mL) was stirred at rt for 24 h. HOBt (129 mg, 0.952 mmol), DMAP (23.2 mg, 0.190 mmol), DIPEA (0.521 mL, 3.05 mmol) and EDC.HCl (219 mg, 1.14 mmol) were added again, and the mixture was stirred for 6 h. $CH_2Cl_2$ was added, and the mixture was washed with aq. 1M HCl and brine. The org. layer was dried over $MgSO_4$, filtered, and the solvents were removed under reduced pressure. Purification of the crude by FC ($MeOH/CH_2Cl_2$ 1:19 with 1% $Et_3N$) yielded the title compound (105 mg, 18%). LC-MS: $t_R$=1.21 min; ES+: 762.49.

(rac.)-(1R*,2R*,3S*,5S*)-2-{[2-Chloro-5-(2-methoxy-ethyl)-benzyl]-cyclopropyl-carbamoyl}-3-{6-[2-(2,6-dichloro-4-methyl-phenoxy)-ethoxy]-pyridin-3-yl}-8-aza-bicyclo[3.2.1]octane-8-carboxylic acid tert-butyl ester (L30)

A mixture of compound K24 (1.08 g, 1.95 mmol), DIPEA (1.34 mL, 7.80 mmol), DMAP (59.6 mg, 0.488 mmol), HOBt (329 mg, 2.44 mmol) and EDC.HCl (561 mg, 2.93 mmol) in $CH_2Cl_2$ (30 mL) was stirred at rt for 15 min. [2-Chloro-5-(2-methoxy-ethyl)-benzyl]-cyclopropyl-amine (701 mg, 2.93 mmol) was added, and the mixture was stirred for 4 days at rt. $CH_2Cl_2$ (250 mL) was added, and the mixture was washed with aq. 1M HCl (2×), and aq. sat. $NaHCO_3$ (1×). The org. layer was dried over $MgSO_4$, filtered, and the solvents were removed under reduced pressure. Purification of the crude by FC (EtOAc/heptane 1:10) yielded the title compound (710 mg, 47%). LC-MS: $t_R$=1.24 min; ES+: 774.41.

(rac.)-(1R*,5S*)-7-{4-[3-(2-Chloro-3,6-difluoro-phenyl)-isoxazol-5-ylmethoxy]-phenyl}-6-{[2-chloro-5-(3-methoxy-propyl)-benzyl]-cyclopropyl-carbamoyl}-3,9-diaza-bicyclo[3.3.1]non-6-ene-3,9-dicarboxylic acid 3-tert-butyl ester 9-(2,2,2-trichloro-1,1-dimethyl-ethyl) ester (L31)

A mixture of compound K17 (940 mg, 1.19 mmol), EDC.HCl (569 mg, 2.67 mmol), HOBt (227 mg, 1.49 mmol), DMAP (36.3 mg, 0.297 mmol) and DIPEA (0.814 mL, 4.75 mmol) in $CH_2Cl_2$ (18 mL) was stirred at rt for 3 h. [2-Chloro-5-(2-methoxy-propyl)-benzyl]-cyclopropyl-amine (558 mg, 2.20 mmol) was added, and the mixture was stirred at rt for 2 days. $CH_2Cl_2$ was added, and the mixture was washed with aq. 1M HCl and with aq. sat. $NaHCO_3$. The org. layer was dried over $MgSO_4$, filtered, and the solvents were removed under reduced pressure. Purification of the residue by FC (heptane/EtOAc 65:35→EtOAc) yielded the title compound (560 mg, 45%). LC-MS: $t_R$=1.30 min; ES+: 1027.30.

(rac.)-(1R*,5S*)-7-{4-[3-(2-Chloro-3,6-difluoro-phenyl)-isoxazol-5-ylmethoxy]-phenyl}-6-{[2-chloro-5-(2-methoxy-ethyl)-benzyl]-cyclopropyl-carbamoyl}-3,9-diaza-bicyclo[3.3.1]non-6-ene-3,9-dicarboxylic acid di-tert-butyl ester (L32)

A mixture of compound K25 (1.45 g, 2.17 mmol), EDC.HCl (1.04 g, 5.42 mmol), HOBt (414 mg, 2.71 mmol), DMAP (66.1 mg, 0.541 mmol) and DIPEA (1.48 μL, 8.67 mmol) in $CH_2Cl_2$ (32 mL) was stirred at rt for 3 h. [2-Chloro-5-(2-methoxy-ethyl)-benzyl]-cyclopropyl-amine (961 mg, 4.01 mmol) was added, and the mixture was stirred at rt for 24 h. EDC.HCl (1.04 g, 5.42 mmol), HOBt (414 mg, 2.71 mmol), and DMAP (cat. amount) were added again, and the mixture was stirred for 6 days. EDC.HCl (1.04 g, 5.42 mmol), HOBt (414 mg, 2.71 mmol), and DMAP (cat. amount) were added again, and the mixture was stirred at rt for 6 days. $CH_2Cl_2$ was added, and the mixture was washed with aq. 1M HCl and with aq. sat. $NaHCO_3$. The org. layer was dried over $MgSO_4$, filtered, and the solvents were removed under reduced pressure. Purification of the residue by FC (heptane/EtOAc 7:3) yielded the title compound (990 mg, 50%). LC-MS: $t_R$=1.22 min; ES+: 909.39.

(rac.)-(1R*,5S*)-3-Acetyl-7-{4-[3-(2-chloro-3,6-difluoro-phenyl)-isoxazol-5-ylmethoxy]-phenyl}-6-{[2-chloro-5-(3-methoxy-propyl)-benzyl]-cyclopropyl-carbamoyl}-3,9-diaza-bicyclo[3.3.1]non-6-ene-9-carboxylic acid tert-butyl ester (L33)

A mixture of compound K26 (720 mg, 1.14 mmol), EDC.HCl (548 mg, 2.86 mmol), HOBt (219 mg, 1.43 mmol), DMAP (34.9 mg, 0.286 mmol) and DIPEA (0.783 mL, 4.75 mmol) in $CH_2Cl_2$ (17 mL) was stirred at rt for 3 h. [2-Chloro-5-(2-methoxy-propyl)-benzyl]-cyclopropyl-amine (537 mg, 2.12 mmol) was added, and the mixture was stirred at rt for 24 h. EDC.HCl (548 mg, 2.86 mmol), HOBt (219 mg, 1.43 mmol), and DMAP (cat. amount) were added again, and the mixture was stirred at rt for 1 day. EDC.HCl (548 mg, 2.86 mmol), HOBt (219 mg, 1.43 mmol), and DMAP (cat. amount) were added again, and the mixture was stirred at rt for 1 day. EDC.HCl (548 mg, 2.86 mmol), HOBt (219 mg, 1.43 mmol), and DMAP (cat. amount) were added again, and the mixture was stirred at rt for 6 days. $CH_2Cl_2$ was added, and the mixture was washed with aq. 1M HCl and with aq. sat. $NaHCO_3$. The org. layer was dried over $MgSO_4$, filtered, and the solvents were removed under reduced pressure. Purification of the residue by FC (EtOAc) yielded the title compound (550 mg, 56%). LC-MS: $t_R$=1.20 min; ES+: 865.11.

(rac.)-(1R*,5S*)-3-Acetyl-7-{4-[3-(2-chloro-3,6-difluoro-phenyl)-isoxazol-5-ylmethoxy]-phenyl}-6-{[2-chloro-5-(2-methoxy-ethyl)-benzyl]-cyclopropyl-carbamoyl}-3,9-diaza-bicyclo[3.3.1]non-6-ene-9-carboxylic acid tert-butyl ester (L34)

A mixture of compound K26 (1.13 g, 1.79 mmol), EDC.HCl (860 mg, 4.49 mmol), HOBt (343 mg, 2.24 mmol), DMAP (54.9 mg, 0.449 mmol) and DIPEA (1.23 mL, 7.18 mmol) in $CH_2Cl_2$ (27 mL) was stirred at rt for 3 h. [2-Chloro-5-(2-methoxy-ethyl)-benzyl]-cyclopropyl-amine (795 mg, 3.32 mmol) was added, and the mixture was stirred at rt for 3 days. EDC.HCl (354 mg, 1.79 mmol), HOBt (242 mg, 1.79 mmol), and DMAP (cat. amount) were added again, and the mixture was stirred at rt for 2 days. EDC.HCl (354 mg, 1.79 mmol), HOBt (242 mg, 1.79 mmol), and DMAP (cat. amount) were added again, and the mixture was stirred at rt for 1 day. EDC.HCl (177 mg, 0.90 mmol), HOBt (121 mg, 0.90 mmol), and DMAP (cat. amount) were added again, and the mixture was stirred at rt for 5 days. $CH_2Cl_2$ was added, and the mixture was washed with aq. 1M HCl and with aq. sat. $NaHCO_3$. The org. layer was dried over $MgSO_4$, filtered, and the solvents were removed under reduced pressure. Purification of the residue by FC (EtOAc/heptane 7:3→EtOAc→$MeOH/CH_2Cl_2$ 1:9) yielded the title compound (560 mg, 37%). LC-MS: $t_R$=1.19 min; ES+: 851.36.

(rac.)-(1R*,5S*)-7-{6-[3-(2-Chloro-3,6-difluoro-phenyl)-isoxazol-5-ylmethoxy]-pyridin-3-yl}-6-{[2-chloro-5-(3-methoxy-propyl)-benzyl]-cyclopropyl-carbamoyl}-3,9-diaza-bicyclo[3.3.1]non-6-ene-3,9-dicarboxylic acid di-tert-butyl ester (L35)

A mixture of compound K27 (689 mg, 1.00 mmol), DIPEA (0.685 mL, 4.00 mmol), DMAP (30.5 mg, 0.250 mmol), HOBt (169 mg, 1.25 mmol) and EDC.HCl (479 mg, 2.50 mmol) in DMF (15 mL) was stirred at rt for 45 min. [2-Chloro-5-(2-methoxy-propyl)-benzyl]-cyclopropyl-amine (381 mg, 1.50 mmol) was added, and the mixture was stirred for 6 days. The mixture was diluted with EtOAc, and was washed with aq. 1M HCl (3×) and aq. sat. NaHCO$_3$ (1×). The org. layer was dried over MgSO$_4$, filtered, and the solvents were removed under reduced pressure. Purification of the crude by FC (heptane→EtOAc/heptane 40:60) yielded the title compound (452 mg, 49%). LC-MS: $t_R$=1.23 min; ES+: 924.18.

Mixture of (1R,2R,3S,5S)-2-{[2-chloro-5-(2-methoxy-ethyl)benzyl]-cyclopropyl-carbamoyl}-3-{4-[(R)-3-(2,6-dichloro-4-methyl-phenoxy)-pyrrolidin-1-yl]-phenyl}-8-aza-bicyclo[3.2.1]octane-8-carboxylic acid tert-butyl ester and (1S,2S,3R,5R)-2-{[2-chloro-5-(2-methoxy-ethyl)-benzyl]-cyclopropyl-carbamoyl}-3-{4-[(R)-3-(2,6-dichloro-4-methyl-phenoxy)-pyrrolidin-1-yl]-phenyl}-8-aza-bicyclo[3.2.1]octane-8-carboxylic Acid tert-butyl ester (L36)

A mixture of compounds K28 (742 mg, 1.29 mmol), DIPEA (0.883 mL, 5.16 mmol), DMAP (39.5 mg, 0.323 mmol), HOBt (218 mg, 1.61 mmol), EDC.HCl (371 mg, 1.94 mmol) and [2-chloro-5-(2-methoxy-ethyl)-benzyl]-cyclopropyl-amine (464 mg, 1.94 mmol) in CH$_2$Cl$_2$ (20 mL) was stirred at rt for 24 h. [2-Chloro-5-(2-methoxy-ethyl)-benzyl]-cyclopropyl-amine (155 mg, 0.647 mmol) was added, and the mixture was stirred for 3 days. CH$_2$Cl$_2$ was added, and the mixture was washed with aq. 1M HCl, and aq. 10% Na$_2$CO$_3$. The org. layer was dried over MgSO$_4$, filtered, and the solvents were removed under reduced pressure. Purification of the crude by FC (EtOAc/heptane 1:9→1:1) yielded the title compounds mixture (470 mg, 46%). LC-MS: $t_R$=1.31 min; ES+: 798.29.

Mixture of (1R,2R,3S,5S)-2-{[2-chloro-5-(2-methoxy-ethyl)-benzyl]-cyclopropyl-carbamoyl}-3-{6-[(R)-3-(2,6-dichloro-4-methyl-phenoxy)-pyrrolidin-1-yl]-pyridin-3-yl}-8-aza-bicyclo[3.2.1]octane-8-carboxylic acid tert-butyl ester and (1S,2S,3R,5R)-2-{[2-chloro-5-(2-methoxy-ethyl)-benzyl]-cyclopropyl-carbamoyl}-3-{6-[(R)-3-(2,6-dichloro-4-methyl-phenoxy)-pyrrolidin-1-yl]-pyridin-3-yl}-8-aza-bicyclo[3.2.1]octane-8-carboxylic acid tert-butyl ester (L37)

A mixture of compounds K29 (577 mg, 1.00 mmol), DIPEA (0.684 mL, 4.00 mmol), DMAP (30.5 mg, 0.250 mmol), HOBt (169 mg, 1.25 mmol), EDC.HCl (288 mg, 1.50 mmol) and [2-chloro-5-(2-methoxy-ethyl)-benzyl]-cyclopropyl-amine (240 mg, 1.00 mmol) in CH$_2$Cl$_2$ (20 mL) was stirred at rt for 7 days. DIPEA (0.171 mL, 1.00 mmol), HOBt (135 mg, 1.00 mmol), and EDC.HCl (197 mg, 1.00 mmol) were added, and the mixture was stirred for 3 days. EDC.HCl (98 mg, 0.50 mmol) was added, and the mixture was stirred for 3 days. The mixture was diluted with CH$_2$Cl$_2$ (80 mL), and was washed with aq. 1M HCl (2×) and aq. 10% Na$_2$CO$_3$ (1×). The org. layer was dried over MgSO$_4$, filtered, and the solvents were removed under reduced pressure. Purification of the crude by FC (EtOAc/heptane 1:3→1:1) yielded the title compounds mixture (150 mg, 19%). LC-MS: $t_R$=1.01 min; ES+: 799.41.

Mixture of (3'R,4'S)-3'-{[2-chloro-5-(2-methoxy-ethyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(2-methoxy-ethyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L38)

A mixture of compounds K30 (600 mg, 1.09 mmol), DIPEA (0.746 mL, 4.36 mmol), DMAP (33.3 mg, 0.273 mmol), HOBt (184 mg, 1.36 mmol), EDC.HCl (313 mg, 1.64 mmol) and [2-chloro-5-(2-methoxy-ethyl)-benzyl]-cyclopropyl-amine (261 mg, 1.09 mmol) in CH$_2$Cl$_2$ (10 mL) was stirred at rt for 3 days. EDC.HCl (200 mg, 1.02 mmol) was added, and the mixture was stirred for 6 days. CH$_2$Cl$_2$ was added, and the mixture was washed with aq. 1M HCl, water and brine, dried over MgSO$_4$, filtered, and the solvents were removed under reduced pressure. Purification of the crude by FC(CH$_2$Cl$_2$→MeOH/CH$_2$Cl$_2$ 1:9) yielded the title compounds mixture (624 mg, 74%). LC-MS: $t_R$=1.05 min; ES+: 771.30.

(rac.)-(1R*,5S*)-2-{[5-Chloro-2-(3-methoxy-propyl)-pyridin-4-ylmethyl]-cyclopropyl-carbamoyl}-3-{4-[2-(2,6-dichloro-4-methyl-phenoxy)ethoxy]-phenyl}-8-aza-bicyclo[3.2.1]oct-2-ene-8-carboxylic acid tert-butyl ester (L39)

To a sol. of compound K1 (548 mg, 1.00 mmol) in DMF (15 mL) were successively added at rt: DIPEA (0.685 mL, 4.00 mmol), DMAP (30.5 mg, 0.250 mmol), HOBt (169 mg, 1.25 mmol) and EDC.HCl (479 mg, 2.50 mmol). The reaction mixture was stirred at rt for 45 min, and [5-chloro-2-(3-methoxy-propyl)-pyridin-4-ylmethyl]-cyclopropyl-amine (361 mg, 1.50 mmol) was added. The mixture was stirred for 6 days. The mixture was diluted with EtOAc, and was washed with aq. 1M HCl (3×) and aq. sat. NaHCO$_3$ (1×). The org. layer was dried over MgSO$_4$, filtered, and the solvents were removed under reduced pressure. Purification of the crude by FC (heptane→EtOAc/heptane 50:50) yielded the title compound (190 mg, 24%). LC-MS: $t_R$=1.22 min; ES+: 786.19.

Mixture of (3'R,4'S)-3'-{[5-chloro-2-(3-methoxy-propyl)-pyridin-4-ylmethyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[5-chloro-2-(3-methoxy-propyl)-pyridin-4-ylmethyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L40)

A mixture of compounds K30 (600 mg, 1.09 mmol), DIPEA (0.746 mL, 4.36 mmol), DMAP (33.3 mg, 0.273 mmol), HOBt (184 mg, 1.36 mmol), EDC.HCl (313 mg, 1.64 mmol) and [5-chloro-2-(3-methoxy-propyl)-pyridin-4-ylmethyl]-cyclopropyl-amine (333 mg, 1.31 mmol) in CH$_2$Cl$_2$ (10 mL) was stirred at rt for 2 days. CH$_2$Cl$_2$ was added, and the mixture was washed with aq. 1M HCl, water and brine, dried over MgSO$_4$, filtered, and the solvents were removed under reduced pressure. Purification of the crude by FC(CH$_2$Cl$_2$→MeOH/CH$_2$Cl$_2$ 1:9) yielded the title compounds mixture (330 mg, 39%). LC-MS: $t_R$=1.01 min; ES+: 788.67.

(rac.)-(1R*,2R*,3S*,5S*)-3-{4-[3-(2-Chloro-3,6-difluoro-phenyl)isoxazol-5-ylmethoxy]-phenyl}-2-{[2-chloro-5-(3-methoxy-propyl)-benzyl]-cyclopropyl-carbamoyl}-8-aza-bicyclo[3.2.1]octane-8-carboxylic acid tert-butyl ester (L41)

To a sol. of compound K31 (706 mg, 1.23 mmol) in CH$_2$Cl$_2$ (18 mL) were added EDC.HCl (589 mg, 3.07 mmol), HOBt (235 mg, 1.53 mmol), DIPEA (0.841 mL, 4.91 mmol) and DMAP (37.3 mg, 0.306 mmol). The mixture was stirred at rt for 2 h, and [2-chloro-5-(2-methoxy-propyl)-benzyl]-cyclopropyl-amine (530 mg, 2.09 mmol) was added. The mixture was stirred at rt for 3 days. EDC.HCl (118 mg, 0.614 mmol), HOBt (82.9 mg, 0.614 mmol), DMAP (15.0 mg, 0.123 mmol) and DIPEA (0.420 mL, 2.46 mmol) were added to the reaction mixture, and the mixture was stirred for 7 days. The mixture was diluted with CH$_2$Cl$_2$, and was washed with aq. 1M HCl. The aq. layer was extracted back with CH$_2$Cl$_2$. The combined org. extracts were washed with aq. sat. NaHCO$_3$, dried over MgSO$_4$, filtered, and the solvents were removed under reduced pressure. Purification of the residue by FC (heptane/EtOAc 2:8) yielded the title compound (360 mg, 36%). LC-MS: t$_R$=1.22 min; ES+: 810.45.

(rac.)-(1R*,2R*,3S*,5S*)-3-{4-[3-(2-Chloro-3,6-difluoro-phenyl)isoxazol-5-ylmethoxy]-phenyl}-2-{[2-chloro-5-(2-methoxy-ethyl)-benzyl]-cyclopropyl-carbamoyl}-8-aza-bicyclo[3.2.1]octane-8-carboxylic acid tert-butyl ester (L42)

To a sol. of compound K31 (1.16 g, 2.02 mmol) in CH$_2$Cl$_2$ (20 mL) were added [2-chloro-5-(2-methoxy-ethyl)-benzyl]-cyclopropyl-amine (484 mg, 2.02 mmol), DIPEA (1.04 mL, 6.05 mmol) and TBTU (968 mg, 3.02 mmol). The mixture was stirred at rt for 3 days. The mixture was partitioned between CH$_2$Cl$_2$ and water, and the aq. layer was extracted with CH$_2$Cl$_2$. The combined org. extracts were dried over MgSO$_4$, filtered, and the solvents were removed under reduced pressure. Purification of the residue by FC (EtOAc/heptane 2:3) yielded the title compound (1.00 g, 62%). LC-MS: t$_R$=1.21 min; ES+: 796.44.

Mixture of (3'R,4'S)-3'-{[2-chloro-5-(2-methoxy-ethyl)-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(2-methoxy-ethyl)-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L43)

A sol. of compounds K32 (1.19 g, 2.17 mmol) in CH$_2$Cl$_2$ (22 mL) was treated with TBTU (833 mg, 2.60 mmol) and DIPEA (1.11 mL, 6.49 mmol), and the resulting sol. was stirred for 30 min at rt. [2-Chloro-5-(2-methoxy-ethyl)-benzyl]-cyclopropyl-amine (649 mg, 2.71 mmol) was added, and the resulting sol. was stirred at rt for 3 h. [2-Chloro-5-(2-methoxy-ethyl)-benzyl]-cyclopropyl-amine (162 mg, 0.678 mmol) was added. The mixture was stirred for 2 h, and was poured in aq. sat. NaHCO$_3$. The resulting mixture was extracted with EtOAc (3×). The combined org. extracts were dried over Na$_2$SO$_4$, filtered, and the solvents were removed under reduced pressure. Purification of the crude by FC (EtOAc/heptane 50:50) yielded the title compounds mixture (2.34 g, quantitative yield). LC-MS: t$_R$=1.01 min; ES+: 773.46.

(rac.)-(1R*,2R*,3S*,5S*)-3-{4-[3-(2-Chloro-3,6-difluoro-phenyl)isoxazol-5-ylmethoxy]-phenyl}-2-{[5-chloro-2-(3-methoxy-propyl)-pyridin-4-ylmethyl]-cyclopropyl-carbamoyl}-8-aza-bicyclo[3.2.1]octane-8-carboxylic acid tert-butyl ester (L44)

To a sol. of compound K31 (620 mg, 1.08 mmol) in CH$_2$Cl$_2$ (6.00 mL) were added [5-chloro-2-(3-methoxy-propyl)-pyridin-4-ylmethyl]-cyclopropyl-amine (275 mg, 1.08 mmol), DIPEA (3.24 mmol) and TBTU (1.61 mmol). The mixture was stirred at rt for 3 days. CH$_2$Cl$_2$ was added, and the mixture was washed with water. The org. layer was dried over MgSO$_4$, filtered, and the solvents were removed under reduced pressure. Purification of the crude by FC (heptane/EtOAc 1:1) yielded the title compound (450 mg, 51%). LC-MS: t$_R$=1.16 min; ES+: 811.48.

(rac.)-(3R*,4S*)-4-{4-[3-(2-Chloro-3,6-difluoro-phenyl)-isoxazol-5-ylmethoxy]-phenyl}-3-{[5-chloro-2-(3-methoxy-propyl)-pyridin-4-ylmethyl]-cyclopropyl-carbamoyl}-piperidine-1-carboxylic acid tert-butyl ester (L45)

A mixture of compound K6 (700 mg, 1.28 mmol), DMF (cat. amount) and oxalyl chloride (0.140 mL, 1.68 mmol) in toluene (20 mL) was stirred for 1 h at rt. The solvents were removed under reduced pressure, and the residue was dissolved in CH$_2$Cl$_2$ (20 mL). Et$_3$N (0.267 mL, 1.92 mmol) and [5-chloro-2-(3-methoxy-propyl)-pyridin-4-ylmethyl]-cyclopropyl-amine (488 mg, 1.92 mmol) were added, and the mixture was stirred for 30 min at rt. The mixture was washed with aq. 1M HCl and brine. The org. layer was dried over MgSO$_4$, filtered, and the solvents were removed under reduced pressure. Drying the residue under high vacuum yielded the crude title compound (670 mg, 67%) that was used further without purification. LC-MS: t$_R$=1.16 min; ES+: 785.31.

(rac.)-(3R*,4S*)-3-{[5-(Acetylamino-methyl)-2-chloro-benzyl]-cyclopropyl-carbamoyl}-4-{4-[3-(2-chloro-3,6-difluoro-phenyl)-isoxazol-5-ylmethoxy]-phenyl}-piperidine-1-carboxylic acid tert-butyl ester (L46)

Oxalyl chloride (0.140 mL, 1.66 mmol) was added to a sol. of compound K6 (700 mg, 1.28 mmol) in toluene (22 mL), and DMF (0.020 mL). The mixture was stirred at rt for 1 h, and the solvents were removed under reduced pressure. The residue was dissolved in CH$_2$Cl$_2$ (17 mL), and Et$_3$N (0.266 mL, 1.91 mmol) was added. The mixture was stirred for 5 min, and a sol. of N-(4-chloro-3-cyclopropylaminomethyl-benzyl)-acetamide (484 mg, 1.91 mmol) in CH$_2$Cl$_2$ (7.0 mL) was added. The mixture was stirred at rt overnight, and was washed with aq. 1M HCl and brine. The org. layer was dried over MgSO$_4$, filtered, and the solvents were removed under reduced pressure. Purification of the crude by FC (MeOH/CH$_2$Cl$_2$ 1:49) yielded the title compound (502 mg, 50%). LC-MS: t$_R$=1.15 min; ES+: 783.27.

Mixture of (3'R,4'S)-3'-{[5-(acetylamino-methyl)-2-chloro-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[5-(acetylamino-methyl)-2-chloro-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L47)

Oxalyl chloride (0.136 mL, 1.57 mmol) was added to a sol. of compounds K30 (720 mg, 1.31 mmol) in toluene (20 mL)

and DMF (3 drops). The mixture was stirred at rt for 80 min. The solvents were removed under reduced pressure, and the residue was diluted in CH$_2$Cl$_2$ (30 mL). Et$_3$N (0.540 mL, 3.90 mmol) was added, and the mixture was stirred for 5 min. A sol. of N-(4-chloro-3-cyclopropylaminomethyl-benzyl)-acetamide (489 mg, 1.94 mmol) in CH$_2$Cl$_2$ (4.00 mL) was added, and the mixture was stirred at rt for 1 h. The mixture was diluted with CH$_2$Cl$_2$, and was washed with aq. sat. NH$_4$Cl and aq. 10% Na$_2$CO$_3$. The org. layer was dried over MgSO$_4$, filtered, and the solvents were removed under reduced pressure. Purification of the crude by FC (EtOAc/heptane 1:1→EtOAc→MeOH/EtOAc 1:9) yielded the title compounds mixture (778 mg, 77%). LC-MS: t$_R$=0.99 min; ES+: 784.23.

Mixture of (3'R,4'S)-3'-{[5-(acetylamino-methyl)-2-chloro-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[5-(acetylamino-methyl)-2-chloro-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L48)

Oxalyl chloride (0.136 mL, 1.57 mmol) was added to a sol. of compounds K32 (720 mg, 1.31 mmol) in toluene (20 mL) and DMF (3 drops). The mixture was stirred at rt for 80 min. The solvents were removed under reduced pressure, and the residue was diluted in CH$_2$Cl$_2$ (30 μL). Et$_3$N (0.540 mL, 3.90 mmol) was added, and the mixture was stirred for 5 min. A sol. of N-(4-chloro-3-cyclopropylaminomethyl-benzyl)-acetamide (489 mg, 1.94 mmol) in CH$_2$Cl$_2$ (4.00 mL) was added, and the mixture was stirred at rt for 1 h. The mixture was diluted with CH$_2$Cl$_2$, and was washed with aq. sat. NH$_4$Cl and aq. 10% Na$_2$CO$_3$. The org. layer was dried over MgSO$_4$, filtered, and the solvents were removed under reduced pressure. Purification of the crude by FC (EtOAc/heptane 1:1→EtOAc→MeOH/EtOAc 1:9) yielded the title compounds mixture (671 mg, 66%). LC-MS: t$_R$=0.99 min; ES+: 784.23.

Mixture of (3'R,4'S)-3'-({2-chloro-5-[(3,3,3-trifluoro-propionylamino)-methyl]-benzyl}-cyclopropyl-carbamoyl)-6-[(R)-3-(2,6-dichloro-4-methyl-phenoxy)pyrrolidin-1-yl]-3',4',5',6'-tetrahydro-2'H-[3,4']bipyridinyl-1'-carboxylic acid tert-butyl ester and (3'S,4'R-3'-({2-chloro-5-[(3,3,3-trifluoro-propionylamino)-methyl]-benzyl}-cyclopropyl-carbamoyl)-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L49)

Oxalyl chloride (0.136 mL, 1.57 mmol) was added to a sol. of compounds K30 (720 mg, 1.31 mmol) in toluene (20 mL) and DMF (3 drops). The mixture was stirred at rt for 80 min. The solvents were removed under reduced pressure, and the residue was diluted in CH$_2$Cl$_2$ (30 mL). Et$_3$N (0.540 mL, 3.90 mmol) was added, and the mixture was stirred for 5 min. A sol. of N-(4-chloro-3-cyclopropylaminomethyl-benzyl)-3,3,3-trifluoro-propionamide (621 mg, 1.94 mmol) in CH$_2$Cl$_2$ (4.00 mL) was added, and the mixture was stirred at rt for 1 h. The mixture was diluted with CH$_2$Cl$_2$, and was washed with aq. sat. NH$_4$Cl and aq. 10% Na$_2$CO$_3$. The org. layer was dried over MgSO$_4$, filtered, and the solvents were removed under reduced pressure. Purification of the crude by FC (EtOAc/heptane 1:1→EtOAc→MeOH/EtOAc 1:9) yielded the title compounds mixture (870 mg, 79%). LC-MS: t$_R$=1.02 min; ES+: 854.24.

Mixture of (3'R,4'S)-3'-({2-chloro-5-[(3,3,3-trifluoro-propionylamino)-methyl]-benzyl}-cyclopropyl-carbamoyl)-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-({2-chloro-5-[(3,3,3-trifluoro-propionylamino)-methyl]-benzyl}-cyclopropyl-carbamoyl)-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L50)

Oxalyl chloride (0.136 mL, 1.57 mmol) was added to a sol. of compounds K32 (720 mg, 1.31 mmol) in toluene (20 mL) and DMF (3 drops). The mixture was stirred at rt for 80 min. The solvents were removed under reduced pressure, and the residue was diluted in CH$_2$Cl$_2$ (30 mL). Et$_3$N (0.540 mL, 3.90 mmol) was added, and the mixture was stirred for 5 min. A sol. of N-(4-chloro-3-cyclopropylaminomethyl-benzyl)-3,3,3-trifluoro-propionamide (625 mg, 1.95 mmol) in CH$_2$Cl$_2$ (4.00 mL) was added, and the mixture was stirred at rt for 1 h. The mixture was diluted with CH$_2$Cl$_2$, and was washed with aq. sat. NH$_4$Cl and aq. 10% Na$_2$CO$_3$. The org. layer was dried over MgSO$_4$, filtered, and the solvents were removed under reduced pressure. Purification of the crude by FC (EtOAc/heptane 1:1→EtOAc→MeOH/EtOAc 1:9) yielded the title compounds mixture (840 mg, 76%). LC-MS: t$_R$=1.02 min; ES+: 854.28.

(rac.)-(3R*,4S*)-3-({5-[(tert-Butoxycarbonyl-cyclopropyl-amino)-methyl]-2-chloro-benzyl}-cyclopropyl-carbamoyl)-4-{4-[3-(2-chloro-3,6-difluoro-phenyl)-isoxazol-5-ylmethoxy]-phenyl}-piperidine-1-carboxylic acid tert-butyl ester (L51)

Oxalyl chloride (0.122 mL, 1.44 mmol) was added to a sol. of compound K6 (659 mg, 1.20 mmol) in toluene (25 mL) and DMF (3 drops). The mixture was stirred at rt for 80 min. The solvents were removed under reduced pressure, and the residue was diluted in CH$_2$Cl$_2$ (30 mL). Et$_3$N (0.459 mL, 3.30 mmol) was added, and the mixture was stirred for 5 min. A sol. of (4-chloro-3-cyclopropylaminomethyl-benzyl)-cyclopropyl-carbamic acid tert-butyl ester (463 mg, 1.32 mmol) in CH$_2$Cl$_2$ (4.00 mL) was added, and the mixture was stirred at rt for 1 h. The mixture was diluted with CH$_2$Cl$_2$, and was washed with aq. sat. NH$_4$Cl and aq. 10% Na$_2$CO$_3$. The org. layer was dried over MgSO$_4$, filtered, and the solvents were removed under reduced pressure. Purification of the crude by FC (EtOAc/heptane 1:1→EtOAc→MeOH/EtOAc 1:9) yielded the title compound (600 mg, 62%). LC-MS: t$_R$=1.23 min; ES+: 881.76.

(rac.)-(3R*,4S*)-4-{4-[3-(2-Chloro-3,6-difluoro-phenyl)-isoxazol-5-ylmethoxy]-phenyl}-3-{[5-chloro-2-(3-methoxy-propyl)-1-oxy-pyridin-4-ylmethyl]-cyclopropyl-carbamoyl}-piperidine-1-carboxylic acid tert-butyl ester (L52)

MCPBA (332 mg, 1.34 mmol) was added to a sol. of compound L45 (960 mg, 1.22 mmol) in CH$_2$Cl$_2$ (12 mL). The mixture was stirred at rt overnight, and MCPBA (50 mg, 0.290 mmol) was added again. The mixture was stirred for 5 h, and EtOAc was added. The mixture was washed with aq. sat. NaHCO$_3$ and brine. The org. layer was dried over MgSO$_4$, filtered, and the solvents were removed under reduced pressure. Purification of the crude by FC (MeOH/CH$_2$Cl$_2$ 1:9) yielded the title compound still mixed with compound L45. This mixture was dissolved in CH$_2$Cl$_2$ (12 mL), and MCPBA (100 mg, 0.406 mmol) was added again. The mixture was stirred for 4 h at rt, and was washed with aq. sat. NaHCO$_3$ and water. The org. layer was dried over Na$_2$SO$_4$, filtered, and the solvents were removed under reduced pressure. Purification of the crude by FC (MeOH/CH$_2$Cl$_2$ 2.5:97.5→5:95, always with 1% Et$_3$N) yielded the title compound (660 mg, 66%). LC-MS: t$_R$=1.15 min; ES+: 800.75.

Mixture of (3'R,4'S)-3'-({5-[(tert-butoxycarbonyl-cyclopropyl-amino)-methyl]-2-chloro-benzyl}-cyclopropyl-carbamoyl)-6-[(S)-3-(2,6-dichloro-4-methyl-phenoxy)pyrrolidin-1-yl]-3',4',5',6'-tetrahydro-2'H-[3,4']bipyridinyl-1'-carboxylic acid tert-butyl ester and (3'S,4'R)-3'-({5-[(tert-butoxycarbonyl-cyclopropyl-amino)methyl]-2-chloro-benzyl}-cyclopropyl-carbamoyl)-6-[(S)-3-(2,6-dichloro-4-methyl-phenoxy)pyrrolidin-1-yl]-3',4',5',6'-tetrahydro-2'H-[3,4']bipyridinyl-1'-carboxylic acid tert-butyl ester (L53)

To a sol. of compounds K32 (623 mg, 1.13 mmol) in toluene (18 mL) were successively added at rt DMF (one drop) and oxalyl chloride (0.117 mL, 1.36 mmol). The mixture was stirred at rt for 1 h. The solvents were removed under reduced pressure, and the crude was dried under high vacuum. The crude product was dissolved in CH$_2$Cl$_2$ (20 mL). Et$_3$N (0.47 mL, 3.39 mmol) was added, and the mixture was stirred for 5 min at rt. A sol. of (4-chloro-3-cyclopropylaminomethyl-benzyl)-cyclopropyl-carbamic acid tert-butyl ester (475 mg, 1.35 mmol) in CH$_2$Cl$_2$ (4 mL) was added, and the mixture was stirred at rt for 45 min. CH$_2$Cl$_2$ (20 mL) was added, and the mixture was washed with aq. sat. NH$_4$Cl (1×) and aq. 10% Na$_2$CO$_3$ (1×). The org. layer was dried over MgSO$_4$, filtered, and the solvents were removed under reduced pressure. Purification of the crude by FC (heptane/EtOAc 1:1→EtOAc) yielded the title compounds mixture (860 mg, 86%). LC-MS: t$_R$=1.08 min; ES+: 884.86.

(rac.)-(3R*,4S*)-3-{[5-(2-Acetylamino-ethyl)-2-chloro-benzyl]-cyclopropyl-carbamoyl}-4-{4-[3-(2-chloro-3,6-difluoro-phenyl)-isoxazol-5-ylmethoxy]-phenyl}-piperidine-1-carboxylic acid tert-butyl ester (L54)

Oxalyl chloride (0.211 mL, 2.49 mmol) was added to a sol. of compound K6 (1.14 g, 2.07 mmol) and DMF (3 drops) in toluene (65 mL). The mixture was stirred at rt for 45 min, and the solvents were removed under reduced pressure. The residue was thoroughly dried under high vacuum, and dissolved in CH$_2$Cl$_2$ (35 mL). Et$_3$N (0.710 mL, 5.10 mmol) was added, and the mixture was stirred for 5 min at rt. A sol. of N-[2-(4-chloro-3-cyclopropylaminomethyl-phenyl)-ethyl]-acetamide (540 mg, 2.04 mmol) in CH$_2$Cl$_2$ (4.00 mL) was added, and the mixture was stirred at rt for 1 h. More CH$_2$Cl$_2$ was added, and the mixture was washed with aq. sat. NH$_4$Cl and aq. 10% Na$_2$CO$_3$. The org. layer was dried over MgSO$_4$, filtered, and the solvents were removed under reduced pressure. Purification of the residue by FC (EtOAc/heptane 1:1<EtOAc) yielded the title compound (490 mg, 36%). LC-MS: t$_R$=1.14 min; ES+: 797.52.

(rac.)-(3R*,4S*)-3-({5-[2-(tert-Butoxycarbonyl-cyclopropyl-amino)-ethyl]-2-chloro-benzyl}-cyclopropyl-carbamoyl)-4-{4-[3-(2-chloro-3,6-difluoro-phenyl)-isoxazol-5-ylmethoxy]-phenyl}-piperidine-1-carboxylic acid tert-butyl ester (L55)

Oxalyl chloride (0.120 mL, 1.42 mmol) was added to a sol. of compound K6 (600 mg, 1.09 mmol) and DMF (1 drop) in toluene (15 mL). The mixture was stirred for 1 h at rt, and the solvents were removed under reduced pressure. The residue was dissolved in CH$_2$Cl$_2$ (10 mL), and Et$_3$N (0.221 mmol, 1.59 mmol) was added. The mixture was stirred for 5 min, and [2-(4-chloro-3-cyclopropylaminomethyl-phenyl)-ethyl]-cyclopropyl-carbamic acid tert-butyl ester (386 mg, 1.06 mmol) was added. The mixture was stirred for 30 min at rt, and was washed with aq. 1M HCl and brine. The org. layer was dried over MgSO$_4$, filtered, and the solvents were removed under reduced pressure. Purification of the crude by FC (EtOAc/heptane 1:4-EtOAc) yielded the title compound (620 mg, 49%). LC-MS: t$_R$=1.25 min; ES+: 895.57.

Mixture of (3'R,4'S)-3'-({5-[2-(tert-butoxycarbonyl-cyclopropyl-amino)-ethyl]-2-chloro-benzyl}-cyclopropyl-carbamoyl)-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-({5-[2-(tert-butoxycarbonyl-cyclopropyl-amino)-ethyl]-2-chloro-benzyl}-cyclopropyl-carbamoyl)-6-[(R)-3-(2,6-dichloro-4-methyl-phenoxy)pyrrolidin-1-yl]-3',4',5',6'-tetrahydro-2'H-[3,4']bipyridinyl-1'-carboxylic acid tert-butyl ester (L56)

Oxalyl chloride (0.120 mL, 1.42 mmol) was added to a sol. of compounds K30 (600 mg, 1.09 mmol) and DMF (1 drop) in toluene (15 mL). The mixture was stirred for 30 min at rt, and the solvents were removed under reduced pressure. The residue was dissolved in CH$_2$Cl$_2$ (10 mL) and Et$_3$N (0.221 mL, 1.59 mmol) was added. The mixture was stirred for 5 min, and [2-(4-chloro-3-cyclopropylaminomethyl-phenyl)-ethyl]-cyclopropyl-carbamic acid tert-butyl ester (405 mg, 1.11 mmol) was added. The mixture was stirred for 30 min at rt, and was washed with aq. 1M HCl and brine. The org. layer was dried over MgSO$_4$, filtered, and the solvents were removed under reduced pressure. Purification of the crude by FC (EtOAc/heptane 1:1→EtOAc) yielded the title compounds mixture (240 mg, 24%). LC-MS: t$_R$=1.09 min; ES+: 898.60.

Mixture of (3'R,4'S)-3'-({5-[2-(tert-butoxycarbonyl-cyclopropyl-amino)-ethyl]-2-chloro-benzyl}-cyclopropyl-carbamoyl)-6-[(S)-3-(2,6-dichloro-4-methyl-phenoxy)pyrrolidin-1-yl]-3',4',5',6'-tetrahydro-2'H-[3,4']bipyridinyl-1'-carboxylic acid tert-butyl ester and (3'S,4'R)-3'-({5-[2-(tert-butoxycarbonyl-cyclopropyl-amino)-ethyl]-2-chloro-benzyl}-cyclopropyl-carbamoyl)-6-[(S)-3-(2,6-dichloro-4-methyl-phenoxy)pyrrolidin-1-yl]-3',4',5',6'-tetrahydro-2'H-[3,4']bipyridinyl-1'-carboxylic acid tert-butyl ester (L57)

Oxalyl chloride (0.150 mL, 1.77 mmol) was added to a sol. of compounds K32 (750 mg, 1.36 mmol) and DMF (1 drop) in toluene (33 mL). The mixture was stirred for 90 min at rt, and the solvents were removed under reduced pressure. The residue was dissolved in CH$_2$Cl$_2$ (26 mL) and Et$_3$N (0.227 mL, 1.63 mmol) was added. The mixture was stirred for 5 min, and [2-(4-chloro-3-cyclopropylaminomethyl-phenyl)-ethyl]-cyclopropyl-carbamic acid tert-butyl ester (398 mg, 1.09 mmol) was added. The mixture was stirred for 30 min at rt, and the solvents were removed under reduced pressure. Purification of the crude by FC (EtOAc/heptane 1:1) yielded the title compounds mixture (796 mg, 65%). LC-MS: $t_R$=1.08 min; ES+: 898.61.

(rac.)-(3'R*,4'S*)-3'-{[5-Chloro-2-(3-methoxy-propyl)-1-oxy-pyridin-4-ylmethyl]-cyclopropyl-carbamoyl}-6-[2-(2,6-dichloro-4-methyl-phenoxy)-ethoxy]-3',4',5',6'-tetrahydro-2'H-[3,4']bipyridinyl-1'-carboxylic acid tert-butyl ester (L58)

Oxalyl chloride (0.147 mL, 1.73 mmol) was added to a sol. of compound K16 (700 mg, 1.33 mmol) and DMF (0.02 mL) in toluene (29 mL). The mixture was stirred for 30 min, and the solvents were removed under reduced pressure. The residue was dried under high vacuum for 30 min, and was diluted with $CH_2Cl_2$ (38 mL). $Et_3N$ (0.345 mL, 2.48 mmol) and [5-chloro-2-(3-methoxy-propyl)-1-oxy-pyridin-4-ylmethyl]-cyclopropyl-amine were added (448 mg, 1.66 mmol). The mixture was stirred at rt for 1.5 h, and more $CH_2Cl_2$ was added. The mixture was washed with aq. 1M HCl and brine. The org. layer was dried over $MgSO_4$, filtered, and the solvents were removed under reduced pressure. Purification of the crude by FC (MeOH/$CH_2Cl_2$ 1:49) yielded the title compound (480 mg, 47%). LC-MS: $t_R$=1.16 min; ES+: 779.56.

(rac.)-(3R*,4S*)-3-[(5-{[tert-Butoxycarbonyl-(2,2-difluoro-ethyl)-amino]-methyl}-2-chloro-benzyl)-cyclopropyl-carbamoyl]-4-{4-[3-(2-chloro-3,6-difluoro-phenyl)-isoxazol-5-ylmethoxy]-phenyl}-piperidine-1-carboxylic acid tert-butyl ester (L59)

Oxalyl chloride (0.120 mL, 1.42 mmol) was added to a sol. of compound K6 (600 mg, 1.09 mmol) and DMF (one drop) in toluene (15 mL). The mixture was stirred for 1 h, and the solvents were removed under reduced pressure. The residue was dissolved in $CH_2Cl_2$ (10 mL) and $Et_3N$ (0.221 mL, 1.59 mmol) was added. The mixture was stirred for 5 min, and a sol. of (4-chloro-3-cyclopropylaminomethyl-benzyl)-(2,2-difluoro-ethyl)-carbamic acid tert-butyl ester (458 mg, 1.27 mmol) in $CH_2Cl_2$ (5 mL) was added. The mixture was stirred for 30 min at rt, and was extracted with aq. 1M HCl and brine. The org. layer was dried over $MgSO_4$, filtered, and the solvents were removed under reduced pressure. Purification of the crude by FC (EtOAc/heptane 1:4→EtOAc) yielded the title compound (700 mg, 71%). LC-MS: $t_R$=1.22 min; ES+: 905.53.

Mixture of (3'R,4'S)-3'-[(5-{[tert-butoxycarbonyl-(2,2-difluoro-ethyl)-amino]-methyl}-2-chloro-benzyl)-cyclopropyl-carbamoyl]-6-[(S-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(5-{[tert-butoxycarbonyl-(2,2-difluoro-ethyl)amino]-methyl}-2-chloro-benzyl)-cyclopropyl-carbamoyl]-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L60)

Oxalyl chloride (0.150 mL, 1.77 mmol) was added to a sol. of compounds K32 (750 mg, 1.36 mmol) and DMF (one drop) in toluene (33 mL). The mixture was stirred for 1 h, and the solvents were removed under reduced pressure. The residue was dissolved in $CH_2Cl_2$ (20 mL) and $Et_3N$ (0.227 mL, 1.63 mmol) was added. The mixture was stirred for 5 min, and a sol. of (4-chloro-3-cyclopropylaminomethyl-benzyl)-(2,2-difluoro-ethyl)-carbamic acid tert-butyl ester (409 mg, 1.09 mmol) in $CH_2Cl_2$ (6 mL) was added. The mixture was stirred for 30 min at rt, and the solvents were removed under reduced pressure. Purification of the crude by FC (EtOAc/heptane 1:1) yielded the title compounds mixture (759 mg, 62%). LC-MS: $t_R$=1.06 min; ES+: 908.57.

Mixture of (3'R,4'S)-3'-[(2-chloro-5-cyclopropylcarbamoylmethyl-benzyl)cyclopropyl-carbamoyl]-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(2-chloro-5-cyclopropylcarbamoylmethyl-benzyl)-cyclopropyl-carbamoyl]-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L61)

Oxalyl chloride (0.150 mL, 1.77 mmol) was added to a sol. of compounds K32 (750 mg, 1.36 mmol) and DMF (one drop) in toluene (33 mL). The mixture was stirred for 1 h, and the solvents were removed under reduced pressure. The residue was dissolved in $CH_2Cl_2$ (20 mL) and $Et_3N$ (0.227 mL, 1.63 mmol) was added. The mixture was stirred for 5 min, and a sol. of 2-(4-chloro-3-cyclopropylaminomethyl-phenyl)-N-cyclopropyl-acetamide (304 mg, 1.09 mmol) in $CH_2Cl_2$ (6 mL) was added. The mixture was stirred for 30 min at rt, and the solvents were removed under reduced pressure. Purification of the crude by FC (EtOAc) yielded the title compounds mixture (737 mg, 72%). LC-MS: $t_R$=1.00 min; ES+: 812.57.

Mixture of (3'R,4'S)-3'-[(2-chloro-5-methylcarbamoylmethyl-benzyl)-cyclopropyl-carbamoyl]-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(2-chloro-5-methylcarbamoylmethyl-benzyl)-cyclopropyl-carbamoyl]-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L62)

Oxalyl chloride (0.143 mL, 1.69 mmol) was added to a sol. of compounds K32 (716 mg, 1.30 mmol) and DMF (0.02 mL) in toluene (30 mL). The mixture was stirred for 2.5 h at rt, and the solvents were removed under reduced pressure. The residue was dissolved in $CH_2Cl_2$ (32 mL), and $Et_3N$ (0.378 mL, 2.70 mmol) was added. A sol. of 2-(4-chloro-3-cyclopropylaminomethyl-phenyl)-N-methyl-acetamide (455 mg, 1.80 mmol) in $CH_2Cl_2$ (10 mL) was added, and the mixture was stirred for 1 h at rt. More $CH_2Cl_2$ was added, and the mixture was washed with aq. 1M HCl and with brine. The org. layer was dried over $MgSO_4$, filtered, and the solvents were removed under reduced pressure. Purification of the crude by FC (MeOH/$CH_2Cl_2$ 1:49) yielded the title compounds mixture (810 mg, 79%). LC-MS: $t_R$=0.94 min; ES+: 786.60.

Mixture of (3'R,4'S)-3'-[(2-chloro-5-ethylcarbamoylmethyl-benzyl)cyclopropyl-carbamoyl]-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(2-chloro-5-ethylcarbamoylmethyl-benzyl)-cyclopropyl-carbamoyl]-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L63)

Oxalyl chloride (0.119 mL, 1.37 mmol) was added to a sol. of compounds K32 (630 mg, 1.14 mmol) and DMF (one drop)

in toluene (25 mL). The mixture was stirred for 2 h, and the solvents were removed under reduced pressure. The residue was dissolved in $CH_2Cl_2$ (31 mL) and $Et_3N$ (0.580 mL, 4.17 mmol) was added. The mixture was stirred for 5 min, and a sol. of 2-(4-chloro-3-cyclopropylaminomethyl-phenyl)-N-ethyl-acetamide (370 mg, 1.39 mmol) in $CH_2Cl_2$ (5 mL) was added. The mixture was stirred for 2 h at rt, and the solvents were removed under reduced pressure. More $CH_2Cl_2$ was added, and the mixture was washed with aq. 10% $Na_2CO_3$. The org. layer was dried over $MgSO_4$, filtered, and the solvents were removed under reduced pressure. Purification of the crude by FC (EtOAc/heptane 4:1) yielded the title compounds mixture (700 mg, 77%). LC-MS: $t_R$=1.01 min; ES+: 800.70.

Mixture of (3'R,4'S)-3'-{[2-chloro-5-(propionylamino-methyl)-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(propionylamino-methyl)-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L64)

Oxalyl chloride (0.152 mL, 1.80 mmol) was added to a sol. of compounds K32 (761 mg, 1.38 mmol) and DMF (one drop) in toluene (32 mL). The mixture was stirred for 75 min, and the solvents were removed under reduced pressure. The residue was dissolved in $CH_2Cl_2$ (42 mL) and $Et_3N$ (0.378 mL, 2.70 mmol) was added. The mixture was stirred for 5 min, and a sol. of N-(4-chloro-3-cyclopropylaminomethyl-benzyl)-propionamide (480 mg, 1.80 mmol) in $CH_2Cl_2$ (10 mL) was added. The mixture was stirred for 1 h at rt, and the solvents were removed under reduced pressure. More $CH_2Cl_2$ was added, and the mixture was washed with aq. 1M HCl and brine. The org. layer was dried over $MgSO_4$, filtered, and the solvents were removed under reduced pressure. Purification of the crude by FC (MeOH/$CH_2Cl_2$ 1:49) yielded the title compounds mixture (990 mg, 90%). LC-MS: $t_R$=0.99 min; ES+: 798.74.

(rac.)-(3R*,4S*)-3-({2-Chloro-5-[(cyclopropanecarbonyl-amino)-methyl]-benzyl}-cyclopropyl-carbamoyl)-4-{4-[3-(2-chloro-3,6-difluoro-phenyl)-isoxazol-5-ylmethoxy]-phenyl}-piperidine-1-carboxylic acid tert-butyl ester (L65)

Oxalyl chloride (0.211 mL, 2.49 mmol) was added to a sol. of compound K6 (1.14 g, 2.07 mmol) and DMF (one drop) in toluene (65 mL). The mixture was stirred for 45 min, the solvents were removed under reduced pressure, and the residue was dried under high vacuum. The residue was dissolved in $CH_2Cl_2$ (35 mL) and $Et_3N$ (0.710 mL, 5.10 mmol) was added. The mixture was stirred for 5 min, and a sol. of cyclopropanecarboxylic acid 4-chloro-3-cyclopropylaminomethyl-benzylamide (474 mg, 1.70 mmol) in $CH_2Cl_2$ (4 mL) was added. The mixture was stirred for 1 h at rt, and more $CH_2Cl_2$ was added. The mixture was washed with aq. sat. $NH_4Cl$, and aq. 10% $Na_2CO_3$. The org. layer was dried over $MgSO_4$, and the solvents were removed under reduced pressure. Purification of the crude by FC (EtOAc/heptane 1:3→1:1) yielded the title compound (610 mg, 36%). LC-MS: $t_R$=1.14 min; ES+: 809.54.

Mixture of (3'R,4'S)-3'-({2-chloro-5-[(cyclopropanecarbonyl-amino)-methyl]-benzyl}-cyclopropyl-carbamoyl)-6-[(S)-3-(2,6-dichloro-4-methyl-phenoxy)-pyrrolidin-1-yl]-3',4',5',6'-tetrahydro-2'H-[3,4'] bipyridinyl-1'-carboxylic acid tert-butyl ester and (3'S,4'R)-3'-({2-chloro-5-[(cyclopropanecarbonyl-amino)-methyl]-benzyl}-cyclopropyl-carbamoyl)-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L66)

Oxalyl chloride (0.141 mL, 1.66 mmol) was added to a sol. of compounds K32 (704 mg, 1.28 mmol) and DMF (one drop) in toluene (30 mL). The mixture was stirred for 2.5 h, the solvents were removed under reduced pressure, and the residue was dried under high vacuum. The residue was dissolved in $CH_2Cl_2$ (39 mL) and $Et_3N$ (0.347 mL, 2.48 mmol) was added. The mixture was stirred for 5 min, and a sol. of cyclopropanecarboxylic acid 4-chloro-3-cyclopropylaminomethyl-benzylamide (461 mg, 1.65 mmol) in $CH_2Cl_2$ (10 mL) was added. The mixture was stirred for 1 h at rt, and more $CH_2Cl_2$ was added. The mixture was washed with aq. 1M HCl, and with brine. The org. layer was dried over $MgSO_4$, filtered, and the solvents were removed under reduced pressure. Purification of the crude by FC (MeOH/$CH_2Cl_2$ 1:49) yielded the title compounds mixture (1.03 g, 99%). LC-MS: $t_R$=1.00 min; ES+: 812.64.

(rac.)-(3R*,4S*)-4-{4-[3-(2-chloro-3,6-difluoro-phenyl)isoxazol-5-ylmethoxy]-phenyl}-3-{[2-chloro-5-(methoxycarbonylamino-methyl)-benzyl]-cyclopropyl-carbamoyl}-piperidine-1-carboxylic acid tert-butyl ester (L67)

Oxalyl chloride (0.211 mL, 7.46 mmol) was added to a sol. of compound K6 (1.14 g, 2.07 mmol) and DMF (1 drop) in toluene (65 mL). The mixture was stirred at rt for 45 min, and the solvents were removed under reduced pressure. The residue was dried under high vacuum, and was dissolved in $CH_2Cl_2$ (35 mL). $Et_3N$ (0.710 mL, 5.10 mmol) was added, and the mixture was stirred at rt for 5 min. A sol. of (4-chloro-3-cyclopropylaminomethyl-benzyl)-carbamic acid methyl ester (457 mg, 1.70 mmol) in $CH_2Cl_2$ (4.00 mL) was added, and the mixture was stirred at rt for 1 h. More $CH_2Cl_2$ was added, and the mixture was washed with aq. sat. $NH_4Cl$ and aq. 10% $Na_2CO_3$. The org. layer was dried over $MgSO_4$, filtered, and the solvents were removed under reduced pressure. Purification of the crude by FC (EtOAc/heptane 1:3→1:1→EtOAc) yielded the title compound (620 mg, 37%). LC-MS: $t_R$=1.15 min; ES+: 799.50.

Mixture of (3'R,4'S)-3'-{[2-chloro-5-(methoxycarbonylamino-methyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(methoxycarbonylamino-methyl)-benzyl]-cyclopropyl-carbamoyl}-6-[(R)-3-(2,6-dichloro-4-methyl-phenoxy)-pyrrolidin-1-yl]-3',4',5', 6'-tetrahydro-2'H-[3,4']bipyridinyl-1'-carboxylic acid tert-butyl ester (L68)

Oxalyl chloride (0.113 mL, 1.31 mmol) was added to a sol. of compounds K30 (600 mg, 1.09 mmol) and DMF (1 drop) in toluene (20 mL). The mixture was stirred at rt for 1.5 h, and the solvents were removed under reduced pressure. The residue was dried under high vacuum, and was dissolved in $CH_2Cl_2$ (26 mL). $Et_3N$ (0.455 mL, 3.27 mmol) was added, and the mixture was stirred for 5 min. A sol. of (4-chloro-3-cyclopropylaminomethyl-benzyl)-carbamic acid methyl ester (293 mg, 1.09 mmol) in $CH_2Cl_2$ (4.00 mL) was added, and the mixture was stirred at rt for 45 min. More $CH_2Cl_2$ was added, and the mixture was washed with aq. sat. $NH_4Cl$ and aq. 10% $Na_2CO_3$. The org. layer was dried over $MgSO_4$, filtered, and the solvents were removed under reduced pressure. Purification of the crude by FC (EtOAc/heptane 1:1→EtOAc) yielded the title compounds mixture (860 mg, 89%). LC-MS: $t_R$=0.98 min; ES+: 802.55.

Mixture of (3'R,4'S)-3'-{[2-chloro-5-(methoxycarbonylamino-methyl)-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(methoxycarbonylamino-methyl)-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L69)

Oxalyl chloride (0.113 mL, 1.31 mmol) was added to a sol. of compounds K32 (600 mg, 1.09 mmol) and DMF (1 drop) in toluene (20 mL). The mixture was stirred at rt for 1.5 h, and the solvents were removed under reduced pressure. The residue was dried under high vacuum, and was dissolved in $CH_2Cl_2$ (26 mL). $Et_3N$ (0.455 mL, 3.27 mmol) was added, and the mixture was stirred for 5 min. A sol. of (4-chloro-3-cyclopropylaminomethyl-benzyl)-carbamic acid methyl ester (293 mg, 1.09 mmol) in $CH_2Cl_2$ (4.00 mL) was added, and the mixture was stirred at rt for 45 min. More $CH_2Cl_2$ was added, and the mixture was washed with aq. sat. $NH_4Cl$ and aq. 10% $Na_2CO_3$. The org. layer was dried over $MgSO_4$, filtered, and the solvents were removed under reduced pressure. Purification of the crude by FC (EtOAc/heptane 1:1→EtOAc) yielded the title compounds mixture (630 mg, 72%). LC-MS: $t_R$=0.98 min; ES+: 802.55.

Mixture of (3'R,4'S)-3'-{[5-(2-acetylamino-ethyl)-2-chloro-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[5-(2-acetylamino-ethyl)-2-chloro-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L70)

Oxalyl chloride (0.240 mL, 2.83 mmol) was added to a sol. of compounds K30 (1.20 g, 2.18 mmol) and DMF (1 drop) in toluene (30 mL). The mixture was stirred for 1 h at rt, the solvents were removed under reduced pressure, and the residue was dried under high vacuum for 15 min. The residue was dissolved in $CH_2Cl_2$ (10 mL), and $Et_3N$ (0.456 mL, 3.28 mmol) was added. The mixture was stirred at rt for 5 min, and a sol. of N-[2-(4-chloro-3-cyclopropylaminomethyl-phenyl)-ethyl]-acetamide (611 mg, 2.29 mmol) in $CH_2Cl_2$ (5 mL) was added. The mixture was stirred for 30 min at rt, and the solvents were removed under reduced pressure. $CH_2Cl_2$ was added, and the mixture was washed with aq. 1M HCl and with brine. The org. layer was dried over $MgSO_4$, filtered, and the solvents were removed under reduced pressure. Purification of the crude by FC (EtOAc/heptane 1:1→7:3) yielded the title compounds mixture (1.36 g, 78%). LC-MS: $t_R$=0.99 min; ES+: 798.37.

Mixture of (3'R,4'S)-3'-{[5-(2-acetylamino-ethyl)-2-chloro-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[5-(2-acetylamino-ethyl)-2-chloro-benzyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L71)

Oxalyl chloride (0.143 mL, 1.69 mmol) was added to a sol. of compounds K32 (716 mg, 1.30 mmol) and DMF (1 drop) in toluene (15 mL). The mixture was stirred for 1 h at rt, the solvents were removed under reduced pressure, and the residue was dried under high vacuum for 15 min. The residue was dissolved in $CH_2Cl_2$ (13 mL), and $Et_3N$ (0.362 mL, 2.60 mmol) was added. The mixture was stirred at rt for 5 min, and a sol. of N-[2-(4-chloro-3-cyclopropylaminomethyl-phenyl)-ethyl]-acetamide (364 mg, 1.37 mmol) in $CH_2Cl_2$ (5 mL) was added. The mixture was stirred for 30 min at rt, and the solvents were removed under reduced pressure. $CH_2Cl_2$ was added, and the mixture was washed with aq. 1M HCl and with brine. The org. layer was dried over $MgSO_4$, filtered, and the solvents were removed under reduced pressure. Purification of the crude by FC ($MeOH/CH_2Cl_2$ 1:19) yielded the title compounds mixture (550 mg, 53%). LC-MS: $t_R$=0.98 min; ES+: 798.36.

Mixture of (3'R,4'S)-3'-[(5-{[tert-butoxycarbonyl-(2,2-difluoro-ethyl)-amino]-methyl}-2-chloro-benzyl)-cyclopropyl-carbamoyl]-6-[(R)-3-(2,6-dichloro-4-methyl-phenoxy)-pyrrolidin-1-yl]-3',4',5',6'-tetrahydro-2'H-[3,4']bipyridinyl-1'-carboxylic Acid tert-butyl ester and (3'S,4'R)-3'-[(5-{[tert-butoxycarbonyl-(2,2-difluoro-ethyl)amino]-methyl}-2-chloro-benzyl)-cyclopropyl-carbamoyl]-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L72)

Oxalyl chloride (0.120 mL, 1.42 mmol) was added to a sol. of compounds K30 (600 mg, 1.09 mmol) and DMF (1 drop) in toluene (30 mL). The mixture was stirred for 1 h at rt, the solvents were removed under reduced pressure, and the residue was dried under high vacuum for 15 min. The residue was dissolved in $CH_2Cl_2$ (10 mL), and $Et_3N$ (0.221 mL, 1.49 mmol) was added. The mixture was stirred at rt for 5 min, and a sol. of (4-chloro-3-cyclopropylaminomethyl-benzyl)-(2,2-difluoro-ethyl)-carbamic acid tert-butyl ester (400 mg, 1.11 mmol) in $CH_2Cl_2$ (5 mL) was added. The mixture was stirred for 30 min at rt, and the solvents were removed under reduced pressure. $CH_2Cl_2$ was added, and the mixture was washed with aq. 1M HCl and with brine. The org. layer was dried over $MgSO_4$, filtered, and the solvents were removed under reduced pressure. The residue was triturated with an 8:2 mixture of heptane and EtOAc, and filtered. The filtrate was evaporated under reduced pressure. Purification of the crude by two FC (EtOAc/heptane 1:4→EtOAc; second time $MeOH/CH_2Cl_2$ 1:19) yielded the title compounds mixture (230 mg, 24%). LC-MS: $t_R$=1.10 min; ES+: 908.32.

Mixture of (3'R,4'S)-3'-[(2-chloro-5-cyclopropylcarbamoylmethyl-benzyl)cyclopropyl-carbamoyl]-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(2-chloro-5-cyclopropylcarbamoylmethyl-benzyl)-cyclopropyl-carbamoyl]-6-[(R-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L73)

Oxalyl chloride (0.146 mL, 1.65 mmol) was added to a sol. of compounds K30 (700 mg, 1.27 mmol) and DMF (1 drop) in toluene (30 mL). The mixture was stirred for 1 h at rt, and the solvents were removed under reduced pressure. The residue was dissolved in $CH_2Cl_2$ (30 mL), and $Et_3N$ (0.266 mL, 1.91 mmol) was added. The mixture was stirred at rt for 5 min, and a sol. of 2-(4-chloro-3-cyclopropylaminomethyl-phenyl)-N-cyclopropyl-acetamide (355 mg, 1.27 mmol) in $CH_2Cl_2$ (5 mL) was added. The mixture was stirred for 90 min at rt, and the mixture was washed with aq. 1M HCl and with brine. The org. layer was dried over $MgSO_4$, filtered, and the solvents were removed under reduced pressure. Purification of the crude by FC (MeOH/$CH_2Cl_2$ 1:19) yielded the title compounds mixture (742 mg, 72%). LC-MS: $t_R$=1.00 min; ES+: 812.67.

Mixture of (3'R,4'S)-3'-[(2-chloro-5-methylcarbamoylmethyl-benzyl)-cyclopropyl-carbamoyl]-6-[(R-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(2-chloro-5-methylcarbamoylmethyl-benzyl)-cyclopropyl-carbamoyl]-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L74)

Oxalyl chloride (0.146 mL, 1.65 mmol) was added to a sol. of compounds K30 (700 mg, 1.27 mmol) and DMF (1 drop) in toluene (30 mL). The mixture was stirred for 1 h at rt, and the solvents were removed under reduced pressure. The residue was dissolved in $CH_2Cl_2$ (30 mL), and $Et_3N$ (0.266 mL, 1.91 mmol) was added. The mixture was stirred at rt for 5 min, and a sol. of 2-(4-chloro-3-cyclopropylaminomethyl-phenyl)-N-methyl-acetamide (322 mg, 1.27 mmol) in $CH_2Cl_2$ (5 mL) was added. The mixture was stirred for 2 h at rt, and the mixture was washed with aq. 1M HCl and with brine. The org. layer was dried over $MgSO_4$, and the solvents were removed under reduced pressure. Purification of the crude by FC (MeOH/$CH_2Cl_2$ 1:19) yielded the title compounds mixture (637 mg, 64%). LC-MS: $t_R$=0.98 min; ES+: 786.62.

Mixture of (3'R,4'S)-3'-({2-chloro-5-[(cyclopropanecarbonyl-amino)-methyl]-benzyl}-cyclopropyl-carbamoyl)-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-({2-chloro-5-[(cyclopropanecarbonyl-amino)-methyl]-benzyl}-cyclopropyl-carbamoyl)-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L75)

Oxalyl chloride (0.146 mL, 1.65 mmol) was added to a sol. of compounds K30 (700 mg, 1.27 mmol) and DMF (1 drop) in toluene (30 mL). The mixture was stirred for 1 h at rt, and the solvents were removed under reduced pressure. The residue was dissolved in $CH_2Cl_2$ (30 mL), and $Et_3N$ (0.266 mL, 1.91 mmol) was added. The mixture was stirred at rt for 5 min, and a sol. of cyclopropanecarboxylic acid 4-chloro-3-cyclopropylaminomethyl-benzylamide (355 mg, 1.27 mmol) in $CH_2Cl_2$ (5 mL) was added. The mixture was stirred for 1 h at rt, and the mixture was washed with aq. 1M HCl and with brine. The org. layer was dried over $MgSO_4$, filtered, and the solvents were removed under reduced pressure. Purification of the crude by FC (MeOH/$CH_2Cl_2$ 1:19) yielded the title compounds mixture (496 mg, 48%). LC-MS: $t_R$=0.99 min; ES+: 812.68.

Mixture of (3'R,4'S)-3'-{[5-chloro-2-(3-methoxy-propyl)-1-oxy-pyridin-4-ylmethyl]-cyclopropyl-carbamoyl}-6-[(R)-3-(2,6-dichloro-4-methyl-phenoxy)pyrrolidin-1-yl]-3',4',5',6'-tetrahydro-2'H-[3,4']bipyridinyl-1'-carboxylic acid tert-butyl ester and (3'S,4'R)-3'-{[5-chloro-2-(3-methoxy-propyl)-1-oxy-pyridin-4-ylmethyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L76)

Oxalyl chloride (0.156 mL, 1.77 mmol) was added to a sol. of compounds K30 (750 mg, 1.36 mmol) and DMF (one drop) in toluene (30 mL). The mixture was stirred at rt for 1 h, and the solvents were removed under reduced pressure. The residue was dissolved in $CH_2Cl_2$ (20 mL), and $Et_3N$ (0.284 mL, 2.04 mmol) was added. The mixture was stirred for 5 min at rt, and a sol. of [5-chloro-2-(3-methoxy-propyl)-1-oxy-pyridin-4-ylmethyl]-cyclopropyl-amine (369 mg, 1.36 mmol) in $CH_2Cl_2$ (10 mL) was added. The mixture was stirred for 1 h at rt, and more $CH_2Cl_2$ was added. The mixture was washed with aq. 1M HCl and with brine. The org. layer was dried over $MgSO_4$, filtered, and the solvents were removed under reduced pressure. Purification of the crude by thick layer chromatography (MeOH/$CH_2Cl_2$ 1:15) yielded the title compounds mixture (418 mg, 38%). LC-MS: $t_R$=0.95 min; ES+: 804.31.

Mixture of (3'R,4'S)-3'-{[5-chloro-2-(3-methoxy-propyl)-1-oxy-pyridin-4-ylmethyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[5-chloro-2-(3-methoxy-propyl)-1-oxy-pyridin-4-ylmethyl]-cyclopropyl-carbamoyl}-6-[(S)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L77)

Oxalyl chloride (0.135 mL, 1.54 mmol) was added to a sol. of compounds K32 (650 mg, 1.18 mmol) and DMF (one drop) in toluene (30 mL). The mixture was stirred at rt for 1 h, and the solvents were removed under reduced pressure. The residue was dissolved in $CH_2Cl_2$ (20 mL), and $Et_3N$ (0.247 mL, 1.77 mmol) was added. The mixture was stirred for 5 min at rt, and a sol. of [5-chloro-2-(3-methoxy-propyl)-1-oxy-pyridin-4-ylmethyl]-cyclopropyl-amine (320 mg, 1.18 mmol) in $CH_2Cl_2$ (10 mL) was added. The mixture was stirred for 1 h at rt, and more $CH_2Cl_2$ was added. The mixture was washed with aq. 1M HCl and with brine. The org. layer was dried over $MgSO_4$, filtered, and the solvents were removed under reduced pressure. Purification of the crude by thick layer chromatography (MeOH/$CH_2Cl_2$ 1:15) yielded the title compounds mixture (402 mg, 42%). LC-MS: $t_R$=0.96 min; ES+: 804.29.

(rac.)-(3R*,4S*)-3-[(2-Chloro-5-cyclopropylcarbamoylmethyl-benzyl)cyclopropyl-carbamoyl]-4-{4-[3-(2-chloro-3,6-difluoro-phenyl)-isoxazol-5-ylmethoxy]-phenyl}-piperidine-1-carboxylic acid tert-butyl ester (L78)

Oxalyl chloride (0.184 mL, 1.42 mmol) was added to a sol. of compound K6 (650 mg, 1.19 mmol) and DMF (3 drops) in toluene (20 mL) at rt. The mixture was stirred for 30 min, and the solvents were removed under reduced pressure. The residue was dried under high vacuum for 1 h, and was dissolved in $CH_2Cl_2$ (30 mL). $Et_3N$ (0.495 mL, 3.56 mmol) was added, and the mixture was stirred for 5 min. A sol. of 2-(4-chloro-3-cyclopropylaminomethyl-phenyl)-N-cyclopropyl-acetamide (331 mg, 1.19 mmol) in $CH_2Cl_2$ (5 mL) was added, and the mixture was stirred overnight. More $CH_2Cl_2$ was added, and the mixture was washed with aq. sat. $NH_4Cl$ and aq. 10% $Na_2CO_3$. The org. layer was dried over $MgSO_4$, filtered, and the solvents were removed under reduced pressure. Purification of the crude by FC (EtOAc/heptane 7:3) yielded the title compound (667 mg, 69%). LC-MS: $t_R$=1.13 min; ES+: 809.17.

(rac.)-(3R*,4S*)-4-{4-[3-(2-Chloro-3,6-difluoro-phenyl)-isoxazol-5-ylmethoxy]-phenyl}-3-[(2-chloro-5-methylcarbamoylmethyl-benzyl)-cyclopropyl-carbamoyl]-piperidine-1-carboxylic acid tert-butyl ester (L79)

Oxalyl chloride (0.184 mL, 1.42 mmol) was added to a sol. of compound K6 (650 mg, 1.19 mmol) and DMF (3 drops) in toluene (20 mL) at rt. The mixture was stirred for 30 min, and the solvents were removed under reduced pressure. The residue was dried under high vacuum for 1 h, and was dissolved in $CH_2Cl_2$ (30 mL). $Et_3N$ (0.495 mL, 3.56 mmol) was added, and the mixture was stirred for 5 min. A sol. of 2-(4-chloro-3-cyclopropylaminomethyl-phenyl)-N-methyl-acetamide (300 mg, 1.19 mmol) in $CH_2Cl_2$ (5 mL) was added, and the mixture was stirred overnight. More $CH_2Cl_2$ was added, and the mixture was washed with aq. sat. $NH_4Cl$ and aq. 10% $Na_2CO_3$. The org. layer was dried over $MgSO_4$, filtered, and the solvents were removed under reduced pressure. Purification of the crude by FC (EtOAc/heptane 4:1) yielded the title compound (597 mg, 64%). LC-MS: $t_R$=1.12 min; ES+: 783.70.

(rac.)-(3R*,4S*)-4-{4-[3-(2-Chloro-3,6-difluoro-phenyl)-isoxazol-5-ylmethoxy]-phenyl}-3-[(2-chloro-5-ethylcarbamoylmethyl-benzyl)-cyclopropyl-carbamoyl]-piperidine-1-carboxylic acid tert-butyl ester (L80)

Oxalyl chloride (0.184 mL, 1.42 mmol) was added to a sol. of compound K6 (650 mg, 1.19 mmol) and DMF (3 drops) in toluene (20 mL) at rt. The mixture was stirred for 30 min, and the solvents were removed under reduced pressure. The residue was dried under high vacuum for 1 h, and was dissolved in $CH_2Cl_2$ (30 mL). $Et_3N$ (0.495 mL, 3.56 mmol) was added, and the mixture was stirred for 5 min. A sol. of 2-(4-chloro-3-cyclopropylaminomethyl-phenyl)-N-ethyl-acetamide (316 mg, 1.19 mmol) in $CH_2Cl_2$ (5 mL) was added, and the mixture was stirred overnight. More $CH_2Cl_2$ was added, and the mixture was washed with aq. sat. $NH_4Cl$ and aq. 10% $Na_2CO_3$. The org. layer was dried over $MgSO_4$, filtered, and the solvents were removed under reduced pressure. Purification of the crude by FC (EtOAc/heptane 7:3) yielded the title compound (441 mg, 47%). LC-MS: $t_R$=1.13 min; ES+: 797.77.

(rac.)-(3R*,4S*)-4-{4-[3-(2-Chloro-3,6-difluoro-phenyl)-isoxazol-5-ylmethoxy]-phenyl}-3-{[2-chloro-5-(propionylamino-methyl)-benzyl]-cyclopropyl-carbamoyl}-piperidine-1-carboxylic acid tert-butyl ester (L81)

Oxalyl chloride (0.184 mL, 1.42 mmol) was added to a sol. of compound K6 (650 mg, 1.19 mmol) and DMF (3 drops) in toluene (20 mL) at rt. The mixture was stirred for 30 min, and the solvents were removed under reduced pressure. The residue was dried under high vacuum for 1 h, and was dissolved in $CH_2Cl_2$ (30 mL). $Et_3N$ (0.495 mL, 3.56 mmol) was added, and the mixture was stirred for 5 min. A sol. of N-(4-chloro-3-cyclopropylaminomethyl-benzyl)-propionamide (316 mg, 1.19 mmol) in $CH_2Cl_2$ (5 mL) was added, and the mixture was stirred overnight. More $CH_2Cl_2$ was added, and the mixture was washed with aq. sat. $NH_4Cl$ and aq. 10% $Na_2CO_3$. The org. layer was dried over $MgSO_4$, filtered, and the solvents were removed under reduced pressure. Purification of the crude by FC (EtOAc/heptane 7:3) yielded the title compound (640 mg, 68%). LC-MS: $t_R$=1.13 min; ES+: 797.75.

Mixture of (3'R,4'S)-3'-[(2-chloro-5-ethylcarbamoyl-methyl-benzyl)cyclopropyl-carbamoyl]-6-[(R-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(2-chloro-5-ethylcarbamoylmethyl-benzyl)-cyclopropyl-carbamoyl]-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L82)

Oxalyl chloride (0.120 mL, 1.42 mmol) was added to a sol. of compounds K30 (600 mg, 1.09 mmol) and DMF (1 drop) in toluene (26 mL). The mixture was stirred at rt for 2 h, and the solvents were removed under reduced pressure. The residue was dissolved in $CH_2Cl_2$ (20 mL), and $Et_3N$ (0.227 mL, 1.63 mmol) was added. The mixture was stirred for 5 min, and a sol. of 2-(4-chloro-3-cyclopropylaminomethyl-phenyl)-N-ethyl-acetamide (291 mg, 1.09 mmol) in $CH_2Cl_2$ (6.00 mL) was added. The mixture was stirred for 30 min, and the solvents were removed under reduced pressure. Purification of the residue by FC (EtOAc) yielded the title compounds mixture (560 mg, 64%). LC-MS: $t_R$=1.03 min; ES+: 798.32.

Mixture of (3'R,4'S)-3'-{[2-chloro-5-(propionylamino-methyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(propionylamino-methyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L83)

Oxalyl chloride (0.152 mL, 1.80 mmol) was added to a sol. of compounds K30 (760 mg, 1.38 mmol) and DMF (1 drop) in toluene (32 mL). The mixture was stirred for 1 h at rt, and the solvents were removed under reduced pressure. The residue was dried under high vacuum for 15 min, and was dissolved in $CH_2Cl_2$ (24 mL). $Et_3N$ (0.292 mL, 2.08 mmol) was added, and the mixture was stirred for 5 min. A sol. of N-(4-chloro-3-cyclopropylaminomethyl-benzyl)-propionamide (370 mg, 1.39 mmol) in CH$_2$Cl$_2$ (10 mL) was added, and the mixture was stirred at rt for 1 h. CH$_2$Cl$_2$ (50 mL) was added, and the mixture was washed with aq. 1M HCl and with brine. The org. layer was dried over MgSO$_4$, filtered, and the solvents were removed under reduced pressure. Purification of the residue by FC(CH$_2$Cl$_2$→MeOH/CH$_2$Cl$_2$ 1:49) yielded the title compounds mixture (530 mg, 48%). LC-MS: t$_R$=0.99 min; ES+: 800.69.

(rac.)-(3R*,4S*)-4-{4-[3-(2-Chloro-3,6-difluoro-phenyl)-isoxazol-5-ylmethoxy]-phenyl}-3-{[2-chloro-5-(2-methylcarbamoyl-ethyl)benzyl]-cyclopropyl-carbamoyl}-piperidine-1-carboxylic acid tert-butyl ester (L84)

Oxalyl chloride (0.177 mL, 2.01 mmol) was added to a sol. of compound K6 (850 mg, 1.55 mmol) and DMF (1 drop) in toluene (30 mL). The mixture was stirred for 1 h at rt, and the solvents were removed under reduced pressure. The residue was dried under high vacuum for 15 min, and was dissolved in CH$_2$Cl$_2$ (20 mL). Et$_3$N (0.323 mL, 2.32 mmol) was added, and the mixture was stirred for 5 min. A sol. of 3-(4-chloro-3-cyclopropylaminomethyl-phenyl)-N-methyl-propionamide (413 mg, 1.55 mmol) in CH$_2$Cl$_2$ (10 mL) was added, and the mixture was stirred at rt for 1 h. CH$_2$Cl$_2$ was added, and the mixture was washed with aq. 1M HCl and with brine. The org. layer was dried over MgSO$_4$, filtered, and the solvents were removed under reduced pressure. Purification of the residue by FC(CH$_2$Cl$_2$→MeOH/CH$_2$Cl$_2$ 1:99→1:49→3:97) yielded the title compound (780 mg, 63%). LC-MS: t$_R$=1.14 min; ES+: 797.69.

(rac.)-(3R*,4S*)-3-[(5-{2-[tert-Butoxycarbonyl-(2,2-difluoro-ethyl)-amino]-ethyl}-2-chloro-benzyl)-cyclopropyl-carbamoyl]-4-{4-[3-(2-chloro-3,6-difluoro-phenyl)-isoxazol-5-ylmethoxy]-phenyl}-piperidine-1-carboxylic acid tert-butyl ester (L85)

Oxalyl chloride (0.177 mL, 2.01 mmol) was added to a sol. of compound K6 (850 mg, 1.55 mmol) and DMF (1 drop) in toluene (30 mL). The mixture was stirred for 1 h at rt, and the solvents were removed under reduced pressure. The residue was dried under high vacuum for 15 min, and was dissolved in CH$_2$Cl$_2$ (20 mL). Et$_3$N (0.323 mL, 2.32 mmol) was added, and the mixture was stirred for 5 min. A sol. of [2-(4-chloro-3-cyclopropylaminomethyl-phenyl)-ethyl]-(2,2-difluoro-ethyl)-carbamic acid tert-butyl ester (602 mg, 1.55 mmol) in CH$_2$Cl$_2$ (10 mL) was added, and the mixture was stirred at rt for 90 min. CH$_2$Cl$_2$ was added, and the mixture was washed with aq. 1M HCl and with brine. The org. layer was dried over MgSO$_4$, filtered, and the solvents were removed under reduced pressure. Purification of the residue by FC(CH$_2$Cl$_2$→MeOH/CH$_2$Cl$_2$ 1:99→1:49→3:97) yielded the title compound (530 mg, 37%). LC-MS: t$_R$=1.24 min; ES+: 919.78.

(rac.)-(3'R*,4'S*)-3'-{[5-(2-Acetylamino-ethyl)-2-chloro-benzyl]-cyclopropyl-carbamoyl}-6-[3-(2-chloro-3,6-difluoro-phenyl)isoxazol-5-ylmethoxy]-3',4',5',6'-tetrahydro-2'H-[3,4']bipyridinyl-1'-carboxylic acid tert-butyl ester (L86)

Oxalyl chloride (0.078 mL, 0.886 mmol) was added to a sol. of compound K33 (375 mg, 0.682 mmol) and DMF (1 drop) in toluene (15 mL). The mixture was stirred for 1 h at rt, and the solvents were removed under reduced pressure. The residue was dried under high vacuum for 15 min, and was dissolved in CH$_2$Cl$_2$ (15 mL). Et$_3$N (0.190 mL, 1.36 mmol) was added, and the mixture was stirred for 5 min. A sol. of N-[2-(4-chloro-3-cyclopropylaminomethyl-phenyl)-ethyl]-acetamide (182 mg, 0.682 mmol) in CH$_2$Cl$_2$ (2 mL) was added, and the mixture was stirred at rt for 1 h. CH$_2$Cl$_2$ was added, and the mixture was washed with aq. 1M HCl and with brine. The org. layer was dried over MgSO$_4$, filtered, and the solvents were removed under reduced pressure. Purification of the residue by FC(CH$_2$Cl$_2$→MeOH/CH$_2$Cl$_2$ 1:99→1:49→3:97→5:95) yielded the title compound (776 mg, 99%). LC-MS: t$_R$=1.14 min; ES+: 798.69.

(rac.)-(3'R*,4S*)-6-[3-(2-Chloro-3,6-difluoro-phenyl)-isoxazol-5-ylmethoxy]-3'-{[5-chloro-2-(3-methoxy-propyl)-pyridin-4-ylmethyl]-cyclopropyl-carbamoyl}-3',4',5',6'-tetrahydro-2'H-[3,4']bipyridinyl-1'-carboxylic acid tert-butyl ester (L87)

Oxalyl chloride (0.175 mL, 1.98 mmol) was added to a sol. of compound K33 (840 mg, 1.53 mmol) and DMF (1 drop) in toluene (33 mL). The mixture was stirred for 45 min at rt, and the solvents were removed under reduced pressure. The residue was dried under high vacuum for 1 h, and was dissolved in CH$_2$Cl$_2$ (30 mL). Et$_3$N (0.425 mL, 3.05 mmol) was added, and the mixture was stirred for 5 min. A sol. of [5-chloro-2-(3-methoxy-propyl)-pyridin-4-ylmethyl]-cyclopropyl-amine (389 mg, 1.53 mmol) in CH$_2$Cl$_2$ (3 mL) was added, and the mixture was stirred at rt for 1.5 h. CH$_2$Cl$_2$ was added, and the mixture was washed with aq. 1M HCl and with brine. The org. layer was dried over MgSO$_4$, filtered, and the solvents were removed under reduced pressure. Purification of the residue by FC (CH$_2$Cl$_2$→MeOH/CH$_2$Cl$_2$ 1:99→1:49) yielded the title compound (619 mg, 52%). LC-MS: t$_R$=1.14 min; ES+: 786.67.

(rac.)-(3'R*,4S*)-6-[3-(2-Chloro-3,6-difluoro-phenyl)-isoxazol-5-ylmethoxy]-3'-{[5-chloro-2-(3-methoxy-propyl)-1-oxy-pyridin-4-ylmethyl]-cyclopropyl-carbamoyl}-3',4',5',6'-tetrahydro-2'H-[3,4']bipyridinyl-1'-carboxylic acid tert-butyl ester (L88)

MCPBA (85%, 212 mg, 0.860 mmol) was added to a sol. of compound L87 (615 mg, 0.782 mmol) in CH$_2$Cl$_2$ (19 mL) at rt. The mixture was stirred for 4.5 h, and more CH$_2$Cl$_2$ was added. The mixture was washed with aq. 1M NaOH and with brine. The combined aq. layers were extracted back with CH$_2$Cl$_2$. The combined org. extracts were dried over MgSO$_4$, filtered, and the solvents were removed under reduced pressure. Purification of the crude by FC (MeOH/CH$_2$Cl$_2$ 1:19) yielded the title compound (621 mg, 82%). LC-MS: t$_R$=1.12 min; ES+: 802.67.

Mixture of (3'R,4'S)-3'-{[2-chloro-5-(2-methylcarbamoyl-ethyl)-benzyl]-cyclopropyl-carbamoyl}-6-[3-(R)-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(2-methylcarbamoyl-ethyl)-benzyl]-cyclopropyl-carbamoyl}-6-[3-(R)-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L89)

Oxalyl chloride (0.178 mL, 2.10 mmol) was added to a sol. of compounds K30 (890 mg, 1.62 mmol) and DMF (1 drop) in toluene (45 mL). The mixture was stirred for 1 h at rt, and the solvents were removed under reduced pressure. The residue was dried under high vacuum for 1 h, and was dissolved in CH$_2$Cl$_2$ (30 mL). Et$_3$N (0.327 mL, 2.35 mmol) was added, and the mixture was stirred for 5 min. A sol. of 3-(4-chloro-3-cyclopropylaminomethyl-phenyl)-N-methyl-propionamide (470 mg, 1.76 mmol) in CH$_2$Cl$_2$ (15 mL) was added, and the mixture was stirred at rt for 1.5 h. CH$_2$Cl$_2$ was added, and the mixture was washed with aq. 1M HCl and with brine. The org. layer was dried over MgSO$_4$, filtered, and the solvents were removed under reduced pressure. Purification of the residue by FC(CH$_2$Cl$_2$→MeOH/CH$_2$Cl$_2$ 3:97) yielded the title compounds mixture (230 mg, 18%). LC-MS: t$_R$=1.00 min; ES+: 800.70.

Mixture of (3'R,4'S)-3'-[(5-{2-[tert-butoxycarbonyl-(2,2-difluoro-ethyl)-amino]-ethyl}-2-chloro-benzyl)-cyclopropyl-carbamoyl]-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(5-{2-[tert-butoxycarbonyl-(2,2-difluoro-ethyl)amino]-ethyl}-2-chloro-benzyl)cyclopropyl-carbamoyl]-6-[(R)-3-(2,6-dichloro-4-methyl-phenoxy)-pyrrolidin-1-yl]-3',4',5', 6'-tetrahydro-2'H-[3,4']bipyridinyl-1'-carboxylic acid tert-butyl ester (L90)

Oxalyl chloride (0.166 mL, 1.96 mmol) was added to a sol. of compounds K30 (830 mg, 1.51 mmol) and DMF (1 drop) in toluene (50 mL). The mixture was stirred for 1 h at rt, and the solvents were removed under reduced pressure. The residue was dried under high vacuum for 1 h, and was dissolved in CH$_2$Cl$_2$ (20 mL). Et$_3$N (0.282 mL, 1.35 mmol) was added, and the mixture was stirred for 5 min. A sol. of [2-(4-chloro-3-cyclopropylaminomethyl-phenyl)-ethyl]-(2,2-difluoroethyl)-carbamic acid tert-butyl ester (526 mg, 1.35 mmol) in CH$_2$Cl$_2$ (20 mL) was added, and the mixture was stirred at rt for 1.5 h. CH$_2$Cl$_2$ was added, and the mixture was washed with aq. 1M HCl and with brine. The org. layer was dried over MgSO$_4$, filtered, and the solvents were removed under reduced pressure. Purification of the residue by FC(CH$_2$Cl$_2$→MeOH/CH$_2$Cl$_2$ 3:97) yielded the title compounds mixture (670 mg, 54%). LC-MS: t$_R$=1.09 min; ES+: 922.88.

Mixture of (3'R,4'S)-3'-[(2-chloro-5-methylcarbamoyloxymethyl-benzyl)-cyclopropyl-carbamoyl]-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-[(2-chloro-5-methylcarbamoyloxymethyl-benzyl)-cyclopropyl-carbamoyl]-6-[(R-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L91)

Oxalyl chloride (0.376 mL, 4.36 mmol) was added to a sol. of compounds K30 (2.00 g, 3.66 mmol) and DMF (1 drop) in toluene (85 mL). The mixture was stirred for 4 h at rt, and the solvents were removed under reduced pressure. The residue was dried under high vacuum for 1 h, and was dissolved in CH$_2$Cl$_2$ (50 mL). Et$_3$N (0.932 mL, 6.70 mmol) was added, and the mixture was stirred for 5 min. A sol. of methylcarbamic acid 4-chloro-3-cyclopropylaminomethyl-benzyl ester (660 mg, 2.46 mmol) in CH$_2$Cl$_2$ (5 mL) was added, and the mixture was stirred at rt overnight. CH$_2$Cl$_2$ was added, and the mixture was washed with aq. sat. NH$_4$Cl and aq. 10% Na$_2$CO$_3$. The org. layer was dried over MgSO$_4$, filtered, and the solvents were removed under reduced pressure. Purification of the residue by FC (EtOAc/heptane 4:1) yielded the title compounds mixture (920 mg, 51%). LC-MS: t$_R$=1.00 min; ES+: 802.73.

Mixture of (3'R,4'S)-3'-{[2-chloro-5-(2-methylcarbamoyloxy-ethyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(2-methylcarbamoyloxy-ethyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester (L92)

Oxalyl chloride (0.376 mL, 4.36 mmol) was added to a sol. of compounds K30 (2.00 g, 3.66 mmol) and DMF (1 drop) in toluene (85 mL). The mixture was stirred for 4 h at rt, and the solvents were removed under reduced pressure. The residue was dried under high vacuum for 1 h, and was dissolved in CH$_2$Cl$_2$ (50 mL). Et$_3$N (0.932 mL, 6.70 mmol) was added, and the mixture was stirred for 5 min. A sol. of methylcarbamic acid 2-(4-chloro-3-cyclopropylaminomethyl-phenyl)-ethyl ester (687 mg, 2.43 mmol) in CH$_2$Cl$_2$ (5 mL) was added, and the mixture was stirred at rt overnight. CH$_2$Cl$_2$ was added, and the mixture was washed with aq. sat. NH$_4$Cl and aq. 10% Na$_2$CO$_3$. The org. layer was dried over MgSO$_4$, filtered, and the solvents were removed under reduced pressure. Purification of the residue by FC (EtOAc/heptane 4:1) yielded the title compounds mixture (920 mg, 51%). LC-MS: t$_R$=1.00 min; ES+: 816.75.

Mixture of (3'R,4'S)-3'-{[2-chloro-5-(2-methoxycarbonylamino-ethyl)-benzyl]-cyclopropyl-carbamoyl}-6-[(R)-3-(2,6-dichloro-4-methyl-phenoxy)-pyrrolidin-1-yl]-3',4',5',6'-tetrahydro-2'H-[3,4']bipyridinyl-1'-carboxylic acid tert-butyl ester and (3'S,4'R)-3'-{[2-chloro-5-(2-methoxycarbonylamino-ethyl)-benzyl]-cyclopropyl-carbamoyl}-6-[(R-3-(2,6-dichloro-4-methyl-phenoxy)-pyrrolidin-1-yl]-3',4',5', 6'-tetrahydro-2'H-[3,4']bipyridinyl-1'-carboxylic acid tert-butyl ester (L93)

Oxalyl chloride (0.182 mL, 2.15 mmol) was added to a sol. of compounds K30 (910 mg, 1.65 mmol) and DMF (1 drop) in toluene (40 mL). The mixture was stirred for 2 h at rt, and the solvents were removed under reduced pressure. The residue was dried under high vacuum for 1 h, and was dissolved in CH$_2$Cl$_2$ (30 mL). Et$_3$N (0.341 mL, 2.45 mmol) was added, and the mixture was stirred for 5 min. A sol. of [2-(4-chloro-3-cyclopropylaminomethyl-phenyl)-ethyl]-carbamic acid methyl ester (597 mg, 1.64 mmol) in CH$_2$Cl$_2$ (6 mL) was added, and the mixture was stirred at rt for 30 min. The solvents were removed under reduced pressure. Purification of the residue by FC (EtOAc/heptane 1:1) yielded the title compounds mixture (830 mg, 62%). LC-MS: t$_R$=1.01 min.

(rac.)-(3'R*,4S*)-6-[3-(2-Chloro-3,6-difluoro-phenyl)-isoxazol-5-ylmethoxy]-3'-{[2-chloro-5-(2-methoxy-ethyl)-benzyl]-cyclopropyl-carbamoyl}-3',4',5', 6'-tetrahydro-2'H-[3,4']bipyridinyl-1'-carboxylic acid tert-butyl ester (L94)

Oxalyl chloride (0.078 mL, 0.886 mmol) was added to a sol. of compound K33 (375 mg, 0.682 mmol) and DMF (1 drop) in toluene (15 mL). The mixture was stirred for 40 min at rt, and the solvents were removed under reduced pressure.

The residue was dried under high vacuum for 1 h, and was dissolved in CH$_2$Cl$_2$ (13 mL). Et$_3$N (0.190 mL, 1.36 mmol) was added, and the mixture was stirred for 5 min. A sol. of [2-chloro-5-(2-methoxy-ethyl)-benzyl]-cyclopropyl-amine (164 mg, 0.682 mmol) in CH$_2$Cl$_2$ (2 mL) was added, and the mixture was stirred at rt for 30 min. The mixture was washed with aq. 1M HCl and brine. The org. layer was dried over MgSO$_4$, filtered, and the solvents were removed under reduced pressure. Purification of the residue by FC(CH$_2$Cl$_2$→MeOH/CH$_2$Cl$_2$ 1:99→1:49) yielded the title compound (377 mg, 48%). LC-MS: t$_R$=1.19 min; ES+: 771.66.

(rac.)-(1R*,5S*)-3-Acetyl-6-{[2-chloro-5-(3-methoxy-propyl)-benzyl]-cyclopropyl-carbamoyl}-7-{6-[2-(2,6-dichloro-4-methyl-phenoxy)-ethoxy]-pyridin-3-yl}-3,9-diaza-bicyclo[3.3.1]non-6-ene-9-carboxylic acid 2,2,2-trichloro-1,1-dimethyl-ethyl ester (M1)

HCl (4M in dioxane, 10 mL) was added to a sol. of compound L5 (582 mg, 0.58 mmol) in CH$_2$Cl$_2$ (10 mL) at 0° C. The mixture was stirred for 1 h at 0° C., and 1 h at rt. The solvents were removed under reduced pressure, and the residue was dried under high vacuum overnight. The foamy residue was dissolved in CH$_2$Cl$_2$ (10 mL), and DIPEA (0.397 mL, 2.32 mmol) was added. The mixture was cooled to −20° C., and AcCl (45 µL, 0.64 mmol) was added. The mixture was stirred for 15 min, and was diluted with more CH$_2$Cl$_2$. The mixture was washed with aq. 1M HCl and aq. 1M NaOH. The org. layer was dried over MgSO$_4$, filtered, and the solvents were removed under reduced pressure. Purification of the residue by FC (EtOAc/heptane 1:4→1:3→1:2→EtOAc→MeOH/EtOAc 1:19) yielded the title compound (456 mg, 53%). LC-MS: t$_R$=1.27 min; ES+: 946.37.

EXAMPLES

Example 1

(rac.)-(1R*,5S*)-7-{4-[2-(2,6-Dichloro-4-methyl-phenoxy)-ethyl]-phenyl}-3,9-diaza-bicyclo[3.3.1]non-6-ene-6-carboxylic acid [2-chloro-5-(3-methoxy-propyl)-benzyl]-cyclopropyl-amide Compound L1 (300 mg, 0.34 mmol) and HCl (4.0M in 1,4-dioxane, 2.55 mL, 10.2 mmol) were mixed together at 21° C. and stirred at 21° C. overnight. The mixture was evaporated under reduced pressure, and the residue was partitioned between EtOAc and aq. 1M NaOH. The org. phase was dried over MgSO$_4$, filtered, and the solvents were removed under reduced pressure. Purification of the crude by FC yielded the title compound (68 mg). MS (M+1) ESI 684.

Example 2

(rac.)-(1R*,5S*)-6-{[2-Chloro-5-(2-methoxy-ethyl)-benzyl]-cyclopropyl-carbamoyl}-7-{4-[2-(2,6-dichloro-4-methyl-phenoxy)-ethyl]-phenyl}-3,9-diaza-bicyclo[3.3.1]non-6-ene From (rac.)-(1R*,5S*)-7-{4-[2-(2,6-dichloro-4-methyl-phenoxy)-ethyl]-phenyl}-3,9-diaza-bicyclo[3.3.1]non-6-ene-3,6,9-tricarboxylic acid 3,9-di-tert-butyl ester, as for compound L1, but using N-[2-chloro-5-(2-methoxyethyl)benzyl]cyclopropanamine instead of N-[2-chloro-5-(3-methoxypropyl)benzyl]cyclopropanamine, then as for Example 1, the desired compound was obtained. MS (M+1) ESI 668.

Example 3

(rac.)-(1R*,5S*)-7-{4-[2-(2,6-Dichloro-4-methyl-phenoxy)-ethoxy]-phenyl}-3,9-diaza-bicyclo[3.3.1]non-6-ene-6-carboxylic acid [2-chloro-5-(3-methoxy-propyl)-benzyl]-cyclopropyl-amide This compound was synthesized from (rac.)-(1R*,5S*)-7-{4-[2-(2,6-dichloro-4-methyl-phenoxy)-ethoxy]-phenyl}-3,9-diaza-bicyclo[3.3.1]non-6-ene-3,6,9-tricarboxylic acid 3,9-di-tert-butyl ester (WO 2005/040165) and N-[2-chloro-5-(3-methoxypropyl)benzyl]cyclopropanamine, as for compound L1, and as described for Example 1. MS (ESI, Q$^+$) m/z 697.9.

Example 4

(1R,5S)-7-{4-[2-(2,6-Dichloro-4-methyl-phenoxy)-ethoxy]-phenyl}-3,9-diaza-bicyclo[3.3.1]non-6-ene-6-carboxylic acid [2-chloro-5-(3-methoxy-propyl)-benzyl]-cyclopropyl-amide This compound was obtained via resolution of Example 3 using chiral HPLC (Chiracel-AD column). Optical rotation: [α]$_D^{23}$=+53.2 (c=0.47, CHCl$_3$). MS (ESI, Q$^+$) m/z 700.1.

Example 5

(1S,5R)-7-{4-[2-(2,6-Dichloro-4-methyl-phenoxy)-ethoxy]-phenyl}-3,9-diaza-bicyclo[3.3.1]non-6-ene-6-carboxylic acid [2-chloro-5-(3-methoxy-propyl)-benzyl]-cyclopropyl-amide This compound was obtained via resolution of Example 3 using chiral HPLC (Chiracel-AD column). Optical rotation: [α]$_D^{23}$=−60.1 (c=0.34, CHCl$_3$). MS (ESI, Q$^+$) m/z 698.3.

Example 6

(rac.)-(1R*,5S*)-7-{4-[2-(2,6-Dichloro-4-methyl-phenoxy)-ethoxy]-phenyl}-3,9-diaza-bicyclo[3.3.1]non-6-ene-6-carboxylic acid [2-chloro-5-(2-methoxy-ethyl)-benzyl]-cyclopropyl-amide This compound was synthesized from (rac.)-(1R*,5S*)-7-{4-[2-(2,6-dichloro-4-methyl-phenoxy)-ethoxy]-phenyl}-3,9-diaza-bicyclo[3.3.1]non-6-ene-3,6,9-tricarboxylic acid 3,9-di-tert-butyl ester (WO 2005/040165) and [2-chloro-5-(2-methoxy-ethyl)-benzyl]-cyclopropyl-amine as for compound L1, and then Example 1. MS (ESI, Q$^+$) m/z 686.0.

Example 7

(1R,5S)-7-{4-[2-(2,6-Dichloro-4-methyl-phenoxy)-ethoxy]-phenyl}-3,9-diaza-bicyclo[3.3.1]non-6-ene-6-carboxylic acid [2-chloro-5-(2-methoxy-ethyl)-benzyl]-cyclopropyl-amide This compound was synthesized from (1R,5S)-7-{4-[2-(2,6-dichloro-4-methyl-phenoxy)-ethoxy]-phenyl}-3,9-diaza-bicyclo[3.3.1]non-6-ene-3,6,9-tricarboxylic acid 3,9-di-tert-butyl ester and [2-chloro-5-(2-methoxy-ethyl)-benzyl]-cyclopropyl-amine as for compound L1, and then Example 1. MS (ESI, Q$^+$) m/z 686.1.

Example 8

(1R,5S)-7-{4-[2-(2,6-Dichloro-4-methyl-phenoxy)-ethoxy]-phenyl}-3,9-diaza-bicyclo[3.3.1]non-6-ene-6-carboxylic acid cyclopropyl-[5-(2-methoxy-ethyl)-2-methyl-benzyl]-amide This compound was synthesized from (1R,5S)-7-{4-[2-(2,6-dichloro-4-methyl-phenoxy)-ethoxy]-phenyl}-3,9-diaza-bicyclo[3.3.1]non-6-ene-3,6,9-tricarboxylic acid 3,9-di-tert-butyl ester and cyclopropyl-[5-(2-methoxy-ethyl)-2-methyl-benzyl]-amine as for compound L1, and then Example 1. MS (ESI, Q+) m/z 664.1.

Example 9

(1R,5S)-7-{4-[2-(2,6-Dichloro-4-methyl-phenoxy)-ethoxy]-phenyl}-3,9-diaza-bicyclo[3.3.1]non-6-ene-6-carboxylic acid cyclopropyl-[5-(3-methoxy-propyl)-2-methyl-benzyl]-amide This compound was synthesized from (1R,5S)-7-{4-[2-(2,6-dichloro-4-methyl-phenoxy)-ethoxy]-phenyl}-3,9-diaza-bicyclo[3.3.1]non-6-ene-3,6,9-tricarboxylic acid 3,9-di-tert-butyl ester and cyclopropyl-[5-(3-methoxy-propyl)-2-methyl-benzyl]-amine as for compound L1, and then Example 1. MS (ESI, Q+) m/z 678.2.

Example 10

(1R,5S)-7-{4-[2-(2,6-Dichloro-4-methyl-phenoxy)-ethoxy]-phenyl}-3,9-diaza-bicyclo[3.3.1]non-6-ene-6-carboxylic acid cyclopropyl-[2,3-dichloro-5-(3-methoxy-propyl)-benzyl]-amide This compound was synthesized from (1R,5S)-7-{4-[2-(2,6-dichloro-4-methyl-phenoxy)-ethoxy]-phenyl}-3,9-diaza-bicyclo[3.3.1]non-6-ene-3,6,9-tricarboxylic acid 3,9-di-tert-butyl ester and cyclopropyl-[2,3-dichloro-5-(3-methoxy-propyl)-benzyl]-amine as for compound L1, and then Example 1. MS (ESI, Q+) m/z 733.9.

Example 11

(1R,5S)-3-Carbamimidoyl-7-{4-[2-(2,6-dichloro-4-methyl-phenoxy)-ethoxy]-phenyl}-3,9-diaza-bicyclo[3.3.1]non-6-ene-6-carboxylic acid cyclopropyl-[2-chloro-5-(3-methoxy-propyl)-benzyl]-amide Hydrochloride Salt A sol. of N,N-bis(tert-butylcarbonyl)urea (112 mg, 0.406 mmol) in DMF (5 mL) was treated with EDC.HCl (121 mg, 0.405 mmol) and DIPEA (164 µL, 0.936 mmol). The resulting sol. was stirred at rt for 1 h and then treated with compound L2 (250 mg, 0.312 mmol). The resulting sol. was stirred at rt for 3 h, then poured into a 250 mL separatory funnel containing H$_2$O (150 mL), and extracted with Et$_2$O (3×50 mL). The combined org. layers were washed with brine, dried over MgSO$_4$, filtered and concentrated under reduced pressure. Purification by FC (hexanes/EtOAc 7:3) yielded the protected urea as a clear oil. The protected material was subjected to deprotection and purification as described previously for Example 1. MS (ESI, Q+) m/z 740.2.

Example 12

(1R,5S)-7-{4-[2-(2,6-Dichloro-4-methyl-phenoxy)-ethoxy]-phenyl}-3,9-diaza-bicyclo[3.3.1]non-6-ene-3,6-dicarboxylic acid 3-[(1-cyano-cyclopropyl)-amide] 6-{cyclopropyl-[2-chloro-5-(3-methoxy-propyl)-benzyl]-amide}

A sol. of CDI (5 eq.), 1-amino-cyclopropanecarbonitrile (5 eq.), and Et$_3$N (5 eq.) in DMF was stirred for 30 min at rt. A sol. of compound L2 in DMF was added, and the mixture was stirred overnight. The mixture was quenched with aq. sat. NH$_4$Cl, and extracted with EtOAc. The org. extracts were washed with brine, dried over MgSO$_4$, filtered, and the solvents were removed under reduced pressure. Purification by FC yielded the protected compound that was then treated as described in Example 1. Characterization by MS (ESI, Q+) m/z 806.4.

Example 13

(1R,5S)-7-{4-[2-(2,6-Dichloro-4-methyl-phenoxy)-ethoxy]-phenyl}-3,9-diaza-bicyclo[3.3.1]non-6-ene-3,6-dicarboxylic acid 3-cyclopropylamide 6-{cyclopropyl-[2-chloro-5-(3-methoxy-propyl)-benzyl]-amide}

As described for Example 12, but using cyclopropylamine instead of 1-amino-cyclopropanecarbonitrile. MS (ESI, Q+) m/z 783.0.

Example 14

(1R,5S)-7-{4-[2-(2,6-Dichloro-4-methyl-phenoxy)-ethoxy]-phenyl}-3,9-diaza-bicyclo[3.3.1]non-6-ene-3,6-dicarboxylic acid 3-[(2-carbamoyl-2-methyl-propyl)-amide] 6-{cyclopropyl-[2-chloro-5-(3-methoxy-propyl)-benzyl]-amide}

As described for Example 12, but using 3-amino-2,2-dimethyl-propionamide instead of 1-amino-cyclopropanecarbonitrile. MS (ESI, Q+) m/z 841.8.

Example 15

(1R,5S)-3-{4-[2-(2,6-Dichloro-4-methyl-phenoxy)-ethoxy]-phenyl}-8-aza-bicyclo[3.2.1]oct-2-ene-2-carboxylic acid [2-chloro-5-(3-methoxy-propyl)-benzyl]-cyclopropyl-amide Compound L3 (3.45 g, 4.40 mmol) was dissolved in CH$_2$Cl$_2$ (60 mL), and the mixture was cooled to 0° C. HCl (4M in dioxane, 15 mL) was added. The mixture was stirred for 1 h at 0° C., then for 2.5 h at rt. The solvents were removed under reduced pressure, and the residue was dried under high vacuum overnight. The residue was dissolved in CH$_2$Cl$_2$, and the mixture was washed with aq. 1M NaOH (2×). The org. layer was dried over MgSO$_4$, filtered, and the solvents were removed under reduced pressure. Purification of the crude by FC (MeOH/CH$_2$Cl$_2$ 4:96 with 0.5% Et$_3$N) yielded the racemic title compound (2.18 g, 72%). This racemate was separated by HPLC (Regis Whelk column, isocratic conditions with 85% eluent B) to yield the title compound (420 mg, 19%). LC-MS: $t_R$=0.97 min; ES+: 683.31. Chiral HPLC column: $t_R$=36.97 min.

Example 16

4-{4-[2-(2,6-Dichloro-4-methyl-phenoxy)-ethoxy]-phenyl}-1,2,5,6-tetrahydro-pyridine-3-carboxylic acid [2-chloro-5-(3-methoxy-propyl)-benzyl]-cyclopropyl-amide To a sol. of compound L4 (405 mg, 0.535 mmol) in $CH_2Cl_2$ (5.2 mL) was added HCl (4M in dioxane, 1.34 mL, 5.36 mmol) at 0° C. The mixture was stirred for 1.5 h at 0° C., and the solvents were evaporated under reduced pressure without heating. The residue was diluted with $CH_2Cl_2$, and washed with aq. sat. $NaHCO_3$ and water, dried over $Na_2SO_4$, filtered, and the solvents were removed under reduced pressure. Purification of the residue by FC (MeOH/$CH_2Cl_2$ 1:19) yielded the title compound (168 mg, 48%). LC-MS: $t_R$=0.96 min; ES+: 657.24.

Example 17

(1R,5S)-3-Acetyl-7-{6-[2-(2,6-dichloro-4-methyl-phenoxy)ethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide Zn (powder, 160 mg, 2.43 mmol) was added to an efficiently stirred sol. of compound M1 (458 mg, 0.485 mmol) in THF (6 mL) and AcOH (2 mL). The mixture was stirred for 3 h, and was filtered. The precipitate was washed with THF, and the filtrate was evaporated under reduced pressure. The residue was dried under high vacuum, and was diluted with $CH_2Cl_2$. This mixture was washed with aq. 1M NaOH (4×), and the org. layer was dried over $MgSO_4$, and filtered. The solvents were removed under reduced pressure. Purification of the residue by FC (MeOH/$CH_2Cl_2$ 1:49) yielded the racemic title compound (210 mg, 61%). This racemate was separated by HPLC (Chiralcel OD, isocratic conditions with 70% eluent B) to yield the title compound (63 mg, 30%). LC-MS: $t_R$=0.927 min; ES+: 743.33. Chiral HPLC column: $t_R$=7.6 min.

Example 18

6-[2-(2,6-Dichloro-4-methyl-phenoxy)-ethoxy]-1',2',5',6'-tetrahydro-[3,4']bipyridinyl-3'-carboxylic acid [2-chloro-5-(3-methoxy-propyl)-benzyl]-cyclopropyl-amide To a sol. of compound L6 (570 mg, 0.752 mmol) in $CH_2Cl_2$ (5 mL) at 0° C. was added HCl (4M in dioxane, 1.88 mL, 7.52 mmol). The mixture was stirred for 30 min at 0° C., and for 2 h at rt. Aq. 1M NaOH was added, and the basic mixture was poured on a syringe with dry Isolute® (HM-N, 5 g) and 1 g $Na_2SO_4$. The product was eluted with $CH_2Cl_2$ until no product came out. The solvents were removed under reduced pressure. Purification of the residue by FC (MeOH/$CH_2Cl_2$ 3:97→5:95 with 1% $Et_3N$) yielded the title compound (157 mg, 32%). LC-MS: $t_R$=0.95 min; ES+: 659.98.

Example 19

4-{4-[3-(2-Chloro-3,6-difluoro-phenyl)-isoxazol-5-ylmethoxy]-phenyl}-1,2,5,6-tetrahydro-pyridine-3-carboxylic acid [2-chloro-5-(3-methoxy-propyl)-benzyl]-cyclopropyl-amide HCl (4M in dioxane, 4.70 mL) was added to a sol. of compound L7 (730 mg, 0.931 mmol) in $CH_2Cl_2$ (4 mL) at 0° C. The mixture was stirred at 0° C. for 90 min, and aq. 1M NaOH was added until a slightly basic pH was reached. The mixture was filtered through Isolute® and eluted with $CH_2Cl_2$. The org. extracts were dried over $MgSO_4$, filtered, and the solvents were removed under reduced pressure. Purification of the crude by HPLC yielded the title compound (130 mg, 20%). LC-MS: $t_R$=0.95 min; ES+: 682.18.

Example 20

4-{4-[2-(2,6-Dichloro-4-methyl-phenoxy)-ethoxy]-phenyl}-1,2,5,6-tetrahydro-pyridine-3-carboxylic acid [5-chloro-2-(3-methoxy-propyl)-pyridin-4-ylmethyl]-cyclopropyl-amide A sol. of compound L8 (150 mg, 0.198 mmol) in $CH_2Cl_2$ (3 mL) was cooled to 0° C. HCl (4M in dioxane, 0.247 mL, 0.988 mmol) was added. The mixture was stirred for 1 h at 0° C. HCl (4M in dioxane, 0.247 mL, 0.988 mmol) was added again, and the mixture was stirred for 2 h at rt. HCl (4M in dioxane, 0.247 mL, 0.988 mmol) was added again, and the mixture was stirred for 2 h at rt. Aq. 1M NaOH was added until the mixture was slightly basic. The mixture was filtered through Isolute® and eluted with $CH_2Cl_2$, and the org. phase was dried over $MgSO_4$, filtered, and the solvents were removed under reduced pressure. Purification of the residue by FC (MeOH/$CH_2Cl_2$ 5:95) yielded the title compound (57 mg, 44%). LC-MS: $t_R$=0.91 min; ES+: 660.40.

Examples 21 and 22

(1R,5S)-7-{6-[2-(2,6-Dichloro-4-methyl-phenoxy)-ethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide, and (1S,5R)-7-{6-[2-(2,6-dichloro-4-methyl-phenoxy)ethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide HCl (4M in dioxane, 3.00 mL) was added to a sol. of compound L5 (819 mg, 0.816 mmol) in $CH_2Cl_2$ (9 mL) at 0° C. The mixture was stirred at 0° C. for 30 min, and was allowed to warm up to rt for 1 h. The mixture was concentrated under reduced pressure, and the residue was dried under high vacuum overnight. The residue was dissolved in $CH_2Cl_2$, and the resulting mixture was washed with aq. 1M NaOH. The org. layer was dried over $MgSO_4$, filtered, and the solvents were removed under reduced pressure. This material was dissolved in a mixture of THF (9 mL) and AcOH (3 mL). Zn powder (534 mg, 8.16 mmol) was added, and the mixture was stirred efficiently for 4 h. The mixture was filtered over celite, and the solvents were removed under reduced pressure. The residue was dissolved in $CH_2Cl_2$, and the resulting mixture was washed with aq. 1M NaOH. The org. layer was dried over $MgSO_4$, filtered, and the solvents were removed under reduced pressure. Purification of the residue by FC($CH_2Cl_2$/MeOH 98:2→96:4→94:6→92:8, with always 1% $Et_3N$) yielded a mixture of the title compounds (439 mg, 76%). This mixture was separated by HPLC (Chiralcel OD, isocratic conditions with 85% eluent B) to yield the title compounds (84 mg, 18%, and 53 mg, 12%, respectively). LC-MS: $t_R$=0.85 min; ES+: 701.23. Chiral HPLC column: $t_R$=11.9 and 20.0 min, respectively.

Example 23

(3R,4S)-4-{4-[3-(2-Chloro-3,6-difluoro-phenyl)isoxazol-5-ylmethoxy]-phenyl}-piperidine-3-carboxylic acid [2-chloro-5-(3-methoxy-propyl)-benzyl]-cyclopropyl-amide HCl (4M in dioxane, 4.90 mL, 19.5 mmol) was added to a sol. of compound L9 (1.02 g, 1.31 mmol) in $CH_2Cl_2$ (5.5 mL) at 0° C. The mixture was stirred for 1 h at rt. The mixture was diluted with $CH_2Cl_2$, and was washed with aq. sat. $NaHCO_3$ and water. The org. layer was dried over $Na_2SO_4$, filtered, and the solvents were removed under reduced pressure. Purification of the residue by FC (EtOAc/heptane 7:3→EtOAc→MeOH/acetone 1:9) yielded the title racemic compound (328 mg, 37%). This racemate was separated by HPLC (Regis Whelk, eluent B 65%-40% over 10 min, then isocratic) to yield the title compound (100 mg, 29%). LC-MS: $t_R$=0.95 min; ES+: 684.49. Chiral HPLC column: $t_R$=20.4 min.

Example 24

6-[3-(2-Chloro-3,6-difluoro-phenyl)isoxazol-5-ylmethoxy]-1',2',5',6'-tetrahydro-[3,4']bipyridinyl-3'-carboxylic acid [2-chloro-5-(3-methoxy-propyl)-benzyl]-cyclopropyl-amide HCl (4M in dioxane, 1.10 mL, 4.39 mmol) was added to a sol. of compound L10 (344 mg, 0.439 mmol) in $CH_2Cl_2$ (1.20 mL) at 0° C. The mixture was stirred for 3 h at rt, and the solvents were removed under reduced pressure. $CH_2Cl_2$ was added, and the mixture was washed with aq. 1M NaOH. The org. layer was dried over $MgSO_4$, filtered, and the solvents were removed under reduced pressure. Purification of the residue by FC (heptane/$CH_2Cl_2$/MeOH 3:6:1 with 1% $Et_3$N→heptane/$CH_2Cl_2$/MeOH 2:7:1 with 1% $Et_3$N) yielded the title compound (31 mg, 10%). LC-MS: $t_R$=0.94 min; ES+: 683.46.

Example 25

(1R,5S)-3-Acetyl-7-{6-[2-(2,6-dichloro-4-methyl-phenoxy)-ethoxy]-pyridin-3-yl}-3,9-diaza-bicyclo[3.3.1]non-6-ene-6-carboxylic acid [5-chloro-2-(3-methoxy-propyl)-pyridin-4-ylmethyl]-cyclopropyl-amide To a sol. of compound L11 (722 mg, 0.763 mmol) in THF (9 mL) and AcOH (3 mL) was added portionwise at rt Zn powder (500 mg, 7.63 mmol). This mixture was stirred efficiently at rt for 1 h. The mixture was filtrated over celite, and the filtrate was concentrated under reduced pressure. The residue was dissolved in $CH_2Cl_2$, and was washed with aq. 1M NaOH. The org. layer was dried over $MgSO_4$, filtered, and concentrated under reduced pressure. Purification of the residue by FC($CH_2Cl_2$/MeOH 98:2→96:4→94:6→92:8 with always 1% $Et_3$N) yielded the racemic title compound (305 mg, 54%). This racemate was separated by HPLC (ChiralCel OD, isocratic conditions with 80% eluent B) to yield the title compound (100 mg, 29%). LC-MS: $t_R$=0.86 min; ES+: 744.19. Chiral HPLC column: $t_R$=10.8 min.

Example 26

(1R,2R,3S,5S)-3-{4-[2-(2,6-Dichloro-4-methyl-phenoxy)-ethoxy]-phenyl}-8-aza-bicyclo[3.2.1]octane-2-carboxylic acid [2-chloro-5-(2-methoxy-ethyl)-benzyl]-cyclopropyl-amide To a sol. of compound L12 (448 mg, 0.570 mmol) in $CH_2Cl_2$ (6.00 mL) at 0° C. was added HCl (4M in dioxane, 2.00 mL). The mixture was stirred for 30 min at 0° C., and for 90 min at rt. The solvents were removed under reduced pressure. The residue was dissolved in $CH_2Cl_2$, and was washed with aq. 1M NaOH. The org. layer was dried over $MgSO_4$, filtered, and concentrated under reduced pressure. Purification of the residue by FC ($CH_2Cl_2$/MeOH 96:4→95:5→94:6→93:7 with always 0.5% $Et_3$N) yielded the racemic title compound (358 mg, 93%). This racemate was separated by HPLC (Regis Whelk, gradient eluent B 75%→30% over 30 min) to yield the title compound (114 mg, 30%). LC-MS: $t_R$=1.00 min; ES+: 673.52. Chiral HPLC column: $t_R$=16.6 min.

Example 27

(1R,2R,3S,5S)-3-{4-[2-(2,6-Dichloro-4-methyl-phenoxy)-ethoxy]-phenyl}-8-aza-bicyclo[3.2.1]octane-2-carboxylic acid [2-chloro-5-(3-methoxy-propyl)-benzyl]-cyclopropyl-amide To a sol. of compound L13 (137 mg, 0.174 mmol) in $CH_2Cl_2$ (2.00 mL) at 0° C. was added HCl (4M in dioxane, 0.70 mL). The mixture was stirred for 30 min at 0° C., and for 90 min at rt. The solvents were removed under reduced pressure. The residue was dissolved in $CH_2Cl_2$, and was washed with aq. 1M NaOH. The org. layer was dried over $MgSO_4$, filtered, and concentrated under reduced pressure. Purification of the residue by FC ($CH_2Cl_2$/MeOH 96:4→95:5→94:6→93:7 with always 0.5% $Et_3$N) yielded the racemic title compound (113 mg, 95%). This racemate was separated by HPLC (Regis Whelk, gradient eluent B 75%-30% over 30 min) to yield the title compound (114 mg, 30%). LC-MS: $t_R$=0.99 min; ES+: 687.20. Chiral HPLC column: $t_R$=18.3 min.

Example 28

(1R,5S)-3-{4-[3-(2-Chloro-3,6-difluoro-phenyl)-isoxazol-5-ylmethoxy]-phenyl}-8-aza-bicyclo[3.2.1]oct-2-ene-2-carboxylic acid [2-chloro-5-(3-methoxy-propyl)-benzyl]-cyclopropyl-amide To a sol. of compound L14 (492 mg, 0.627 mmol) in $CH_2Cl_2$ (6.30 mL) at 0° C. was added HCl (4M in dioxane, 6.30 mL). The mixture was stirred for 1 h at rt, and the solvents were removed under reduced pressure. The residue was dissolved in $CH_2Cl_2$, and was washed with aq. 1M NaOH. The org. layer was dried over $MgSO_4$, filtered, and concentrated under reduced pressure. Purification of the residue by FC($CH_2Cl_2$→$CH_2Cl_2$/MeOH 9:1) yielded the racemic title compound (296 mg, 67%). This racemate was separated by HPLC (Chiracel OD, isocratic, eluent B 85%) to yield the title compound (80 mg, 28%). LC-MS: $t_R$=0.94 min; ES+: 708.20. Chiral HPLC column: $t_R$=17.0 min.

Example 29

(1R,5S)-3-Acetyl-7-{6-[3-(2-chloro-3,6-difluoro-phenyl)isoxazol-5-ylmethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide Zn (powder, 192 mg, 2.94 mmol) was added to a sol. of compound L15 (569 mg, 0.587 mmol) in THF (8.01 mL) and AcOH (2.67 mL). The mixture was stirred efficiently at rt for 3 h, and Zn (192 mg, 2.94 mmol) was added again. The mixture was stirred for 1 h, and was filtered through celite. The solvents were removed under reduced pressure, and the residue was dried under high vacuum. The residue was dissolved in $CH_2Cl_2$, and the mixture was washed with aq. 1M NaOH (4×). The org. layer was dried over $MgSO_4$, filtered, and the solvents were removed under reduced pressure. Purification of the residue by FC($CH_2Cl_2$/MeOH 9:1) yielded the racemic title compound (160 mg, 36%). This racemate was separated by HPLC (Chiracel OD, gradient, eluent B 95%<50% over 30 min) to yield the title compound (80 mg, 28%). LC-MS: $t_R$=0.91 min; ES+: 766.17. Chiral HPLC column: $t_R$=19.3 min.

Example 30

6-[2-(2,6-Dichloro-4-methyl-phenoxy)-ethoxy]-1',2',5',6'-tetrahydro-[3,4']bipyridinyl-3'-carboxylic acid [5-chloro-2-(3-methoxy-propyl)-pyridin-4-ylmethyl]-cyclopropyl-amide HCl (4M in dioxane, 0.50 mL) was added to a sol. of compound L20 (249 mg, 0.328 mmol) in $CH_2Cl_2$ (2.00 mL) at 0° C. The mixture was stirred for 1.5 h at 0° C., and aq. 1M NaOH was added until the mixture was slightly basic. The mixture was filtered through Isolute® and the org. layer was dried over $MgSO_4$, filtered, and the solvents were removed under reduced pressure. Purification of the residue by HPLC (x-Bridge column, acetonitrile/$H_2O$+0.05% $NH_4OH$, 10:90→90:10, over 6 min) yielded the title compound (20 mg, 9%).

Example 31

(3'R,4'S)-6-[2-(2,6-Dichloro-4-methyl-phenoxy)-ethoxy]-1',2',3',4',5',6'-hexahydro-[3,4']bipyridinyl-3'-carboxylic acid [5-chloro-2-(3-methoxy-propyl)-pyridin-4-ylmethyl]-cyclopropyl-amide HCl (4M in dioxane, 1.36 mL) was added to a sol. of compound L21 (414 mg, 0.543 mmol) in $CH_2Cl_2$ (1.50 mL) at 0° C. The mixture was stirred for 3 h at rt. $CH_2Cl_2$ was added, and the mixture was washed with aq. 1M NaOH. The org. layer was dried over $MgSO_4$, filtered, and the solvents were removed under reduced pressure. Purification of the residue by HPLC yielded the racemic title compound (211 mg, 59%). This racemate was separated by HPLC (Regis Whelk, 70% B→30% B over 30 min) to yield the title compound (52 mg, 24%). LC-MS: $t_R$=0.88 min; ES+: 663.51. Chiral HPLC column: $t_R$=18.9 min.

Examples 32 and 33

(1R,5S)-7-{4-[3-(2-Chloro-3,6-difluoro-phenyl)-isoxazol-5-ylmethoxy]-phenyl}-3,9-diaza-bicyclo[3.3.1]non-6-ene-6-carboxylic acid [5-chloro-2-(3-methoxy-propyl)-pyridin-4-ylmethyl]-cyclopropyl-amide and (1S,5R)-7-{4-[3-(2-Chloro-3,6-difluoro-phenyl)-isoxazol-5-ylmethoxy]-phenyl}-3,9-diaza-bicyclo[3.3.1]non-6-ene-6-carboxylic acid [5-chloro-2-(3-methoxy-propyl)-pyridin-4-ylmethyl]-cyclopropyl-amide HCl (4M in dioxane, 8.50 mL) was added to a sol. of compound L22 (850 mg, 0.827 mmol) in $CH_2Cl_2$ (8.50 mL) at 0° C. The mixture was stirred at rt for 60 min. The solvents were removed under reduced pressure, and the residue was diluted with $CH_2Cl_2$. The resulting mixture was washed with aq. 1M NaOH and with brine. The org. layer was dried over $MgSO_4$, filtered, and the solvents were removed under reduced pressure. Purification of the residue by FC($CH_2Cl_2$/MeOH 98:2-95:5) yielded a brown oil. This oil was dissolved in THF (4.00 mL) and AcOH (0.50 mL). Zn (261 mg, 3.99 mmol) was added and the reaction mixture was then stirred efficiently at rt for 3 h. The mixture was filtered through celite, and the filtrate was diluted with EtOAc. This mixture was washed with aq. sat. $NaHCO_3$. The org. layer was dried over $MgSO_4$, filtered, and the solvents were removed under reduced pressure. Purification of the crude by FC($CH_2Cl_2$/MeOH 8:2→$CH_2Cl_2$/$NH_3$ 7M in methanol 8:2) yielded the racemic title compound (90 mg, 11%). This mixture was separated by HPLC (Regis Whelk, isocratic eluent B 45%) to yield the title compounds (21 mg and 18 mg, 23% and 20%, respectively). LC-MS: $t_R$=0.80 min; ES+: 724.22. Chiral HPLC column: $t_R$=18.3 min and 20.9 min, respectively.

Example 34

4-{4-[3-(2-Chloro-3,6-difluoro-phenyl)-isoxazol-5-ylmethoxy]-phenyl}-1,2,5,6-tetrahydro-pyridine-3-carboxylic acid [5-chloro-2-(3-methoxy-propyl)-pyridin-4-ylmethyl]-cyclopropyl-amide HCl (4M in dioxane, 1.00 mL) was added to a sol. of compound L23 (548 mg, 0.699 mmol) in $CH_2Cl_2$ (4.00 mL) at 0° C. The mixture was stirred for 1.5 h at 0° C. Aq. 1M NaOH was added until the mixture was slightly basic. The org. layer was separated, dried over $MgSO_4$, filtered, and the solvents were removed under reduced pressure. Purification of the residue by HPLC yielded the title compound (27 mg, 6%). LC-MS: $t_R$=0.88 min; ES+: 683.50.

Example 35

(1R,5S)-3-{6-[2-(2,6-Dichloro-4-methyl-phenoxy)-ethoxy]-pyridin-3-yl}-8-aza-bicyclo[3.2.1]oct-2-ene-2-carboxylic acid [2-chloro-5-(3-methoxy-propyl)-benzyl]-cyclopropyl-amide A mixture of compound K18 (500 mg, 0.910 mmol), EDC.HCl (209 mg, 1.09 mmol) and HOBt (135 mg, 1.00 mmol) in DMF (5 mL) was stirred at rt for 30 min. N-Methylmorpholine (0.502 mL, 4.55 mmol) and [5-chloro-2-(3-methoxy-propyl)-pyridin-4-ylmethyl]-cyclopropyl-amine (462 mg, 1.82 mmol) were added. The mixture was stirred at rt for 3 days, and EDC.HCl (210 mg, 1.09 mmol), HOBt (135 mg, 1.00 mmol), N-methylmorpholine (0.500 mL, 4.54 mmol) and [5-chloro-2-(3-methoxy-propyl)-pyridin-4-ylmethyl]-cyclopropyl-amine (230 mg, 0.91 mmol) were added again. The mixture was stirred at rt for 3 days. The mixture was diluted with EtOAc, and washed with aq. 10% citric acid, with aq. sat. $NaHCO_3$, and with brine. The org. layer was dried over $MgSO_4$, filtered, and the solvents were removed under reduced pressure. Purification of the residue by FC (EtOAc/heptane 1:3) yielded the amide coupling product that was dried under high vacuum. This product was dissolved in HCl (4M in dioxane, 2 mL), and this mixture was stirred at rt for 1 h. The solvents were removed under reduced pressure, and the residue was diluted with EtOAc. This mixture was washed with aq. sat. $NaHCO_3$. The aq. layer was extracted back with EtOAc. The combined org. extracts were dried over $MgSO_4$, filtered, and the solvents were removed under reduced pressure to yield the crude racemic title compound. This racemate was separated by HPLC (Regis Whelk, isocratic eluent B 60%) to yield the title compound (41 mg, 20%). LC-MS: $t_R$=0.96 min; ES+: 686.18. Chiral HPLC column: $t_R$=12.6 min.

Example 36

(1R,5S)-3-{6-[3-(2-Chloro-3,6-difluoro-phenyl)-isoxazol-5-ylmethoxy]-pyridin-3-yl}-8-aza-bicyclo[3.2.1]oct-2-ene-2-carboxylic acid [2-chloro-5-(3-methoxy-propyl)benzyl]-cyclopropyl-amide

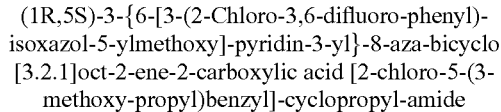

Compound L24 (486 mg, 0.600 mmol) was dissolved in CH$_2$Cl$_2$ (6.00 mL). HCl (4M in dioxane, 6.00 mL) was added at rt. The reaction was stirred for 1 h at rt. The solvents were evaporated under reduced pressure, and the resulting oil was dried under high vacuum. Purification of the residue by FC(CH$_2$Cl$_2$→CH$_2$Cl$_2$/MeOH 90:10) yielded the title racemic compound. This racemate was separated by HPLC (Regis Whelk, isocratic eluent B 60%) to yield the title compound (71 mg, 17%). LC-MS: $t_R$=0.93 min; ES+: 709.18. Chiral HPLC column: $t_R$=16.3 min.

Example 37

(1R,5S)-3-{4-[(R-3-(2,6-Dichloro-4-methyl-phenoxy)-pyrrolidin-1-yl]-phenyl}-8-aza-bicyclo[3.2.1]oct-2-ene-2-carboxylic acid [2-chloro-5-(3-methoxy-propyl)-benzyl]-cyclopropyl-amide

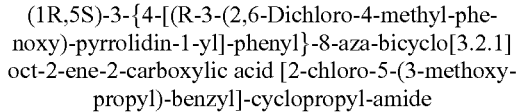

Compounds L25 (525 mg, 0.649 mmol) were dissolved in CH$_2$Cl$_2$ (6.50 mL). HCl (4M in dioxane, 6.50 mL) was added at rt. The reaction was stirred for 1 h at rt. The solvents were evaporated under reduced pressure, and the resulting oil was dried under high vacuum. Purification of the residue by FC(CH$_2$Cl$_2$→CH$_2$Cl$_2$/MeOH 90:10) yielded the title compound with its corresponding (1S,5R)-diastereoisomer (348 mg, 76%). This racemate was separated by HPLC (Regis Whelk, isocratic eluent B 50%) to yield the title compound (92 mg, 20%). LC-MS: $t_R$=1.01 min; ES+: 708.21. Chiral HPLC column: $t_R$=9.83 min.

Examples 38 and 39

(1R,5S)-7-{6-[(R)-3-(2,6-Dichloro-4-methyl-phenoxy)pyrrolidin-1-yl]-pyridin-3-yl}-3,9-diaza-bicyclo[3.3.1]non-6-ene-6-carboxylic acid [2-chloro-5-(2-methoxy-ethyl)benzyl]-cyclopropyl-amide and (1S,5R)-7-{6-[(R)-3-(2,6-dichloro-4-methyl-phenoxy)pyrrolidin-1-yl]-pyridin-3-yl}-3,9-diaza-bicyclo[3.3.1]non-6-ene-6-carboxylic acid [2-chloro-5-(2-methoxy-ethyl)-benzyl]-cyclopropyl-amide

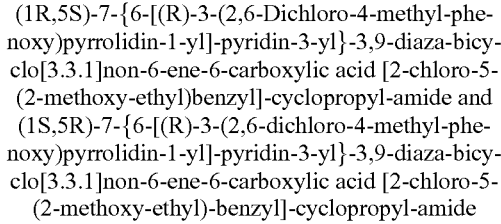

HCl (4M in dioxane, 2.00 mL) was added to a sol. of compound L26 (559 mg, 0.570 mmol) in CH$_2$Cl$_2$ (6.00 mL) at 0° C. The mixture was stirred for 30 min at 0° C., and overnight at rt. The solvents were removed under reduced pressure, and the resulting oil was dried under high vacuum. The residue was diluted with CH$_2$Cl$_2$, and the resulting mixture was washed with aq. 1M NaOH. The org. layer was dried over MgSO$_4$, filtered, and the solvents were removed under reduced pressure. Purification of the residue by FC (CH$_2$Cl$_2$/MeOH 96:4→94:6→98:2→90:10) yielded the mixed title compounds (402 mg, 99%). This mixture was separated by HPLC (Regis Whelk, isocratic eluent B 45%) to yield the title compounds (70 mg and 68 mg, 23% and 22%, respectively). LC-MS: $t_R$=0.80 min; ES+: 712.59. Chiral HPLC column: $t_R$=19.7 min and 24.6 min, respectively.

Examples 40 and 41

(1R,5S)-7-{6-[(R)-3-(2-Chloro-3,6-difluoro-phenoxy)-pyrrolidin-1-yl]-pyridin-3-yl}-3,9-diaza-bicyclo[3.3.1]non-6-ene-6-carboxylic acid [2-chloro-5-(2-methoxy-ethyl)benzyl]-cyclopropyl-amide and (1S,5R)-7-{6-[(R)-3-(2-Chloro-3,6-difluoro-phenoxy)pyrrolidin-1-yl]-pyridin-3-yl}-3,9-diaza-bicyclo[3.3.1]non-6-ene-6-carboxylic acid [2-chloro-5-(2-methoxy-ethyl)-benzyl]-cyclopropyl-amide

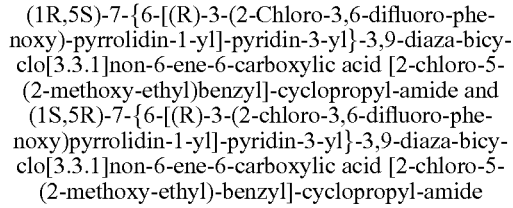

HCl (4M in dioxane, 2.00 mL) was added to a sol. of compounds L27 (581 mg, 0.646 mmol) in CH$_2$Cl$_2$ (6.00 mL) at 0° C. The mixture was stirred for 30 min at 0° C., and overnight at rt. The solvents were removed under reduced pressure, and the resulting oil was dried under high vacuum. The residue was diluted with CH$_2$Cl$_2$, and the resulting mixture was washed with aq. 1M NaOH. The org. layer was dried over MgSO$_4$, filtered, and the solvents were removed under reduced pressure. Purification of the residue by FC (CH$_2$Cl$_2$/MeOH 96:4→94:6→98:2→90:10) yielded the mixed title compounds (344 mg, 76%). This mixture was separated by HPLC (Regis Whelk, isocratic eluent B 45%) to yield the title compounds (53 mg and 60 mg, 18% and 20%, respectively). LC-MS: $t_R$=0.78 min; ES+: 698.57. Chiral HPLC column: $t_R$=15.5 min and 20.3 min, respectively.

Examples 42 and 43

(1R,5S)-7-{6-[2-(2,6-Dichloro-4-methyl-phenoxy)-ethoxy]-pyridin-3-yl}-3,9-diaza-bicyclo[3.3.1]non-6-ene-6-carboxylic acid [5-chloro-2-(3-methoxy-propyl)-pyridin-4-ylmethyl]-cyclopropyl-amide and (1S,5R)-7-{6-[2-(2,6-dichloro-4-methyl-phenoxy)ethoxy]-pyridin-3-yl}-3,9-diaza-bicyclo[3.3.1]non-6-ene-6-carboxylic acid [5-chloro-2-(3-methoxy-propyl)-pyridin-4-ylmethyl]-cyclopropyl-amide

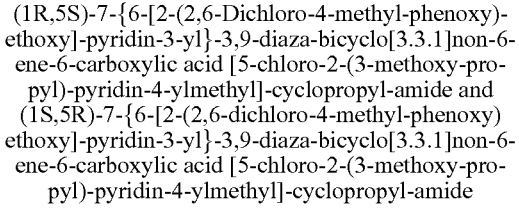

HCl/dioxane (4M, 5.00 mL) was added to a sol. of compound L28 (764 mg, 0.760 mmol) in CH$_2$Cl$_2$ (5.00 mL). The mixture was stirred for 1 h at rt, and the mixture was evaporated under reduced pressure. The residue was dried under high vacuum. The residue was dissolved in a mixture of THF (6.00 mL) and AcOH (2.00 μL). Zn (497 mg, 7.60 mmol) was added, and the mixture was stirred for 3 h. The mixture was filtered, washed with THF, and the solvents were removed under reduced pressure. The residue was dried under high vacuum. The residue was diluted with EtOAc and washed with aq. 1M NaOH (3×). The combined aq. layers were extracted with EtOAc (1×). The combined org. layers were dried over MgSO$_4$, filtered, and the solvents were removed under reduced pressure. Purification of the residue by FC (MeOH/CH$_2$Cl$_2$ 1:9→2:8, with always 1% Et$_3$N) yielded the title racemic compound (109 mg, 20%). This racemate was separated by HPLC (Regis Whelk, isocratic eluent B 50%) to yield the title compounds (4.5 mg and 4.1 mg, 5% and 4%, respectively). LC-MS: $t_R$=0.80 min; ES+: 702.10. Chiral HPLC column: $t_R$=15.5 min and 17.9 min, respectively.

Example 44

(3R,4S)-4-{4-[2-(2,6-Dichloro-4-methyl-phenoxy)-ethoxy]-phenyl}-piperidine-3-carboxylic acid [5-chloro-2-(3-methoxy-propyl)-pyridin-4-ylmethyl]-cyclopropyl-amide

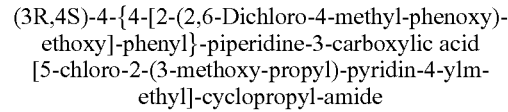

HCl (4M in dioxane, 5.00 mL) was added to a sol. of compound L29 (103 mg, 0.135 mmol) in CH$_2$Cl$_2$ (5.00 mL) at 0° C. The mixture was stirred for 1 h at 0° C. and for 1 h at rt. The solvents were removed under reduced pressure, and the resulting oil was dried under high vacuum. The residue was diluted with CH$_2$Cl$_2$, and the resulting mixture was washed with aq. 1M NaOH (3×). The org. layer was dried over MgSO$_4$, filtered, and the solvents were removed under reduced pressure. Purification of the residue by FC (CH$_2$Cl$_2$/MeOH 98:2→96:4 with 1% Et$_3$N) yielded the title compound (52 mg, 58%). LC-MS: t$_R$=0.89 min; ES+: 662.17.

Example 45

(1R,2R,3S,5S)-3-{6-[2-(2,6-Dichloro-4-methyl-phenoxy)-ethoxy]-pyridin-3-yl}-8-aza-bicyclo[3.2.1]octane-2-carboxylic acid [2-chloro-5-(2-methoxy-ethyl)-benzyl]-cyclopropyl-amide HCl (4M in dioxane, 18 mL) was added to a sol. of compound L30 (711 mg, 0.920 mmol) in CH$_2$Cl$_2$ (18 mL). The mixture was stirred for 30 min at 0° C., and for 1 h at rt. The solvents were removed under reduced pressure, and the residue was dried under high vacuum. The resulting material was dissolved in CH$_2$Cl$_2$, and this mixture was washed with aq. 1M NaOH (3×). The org. layer was dried over MgSO$_4$, filtered, and the solvents were removed under reduced pressure. Drying the residue under high vacuum yielded the crude racemic compound (580 mg, 94%). This racemate was separated by HPLC (Regis Whelk, isocratic eluent B 50%) to yield the title compound (200 mg, 35%). LC-MS: t$_R$=0.97 min; ES+: 674.24. Chiral HPLC column: t$_R$=10.5 min.

Examples 46 and 47

(1R,5S)-7-{4-[3-(2-Chloro-3,6-difluoro-phenyl)-isoxazol-5-ylmethoxy]-phenyl}-3,9-diaza-bicyclo[3.3.1]non-6-ene-6-carboxylic acid [2-chloro-5-(3-methoxy-propyl)-benzyl]-cyclopropyl-amide and (1S,5R)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(3-methoxy-propyl)-benzyl]-cyclopropyl-amide Zn (powder, 356 mg, 5.45 mmol) was added to a sol. of compound L31 (560 mg, 0.545 mmol) in THF (5.00 mL) and glacial AcOH (0.700 mL). The mixture was stirred efficiently at rt for 5 h. The mixture was filtered through celite, and was combined with EtOAc. The resulting mixture was washed with aq. sat. NaHCO$_3$. The org. layer was dried over MgSO$_4$, filtered, and the solvents were removed under reduced pressure. This crude material was dissolved in CH$_2$Cl$_2$ (4.00 mL), and HCl (4M in dioxane, 4.00 mL) was added. The mixture was stirred for 1 h at rt, and the solvents were removed under reduced pressure. The residue was diluted with EtOAc, and the resulting mixture was washed with aq. 1M NaOH. The org. layer was dried over MgSO$_4$, filtered, and the solvents were removed under reduced pressure. Purification of the crude by FC (MeOH/CH$_2$Cl$_2$ 1:4) yielded the racemic title compounds mixture (150 mg, 38%). This racemate was separated by HPLC (Regis Whelk, isocratic eluent B 50%) to yield the title compounds (45 mg and 46 mg, 30% and 30%, respectively). LC-MS: t$_R$=0.85 min; ES+: 723.23. Chiral HPLC column: t$_R$=18.7 min and 22.9 min, respectively.

Examples 48 and 49

(1R,5S)-7-{4-[3-(2-Chloro-3,6-difluoro-phenyl)-isoxazol-5-ylmethoxy]-phenyl}-3,9-diaza-bicyclo[3.3.1]non-6-ene-6-carboxylic acid [2-chloro-5-(2-methoxy-ethyl)-benzyl]-cyclopropyl-amide and (1S,5R)-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(2-methoxy-ethyl)-benzyl]-cyclopropyl-amide HCl (4M in dioxane, 10 mL) was added to a sol. of compound L32 (991 mg, 1.09 mmol) in CH$_2$Cl$_2$ (10 mL) at 0° C. The mixture was stirred for 1 h at 0° C., and for 2 h at rt. The solvents were removed under reduced pressure, and the residue was partitioned between CH$_2$Cl$_2$ and aq. 1M NaOH. The org. layer was dried over MgSO$_4$, filtered, and the solvents were removed under reduced pressure. Purification of the crude by FC (CH$_2$Cl$_2$/7M NH$_3$ in MeOH 9:1→8:2) yielded the mixed title compounds (574 mg, 74%). This racemate was separated by HPLC (Regis Whelk, isocratic eluent B 50%) to yield the title compounds (185 mg and 188 mg, 36% and 37%, respectively). LC-MS: t$_R$=0.83 min; ES+: 709.33. Chiral HPLC column: t$_R$=19.7 min and 23.3 min, respectively.

Example 50

(1R,5S)-3-Acetyl-7-{4-[3-(2-chloro-3,6-difluoro-phenyl)-isoxazol-5-ylmethoxy]-phenyl}-3,9-diaza-bicyclo[3.3.1]non-6-ene-6-carboxylic acid [2-chloro-5-(3-methoxy-propyl)benzyl]-cyclopropyl-amide HCl (4M in dioxane, 5.50 mL) was added to a sol. of compound L33 (551 mg, 0.636 mmol) in CH$_2$Cl$_2$ (5.50 mL) at 0° C. The mixture was stirred for 1 h at 0° C., and for 2 h at rt. The solvents were removed under reduced pressure, and the residue was partitioned between CH$_2$Cl$_2$ and aq. 1M NaOH. The org. layer was dried over MgSO$_4$, filtered, and the solvents were removed under reduced pressure. Purification of the crude by FC (CH$_2$Cl$_2$/7M NH$_3$ in MeOH 9:1) yielded the racemic title compound (270 mg, 55%). This racemate was separated by HPLC (Regis Whelk, isocratic eluent B 50%) to yield the title compound (135 mg, 31%). LC-MS: t$_R$=0.91 min; ES+: 765.14. Chiral HPLC column: t$_R$=27.4 min.

Example 51

(1R,5S)-3-Acetyl-7-{4-[3-(2-chloro-3,6-difluoro-phenyl)isoxazol-5-ylmethoxy]-phenyl}-3,9-diaza-bicyclo[3.3.1]non-6-ene-6-carboxylic acid [2-chloro-5-(2-methoxy-ethyl)-benzyl]-cyclopropyl-amide HCl (4M in dioxane, 5.60 mL), was added to a sol. of compound L34 (560 mg, 0.657 mmol) in CH$_2$Cl$_2$ (5.60 mL) at 0° C. The mixture was stirred for 1 h at 0° C., and for 2 h at rt. The solvents were removed under reduced pressure, and the residue was partitioned between EtOAc and aq. 1M NaOH. The org. layer was dried over MgSO$_4$, filtered, and the solvents were removed under reduced pressure. Purification of the residue by FC (CH$_2$Cl$_2$/7M NH$_3$ in MeOH 9:1) yielded the racemic title compound (385 mg, 78%). This racemate was separated by HPLC (Regis Whelk, isocratic eluent B 50%) to yield the title compound (102 mg, 26%). LC-MS: t$_R$=0.89 min; ES+: 751.37. Chiral HPLC column: t$_R$=27.8 min.

Examples 52 and 53

(1R,5S)-7-{6-[3-(2-Chloro-3,6-difluoro-phenyl)-isoxazol-5-ylmethoxy]-7-pyridin-3-yl}-3,9-diaza-bicyclo[3.3.1]non-6-ene-6-carboxylic acid [2-chloro-5-(3-methoxy-propyl)benzyl]-cyclopropyl-amide and (1S,5R)-7-{6-[3-(2-chloro-3,6-difluoro-phenyl)-isoxazol-5-ylmethoxy]-pyridin-3-yl}-3,9-diaza-bicyclo[3.3.1]non-6-ene-6-carboxylic acid [2-chloro-5-(3-methoxy-propyl)-benzyl]-cyclopropyl-amide HCl (4M in dioxane, 9.80 mL) was added to a sol. of compound L35 (452 mg, 489 mmol) in $CH_2Cl_2$ (4.90 mL) at rt. The mixture was stirred for 1 h at rt, and the solvents were removed under reduced pressure. The residue was dried under high vacuum. Purification of the crude by FC($CH_2Cl_2 \rightarrow CH_2Cl_2$/MeOH 80:20) yielded the racemic title compounds mixture (277 mg, 78%). This racemate was separated by HPLC (Regis Whelk, isocratic eluent B 45%) to yield the title compounds (24 mg and 30 mg, 9% and 11%, respectively). LC-MS: $t_R$=0.85 min; ES+: 724.19. Chiral HPLC column: $t_R$=13.7 min and 16.9 min, respectively.

Example 54

(1R,2R,3S,5S)-3-{4-[(R)-3-(2,6-Dichloro-4-methyl-phenoxy)-pyrrolidin-1-yl]-phenyl}-8-aza-bicyclo[3.2.1]octane-2-carboxylic acid [2-chloro-5-(2-methoxy-ethyl)benzyl]-cyclopropyl-amide HCl (4M in dioxane 8.00 mL) was added to a sol. of compounds L36 (474 mg, 0.595 mmol) in $CH_2Cl_2$ (8.00 mL). The mixture was stirred for 30 min at 0° C., and for 1 h at rt. The solvents were removed under reduced pressure, and the residue was dried under high vacuum. The residue was dissolved in $CH_2Cl_2$, and the mixture was washed with aq. 1M NaOH (3×). The org. layer was dried over $MgSO_4$, filtered, and the solvents were removed under reduced pressure. Purification of the crude by FC (2M $NH_3$ in MeOH/$CH_2Cl_2$ 1:30→13:300→15:300→36:300) yielded the title compound with its corresponding (1S,2S,3R,5R)-diastereoisomer (295 mg, 71%). This mixture was separated by HPLC (Regis Whelk, isocratic eluent B 50%) to yield the title compound (85 mg, 29%). LC-MS: $t_R$=1.03 min; ES+: 698.27. Chiral HPLC column: $t_R$=18.6 min.

Example 55

(1R,2R,3S,5S)-3-{6-[(R)-3-(2,6-Dichloro-4-methyl-phenoxy)-pyrrolidin-1-yl]-pyridin-3-yl}-8-aza-bicyclo[3.2.1]octane-2-carboxylic acid [2-chloro-5-(2-methoxy-ethyl)-benzyl]-cyclopropyl-amide HCl (4M in dioxane, 10.0 mL) was added to a sol. of compounds L37 (152 mg, 0.190 mmol) in $CH_2Cl_2$ (10.0 mL) at 0° C. The mixture was stirred for 30 min at 0° C., and for 1 h at rt. The solvents were removed under reduced pressure, and the residue was dried under high vacuum. The residue was diluted with $CH_2Cl_2$, and the mixture was washed with aq. 1M NaOH (3×). The org. layer was dried over $MgSO_4$, filtered, and the solvents were removed under reduced pressure to yield a crude mixture of the title compound with its corresponding (1S,2S,3R,5R)-diastereoisomer (125 mg, 94%). This mixture was separated by HPLC (Regis Whelk, isocratic eluent B 50%) to yield the title compound (24 mg, 21%). LC-MS: $t_R$=0.78 min; ES+: 697.39. Chiral HPLC column: $t_R$=13.7 min.

Example 56

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid [2-chloro-5-(2-methoxy-ethyl)-benzyl]-cyclopropyl-amide HCl (4M in dioxane, 2.00 mL) was added to a sol. of compounds L38 (624 mg, 0.793 mmol) in $CH_2Cl_2$ (2.50 mL) at 0° C. The mixture was stirred for 3 h at rt, and the solvents were removed under reduced pressure. $CH_2Cl_2$ was added, and the mixture was washed with aq. 1M NaOH. The org. layer was dried with $MgSO_4$, filtered, and the solvents were removed under reduced pressure. Purification of the crude by FC (EtOAc/heptane 7:3→EtOAc/MeOH 9:1) yielded the title compound mixed with its (3'S,4'R)-diastereoisomer (380 mg, 71%). This mixture was separated by HPLC (Regis Whelk, isocratic eluent B 50%) to yield the title compound (78 mg, 21%). LC-MS: $t_R$=0.82 min; ES+: 671.22. Chiral HPLC column: $t_R$=18.3 min.

Example 57

(1R,5S)-3-{4-[2-(2,6-Dichloro-4-methyl-phenoxy)-ethoxy]-phenyl}-8-aza-bicyclo[3.2.1]oct-2-ene-2-carboxylic acid [5-chloro-2-(3-methoxy-propyl)-pyridin-4-ylmethyl]-cyclopropyl-amide HCl (4M in dioxane, 2.40 mL) was added to a sol. of compound L39 (190 mg, 0.242 mmol) in $CH_2Cl_2$ (2.40 mL). The mixture was stirred for 1 h at rt. The solvents were removed under reduced pressure, and the resulting oil was dried under high vacuum. Purification of the residue by FC($CH_2Cl_2 \rightarrow CH_2Cl_2$/MeOH 90:10) yielded the racemic title compound (148 mg, 89%). This mixture was separated by HPLC (Regis Whelk, isocratic eluent B 70%) to yield the title compound (7.1 mg, 5%). LC-MS: $t_R$=0.92 min; ES+: 684.23. Chiral HPLC column: $t_R$=20.9 min.

Example 58

(3'R,4'S)-6-[(R)-3-(2,6-Dichloro-4-methyl-phenoxy)pyrrolidin-1-yl]-1',2',3',4',5',6'-hexahydro-[3,4']bipyridinyl-3'-carboxylic acid [5-chloro-2-(3-methoxypropyl)pyridin-4-ylmethyl]-cyclopropyl-amide HCl (4M in dioxane, 1.10 mL) was added to a sol. of compounds L40 (360 mg, 0.457 mmol) in $CH_2Cl_2$ at 0° C. The mixture was stirred for 3 h at rt, and the solvents were removed under reduced pressure. $CH_2Cl_2$ was added, and the mixture was washed with aq. 1M NaOH. The org. layer was dried over $MgSO_4$, filtered, and the solvents were removed under reduced pressure to yield the title compound with its corresponding (3'S,4'R)-diastereoisomer (310 mg, 99%). This racemate was separated by HPLC (Regis Whelk, isocratic eluent B 70%) to yield the title compound (49 mg, 16%). LC-MS: $t_R$=0.76 min; ES+: 688.20. Chiral HPLC column: $t_R$=19.3 min.

Example 59

(1R,2R,3S,5S)-3-{4-[3-(2-Chloro-3,6-difluoro-phenyl)isoxazol-5-ylmethoxy]-phenyl}-8-aza-bicyclo[3.2.1]octane-2-carboxylic acid [2-chloro-5-(3-methoxy-propyl)-benzyl]-cyclopropyl-amide To a sol. of compound L41 (360 mg, 0.444 mmol) in $CH_2Cl_2$ (4.00 mL) at rt was added HCl (4M in dioxane, 4.00 if L). The mixture was stirred at rt for 2 h, and the mixture was evaporated under reduced pressure. CH$_2$Cl$_2$ was added, and the mixture was washed with aq. 1M NaOH. The aq. layer was extracted back with CH$_2$Cl$_2$. The combined org. extracts were dried over MgSO$_4$, filtered, and the solvents were removed under reduced pressure. Purification of the residue by FC(CH$_2$Cl$_2$/MeOH 9:1) yielded the racemic title compound (120 mg, 38%). This racemate was separated by HPLC (Regis Whelk, isocratic eluent B 50%) to yield the title compound (17 mg, 17%). LC-MS: t$_R$=0.96 min; ES+: 710.37. Chiral HPLC column: t$_R$=15.1 min.

Example 60

(1R,2R,3S,5S)-3-{4-[3-(2-Chloro-3,6-difluoro-phenyl)isoxazol-5-ylmethoxy]-phenyl}-8-aza-bicyclo [3.2.1]octane-2-carboxylic acid [2-chloro-5-(2-methoxy-ethyl)benzyl]-cyclopropyl-amide To a sol. of compound L42 (1.00 g, 1.26 mmol) in CH$_2$Cl$_2$ (10 mL) at rt was added HCl (4M in dioxane, 10 mL). The mixture was stirred at rt for 3 h. The mixture was evaporated to dryness, then CH$_2$Cl$_2$ was added. The mixture was washed with aq. 1M NaOH. The aq. layer was extracted back with CH$_2$Cl$_2$. The combined org. extracts were dried over MgSO$_4$, filtered, and the solvents were removed under reduced pressure. Purification of the residue by FC(CH$_2$Cl$_2$/7M NH$_3$ in MeOH 9:1) yielded the racemic title compound (760 mg, 87%). This racemate was separated by HPLC (Regis Whelk, isocratic eluent B 50%) to yield the title compound (17 mg, 17%). LC-MS: t$_R$=0.94 min; ES+: 696.40. Chiral HPLC column: t$_R$=15.1 min.

Example 61

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid [2-chloro-5-(2-methoxy-ethyl)-benzyl]-cyclopropyl-amide A sol. of compound L43 (2.14 g, 2.77 mmol) in CH$_2$Cl$_2$ (27 mL) at 0° C. was treated with HCl (4M in dioxane, 13.5 mL), and the mixture was stirred for 2 h while warming up to rt. The mixture was poured in aq. 1M NaOH, and the resulting mixture was extracted with EtOAc (3×). The combined org. extracts were dried over Na$_2$SO$_4$, filtered, and the solvents were removed under reduced pressure. Purification of the residue by FC(CH$_2$Cl$_2$/MeOH 85:15) yielded the title compound with its corresponding (3'S,4'R)-diastereoisomer (904 mg, 48%). This mixture was separated by HPLC (Regis Whelk, isocratic eluent B 50%) to yield the title compound (42 mg, 5%). LC-MS: t$_R$=0.80 min; ES+: 673.47. Chiral HPLC column: t$_R$=19.7 min.

Example 62

(1R,2R,3S,5S)-3-{4-[3-(2-Chloro-3,6-difluoro-phenyl)isoxazol-5-ylmethoxy]-phenyl}-8-aza-bicyclo [3.2.1]octane-2-carboxylic acid [5-chloro-2-(3-methoxy-propyl)pyridin-4-ylmethyl]-cyclopropyl-amide To a sol. of compound L44 (450 mg, 0.555 mmol) in CH$_2$Cl$_2$ (4.50 mL) at rt was added HCl (4M in dioxane, 4.50 mL). The mixture was then stirred at rt for 2 h. The solvents were removed under reduced pressure, and CH$_2$Cl$_2$ was added. The org. layer was washed with aq. 1M NaOH. The aq. layer was extracted back with CH$_2$Cl$_2$. The combined org. extracts were dried over MgSO$_4$, filtered, and the solvents were removed under reduced pressure. Purification of the crude by FC(CH$_2$Cl$_2$/MeOH 9:1) yielded the racemic title compound (270 mg, 68%). This racemate was separated by HPLC (Regis Whelk, isocratic eluent B 50%) to yield the title compound (88 mg, 33%). LC-MS: t$_R$=0.89 min; ES+: 711.39. Chiral HPLC column: t$_R$=15.7 min.

Example 63

(3R,4S)-4-{4-[3-(2-Chloro-3,6-difluoro-phenyl)-isoxazol-5-ylmethoxy]-phenyl}-piperidine-3-carboxylic acid [5-chloro-2-(3-methoxy-propyl)-pyridin-4-ylmethyl]-cyclopropyl-amide HCl (4M in dioxane, 2.13 mL) was added to a sol. of compound L45 (670 mg, 0.853 mmol) in CH$_2$Cl$_2$ (2.00 µL) at 0° C. The mixture was stirred for 30 min at 0° C., and for 1.5 h at rt. The mixture was washed with aq. 10% Na$_2$CO$_3$ and brine. The org. layer was dried over MgSO$_4$, filtered, and the solvents were removed under reduced pressure. Purification of the crude by HPLC (acetonitrile/0.05% aq. NH$_3$ 10:90→90:10, X-bridge column) yielded the racemic title compound (406 mg, 69%). This racemate was separated by HPLC (Regis Whelk, isocratic eluent B 50%) to yield the title compound (90 mg, 23%). LC-MS: t$_R$=0.86 min; ES+: 685.59. Chiral HPLC column: t$_R$=18.6 min.

Example 64

(3R,4S)-4-{4-[3-(2-Chloro-3,6-difluoro-phenyl)isoxazol-5-ylmethoxy]-phenyl}-piperidine-3-carboxylic acid [5-(acetylamino-methyl)-2-chloro-benzyl]-cyclopropyl-amide HCl (4M in dioxane, 1.60 mL) was added to a sol. of compound L46 (500 mg, 0.638 mmol) in CH$_2$Cl$_2$ (1.50 µL) at 0° C. The mixture was stirred at 0° C. for 90 min, and was diluted with more CH$_2$Cl$_2$. The mixture was washed with aq. sat. NaHCO$_3$ and with brine. The org. layer was dried over MgSO$_4$, filtered, and the solvents were removed under reduced pressure to yield the crude racemic title compound (430 mg, 99%). This crude racemate was separated by HPLC (Regis Whelk, isocratic eluent B 50%) to yield the title compound (115 mg, 27%). LC-MS: t$_R$=0.87 min; ES+: 683.21. Chiral HPLC column: t$_R$=25.1 min.

Example 65

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid [5-(acetylamino-methyl)-2-chloro-benzyl]-cyclopropyl-amide HCl (4M in dioxane, 4.90 mL) was added to a sol. of compounds L47 (770 mg, 0.990 mmol) in CH$_2$Cl$_2$ (9.90 mL) at 0° C. The mixture was stirred for 30 min at 0° C., and for 1 h at rt. The mixture was poured onto an efficiently stirred mixture of aq. 10% Na$_2$CO$_3$ (40 mL) and EtOAc (100 mL). The phases were separated, and the aq. phase was extracted back with EtOAc (2×). The combined org. extracts were dried over Na$_2$SO$_4$, filtered, and the solvents were removed under reduced pressure to yield the crude title compound mixed with its corresponding (3'S,4'R)-diastereoisomer (510 mg, 76%). This crude mixture was separated by HPLC (Regis Whelk, isocratic eluent B 50%) to yield the title compound (160 mg, 32%). LC-MS: $t_R$=0.77 min; ES+: 684.30. Chiral HPLC column: $t_R$=25.0 min.

Example 66

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid [5-(acetylamino-methyl)-2-chloro-benzyl]-cyclopropyl-amide HCl (4M in dioxane, 4.25 mL) was added to a sol. of compounds L48 (667 mg, 0.850 mmol) in $CH_2Cl_2$ (8.50 mL) at 0° C. The mixture was stirred for 30 min at 0° C., and for 1 h at rt. The mixture was poured onto an efficiently stirred mixture of aq. 10% $Na_2CO_3$ (40 mL) and EtOAc (100 mL). The phases were separated, and the aq. phase was extracted back with EtOAc (2×). The combined org. extracts were dried over $Na_2SO_4$, filtered, and the solvents were removed under reduced pressure to yield the crude title compound mixed with its corresponding (3'S,4'R)-diastereoisomer (515 mg, 88%). This crude mixture was separated by HPLC (Regis Whelk, isocratic eluent B 50%) to yield the title compound (160 mg, 32%). LC-MS: $t_R$=0.77 min; ES+: 684.30. Chiral HPLC column: $t_R$=26.3 min.

Example 67

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid {2-chloro-5-[(3,3,3-trifluoro-propionylamino)-methyl]-benzyl}-cyclopropyl-amide HCl (4M in dioxane, 5.10 mL) was added to a sol. of compounds L49 (870 mg, 1.02 mmol) in $CH_2Cl_2$ (10.2 mL) at 0° C. The mixture was stirred for 30 min at 0° C., and for 1 h at rt. The mixture was poured onto an efficiently stirred mixture of aq. 10% $Na_2CO_3$ (40 mL) and EtOAc (100 mL). The phases were separated, and the aq. phase was extracted back with EtOAc (2×). The combined org. extracts were dried over $Na_2SO_4$, filtered, and the solvents were removed under reduced pressure to yield the crude title compound mixed with its corresponding (3'S,4'R)-diastereoisomer (610 mg, 79%). This crude mixture was separated by HPLC (Regis Whelk, isocratic eluent B 50%) to yield the title compound (200 mg, 33%). LC-MS: $t_R$=0.81 min; ES+: 752.31. Chiral HPLC column: $t_R$=21.5 min.

Example 68

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid {2-chloro-5-[(3,3,3-trifluoro-propionylamino)-methyl]-benzyl}-cyclopropyl-amide HCl (4M in dioxane, 4.80 mL) was added to a sol. of compounds L50 (828 mg, 0.970 mmol) in $CH_2Cl_2$ (9.70 mL) at 0° C. The mixture was stirred for 30 min at 0° C., and for 1 h at rt. The mixture was poured onto an efficiently stirred mixture of aq. 10% $Na_2CO_3$ (40 mL) and EtOAc (100 mL). The phases were separated, and the aq. phase was extracted back with EtOAc (2×). The combined org. extracts were dried over $Na_2SO_4$, filtered, and the solvents were removed under reduced pressure to yield the crude title compound mixed with its corresponding (3'S,4'R)-diastereoisomer (715 mg, 98%). This crude mixture was separated by HPLC (Regis Whelk, isocratic eluent B 50%) to yield the title compound (215 mg, 29%). LC-MS: $t_R$=0.81 min; ES+: 754.23. Chiral HPLC column: $t_R$=20.9 min.

Example 69

(3R,4S)-4-{4-[3-(2-Chloro-3,6-difluoro-phenyl)isoxazol-5-ylmethoxy]-phenyl}-piperidine-3-carboxylic acid (2-chloro-5-cyclopropylaminomethyl-benzyl)-cyclopropyl-amide HCl (4M in dioxane, 3.40 mL) was added to a sol. of compound L51 (600 mg, 0.680 mmol) in $CH_2Cl_2$ (6.80 mL) at 0° C. The mixture was stirred for 30 min at 0° C., and for 1 h at rt. The mixture was poured onto an efficiently stirred mixture of aq. 10% $Na_2CO_3$ (40 mL) and EtOAc (100 mL). The phases were separated, and the aq. phase was extracted back with EtOAc (2×). The combined org. extracts were dried over $Na_2SO_4$, filtered, and the solvents were removed under reduced pressure to yield the crude racemic title compound (410 mg, 88%). This racemate was separated by HPLC (Regis Whelk, isocratic eluent B 50%) to yield the title compound (117 mg, 29%). LC-MS: $t_R$=0.78 min; ES+: 681.66. Chiral HPLC column: $t_R$=15.6 min.

Example 70

(3R,4S)-4-{4-[3-(2-Chloro-3,6-difluoro-phenyl)isoxazol-5-ylmethoxy]-phenyl}-piperidine-3-carboxylic acid [5-chloro-2-(3-methoxy-propyl)-1-oxy-pyridin-4-ylmethyl]-cyclopropyl-amide HCl (4M in dioxane, 5.00 mL) was added to a sol. of compound L52 (660 mg, 0.823 mmol) in $CH_2Cl_2$ (5.00 mL) at 0° C. The mixture was stirred for 30 min at 0° C., and for 1 h at rt. The mixture was diluted with $CH_2Cl_2$, washed with aq. sat. $NaHCO_3$ and brine. The org. layer was dried over $Na_2SO_4$, filtered, and the solvents were evaporated under reduced pressure. Purification of the crude by FC (MeOH/$CH_2Cl_2$ 1:9→3:7) yielded the racemic title compound (528 mg, 91%). This racemate was separated by HPLC (Regis Whelk, isocratic eluent B 30%) to yield the title compound (65 mg, 13%). LC-MS: $t_R$=0.85 min; ES+: 701.18. Chiral HPLC column: $t_R$=25.4 min.

Example 71

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid (2-chloro-5-cyclopropylaminomethyl-benzyl)-cyclopropyl-amide To a sol. of compounds L53 (860 mg, 0.97 mmol) in $CH_2Cl_2$ (9.7 mL) at 0° C. was added a HCl (4M in dioxane, 4.85 mL). The mixture was stirred at 0° C. for 30 min, and for 45 min at rt. The mixture was poured onto a mixture of aq. 10% $Na_2CO_3$ (28 mL) and EtOAc (140 ml) under stirring. The layers were separated. The org. extract was dried over $MgSO_4$, filtered, and the solvents were removed under reduced pressure to yield the crude title compound mixed with its corresponding (3'S,4'R)-diastereoisomer (631 mg, 95%). This mixture was separated by HPLC (Regis Whelk, isocratic eluent B 50%) to yield the title compound (175 mg, 29%). LC-MS: $t_R$=0.70 min; ES+: 683.10. Chiral HPLC column: $t_R$=16.9 min.

Example 72

(3R,4S)-4-{4-[3-(2-Chloro-3,6-difluoro-phenyl)isoxazol-5-ylmethoxy]-phenyl}-piperidine-3-carboxylic acid [5-(2-acetylamino-ethyl)-2-chloro-benzyl]-cyclopropyl-amide HCl (4M in dioxane, 3.00 mL) was added to a sol. of compound L54 (486 mg, 0.610 mmol) in $CH_2Cl_2$ (6.10 mL) at 0° C. The mixture was stirred for 30 min at 0° C., and for 1 h at rt. The mixture was poured onto efficiently stirred aq. 10% $Na_2CO_3$ (20 mL), and EtOAc (100 mL) was added. The layers were separated, and the aq. layer was extracted with EtOAc (2×). The combined org. extracts were dried over $MgSO_4$, filtered, and the solvents were removed under reduced pressure to yield the crude, racemic title compound (500 mg, quantitative yield). This racemate was separated by HPLC (Regis Whelk, isocratic eluent B 50%) to yield the title compound (60 mg, 12%). LC-MS: $t_R$=0.89 min; ES+: 697.26. Chiral HPLC column: $t_R$=22.8 min.

Example 73

(3R,4S)-4-{4-[3-(2-Chloro-3,6-difluoro-phenyl)isoxazol-5-ylmethoxy]-phenyl}-piperidine-3-carboxylic acid [2-chloro-5-(2-cyclopropylamino-ethyl)-benzyl]-cyclopropyl-amide HCl (4M in dioxane, 1.73 mL) was added to a sol. of compound L55 (620 mg, 0.692 mmol) in $CH_2Cl_2$ (5.00 mL) at 0° C. The mixture was stirred for 1 h at 0° C., and aq. sat. $NaHCO_3$ was added until the pH was neutral. The layers were separated, and the aq. layer was extracted with $CH_2Cl_2$. The combined org. extracts were washed with water and brine, were dried over $MgSO_4$, filtered, and the solvents were removed under reduced pressure to yield the crude, racemic title compound (485 mg, quantitative yield). This racemate was separated by HPLC (Regis Whelk, isocratic eluent B 50%) to yield the title compound (85 mg, 17%). LC-MS: $t_R$=0.79 min; ES+: 695.22. Chiral HPLC column: $t_R$=16.7 min.

Example 74

(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-cyclopropylamino-ethyl)-benzyl]-cyclopropyl-amide HCl (4M in dioxane, 2.00 mL) was added to a sol. of compounds L56 (227 mg, 0.253 mmol) in $CH_2Cl_2$ (4.00 mL) at 0° C. The mixture was stirred for 1 h at 0° C., and was neutralized with aq. sat. $NaHCO_3$. The layers were separated, and the org. layer was extracted with $CH_2Cl_2$. The combined org. extracts were washed with aq. 10% $Na_2CO_3$ and brine, were dried over $MgSO_4$, filtered, and the solvents were removed under reduced pressure to yield the crude title compound mixed with its corresponding (3'S, 4'R)-diastereoisomer (174 mg, 98%). This mixture was separated by HPLC (Regis Whelk, isocratic eluent B 45%) to yield the title compound (18 mg, 11%). LC-MS: $t_R$=0.72 min; ES+: 696.28. Chiral HPLC column: $t_R$=15.0 min.

Example 75

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid [2-chloro-5-(2-cyclopropylamino-ethyl)-benzyl]-cyclopropyl-amide HCl (4M in dioxane, 2.50 mL) was added to a sol. of compounds L57 (796 mg, 0.887 mmol) in $CH_2Cl_2$ (5.00 mL) at 0° C. The mixture was stirred for 1 h at 0° C., and was neutralized with aq. sat. $NaHCO_3$. The layers were separated, and the aq. layer was extracted with $CH_2Cl_2$ (2×). The combined org. extracts were washed with water and brine, dried over $MgSO_4$, filtered, and the solvents were removed under reduced pressure to yield the crude title compound mixed with its corresponding (3'S,4'R)-diastereoisomer (582 mg, 93%). This mixture was separated by HPLC (Regis Whelk, isocratic eluent B 50%) to yield the title compound (127 mg, 24%). LC-MS: $t_R$=0.72 min; ES+: 696.30. Chiral HPLC column: $t_R$=17.9 min.

Example 76

(3'R,4'S)-6-[2-(2,6-Dichloro-4-methyl-phenoxy)-ethoxy]-1',2',3',4',5',6'-hexahydro-[3,4']bipyridinyl-3'-carboxylic acid [5-chloro-2-(3-methoxy-propyl)-1-oxy-pyridin-4-ylmethyl]-cyclopropyl-amide HCl (4M in dioxane, 11.00 mL) was added to a sol. of compound L58 (780 mg, 1.00 mmol) in $CH_2Cl_2$ (11.00 mL) at 0° C. The mixture was stirred for 1.5 h at 0° C., and was poured onto efficiently stirred aq. 1M NaOH. The layers were separated, and the aq. layer was extracted with $CHCl_3$. The combined org. extracts were washed with brine, dried over $MgSO_4$, filtered, and the solvents were removed under reduced pressure to yield the crude racemic title compound (428 mg, 63%). This racemate was separated by HPLC (Regis Whelk, isocratic eluent B 50%) to yield the title compound (42 mg, 11%). LC-MS: $t_R$=0.85 min; ES+: 677.26. Chiral HPLC column: $t_R$=40.2 min.

Example 77

(3R,4S)-4-{4-[3-(2-Chloro-3,6-difluoro-phenyl)isoxazol-5-ylmethoxy]-phenyl}-piperidine-3-carboxylic acid {2-chloro-5-[(2,2-difluoro-ethylamino)-methyl]-benzyl}-cyclopropyl-amide HCl (4M in dioxane, 1.93 mL) was added to a sol. of compound L59 (700 mg, 0.773 mmol) in $CH_2Cl_2$ (5.00 mL) at 0° C. The mixture was stirred for 1 h at 0° C., and neutralized with aq. 10% $Na_2CO_3$. The layers were separated, and the aq. layer was extracted with $CH_2Cl_2$. The combined org. extracts were washed with brine, dried over $MgSO_4$, filtered, and the solvents were removed under reduced pressure to yield the crude racemic title compound (410 mg, 75%). This racemate was separated by HPLC (Regis Whelk, isocratic eluent B 50%) to yield the title compound (83 mg, 18%). LC-MS: $t_R$=0.79 min; ES+: 705.18. Chiral HPLC column: $t_R$=15.5 min.

Example 78

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid {2-chloro-5-[(2,2-difluoro-ethylamino)methyl]-benzyl}-cyclopropyl-amide HCl (4M in dioxane, 2.83 mL) was added to a sol. of compounds L60 (739 mg, 0.814 mmol) in $CH_2Cl_2$ (5.66 mL) at 0° C. The mixture was stirred for 1 h at rt, and aq. 10% $Na_2CO_3$ was added to neutralize the mixture. The layers were separated, and the aq. layer was extracted with $CH_2Cl_2$ (2×). The combined org. extracts were washed with water and brine, dried over $MgSO_4$, filtered, and the solvents were removed under reduced pressure to yield the crude title compound mixed with its corresponding (3'S,4'R)-diastereoisomer (534 mg, 93%). This mixture was separated by HPLC (Regis Whelk, isocratic eluent B 50%) to yield the title compound (118 mg, 23%). LC-MS: $t_R$=0.72 min; ES+: 708.27. Chiral HPLC column: $t_R$=16.2 min.

Example 79

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid (2-chloro-5-cyclopropyl-carbamoylmethyl-benzyl)-cyclopropyl-amide HCl (4M in dioxane, 2.83 mL) was added to a sol. of compounds L61 (637 mg, 0.785 mmol) in CH$_2$Cl$_2$ (5.66 mL) at 0° C. The mixture was stirred for 1 h at rt, and aq. sat. NaHCO$_3$ was added until a pH=7 was reached. The layers were separated, and the aq. layer was extracted with CH$_2$Cl$_2$ (2×). The combined org. extracts were washed with water and brine, were dried over MgSO$_4$, filtered, and the solvents were removed under reduced pressure to yield the crude title compound mixed with its corresponding (3'S,4'R)-diastereoisomer (466 mg, 83%). This mixture was separated by HPLC (Regis Whelk, isocratic eluent B 45%) to yield the title compound (55 mg, 13%). LC-MS: $t_R$=0.80 min; ES+: 710.21. Chiral HPLC column: $t_R$=36.7 min.

Example 80

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid (2-chloro-5-methylcarbamoylmethyl-benzyl)-cyclopropyl-amide HCl (4M in dioxane, 11.0 mL) was added to a sol. of compounds L62 (810 mg, 1.03 mmol) in CH$_2$Cl$_2$ (11.0 mL) at 0° C. The mixture was stirred for 1 h at 0° C., and aq. 1M NaOH (40 mL) was added. The layers were separated, and the aq. layer was extracted with CHCl$_3$. The combined org. extracts were washed with brine, dried over MgSO$_4$, filtered, and the solvents were removed under reduced pressure to yield the crude title compound mixed with its corresponding (3'S,4'R)-diastereoisomer (670 mg, 95%). This mixture was separated by HPLC (Regis Whelk, isocratic eluent B 50%) to yield the title compound (112 mg, 17%). LC-MS: $t_R$=0.75 min; ES+: 686.59. Chiral HPLC column: $t_R$=40.5 min.

Example 81

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid (2-chloro-5-ethylcarbamoylmethyl-benzyl)-cyclopropyl-amide HCl (4M in dioxane, 7.0 mL) was added to a sol. of compounds L63 (700 mg, 0.876 mmol) in CH$_2$Cl$_2$ (7.0 mL) at 0° C. The mixture was stirred for 2 h at 0° C., and aq. 1M NaOH was added until a pH>12 was reached. The layers were separated, and the aq. layer was extracted with CH$_2$Cl$_2$. The combined org. extracts were washed with brine, dried over MgSO$_4$, filtered, and the solvents were removed under reduced pressure to yield the crude title compound mixed with its corresponding (3'S,4'R)-diastereoisomer (605 mg, 99%). This mixture was separated by HPLC (Regis Whelk, isocratic eluent B 45%) to yield the title compound (110 mg, 19%). LC-MS: $t_R$=0.80 min; ES+: 698.32. Chiral HPLC column: $t_R$=39.1 min.

Example 82

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid [2-chloro-5-(propionylamino-methyl)-benzyl]-cyclopropyl-amide HCl (4M in dioxane, 13.0 mL) was added to a sol. of compounds L64 (990 mg, 1.24 mmol) in CH$_2$Cl$_2$ (13.0 mL) at 0° C. The mixture was stirred for 1 h at 0° C., and aq. 1M NaOH (40 mL) was added. The layers were separated, and the aq. layer was extracted with CHCl$_3$. The combined org. extracts were washed with brine, dried over MgSO$_4$, filtered, and the solvents were removed under reduced pressure. Purification of the crude by FC (MeOH/CH$_2$Cl$_2$ 1:19) yielded the title compound mixed with its corresponding (3'S,4'R)-diastereoisomer (571 mg, 66%). This mixture was separated by HPLC (Regis Whelk, isocratic eluent B 50%) to yield the title compound (100 mg, 18%). LC-MS: $t_R$=0.78 min; ES+: 698.60. Chiral HPLC column: $t_R$=27.5 min.

Example 83

(3R,4S)-4-{4-[3-(2-Chloro-3,6-difluoro-phenyl)-isoxazol-5-ylmethoxy]-phenyl}-piperidine-3-carboxylic acid {2-chloro-5-[(cyclopropanecarbonyl-amino)-methyl]-benzyl}-cyclopropyl-amide HCl (4M in dioxane, 3.70 mL) was added to a sol. of compound L65 (607 mg, 0.75 mmol) in CH$_2$Cl$_2$ (7.50 mL) at 0° C. The mixture was stirred for 1 h at rt, and was poured onto efficiently stirred aq. 10% Na$_2$CO$_3$. The layers were separated, and the aq. layer was extracted with EtOAc (2×). The combined org. extracts were dried over Na$_2$SO$_4$, filtered, and the solvents were removed under reduced pressure to yield the crude, racemic title compound (530 mg, 99%). This racemate was separated by HPLC (Regis Whelk, isocratic eluent B 50%) to yield the title compound (53 mg, 10%). LC-MS: $t_R$=0.90 min; ES+: 709.22. Chiral HPLC column: $t_R$=27.1 min.

Example 84

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid {2-chloro-5-[(cyclopropanecarbonyl-amino)-methyl]-benzyl}-cyclopropyl-amide HCl (4M in dioxane, 14 mL) was added to a sol. of compounds L66 (1030 mg, 1.27 mmol) in CH$_2$Cl$_2$ (14 mL) at 0° C. The mixture was stirred for 1 h at rt, and was poured onto efficiently stirred aq. 10% Na$_2$CO$_3$. The layers were separated, and aq. 1M NaOH (40 mL) was added. The layers were separated, and the aq. layer was extracted with CHCl$_3$. The combined org. extracts were washed with brine, dried over MgSO$_4$, filtered, and the solvents were removed under reduced pressure to yield the crude title compound mixed with its corresponding (3'S,4'R)-diastereoisomer (630 mg, 70%). This mixture was separated by HPLC (Regis Whelk, isocratic eluent B 50%) to yield the title compound (140 mg, 22%). LC-MS: $t_R$=0.79 min; ES+: 712.56. Chiral HPLC column: $t_R$=27.0 min.

Example 85

(4-Chloro-3-{[((3R,4S)-4-{4-[3-(2-chloro-3,6-difluoro-phenyl)-isoxazol-5-ylmethoxy]-phenyl}-piperidine-3-carbonyl)-cyclopropyl-amino]-methyl}-benzyl)-carbamic Acid Methyl ester HCl (4M in dioxane, 4.80 mL) was added to a sol. of compound L67 (616 mg, 0.770 mmol) in CH$_2$Cl$_2$ (7.70 mL) at 0° C. The mixture was stirred for 1 h at rt, and was poured onto efficiently stirred aq. 10% Na$_2$CO$_3$ (20 mL). The layers were separated, and the aq. layer was extracted with EtOAc. The combined org. extracts were dried over Na$_2$SO$_4$, filtered, and the solvents were removed under reduced pressure to yield the crude, racemic title compound (530 mg, 98%). This mixture was separated by HPLC (Regis Whelk, isocratic eluent B 50%) to yield the title compound (50 mg, 10%). LC-MS: t$_R$=0.89 min; ES+: 699.17. Chiral HPLC column: t$_R$=27.4 min.

Example 86

{4-Chloro-3-[(cyclopropyl-{(3'R,4'S)-6-[(R)-3-(2,6-dichloro-4-methyl-phenoxy)pyrrolidin-1-yl]-1',2',3',4',5',6'-hexahydro-[3,4']bipyridinyl-3'-carbonyl}-amino)-methyl]-benzyl}-carbamic Acid Methyl ester HCl (4M in dioxane, 1.25 mL) was added to a sol. of compounds L68 (190 mg, 0.237 mmol) in CH$_2$Cl$_2$ (2.37 mL) at 0° C. The mixture was stirred for 30 min at 0° C. and for 80 min at rt, and was poured onto efficiently stirred aq. 10% Na$_2$CO$_3$ (7.00 mL). The layers were separated, and the aq. layer was extracted with EtOAc. The combined org. extracts were dried over Na$_2$SO$_4$, filtered, and the solvents were removed under reduced pressure to yield the crude title compound mixed with its corresponding (3'S,4'R)-diastereoisomer (163 mg, 98%). This mixture was separated by HPLC (Regis Whelk, isocratic eluent B 50%) to yield the title compound (23 mg, 14%). LC-MS: t$_R$=0.80 min; ES+: 702.25. Chiral HPLC column: t$_R$=23.5 min.

Example 87

{4-Chloro-3-[(cyclopropyl-{(3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-benzyl}-carbamic Acid Methyl ester HCl (4M in dioxane, 3.25 mL) was added to a sol. of compounds L69 (630 mg, 0.786 mmol) in CH$_2$Cl$_2$ (7.90 mL) at 0° C. The mixture was stirred for 30 min at 0° C. and for 80 min at rt, and was poured onto efficiently stirred aq. 10% Na$_2$CO$_3$ (23.0 mL). The layers were separated, and the aq. layer was extracted with EtOAc. The combined org. extracts were dried over Na$_2$SO$_4$, filtered, and the solvents were removed under reduced pressure to yield the crude title compound mixed with its corresponding (3'S,4'R)-diastereoisomer (550 mg, 99%). This mixture was separated by HPLC (Regis Whelk, isocratic eluent B 50%) to yield the title compound (120 mg, 22%). LC-MS: t$_R$=0.78 min; ES+: 702.48. Chiral HPLC column: t$_R$=26.6 min.

Example 88

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid [5-(2-acetylamino-ethyl)-2-chloro-benzyl]-cyclopropyl-amide HCl (4M in dioxane, 6.4 mL) was added to a sol. of compounds L70 (1.36 g, 1.70 mmol) in CH$_2$Cl$_2$ (6 mL) at 0° C. The mixture was stirred for 1 h at 0° C., and aq. sat. NaHCO$_3$ was added to neutralization. CH$_2$Cl$_2$ was added, and the mixture was extracted with aq. 1M HCl and brine. The org. layer was dried over MgSO$_4$, filtered, and the solvents were removed under reduced pressure. Purification by HPLC yielded the title compound mixed with its corresponding (3'S,4'R)-diastereoisomer (658 mg, 55%). This mixture was separated by HPLC (Regis Whelk, isocratic eluent B 50%) to yield the title compound (184 mg, 28%). LC-MS: t$_R$=0.76 min; ES+: 700.58. Chiral HPLC column: t$_R$=21.0 min.

Example 89

(3'R,4'S)-6-[(S)-3-(2,6-Dichloro-4-methyl-phenoxy)-pyrrolidin-1-yl]-1',2',3',4',5',6'-hexahydro-[3,4']bipyridinyl-3'-carboxylic acid [5-(2-acetylamino-ethyl)-2-chloro-benzyl]-cyclopropyl-amide HCl (4M in dioxane, 2.35 mL) was added to a sol. of compounds L71 (500 mg, 0.626 mmol) in CH$_2$Cl$_2$ (3.00 mL) at 0° C. The mixture was stirred for 1 h at 0° C., and aq. sat. NaHCO$_3$ was added to neutralization. CH$_2$Cl$_2$ was added, and the mixture was extracted with aq. 1M HCl and brine. The org. layer was dried over MgSO$_4$, filtered, and the solvents were removed under reduced pressure. Purification by HPLC yielded the title compound mixed with its corresponding (3'S,4'R)-diastereoisomer (209 mg, 48%). This mixture was separated by HPLC (Regis Whelk, isocratic eluent B 50%) to yield the title compound (60 mg, 30%). LC-MS: t$_R$=0.78 min; ES+: 700.66. Chiral HPLC column: t$_R$=22.8 min.

Example 90

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid {2-chloro-5-[(2,2-difluoro-ethylamino)methyl]-benzyl}-cyclopropyl-amide HCl (4M in dioxane, 4.00 mL) was added to a sol. of compounds L72 (460 mg, 0.506 mmol) in CH$_2$Cl$_2$ (8.00 mL) at 0° C. The mixture was stirred for 1 h at 0° C., and aq. sat. NaHCO$_3$ was added to neutralization. CH$_2$Cl$_2$ was added, and the mixture was extracted with aq. 1M HCl and brine. The org. layer was dried over MgSO$_4$, filtered, and the solvents were removed under reduced pressure. Purification by HPLC yielded the title compound mixed with its corresponding (3'S,4'R)-diastereoisomer (270 mg, 75%). This mixture was separated by HPLC (Regis Whelk, isocratic eluent B 50%) to yield the title compound (34 mg, 15%). LC-MS: t$_R$=0.72 min; ES+: 706.23. Chiral HPLC column: t$_R$=14.0 min.

Example 91

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid (2-chloro-5-cyclopropylcarbamoylmethyl-benzyl)-cyclopropyl-amide HCl (4M in dioxane, 8.00 mL) was added to a sol. of compounds L73 (740 mg, 0.912 mmol) in CH$_2$Cl$_2$ (8.00 mL) at 0° C. The mixture was stirred for 30 min at 0° C., and for 1 h at rt. The solvents were removed under reduced pressure, and the residue was dried under high vacuum. The residue was dissolved in CHCl$_3$, and the mixture was washed with aq. 1M NaOH. The org. layer was dried over MgSO$_4$, filtered, and the solvents were removed under reduced pressure to yield the crude title compound mixed with its corresponding (3'S,4'R)-diastereoisomer (707 mg, quantitative yield). This mixture was separated by HPLC (Regis Whelk, isocratic eluent B 50%) to yield the title compound (180 mg, 28%). LC-MS: $t_R$=0.78 min; ES+: 712.60. Chiral HPLC column: $t_R$=38.5 min.

Example 92

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid (2-chloro-5-methyl-carbamoylmethyl-benzyl)-cyclopropyl-amide HCl (4M in dioxane, 7.00 mL) was added to a sol. of compounds L74 (632 mg, 0.805 mmol) in $CH_2Cl_2$ (7.00 mL) at 0° C. The mixture was stirred for 30 min at 0° C., and for 1 h at rt. The solvents were removed under reduced pressure, and the residue was dried under high vacuum. The residue was dissolved in $CHCl_3$, and the mixture was washed with aq. 1M NaOH. The org. layer was dried over $MgSO_4$, filtered, and the solvents were removed under reduced pressure to yield the crude title compound mixed with its corresponding (3'S,4'R)-diastereoisomer (544 mg, 99%). This mixture was separated by HPLC (Regis Whelk, isocratic eluent B 50%) to yield the title compound (62 mg, 12%). LC-MS: $t_R$=0.78 min; ES+: 684.66. Chiral HPLC column: $t_R$=38.6 min.

Example 93

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic acid {2-chloro-5-[(cyclopropanecarbonyl-amino)-methyl]-benzyl}-cyclopropyl-amide HCl (4M in dioxane, 5.00 mL) was added to a sol. of compounds L75 (491 mg, 0.605 mmol) in $CH_2Cl_2$ (5.00 mL) at 0° C. The mixture was stirred for 30 min at 0° C., and for 1 h at rt. The solvents were removed under reduced pressure, and the residue was dried under high vacuum. The residue was dissolved in $CHCl_3$, and the mixture was washed with aq. 1M NaOH. The org. layer was dried over $MgSO_4$, filtered, and the solvents were removed under reduced pressure to yield the crude title compound mixed with its corresponding (3'S,4'R)-diastereoisomer (544 mg, 99%). This mixture was separated by HPLC (Regis Whelk, isocratic eluent B 50%) to yield the title compound (71 mg, 16%). LC-MS: $t_R$=0.79 min; ES+: 712.63. Chiral HPLC column: $t_R$=24.6 min.

Example 94

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic Acid [5-chloro-2-(3-methoxy-propyl)-1-oxy-pyridin-4-ylmethyl]-cyclopropyl-amide HCl (4M in dioxane, 4.20 mL) was added to a sol. of compounds L76 (414 mg, 0.515 mmol) in $CH_2Cl_2$ (4.20 mL) at 0° C. The mixture was stirred for 30 min at 0° C., and for 1 h at rt. The solvents were removed under reduced pressure, and the residue was dried under high vacuum. The residue was dissolved in $CHCl_3$, and the mixture was washed with aq. 1M NaOH. The org. layer was dried over $MgSO_4$, filtered, and the solvents were removed under reduced pressure to yield the crude title compound mixed with its corresponding (3'S,4'R)-diastereoisomer (383 mg, quantitative yield). This mixture was separated by HPLC (Chiralcel OD, isocratic eluent B 80%) to yield the title compound (107 mg, 30%). LC-MS: $t_R$=0.74 min; ES+: 704.27. Chiral HPLC column: $t_R$=22.1 min.

Example 95

(3'R,4'S)-6-[(S)-3-(2,6-Dichloro-4-methyl-phenoxy)-pyrrolidin-1-yl]-1',2',3',4',5',6'-hexahydro-[3,4]bipyridinyl-3'-carboxylic Acid [5-chloro-2-(3-methoxy-propyl)-1-oxy-pyridin-4-ylmethyl]-cyclopropyl-amide HCl (4M in dioxane, 4.00 mL) was added to a sol. of compounds L77 (398 mg, 0.496 mmol) in $CH_2Cl_2$ (4.00 mL) at 0° C. The mixture was stirred for 30 min at 0° C., and for 1 h at rt. The solvents were removed under reduced pressure, and the residue was dried under high vacuum. The residue was dissolved in $CHCl_3$, and the mixture was washed with aq. 1M NaOH. The org. layer was dried over $MgSO_4$, filtered, and the solvents were removed under reduced pressure to yield the crude title compound mixed with its corresponding (3'S,4'R)-diastereoisomer (360 mg, quantitative yield). This mixture was separated by HPLC (Chiralcel OD, isocratic eluent B 80%) to yield the title compound (80 mg, 26%). LC-MS: $t_R$=0.75 min; ES+: 704.27. Chiral HPLC column: $t_R$=19.1 min.

Example 96

(3R,4S)-4-{4-[3-(2-Chloro-3,6-difluoro-phenyl)isoxazol-5-ylmethoxy]-phenyl}-piperidine-3-carboxylic Acid (2-chloro-5-cyclopropylcarbamoylmethyl-benzyl)-cyclopropyl-amide HCl (4M in dioxane, 7.00 mL) was added to a sol. of compound L78 (667 mg, 0.824 mmol) in $CH_2Cl_2$ (7.00 mL) at 0° C. The mixture was stirred at 0° C. for 3 h, and aq. 1M NaOH was added until the aq. layer showed a pH=14. The layers were separated, and the aq. phase was extracted with $CH_2Cl_2$. The combined org. extracts were dried over $MgSO_4$, filtered, and the solvents were removed under reduced pressure to yield the crude, racemic title compound (581 mg, 99%). This racemate was separated by HPLC (Regis Whelk, isocratic eluent B 50%) to yield the title compound (142 mg, 25%). LC-MS: $t_R$=0.88 min; ES+: 709.54. Chiral HPLC column: $t_R$=34.6 min.

Example 97

(3R,4S)-4-{4-[3-(2-Chloro-3,6-difluoro-phenyl)-isoxazol-5-ylmethoxy]-phenyl}-piperidine-3-carboxylic Acid (2-chloro-5-methylcarbamoylmethyl-benzyl)-cyclopropyl-amide HCl (4M in dioxane, 6.00 mL) was added to a sol. of compound L79 (597 mg, 0.762 mmol) in $CH_2Cl_2$ (6.00 mL) at 0° C. The mixture was stirred at 0° C. for 3 h, and aq. 1M NaOH was added until the aq. layer showed a pH=14. The layers were separated, and the aq. phase was extracted with $CH_2Cl_2$. The combined org. extracts were dried over $MgSO_4$, filtered, and the solvents were removed under reduced pressure to yield the crude, racemic title compound (518 mg, 99%). This racemate was separated by HPLC (Regis Whelk,

Example 98

(3R,4S)-4-{4-[3-(2-Chloro-3,6-difluoro-phenyl-isoxazol-5-ylmethoxy]-phenyl}-piperidine-3-carboxylic Acid (2-chloro-5-ethylcarbamoylmethyl-benzyl)-cyclopropyl-amide HCl (4M in dioxane, 5.00 mL) was added to a sol. of compound L80 (441 mg, 0.553 mmol) in $CH_2Cl_2$ (5.00 µL) at 0° C. The mixture was stirred at 0° C. for 3 h, and aq. 1M NaOH was added until the aq. layer showed a pH=14. The layers were separated, and the aq. phase was extracted with $CH_2Cl_2$. The combined org. extracts were dried over $MgSO_4$, filtered, and the solvents were removed under reduced pressure to yield the crude, racemic title compound (398 mg, quantitative yield). This racemate was separated by HPLC (Regis Whelk, isocratic eluent B 50%) to yield the title compound (82 mg, 21%). LC-MS: $t_R$=0.87 min; ES+: 697.56. Chiral HPLC column: $t_R$=32.2 min.

Example 99

(3R,4S)-4-{4-[3-(2-Chloro-3,6-difluoro-phenyl)-isoxazol-5-ylmethoxy]-phenyl}-piperidine-3-carboxylic Acid [2-chloro-5-(propionylamino-methyl)-benzyl]-cyclopropyl-amide HCl (4M in dioxane, 7.00 mL) was added to a sol. of compound L81 (640 mg, 0.802 mmol) in $CH_2Cl_2$ (7.00 mL) at 0° C. The mixture was stirred at 0° C. for 3 h, and aq. 1M NaOH was added until the aq. layer showed a pH=14. The layers were separated, and the aq. phase was extracted with $CH_2Cl_2$. The combined org. extracts were dried over $MgSO_4$, filtered, and the solvents were removed under reduced pressure to yield the crude, racemic title compound (584 mg, quantitative yield). This racemate was separated by HPLC (Regis Whelk, isocratic eluent B 50%) to yield the title compound (141 mg, 25%). LC-MS: $t_R$=0.88 min; ES+: 697.55. Chiral HPLC column: $t_R$=24.0 min.

Example 100

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic Acid (2-chloro-5-ethylcarbamoylmethyl-benzyl)cyclopropyl-amide HCl (4M in dioxane, 2.50 mL) was added to a sol. of compounds L82 (560 mg, 0.701 mmol) in $CH_2Cl_2$ (5.00 mL) at 0° C. The mixture was stirred at 0° C. for 1 h, and aq. sat. $NaHCO_3$ was added. The layers were separated, and the aq. phase was extracted with $CH_2Cl_2$. The combined org. extracts were dried over $MgSO_4$, filtered, and the solvents were removed under reduced pressure to yield the crude, title compound mixed with its corresponding (3'S,4'R)-diastereoisomer (300 mg, 61%). This mixture was separated by HPLC (Regis Whelk, isocratic eluent B 50%) to yield the title compound (75 mg, 27%). LC-MS: $t_R$=0.81 min; ES+: 700.27. Chiral HPLC column: $t_R$=18.4 min.

Example 101

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic Acid [2-chloro-5-(propionylamino-methyl)benzyl]-cyclopropyl-amide HCl (4M in dioxane, 7.00 mL) was added to a sol. of compounds L83 (530 mg, 0.663 mmol) in $CH_2Cl_2$ (7.00 mL) at 0° C. The mixture was stirred for 2 h at 0° C., and was poured onto aq. 1M NaOH. The layers were separated, and the aq. layer was extracted with $CHCl_3$. The combined org. extracts were dried over $MgSO_4$, filtered, and the solvents were removed under reduced pressure to yield the crude title compound mixed with its corresponding (3'S,4'R)-diastereoisomer (410 mg, 88%). This mixture was separated by HPLC (Regis Whelk, isocratic eluent B 50%) to yield the title compound (50 mg, 12%). LC-MS: $t_R$=0.77 min; ES+: 698.62. Chiral HPLC column: $t_R$=24.6 min.

Example 102

(3R,4S)-4-{4-[3-(2-Chloro-3,6-difluoro-phenyl)isoxazol-5-ylmethoxy]-phenyl}-piperidine-3-carboxylic Acid [2-chloro-5-(2-methylcarbamoyl-ethyl)benzyl]-cyclopropyl-amide HCl (4M in dioxane, 8.00 mL) was added to a sol. of compound L84 (775 mg, 0.972 mmol) in $CH_2Cl_2$ (8.00 mL) at 0° C. The mixture was stirred for 30 min at 0° C. and for 1.5 h at rt. The solvents were removed under reduced pressure, and the residue was dried under high vacuum. The residue was dissolved with $CHCl_3$, and the mixture was washed with aq. 1M NaOH. The org. layer was dried over $MgSO_4$, filtered, and the solvents were removed under reduced pressure to yield the crude, racemic title compound (792 mg, quantitative yield). This racemate was separated by HPLC (Regis Whelk, isocratic eluent B 50%) to yield the title compound (227 mg, 30%). LC-MS: $t_R$=0.87 min; ES+: 697.62. Chiral HPLC column: $t_R$=21.4 min.

Example 103

(3R,4S)-4-{4-[3-(2-Chloro-3,6-difluoro-phenyl)isoxazol-5-ylmethoxy]-phenyl}-piperidine-3-carboxylic Acid {2-chloro-5-[2-(2,2-difluoro-ethylamino)-ethyl]-benzyl}-cyclopropyl-amide HCl (4M in dioxane, 6.00 mL) was added to a sol. of compound L85 (525 mg, 0.571 mmol) in $CH_2Cl_2$ (6.00 mL) at 0° C. The mixture was stirred for 30 min at 0° C. and for 1.5 h at rt. The solvents were removed under reduced pressure, and the residue was dried under high vacuum. The residue was dissolved with $CHCl_3$, and the mixture was washed with aq. 1M NaOH. The org. layer was dried over $MgSO_4$, filtered, and the solvents were removed under reduced pressure to yield the crude, racemic title compound (460 mg, quantitative yield). This racemate was separated by HPLC (Regis Whelk, isocratic eluent B 50%) to yield the title compound (122 mg, 30%). LC-MS: $t_R$=0.78 min; ES+: 719.60. Chiral HPLC column: $t_R$=14.4 min.

Example 104

(3'R,4'S)-6-[3-(2-Chloro-3,6-difluoro-phenyl)isoxazol-5-ylmethoxy]-1',2',3',4',5',6'-hexahydro-[3,4']bipyridinyl-3'-carboxylic Acid [5-(2-acetylamino-ethyl)-2-chloro-benzyl]-cyclopropyl-amide HCl (4M in dioxane, 8 mL) was added to a sol. of compound L86 (770 mg, 0.964 mmol) in $CH_2Cl_2$ (8 mL) at 0° C.

The mixture was stirred for 30 min at 0° C., and for 1 h at rt. The solvents were removed under reduced pressure, and the residue was dried under high vacuum. The residue was diluted with CHCl$_3$, and the mixture was washed with aq. 1M NaOH. The org. layer was dried over MgSO$_4$, filtered, and the solvents were removed under reduced pressure to yield the crude racemic title compound (692 mg, quantitative yield). This racemate was separated by HPLC (Regis Whelk, isocratic eluent B 50%) to yield the title compound (211 mg, 31%). LC-MS: t$_R$=0.86 min; ES+: 698.60. Chiral HPLC column: t$_R$=18.9 min.

Example 105

(3'R,4'S)-6-[3-(2-Chloro-3,6-difluoro-phenyl)-isoxazol-5-ylmethoxy]-1',2',3',4',5',6'-hexahydro-[3,4']bipyridinyl-3'-carboxylic Acid [5-chloro-2-(3-methoxy-propyl)-1-oxy-pyridin-4-ylmethyl]-cyclopropyl-amide HCl (4M in dioxane, 6 mL) was added to a sol. of compound L88 (550 mg, 0.685 mmol) in CH$_2$Cl$_2$ (6 mL) at 0° C. The mixture was stirred for 30 min at 0° C., and for 1 h at rt. The solvents were removed under reduced pressure, and the residue was dried under high vacuum. The residue was diluted with CHCl$_3$, and the mixture was washed with aq. 1M NaOH. The org. layer was dried over MgSO$_4$, filtered, and the solvents were removed under reduced pressure to yield the crude racemic title compound (692 mg, quantitative yield). This racemate was separated by HPLC (Regis Whelk, isocratic eluent B 50%) to yield the title compound (83 mg, 17%). LC-MS: t$_R$=0.81 min; ES+: 702.54. Chiral HPLC column: t$_R$=41.4 min.

Example 106

(3'R,4'S)-6-[3-(2-Chloro-3,6-difluoro-phenyl)-isoxazol-5-ylmethoxy]-1',2',3',4',5',6'-hexahydro-[3,4']bipyridinyl-3'-carboxylic Acid [5-chloro-2-(3-methoxy-propyl)pyridin-4-ylmethyl]-cyclopropyl-amide HCl (4M in dioxane, 6 mL) was added to a sol. of compound L87 (600 mg, 0.763 mmol) in CH$_2$Cl$_2$ (6 mL) at 0° C. The mixture was stirred for 30 min at 0° C., and for 1 h at rt. The solvents were removed under reduced pressure, and the residue was dried under high vacuum. The residue was diluted with CHCl$_3$, and the mixture was washed with aq. 1M NaOH. The org. layer was dried over MgSO$_4$, filtered, and the solvents were removed under reduced pressure to yield the crude racemic title compound (534 mg, quantitative yield). This racemate was separated by HPLC (Regis Whelk, isocratic eluent B 50%) to yield the title compound (164 mg, 31%). LC-MS: t$_R$=0.84 min; ES+: 686.61. Chiral HPLC column: t$_R$=15.8 min.

Example 107

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic Acid [2-chloro-5-(2-methylcarbamoyl-ethyl)-benzyl]-cyclopropyl-amide HCl (4M in dioxane, 10 mL) was added to a sol. of compounds L89 (230 mg, 0.288 mmol) in CH$_2$Cl$_2$ (10 mL) at 0° C. The mixture was stirred for 30 min at 0° C., and for 1 h at rt. The solvents were removed under reduced pressure, and the residue was dried under high vacuum. The residue was diluted with CHCl$_3$, and the mixture was washed with aq. 1M NaOH. The org. layer was dried over MgSO$_4$, filtered, and the solvents were removed under reduced pressure to yield the crude title compound mixed with its corresponding (3'S,4'R)-diastereoisomer (130 mg, 65%). This mixture was separated by HPLC (Regis Whelk, isocratic eluent B 50%) to yield the title compound (30 mg, 21%). LC-MS: t$_R$=0.78 min; ES+: 700.63. Chiral HPLC column: t$_R$=22.1 min.

Example 108

(3'R,4'S)-6-[(R)-3-(2,6-Dichloro-4-methyl-phenoxy)-pyrrolidin-1-yl]-1',2',3',4',5',6'-hexahydro-[3,4']bipyridinyl-3'-carboxylic Acid {2-chloro-5-[2-(2,2-difluoro-ethylamino)-ethyl]-benzyl}-cyclopropyl-amide HCl (4M in dioxane, 16 mL) was added to a sol. of compounds L90 (772 mg, 0.838 mmol) in CH$_2$Cl$_2$ (16 mL) at 0° C. The mixture was stirred for 30 min at 0° C., and for 1 h at rt. The solvents were removed under reduced pressure, and the residue was dried under high vacuum. The residue was diluted with CHCl$_3$, and the mixture was washed with aq. 1M NaOH. The org. layer was dried over MgSO$_4$, filtered, and the solvents were removed under reduced pressure. Purification of the crude by FC (MeOH/CH$_2$Cl$_2$ 1:19) yielded the title compound mixed with its corresponding (3'S,4'R)-diastereoisomer (210 mg, 35%). This mixture was separated by HPLC (Regis Whelk, isocratic eluent B 50%) to yield the title compound (80 mg, 37%). LC-MS: t$_R$=0.70 min; ES+: 722.65. Chiral HPLC column: t$_R$=14.0 min.

Example 109

Methyl-carbamic Acid 4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-benzyl Ester HCl (4M in dioxane, 10 mL) was added to a sol. of compounds L91 (920 mg, 1.15 mmol) in CH$_2$Cl$_2$ (10 mL) at 0° C. The mixture was stirred for 3 h at 0° C. The mixture was diluted with more CH$_2$Cl$_2$, and the mixture was washed with aq. 1M NaOH. The org. layer was dried over MgSO$_4$, filtered, and the solvents were removed under reduced pressure. Drying the residue under high vacuum yielded the crude title compound mixed with its corresponding (3'S,4'R)-diastereoisomer (850 mg, quantitative yield). This mixture was separated by HPLC (Regis Whelk, isocratic eluent B 50%) to yield the title compound (175 mg, 22%). LC-MS: t$_R$=0.78 min; ES+: 700.61. Chiral HPLC column: t$_R$=26.1 min.

Example 110

Methyl-carbamic Acid 2-{4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-phenyl}-ethyl Ester HCl (4M in dioxane, 10 mL) was added to a sol. of compounds L92 (920 mg, 1.13 mmol) in CH$_2$Cl$_2$ (10 mL) at 0° C. The mixture was stirred for 3 h at 0° C. The mixture was diluted with more CH$_2$Cl$_2$, and the mixture was washed with aq. 1M NaOH. The org. layer was dried over MgSO$_4$, filtered, and the solvents were removed under reduced pressure. Drying the residue under high vacuum yielded the crude title compound mixed with its corresponding (3'S,4'R)-diastereoisomer (730 mg, 90%). This mixture was separated by HPLC (Regis Whelk, isocratic eluent B 50%) to yield the title compound (159 mg, 22%). LC-MS: $t_R$=0.79 min; ES+: 716.61. Chiral HPLC column: $t_R$=21.4 min.

Example 111

(2-{4-Chloro-3-[(cyclopropyl-{(3'R,4'S)-6-[(R-3-(2,6-dichloro-4-methyl-phenoxy)pyrrolidin-1-yl]-1',2',3',4',5',6'-hexahydro-[3,4']bipyridinyl-3'-carbonyl}-amino)-methyl]-phenyl}-ethyl)-carbamic Acid Methyl Ester HCl (4M in dioxane, 3.70 mL) was added to a sol. of compounds L93 (830 mg, 1.47 mmol) in $CH_2Cl_2$ (6.00 mL) at 0° C. The mixture was stirred for 1.5 h at rt. The mixture was diluted with more $CH_2Cl_2$, and the mixture was washed with aq. 1M NaOH. The org. layer was dried over $MgSO_4$, filtered, and the solvents were removed under reduced pressure. Drying the residue under high vacuum yielded the crude title compound mixed with its corresponding (3'S,4'R)-diastereoisomer (496 mg, 47%). This mixture was separated by HPLC (Regis Whelk, isocratic eluent B 50%) to yield the title compound (83 mg, 18%). LC-MS: $t_R$=0.80 min; ES+: 716.66. Chiral HPLC column: $t_R$=20.7 min.

Example 112

(3'R,4'S)-6-[3-(2-Chloro-3,6-difluoro-phenyl)-isoxazol-5-ylmethoxy]-1',2',3',4',5',6'-hexahydro-[3,4']bipyridinyl-3'-carboxylic Acid [2-chloro-5-(2-methoxy-ethyl)-benzyl]-cyclopropyl-amide HCl (4M in dioxane, 4.00 mL) was added to a sol. of compound L94 (370 mg, 0.479 mmol) in $CH_2Cl_2$ (4.00 mL) at 0° C. The mixture was stirred for 30 min at 0° C. and for 1 h at rt. The solvents were removed under reduced pressure, and the residue was dried under high vacuum. The residue was diluted with $CHCl_3$, and the mixture was washed with aq. 1M NaOH. The org. layer was dried over $MgSO_4$, filtered, and the solvents were removed under reduced pressure to yield the crude racemic title compound (344 mg, quantitative yield). This racemate was separated by HPLC (Regis Whelk, isocratic eluent B 50%) to yield the title compound (70 mg, 22%). LC-MS: $t_R$=0.90 min; ES+: 671.61. Chiral HPLC column: $t_R$=15.2 min.

Biological Assays
1. Enzyme Immuno Assay (EIA) to Estimate AngI Accumulation and Renin Inhibition
1.1 Preparation of AngI-BSA Conjugate 1.3 mg (1 µmol) of AngI [1-10 (Bachem, H-1680)] and 17 mg (0.26 µmol) of BSA (Fluka, 05475) were dissolved in 4 mL of 0.1M phosphate buffer, pH 7.4, after which 2 mL of a 1:100 dilution of glutaraldehyde in $H_2O$ (Sigma G-5882) was added dropwise. The mixture was incubated overnight at 4° C., then dialyzed against 2 liters of 0.9% NaCl, twice for 4 h at rt, followed by dialysis against 2 liters of PBS 1× overnight at rt. The solution was then filtered with a Syringe filter, 0.45 µm (Nalgene, Cat. No. 194-2545). The conjugate can be stored in polypropylene tubes in 0.05% sodium azide at 4° C. for at least 12 months.
1.2 Preparation of BSA-AngI Coated MTP Microtiter plates (MPT384, MaxiSorp™, Nunc) were incubated overnight at 4° C. with 80 µl of AngI (1-10)/BSA conjugate, diluted 1:100'000 in PBS 1× in a teflon beaker (exact dilution dependent on batch of conjugate), emptied, filled with 90 µl of blocking solution [0.5% BSA (Sigma A-2153) in PBS 1×, 0.02% $NaN_3$], and incubated for at least 2 h at rt, or overnight at 4° C. 96 well MTP (MaxiSorp™, Nunc) were coated with 200 µl conjugate and blocked with 250 µl blocking solution as above, except that the blocking solution contained 3% BSA. The plates can be stored in blocking solution at 4° C. for 1 month.
1.3 AngI-EIA in 384 Well MTP The AngI (1-10)/BSA coated MTP were washed 3 times with wash buffer (PBS 1×, 0.01% Tween 20) and filled with 75 µl of primary antibody solution (anti-AngI antiserum, pre-diluted 1:10 in horse serum), diluted to a final concentration of 1:100'000 in assay buffer (PBS 1×, 1 mM EDTA, 0.1% BSA, pH 7.4). 5 µl of the renin reaction (or standards in assay buffer) (see below) were added to the primary antibody solution and the plates were incubated overnight at 4° C. After the incubation the plates were washed 3 times with wash buffer and incubated with secondary antibody [anti-rabbit IgG, linked to horseradish peroxidase (Amersham Bioscience, NA 934V), diluted 1:2'000 in wash buffer] for 2 h at rt. The plates were washed 3 times with wash buffer and then incubated for 1 h at rt with substrate solution [1.89 mM ABTS (2,2'-azino-di-(3-ethyl-benzthiazolinsulfonate)] (Roche Diagnostics, 102 946) and 2.36 mM $H_2O_2$ [30%, (Fluka, 95300] in substrate buffer (0.1M sodium acetate, 0.05M sodium dihydrogen phosphate, pH 4.2). The OD of the plate was read at 405 nm in a microplate reader (FLUOStar Optima from BMG). The production of AngI during the renin reaction was quantified by comparing the OD of the sample with the OD of a standard curve of AngI(1-10), measured in parallel.
2. Primary Renin Inhibition Assay: $IC_{50}$ in Buffer, 384 Well MTP The renin assay was adapted from an assay described before (Fischli W. et al., *Hypertension,* 1991, 18:22-31) and consists of two steps: in the first step, recombinant human renin is incubated with its substrate (commercial human tetradecapeptide renin substrate) to create the product Angiotensin I (AngI). In the second step, the accumulated AngI is measured by an immunological assay (enzyme immuno assay, EIA). The detailed description of this assay is found below. The EIA is very sensitive and well suited for renin activity measurements in buffer or in plasma. Due to the low concentration of renin used in this assay (2 fmol per assay tube or 10 pM) it is possible to measure inhibitor affinities in this primary assay down to low pM concentration.
2.1 Methodology Recombinant human renin (3 pg/µl) in assay buffer (PBS 1×, 1 mM EDTA, 0.1% BSA, pH 7.4), human tetradecapeptide (1-14) substrate (Bachem, M-1120) [5 µM in 10 mM HCl], hydroxyquinoline sulfate (Fluka, 55100) [30 mM in $H_2O$] and assay buffer were premixed at 4° C. at a ratio of 100:30:10:145. 47.5 µl per well of this premix was transferred into polypropylene plates (MTP384, Nunc). Test compounds were dissolved and diluted in 100% DMSO and 2.5 µl added to the premix, then incubated at 37° C. for 3 h. At the end of the incubation period, 5 µl of the renin reaction (or standards in assay buffer) were transferred into EIA assays (as described above) and AngI produced by renin was quantified. The percentage of renin inhibition (AngI decrease) was calculated for each concentration of compound and the concentration of renin inhibition was determined that inhibited the enzyme activity by 50% ($IC_{50}$). The compounds of the present invention also exhibit a very good bioavailability and are metabolically more stable than prior art compounds.

Examples of Inhibition:

| Compound of Example No. | IC$_{50}$ values [nM] |
|---|---|
| 1 | 0.2 |
| 4 | 0.2 |
| 11 | 0.3 |
| 13 | 0.8 |
| 18 | 0.5 |
| 26 | 0.14 |
| 34 | 0.1 |
| 42 | 0.26 |
| 50 | 0.24 |
| 60 | 0.26 |
| 67 | 0.63 |
| 77 | 0.22 |
| 83 | 0.18 |
| 93 | 0.38 |
| 102 | 0.08 |
| 110 | 0.39 |

The invention claimed is:

1. A compound of the formula (I)

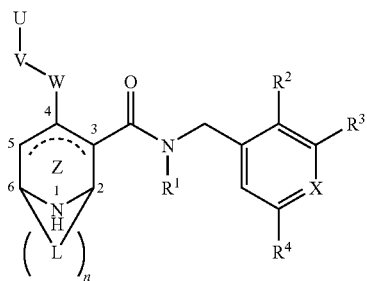

Formula (I)

wherein the dotted line in the 6-membered nitrogen containing ring Z of formula (I) (said ring Z consisting of the numbered ring atoms 1 to 6) indicates that either a double bond is present at the 3,4- or at the 4,5-position of the ring Z of formula (I) or that no double bond is present in the ring Z of formula (I); and wherein a double bond can be present at the 3,4- or at the 4,5-position of the ring Z of formula (I); or:

no double bond may be present in the ring Z of formula (I) if:
i) X represents N or N$^+$—O$^-$, or
ii) V represents —O—CH$_2$-Q-, or
iii) W represents para-substituted phenyl or para-substituted pyridinyl, and V represents a pyrrolidinyl of the formula:

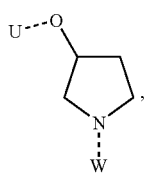

X represents CH, N, or N$^+$—O$^-$;
W represents a para-substituted phenyl, a para-substituted pyridinyl, or a thiazolyl;

V represents —O—CH$_2$-Q-, wherein Q is bound to the group U of formula (I); or:
V represents a pyrrolidinyl of the formula:

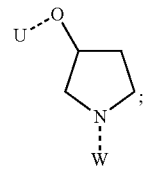

U represents unsubstituted aryl; mono-, di-, tri- or tetra-substituted aryl, wherein the substituents are independently selected from C$_{1-7}$-alkyl, —CF$_3$, halogen and hydroxy-C$_{1-7}$-alkyl; or five-membered heteroaryl containing two heteroatoms independently selected from nitrogen, oxygen and sulfur, wherein said heteroaryl radical is optionally mono-, di- or tri-substituted, wherein the substitutents are independently selected from C$_{1-7}$-alkyl, C$_{1-7}$-alkoxy, —CF$_3$, —OCF$_3$, and halogen;
Q represents a five-membered heteroaryl with two or three heteroatoms independently selected from O and N;
R$^1$ represents C$_{1-7}$-alkyl or cycloalkyl;
R$^2$ represents halogen or C$_{1-7}$-alkyl;
R$^3$ represents halogen, C$_{1-7}$-alkyl, C$_{1-7}$-alkoxy, —CF$_3$, or hydrogen;
R$^4$ represents C$_{1-7}$-alkyl-O—(CH$_2$)$_{0-4}$—CH$_2$—; CF$_3$—O—(CH$_2$)$_{0-4}$—CH$_2$—; R'R''N—(CH$_2$)$_{0-4}$—CH$_2$—, wherein R' and R'' are independently selected from the group consisting of hydrogen, C$_{1-7}$-alkyl (optionally substituted by one to three fluorine), cyclopropyl (optionally substituted by one to three fluorine), cyclopropyl-C$_{1-7}$-alkyl (optionally substituted by one to three fluorine), and —C(=O)—R''' wherein R''' is C$_{1-4}$-alkyl, C$_{1-4}$-alkoxy, —CF$_3$, —CH$_2$—CF$_3$, or cyclopropyl; or R$^{12}$NH—C(=O)—(O)O—, —(CH$_2$)$_{0-4}$—, wherein R$^{12}$ is C$_{1-4}$-alkyl, C$_{1-4}$-alkoxy, or cyclopropyl;
n represents the integer 0;
and salts thereof.

2. A compound according to claim 1, wherein
a double bond can be present at the 3,4- or at the 4,5-position of the ring Z of formula (I); or
no double bond may be present in the ring Z of formula (I) if:
i) X represents N, or
ii) V represents —O—CH$_2$-Q-
X represents CH or N;
V represents —O—CH$_2$-Q-, wherein Q is bound to the group U of formula (I); or:
V represent a pyrrolidinyl of the formula:

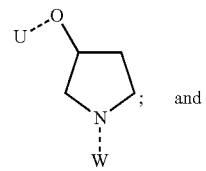

and

R$^4$ represents C$_{1-7}$-alkyl-O—(CH$_2$)$_{0-4}$—CH$_2$—; CF$_3$—O—(CH$_2$)$_{0-4}$—CH$_2$—; or R'R''N—(CH$_2$)$_{0-4}$—CH$_2$—, wherein R' and R'' are independently selected from the group consisting of hydrogen, C$_{1-7}$-alkyl (optionally substituted by one to three fluorine), cyclopropyl (optionally substituted by one to three fluorine), cyclopropyl-$C_{1-7}$-alkyl (optionally substituted by one to three fluorine), and —C(=O)—R''' wherein R''' is $C_{1-4}$-alkyl, —CF$_3$, —CH$_2$—CF$_3$, or cyclopropyl;

or a salt of such a compound.

3. A compound according to claim 1, wherein X represents CH or N$^+$—O$^-$, or a salt of such a compound.

4. A compound according to claim 1, wherein R$^1$ represents cyclopropyl, or a salt of such a compound.

5. A compound according to claim 1, wherein W represents a para-substituted phenyl, or

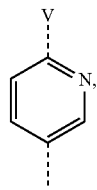

or a salt of such a compound.

6. A compound according to claim 1, wherein V represents —O—CH$_2$-Q-, or a salt of such a compound.

7. A compound according to claim 1, wherein V—W represents:

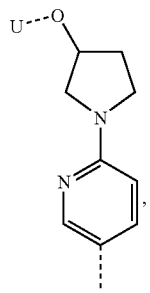

or a salt of such a compound.

8. A compound according to claim 1, wherein U represents

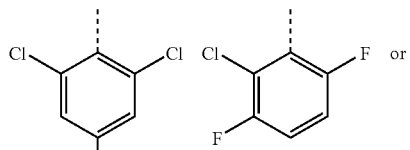

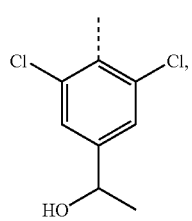

or a salt of such a compound.

9. A compound according to claim 8, wherein U represents

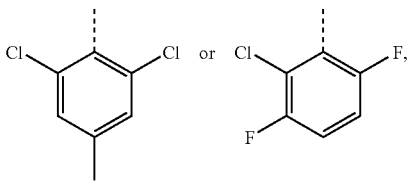

or a salt of such a compound.

10. A compound according to claim 1, wherein Q represents an isoxazolyl or an oxadiazolyl, or a salt of such a compound.

11. A compound according to claim 10, wherein Q represents an isoxazolyl, or a salt of such a compound.

12. A compound according to claim 1, wherein R$^2$ represents Cl, and R$^3$ represents hydrogen, or a salt of such a compound.

13. A compound according to claim 1, wherein R$^4$ represents CH$_3$—O—(CH$_2$)$_{2-3}$—, or CH$_3$—C(=O)—NH—CH$_2$—CH$_2$—, or a salt of such a compound.

14. A compound according to claim 1, wherein R$^4$ represents —CH$_2$CH$_2$CH$_2$—O—CH$_3$ or —CH$_2$CH$_2$—O—CH$_3$, or a salt of such a compound.

15. A compound according to claim 14, wherein R$^4$ represents —CH$_2$CH$_2$—O—CH$_3$, or a salt of such a compound.

16. A compound according to claim 1, wherein the moiety

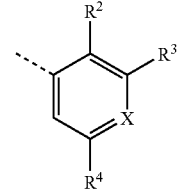

represents one of the following possibilities:

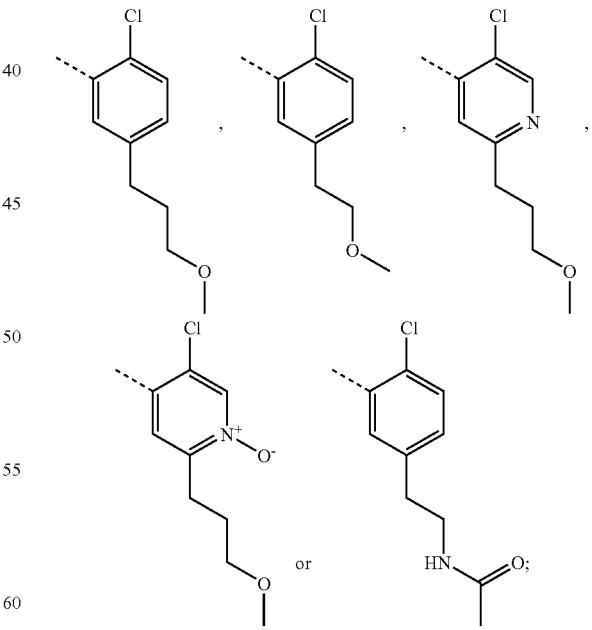

or a salt of such a compound.

17. A compound according to claim 1, wherein no double bond is present in the ring Z of formula (I), or a double bond is present at the 3,4-position of the ring Z of formula (I), or a salt of such a compound.

18. A compound according to claim 1, wherein a double bond can be present at the 3,4-position of the ring Z of formula (I);
or:
no double bond may be present in the ring Z of formula (I) if:
  i) X represents N or N⁺—O⁻, or
  ii) V represents —O—CH₂-Q-, or
  iii) W represents para-substituted pyridinyl and V represents a pyrrolidinyl of the formula:

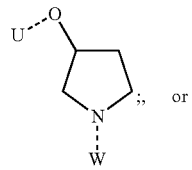

X represents CH, N, or N⁺—O⁻;
W represents a para-substituted phenyl, or a para-substituted pyridinyl;
V represents O—CH₂-Q-, wherein Q is bound to the group U of formula (I), or
V represent a pyrrolidinyl of the formula:

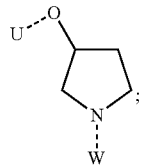

U represents tri-substituted phenyl, wherein the substituents are independently selected from $C_{1-7}$-alkyl and halogen;
Q represents an isoxazolyl;
$R^1$ represents cyclopropyl;
$R^2$ represents halogen or $C_{1-7}$-alkyl;
$R^3$ represents halogen or hydrogen;
$R^4$ represents $C_{1-7}$-alkyl-O—(CH₂)₀₋₄—CH₂—; R'R"N—(CH₂)₀₋₄—CH₂—, wherein R' and R" are independently selected from the group consisting of hydrogen, $C_{1-7}$-alkyl substituted by one to three fluorine, cyclopropyl, and —C(═O)—R'" wherein R'" is $C_{1-4}$-alkyl, $C_{1-4}$-alkoxy, —CH₂—CF₃, or cyclopropyl; or $R^{12}$NH—C(═O)—(O)O—, —(CH₂)₀₋₄—, wherein $R^{12}$ is $C_{1-4}$-alkyl or cyclopropyl; with the proviso that R' and R" cannot both simultaneously represent hydrogen;
$R^6$ represents —H, $C_{1-7}$-alkyl-CO—, —CONHR⁸, or —C(H)NH₂;
$R^8$ represents cycloalkyl; or $C_{1-7}$-alkyl or cycloalkyl which are both mono-substituted with cyano or —CONH₂; and
n represents the integer 0;
or a salt of such a compound.

19. A compound according to claim 1, wherein
no double bond is present in the ring Z of formula (I), and the 3- and 4-substituents of the ring Z of formula (I) are trans to each others, or a salt of such a compound.

20. A compound according to claim 1, wherein
no double bond is present in the ring Z of formula (I), and the absolute configuration is (R) at the position 3 of the ring Z of formula (I), and the 4-substituent of the ring Z of formula (I) is trans to the 3-substituent of the ring Z of formula (I), or a salt of such a compound.

21. A compound according to claim 1 selected from the group consisting of:
4-{4-[3-(2-chloro-3,6-difluoro-phenyl)-isoxazol-5-yl-methoxy]-phenyl}-1,2,5,6-tetrahydro-pyridine-3-carboxylic acid [2-chloro-5-(3-methoxy-propyl)-benzyl]-cyclopropyl-amide,
(3R,4S)-4-{4-[3-(2-chloro-3,6-difluoro-phenyl)-isoxazol-5-ylmethoxy]-phenyl}-piperidine-3-carboxylic acid [2-chloro-5-(3-methoxy-propyl)-benzyl]-cyclopropyl-amide, and
6-[3-(2-chloro-3,6-difluoro-phenyl)-isoxazol-5-ylmethoxy]-1',2',5',6'-tetrahydro-[3,4']bipyridinyl-3'-carboxylic acid [2-chloro-5-(3-methoxy-propyl)-benzyl]-cyclopropyl-amide,
and salts of these compounds.

22. A compound according to claim 1 selected from the group consisting of:
4-{4-[3-(2-chloro-3,6-difluoro-phenyl)-isoxazol-5-ylmethoxy]-phenyl}-1,2,5,6-tetrahydro-pyridine-3-carboxylic acid [5-chloro-2-(3-methoxy-propyl)-pyridin-4-ylmethyl]-cyclopropyl-amide,
(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-methoxy-ethyl)-benzyl]-cyclopropyl-amide,
(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [5-chloro-2-(3-methoxy-propyl)-pyridin-4-ylmethyl]-cyclopropyl-amide,
(3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-methoxy-ethyl)-benzyl]-cyclopropyl-amide, -cyclopropyl-amide,
(3R,4S)-4-{4-[3-(2-chloro-3,6-difluoro-phenyl)-isoxazol-5-ylmethoxy]-phenyl}-piperidine-3-carboxylic acid [5-chloro-2-(3-methoxy-propyl)-pyridin-4-ylmethyl]-cyclopropyl-amide,
(3R,4S)-4-{4-[3-(2-chloro-3,6-difluoro-phenyl)-isoxazol-5-ylmethoxy]-phenyl}-piperidine-3-carboxylic acid [5-(acetylamino-methyl)-2-chloro-benzyl]-cyclopropyl-amide,
(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [5-(acetylamino-methyl)-2-chloro-benzyl]-cyclopropyl-amide,
(3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid [5-(acetylamino-methyl)-2-chloro-benzyl]-cyclopropyl-amide,
(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[(3,3,3-trifluoro-propionylamino)-methyl]-benzyl}-cyclopropyl-amide,
(3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[(3,3,3-trifluoro-propionylamino)-methyl]-benzyl}-cyclopropyl-amide,
(3R,4S)-4-{4-[3-(2-chloro-3,6-difluoro-phenyl)-isoxazol-5-ylmethoxy]-phenyl}-piperidine-3-carboxylic acid (2-chloro-5-cyclopropylaminomethyl-benzyl)-cyclopropyl-amide,
(3R,4S)-4-{4-[3-(2-chloro-3,6-difluoro-phenyl)-isoxazol-5-ylmethoxy]-phenyl}-piperidine-3-carboxylic acid [5-chloro-2-(3-methoxy-propyl)-1-oxy-pyridin-4-ylmethyl]-cyclopropyl-amide,
(3'R,4'S)-6-[(S)-3-(2,6-dichloro-4-methyl-phenoxy)-pyrrolidin-1-yl]-1',2',3',4',5',6'-hexahydro-[3,4']bipyridinyl-3'-carboxylic acid (2-chloro-5-cyclopropylami-nomethyl-benzyl)-cyclopropyl-amide, (3R,4S)-4-{4-[3-(2-chloro-3,6-difluoro-phenyl)-isox-azol-5-ylmethoxy]-phenyl}-piperidine-3-carboxylic acid [5-(2-acetylamino-ethyl)-2-chloro-benzyl]-cyclo-propyl-amide, (3R,4S)-4-{4-[3-(2-chloro-3,6-difluoro-phenyl)-isox-azol-5-ylmethoxy]-phenyl}-piperidine-3-carboxylic acid [2-chloro-5-(2-cyclopropylamino-ethyl)-benzyl]-cyclopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid [2-chloro-5-(2-cyclopropy-lamino-ethyl)-benzyl]-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid [2-chloro-5-(2-cyclopropy-lamino-ethyl)-benzyl]-cyclopropyl-amide, (3R,4S)-4-{4-[3-(2-chloro-3,6-difluoro-phenyl)-isox-azol-5-ylmethoxy]-phenyl}-piperidine-3-carboxylic acid {2-chloro-5-[(2,2-difluoro-ethylamino)-methyl]-benzyl}-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid {2-chloro-5-[(2,2-difluoro-ethy-lamino)-methyl]-benzyl}-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid (2-chloro-5-cyclopropylcarbam-oylmethyl-benzyl)-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid (2-chloro-5-methylcarbamoylm-ethyl-benzyl)-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid (2-chloro-5-ethylcarbamoylm-ethyl-benzyl)-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid [2-chloro-5-(propionylamino-methyl)-benzyl]-cyclopropyl-amide, (3R,4S)-4-{4-[3-(2-chloro-3,6-difluoro-phenyl)-isox-azol-5-ylmethoxy]-phenyl}-piperidine-3-carboxylic acid {2-chloro-5-[(cyclopropanecarbonyl-amino)-me-thyl]-benzyl}-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid {2-chloro-5-[(cyclopropanecar-bonyl-amino)-methyl]-benzyl}-cyclopropyl-amide, (4-chloro-3-{[((3R,4S)-4-{4-[3-(2-chloro-3,6-difluoro-phenyl)-isoxazol-5-ylmethoxy]-phenyl}-piperidine-3-carbonyl)-cyclopropyl-amino]-methyl}-benzyl)-car-bamic acid methyl ester, {4-chloro-3-[(cyclopropyl-{(3'R,4'S)-6-[(R)-3-(2,6-dichloro-4-methyl-phenoxy)-pyrrolidin-1-yl]-1',2',3', 4',5',6'-hexahydro-[3,4']bipyridinyl-3'-carbonyl}-amino)-methyl]-benzyl}-carbamic acid methyl ester, {4-chloro-3-[(cyclopropyl-{(3'R,4'S)-6-[(S)-3-(2,6-dichloro-4-methyl-phenoxy)-pyrrolidin-1-yl]-1',2',3', 4',5',6'-hexahydro-[3,4']bipyridinyl-3'-carbonyl}-amino)-methyl]-benzyl}-carbamic acid methyl ester, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid [5-(2-acetylamino-ethyl)-2-chloro-benzyl]-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid [5-(2-acetylamino-ethyl)-2-chloro-benzyl]-cyclopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid {2-chloro-5-[(2,2-difluoro-ethy-lamino)-methyl]-benzyl}-cyclopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid (2-chloro-5-cyclopropylcarbam-oylmethyl-benzyl)-cyclopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid (2-chloro-5-methylcarbamoylm-ethyl-benzyl)-cyclopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid {2-chloro-5-[(cyclopropanecar-bonyl-amino)-methyl]-benzyl}-cyclopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid [5-chloro-2-(3-methoxy-propyl)-1-oxy-pyridin-4-ylmethyl]-cyclopropyl-amide, (3'R,4'S)-6-[(S)-3-(2,6-dichloro-4-methyl-phenoxy)-pyr-rolidin-1-yl]-1',2',3',4',5',6'-hexahydro-[3,4']bipyridi-nyl-3'-carboxylic acid [5-chloro-2-(3-methoxy-propyl)-1-oxy-pyridin-4-ylmethyl]-cyclopropyl-amide, (3R,4S)-4-{4-[3-(2-chloro-3,6-difluoro-phenyl)-isox-azol-5-ylmethoxy]-phenyl}-piperidine-3-carboxylic acid (2-chloro-5-cyclopropylcarbamoylmethyl-ben-zyl)-cyclopropyl-amide, (3R,4S)-4-{4-[3-(2-chloro-3,6-difluoro-phenyl)-isox-azol-5-ylmethoxy]-phenyl}-piperidine-3-carboxylic acid (2-chloro-5-methylcarbamoylmethyl-benzyl)-cy-clopropyl-amide, (3R,4S)-4-{4-[3-(2-chloro-3,6-difluoro-phenyl)-isox-azol-5-ylmethoxy]-phenyl}-piperidine-3-carboxylic acid (2-chloro-5-ethylcarbamoylmethyl-benzyl)-cyclo-propyl-amide, (3R,4S)-4-{4-[3-(2-chloro-3,6-difluoro-phenyl)-isox-azol-5-ylmethoxy]-phenyl}-piperidine-3-carboxylic acid [2-chloro-5-(propionylamino-methyl)-benzyl]-cy-clopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid (2-chloro-5-ethylcarbamoylm-ethyl-benzyl)-cyclopropyl-amide, (3'R,4'S)-6-[(R)-3-(2,6-dichloro-4-methyl-phenoxy)-pyr-rolidin-1-yl]-1',2',3',4',5',6'-hexahydro-[3,4']bipyridi-nyl-3'-carboxylic acid [2-chloro-5-(propionylamino-methyl)-benzyl]-cyclopropyl-amide, (3R,4S)-4-{4-[3-(2-chloro-3,6-difluoro-phenyl)-isox-azol-5-ylmethoxy]-phenyl}-piperidine-3-carboxylic acid [2-chloro-5-(2-methylcarbamoyl-ethyl)-benzyl]-cyclopropyl-amide, (3R,4S)-4-{4-[3-(2-chloro-3,6-difluoro-phenyl)-isox-azol-5-ylmethoxy]-phenyl}-piperidine-3-carboxylic acid {2-chloro-5-[2-(2,2-difluoro-ethylamino)-ethyl]-benzyl}-cyclopropyl-amide, (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [5-(2-acetylamino-ethyl)-2-chloro-benzyl]-cyclopropyl-amide, (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [5-chloro-2-(3-methoxy-propyl)-1-oxy-pyridin-4-ylmethyl]-cyclopropyl-amide, (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [5-chloro-2-(3-methoxy-propyl)-pyridin-4-ylmethyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid [2-chloro-5-(2-methylcarbamoyl-ethyl)-benzyl]-cyclopropyl-amide, (3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carboxylic acid {2-chloro-5-[2-(2,2-difluoro-ethylamino)-ethyl]-benzyl}-cyclopropyl-amide, methyl-carbamic acid 4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-benzyl ester, methyl-carbamic acid 2-{4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-phenyl}-ethyl ester, (2-{4-chloro-3-[(cyclopropyl-{(3'R,4'S)-6-[(R)-3-(2,6-dichloro-4-methyl-phenoxy)-pyrrolidin-1-yl]-1',2',3',4',5',6'-hexahydro-[3,4']bipyridinyl-3'-carbonyl}-amino)-methyl]-phenyl}-ethyl)-carbamic acid methyl ester, and (3'R,4'S)-6-[3-(2-chloro-3,6-difluoro-phenyl)-isoxazol-5-ylmethoxy]-1',2',3',4',5',6'-hexahydro-[3,4']bipyridinyl-3'-carboxylic acid [2-chloro-5-(2-methoxy-ethyl)-benzyl]-cyclopropyl-amide, and salts of these compounds.

23. A pharmaceutical composition comprising a compound according to claim 1, or a pharmaceutically acceptable salt thereof, and a pharmaceutically acceptable carrier material.

* * * * *